(12) United States Patent
Edmunds et al.

(10) Patent No.: US 6,498,125 B2
(45) Date of Patent: Dec. 24, 2002

(54) PYRIDINE KETONES USEFUL AS HERBICIDES

(75) Inventors: Andrew Edmunds, Basel (CH); Karl Seckinger, Riegel (DE); Christoph Lüthy, Münchenstein (CH); Walter Kunz, Oberwil (CH); Alain De Mesmaeker, Kaenerkinden (CH); Jürgen Schaetzer, Rheinfelden (DE)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/804,507

(22) Filed: Mar. 12, 2001

(65) Prior Publication Data

US 2002/0016345 A1 Feb. 7, 2002

Related U.S. Application Data

(63) Continuation of application No. PCT/EP99/06761, filed on Sep. 13, 1999.

(30) Foreign Application Priority Data

Sep. 15, 1998 (CH) .............................................. 1873/98

(51) Int. Cl.[7] .................. C07D 213/61; C07D 401/12; A01N 43/40
(52) U.S. Cl. .................. 504/130; 504/138; 544/63; 546/272.1; 546/340
(58) Field of Search ................. 504/130, 138; 546/340, 272.1; 544/63

(56) References Cited

U.S. PATENT DOCUMENTS 4,747,871 A   5/1988   Ruminski et al. ........... 546/318

FOREIGN PATENT DOCUMENTS

| DE | 3818958 | 8/1989 |
|---|---|---|
| DE | 3902818 | 8/1989 |
| EP | 0338992 | 4/1989 |
| EP | 701572 A1 * | 8/1997 |
| EP | 369 803 | 11/1999 |
| GB | 2 305 174 A | 4/1997 |
| WO | WO929078 | 5/1992 |
| WO | WO 97 34485 A | 9/1997 |
| WO | WO 97 43270 | 11/1997 |
| WO | WO 97 46530 A | 12/1997 |

OTHER PUBLICATIONS

Chem. Lett. 1975, 1045.
House, "Modern Synthetic Reactions," Benjamin, Inc., Menlo Par, CA, 1972, pp. 334–335 and 353–354.
Ferri, "Reaktionen der organischen Synthese" (Reactions of Organic Synthesis), Verlag, Stuttgart, 1978, p. 461 ff.
Heterocycles, 24, 2169 (1986).
Heterocycles, 46, 129 (1997).
Heterocycles, 48, 779 (1997).
Helvetica Chimica Acta 71, 596 (1988).
Org. Process Research & Development, vol. 1, 370 (1997).
Org. React., vol. 50, 1 (Stille reaction), 1997.

* cited by examiner

Primary Examiner—Zinna Northington Davis
(74) Attorney, Agent, or Firm—Wililam A. Teoli, Jr.; Thomas Hamilton

(57) ABSTRACT

Compounds of formula (I) in which the substituents are as defined in claim 1 are suitable for use as herbicides.

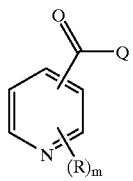

(I)

4 Claims, No Drawings

PYRIDINE KETONES USEFUL AS HERBICIDES

This application is a Continuation of PCT/EP99/06761 filed Sep. 13, 1999.

The present invention relates to novel herbicidally active pyridine ketones, to processes for their preparation, to compositions which comprise these compounds, and to their use for controlling weeds, in particular in crops of useful plants, or for inhibiting plant growth.

Pyridine ketones having herbicidal action are described, for example, in WO 97/46530. We have now found novel pyridine ketones having herbicidal and growth-inhibiting properties.

The present invention thus provides compounds of the formula I

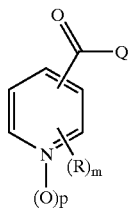

(I)

in which each R independently is $C_1-C_6$alkyl, $C_2-C_6$alkenyl, $C_2-C_6$haloalkenyl, $C_2-C_6$alkynyl, $C_2-C_6$haloalkynyl, $C_3-C_6$cycloalkyl, $C_1-C_6$alkoxy, $C_1-C_6$haloalkoxy, $C_1-C_6$alkylthio, $C_1-C_6$alkylsulfinyl, $C_1-C_6$alkylsulfonyl, $C_1-C_6$haloalkyl, $C_1-C_6$haloalkylthio, $C_1-C_6$haloalkylsulfinyl, $C_1-C_6$haloalkylsulfonyl, $C_1-C_6$alkoxycarbonyl, $C_1-C_6$alkylcarbonyl, $C_1-C_6$alkylamino, di-$C_1-C_6$alkylamino, $C_1-C_6$alkylaminosulfonyl, di-$C_1-C_6$alkylaminosulfonyl, —N(R$_1$)—S—R$_2$, —N(R$_3$)—SO—R$_4$, —N(R$_5$)—SO$_2$—R$_6$, nitro, cyano, halogen, hydroxy, amino, formyl, hydroxy-$C_1-C_6$alkyl, $C_1-C_6$alkoxy-$C_1-C_6$alkyl, $C_1-C_6$alkoxycarbonyloxy-$C_1-C_6$alkyl, $C_1-C_6$alkylthio-$C_1-C_6$alkyl, $C_1-C_6$alkylsulfinyl-$C_1-C_6$alkyl, $C_1-C_6$alkylsulfonyl-$C_1-C_6$alkyl, thiocyanato-$C_1-C_6$alkyl, cyano-$C_1-C_6$alkyl, oxiranyl, $C_3-C_6$alkenyloxy, $C_3-C_6$alkynyloxy, $C_1-C_6$alkoxy-$C_1-C_6$alkoxy, cyano-$C_1-C_6$alkenyloxy, $C_1-C_6$alkoxycarbonyloxy-$C_1-C_6$alkoxy, $C_3C_6$alkynyloxy, cyano-$C_1-C_6$alkoxy, $C_1-C_6$ alkoxycarbonyl-$C_1-C_6$alkoxy, $C_1-C_6$alkylthio-$C_1-C_6$alkoxy, alkoxycarbonyl-$C_1-C_6$alkylthio, alkoxycarbonyl-$C_1-C_6$alkylsulfinyl, alkoxycarbonyl-$C_1-C_6$alkylsulfonyl, $C_1-C_6$alkylsulfonyloxy, $C_1-C_6$haloalkylsulfonyloxy, phenyl, benzyl, phenoxy, phenylthio, phenylsulfinyl, phenylsulfonyl, benzylthio, benzylsulfinyl or benzylsulfonyl, where the phenyl groups may be mono- or polysubstituted by halogen, methyl, ethyl, trifluoromethyl, methoxy or nitro, or R is a five- to ten-membered monocyclic or fused bicyclic ring system, which may be aromatic or partially saturated and may contain 1 to 4 heteroatoms selected from the group consisting of nitrogen, oxygen and sulfur, where the ring system is either attached directly to the pyridine ring or attached to the pyridine ring via a $C_1-C_4$alkylene group, and where each ring system may not contain more than 2 oxygen atoms and not more than two sulfur atoms, and where the ring system for its part may be mono-, di- or trisubstituted by $C_1-C_6$alkyl, $C_1-C_6$haloalkyl, $C_3-C_6$alkenyl, $C_3-C_6$haloalkenyl, $C_3-C_6$alkynyl, $C_3-C_6$haloalkynyl, $C_1-C_6$alkoxy, $C_1-C_6$haloalkoxy, $C_3-C_6$alkenyloxy, $C_3-C_6$alkynyloxy, mercapto, $C_1-C_6$alkylthio, $C_1-C_6$haloalkylthio, $C_3-C_6$alkenylthio, $C_3-C_6$haloalkenylthio, $C_3-C_6$alkynylthio, $C_2-C_5$alkoxyalkylthio, $C_3-C_5$acetylalkylthio, $C_3-C_6$alkoxycarbonylalkylthio, $C_2-C_4$cyanoalkylthio, $C_1-C_6$alkylsulfinyl, $C_1-C_6$haloalkylsulfinyl, $C_1-C_6$alkylsulfonyl, $C_1-C_6$haloalkylsulfonyl, aminosulfonyl, $C_1-C_6$alkylaminosulfonyl, $C_1-C_6$dialkylaminosulfonyl, $C_1-C_6$alkylene-R$_7$, NR$_8$R$_9$, halogen, cyano, nitro, phenyl and benzylthio, where phenyl and benzylthio for their part may be substituted on the phenyl ring by $C_1-C_3$alkyl, $C_1-C_3$haloalkyl, $C_1-C_3$alkoxy, $C_1-C_3$haloalkoxy, halogen, cyano or nitro, and where substituents on the nitrogen in the heterocyclic ring are different from halogen;

m is 1, 2, 3 or 4;

p is 0 or 1;

R$_1$, R$_3$ and R$_5$ independently of one another are hydrogen or $C_1-C_6$alkyl;

R$_2$ is NR$_{10}$R$_{11}$, $C_1-C_6$alkoxy, $C_1-C_6$haloalkoxy, $C_1-C_6$alkyl, $C_1-C_6$haloalkyl, $C_3-C_6$alkenyl, $C_3-C_6$haloalkenyl, $C_3-C_6$alkynyl, $C_3-C_6$haloalkynyl, $C_3-C_6$cycloalkyl or phenyl, where phenyl for its part may be substituted by $C_1-C_3$alkyl, $C_1-C_6$haloalkyl, $C_1-C_6$alkoxy, $C_1-C_3$haloalkoxy, halogen, cyano or nitro;

R$_4$ is NR$_{12}$R$_{13}$, $C_1-C_6$alkoxy, $C_1-C_6$haloalkoxy, $C_1-C_6$alkyl, $C_1-C_6$haloalkyl, $C_3-C_6$alkenyl, $C_3-C_6$haloalkenyl, $C_3-C_6$alkynyl, $C_3-C_6$haloalkynyl, $C_3-C_6$cycloalkyl or phenyl, where phenyl for its part may be substituted by $C_1-C_3$alkyl, $C_1-C_3$haloalkyl, $C_1-C_3$alkoxy, $C_1-C_3$haloalkoxy, halogen, cyano or nitro;

R$_6$ is NR$_{14}$R$_{15}$, $C_1-C_6$alkoxy, $C_1-C_6$haloalkoxy, $C_1-C_6$alkyl, $C_1-C_6$haloalkyl, $C_3-C_6$alkenyl, $C_3-C_6$haloalkenyl, $C_3-C_6$alkynyl, $C_3-C_6$haloalkynyl, $C_3-C_6$cycloalkyl or phpnyl, where phenyl for its part may be substituted by $C_1-C_3$alkyl, $C_1-C_3$haloalkyl, $C_1-C_3$alkoxy, $C_1-C_3$haloalkoxy, halogen, cyano or nitro;

R$_7$ is $C_1-C_3$alkoxy, $C_2-C_4$alkoxycarbonyl, $C_1-C_3$alkylthio, $C_1-C_3$alkylsulfinyl, $C_1-C_3$alkylsulfonyl or phenyl, where phenyl for its part may be substituted by $C_1-C_3$alkyl, $C_1-C_3$haloalkyl, $C_1-C_3$alkoxy, $C_1-C_3$haloalkoxy, halogen, cyano or nitro;

R$_8$, R$_{10}$, R$_{12}$ and R$_{14}$ independently of one another are hydrogen or $C_1-C_6$alkyl;

R$_9$, R$_{11}$, R$_{13}$ and R$_{15}$ is independently of one another are $C_1-C_6$alkyl or $C_1-C_6$alkoxy;

Q is the group $Q_1$

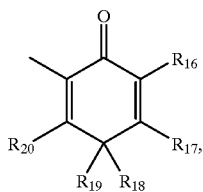

(Q₁)

in which $R_{16}$, $R_{17}$, $R_{18}$ and $R_{19}$ independently of one another are hydrogen, hydroxyl, $C_1-C_4$alkyl, $C_2-C_6$alkenyl, $C_2-C_6$alkynyl, $C_1-C_4$alkoxycarbonyl, $C_1-C_6$alkylthio, $C_1-C_6$alkylsulfinyl, $C_1-C_6$alkylsulfonyl, $C_1-C_4$alkyl-NHS(O)$_2$, $C_1-C_4$haloalkyl, —NH—$C_1-C_4$alkyl, —N($C_1-C_4$alkyl)$_2$, $C_1-C_6$alkoxy, cyano, nitro, halogen or phenyl, which for its part may be substituted by $C_1-C_4$alkyl, $C_1-C_4$haloalkyl, $C_1-C_4$alkoxy, $C_1-C_4$haloalkoxy, $C_1-C_4$alkylcarbonyl, $C_1-C_4$alkoxycarbonyl, amino, $C_1-C_4$alkylamino, di-$C_1-C_4$alkylamino, $C_1-C_6$alkylthio, $C_1-C_6$alkylsulfinyl, $C_1-C_6$alkylsulfonyl, $C_1-C_4$alkyl-S(O)$_2$O, $C_1-C_4$haloalkylthio, $C_1-C_4$haloalkylsulfinyl, $C_1-C_4$haloalkylsulfonyl, $C_1-C_4$haloalkyl-S(O)$_2$O, $C_1-C_4$alkyl-S(O)$_2$NH, $C_1-C_4$alkyl-S(O)$_2$N($C_1-C_4$alkyl), halogen, nitro, COOH or cyano; or two adjacent substituents from the group consisting of $R_{16}$, $R_{17}$, $R_{18}$ and $R_{19}$ form a $C_2-C_6$alkyiene bridge;

$R_{20}$ is hydroxyl, O⁻M⁺, halogen, cyano, SCN, OCN, $C_1-C_{12}$alkoxy, $C_1-C_4$alkoxycarbonyl-$C_1-C_4$alkoxy, $C_1-C_{12}$alkylthio, $C_1-C_{12}$alkylsulfinyl, $C_1-C_{12}$alkylsulfonyl, $C_1-C_{12}$haloalkylthio, $C_1-C_{12}$haloalkylsulfinyl, $C_1-C_{12}$haloalkylsulfonyl, $C_1-C_6$alkoxy-$C_1-C_6$alkylthio, $C_1-C_6$alkoxy-$C_1-C_6$alkylsulfinyl, $C_1-C_6$alkoxy-$C_1-C_6$alkylsulfonyl, $C_2-C_{12}$alkenylthio, $C_2-C_{12}$alkeny isulfinyl, $C_2-C_{12}$alkenylsulfonyl, $C_2-C_{12}$alkynylthio, $C_2-C_{12}$alkynylsulfinyl, $C_2-C_{12}$alkynylsulfonyl, $C_2-C_{12}$haloalkenylthio, $C_2-C_{12}$haloalkenylsulfinyl, $C_2-C_{12}$haloalkenylsulfonyl, $C_1-C_4$alkoxycarbonyl-$C_1-C_4$alkylthio, $C_1-C_4$alkoxycarbonyl-$C_1-C_4$alkylsulfinyl, $C_1-C_4$alkoxycarbonyl-$C_1-C_4$alkylsulfonyl, ($C_1-C_4$alkoxy)$_2$P(O)O, $C_1-C_4$alkyl-($C_1-C_4$alkoxy)P(Q)O, H($C_1-C_4$alkoxy)P(O)O, $R_{37}R_{38}N$, $R_{71}R_{72}$NNH—, $R_{73}R_{74}$NC(O)NH—, $C_1-C_4$alkyl-S(O)$_{39}$, $C_1-C_4$haloalkyl-S(O)$_2$NR$_{40}$, $C_1-C_6$alkyl-S(O)$_2$O, $C_1-C_4$haloalkyl-S(O)$_2$O, $C_1-C_{18}$alkylcarbonyloxy, where the alkyl group may be substituted by halogen, $C_1-C_6$alkoxy, $C_1-C_6$alkylthio or cyano, $C_2-C_{18}$alkenylcarbonyloxy, $C_2-C_{18}$alkynylcarbonyloxy, $C_3-C_6$cycloalkylcarbonyloxy, $C_1-C_{12}$alkoxycarbonyloxy, $C_1-C_{12}$alkylthiocarbonyloxy, $C_1-C_{12}$alkylthiocarbamoyl, $C_1-C_6$alkyl-NH(CS)N($C_1-C_6$alkyl)—NH—, di-$C_1-C_6$alkyl-N(CS)N($C_1-C_6$alkyl)-NH—, benzyloxy, benzylthio, benzylsulfinyl, benzyisulfonyl, phenoxy, phenylthio, phenylsulfinyl, phenylsulfonyl, phenylsulfonyloxy or benzoyloxy, where the phenyl groups for their part may each be substituted by $C_1-C_4$alkyl, $C_1-C_4$haloalkyl, $C_1-C_4$alkoxy, $C_1-C_4$haloalkoxy, $C_1-C_4$alkylcarbonyl, $C_1-C_4$alkoxycarbonyl, $C_1-C_4$alkylamino, di-$C_1-C_4$alkylamino, $C_1-C_4$alkylthio, $C_1-C_4$alkylsulfinyl, $C_1-C_4$alkylsulfonyl, $C_1-C_4$alkyl-S(O)$_2$O, $C_1-C_4$haloalkylthio, $C_1-C_4$haloalkylsulfinyl, $C_1-C_4$haloalkylsulfonyl, $C_1-C_4$haloalkyl-S(O)$_2$O, $C_1-C_4$alkyl-S(O)$_2$NH, $C_1-C_4$alkyl-S(O)$_2$N($C_1-C_4$alkyl), halogen, nitro or cyano, or a group $Ar_1$-thio, $Ar_2$-sulfinyl, $Ar_3$-sulfonyl, —OCO—$Ar_4$ or NH—$Ar_s$ in which $Ar_1$, $Ar_2$, $Ar_3$, $Ar_4$ and $Ar_5$ independently of one another are a five- to ten-membered monocyclic or fused bicyclic ring system which may be aromatic or partially saturated and may contain 1 to 4 heteroatoms selected from the group consisting of nitrogen, oxygen and sulfur, and in which each ring system may not contain more than 2 oxygen atoms and not more than two sulfur atoms, and in which the ring system for its part may be mono-, di- or trisubstituted by $C_1-C_6$alkyl, $C_1-C_6$haloalkyl, $C_3-C_6$alkenyl, $C_3-C_6$haloalkenyl, $C_3-C_6$alkynyl, $C_3-C_6$haloalkynyl, $C_1-C_6$alkoxy, $C_1-C_6$haloalkoxy, $C_3-C_6$alkenyloxy, $C_3-C_6$alkynyloxy, mercapto, $C_1-C_6$alkylthio, $C_1-C_6$haloalkylthio, $C_3-C_6$alkenylthio, $C_3-C_6$haloalkenylthio, $C_3-C_6$alkynylthio, $C_2-C_5$alkoxyalkylthio, $C_3-C_5$acetylalkylthio, $C_3-C_6$alkoxycarbonylalkylthio, $C_2-C_4$cyanoalkylthio, $C_1-C_6$alkylsulfinyl, $C_1-C_6$haloalkylsulfinyl, $C_1-C_6$alkylsulfonyl, $C_1-C_6$haloalkylsulfonyl, aminosulfonyl, $C_1-C_2$alkylaminosufonyl, $C_2-C_4$dialkylaminosulfonyl, $C_1-C_3$alkylene-$R_{41}$, NR$_{42}$R$_{43}$, halogen, cyano, nitro, phenyl and benzylthio, where phenyl and benzylthio for their part may be substituted on the phenyl ring by $C_1-C_3$alkyl, $C_1-C_3$haloalkyl, $C_1-C_3$alkoxy, $C_1-C_3$haloalkoxy, halogen, cyano or nitro, and where substituents on the nitrogen in the heterocyclic ring are different from halogen;

$R_{41}$ is $C_1-C_3$alkoxy, $C_2-C_4$alkoxycarbonyl, $C_1-C_3$alkylthio, $C_1-C_3$alkylsulfinyl, $C_1-C_3$alkylsulfonyl or phenyl, where phenyl for its part may be substituted by $C_1-C_3$alkyl, $C_1-C_3$haloalkyl, $C_1-C_3$alkoxy, $C_1-C_3$haloalkoxy, halogen, cyano or nitro;

$R_{42}$ is hydrogen or $C_1-C_6$alkyl;

$R_{43}$ is $C_1-C_6$alkyl or $C_1-C_6$alkoxy;

$R_{21}$, $R_{37}$, $R_{39}$, $R_{40}$, $R_{71}$ and $R_{73}$ independently of one another are hydrogen or $C_1-C_4$alkyl;

$R_{22}$, $R_{38}$, $R_{72}$ and $R_{74}$ independently of one another are hydrogen, $C_1-C_{12}$alkyl, hydroxyl, $C_1-C_{12}$alkoxy, $C_3-C_6$alkenyloxy or $C_3-C_6$alkynyloxy; or $R_{21}$ and $R_{22}$ together or $R_{37}$ and $R_{38}$ together or $R_{71}$ and $R_{72}$ together or $R_{73}$ and $R_{74}$ together are pyrrolidino, piperidino, morpholino, thiomorpholino, which may be mono- or polysubstituted by methyl groups; or are the group $Q_2$

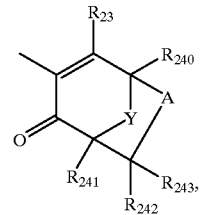

(Q₂)

in which
Y is a chemical bond, an alkylene group $A_1$, carbonyl, oxygen, sulfur, sulfinyl, sulfonyl, —$NHR_{248}$ or $NH(CO)R_{249}$;

$A_1$ is $C(R_{246}R_{247})m_{01}$;

A is $C(R_{244}R_{245})r$;

r and $m_{01}$ independently of one another are 1 or 2;

$R_{240}$ is hydrogen, methyl or $C_1$–$C_3$alkoxycarbonyl;

$R_{241}$, $R_{242}$, $R_{243}$, $R_{244}$, $R_{245}$, $R_{246}$ and $R_{247}$ independently of one another are hydrogen, halogen or methyl, or $R_{243}$ together with an adjacent group $R_{245}$ or $R_{247}$ is a chemical bond;

$R_{248}$ and $R_{249}$ independently of one another are hydrogen or $C_1$–$C_4$alkyl;

$R_{23}$ is hydroxyl, $O^-M^+$, halogen, cyano, SCN, OCN, $C_1$–$C_{12}$alkoxy, $C_1$–$C_4$alkoxycarbonyl-$C_1$–$C_4$alkoxy, $C_1$–$C_{12}$alkylthio, $C_1$–$C_{12}$alkylsulfinyl, $C_1$–$C_{12}$alkylsulfonyl, $C_1$–$C_{12}$haloalkylthio, $C_1$–$C_{12}$haloalkylsulfinyl, $C_1$–$C_{12}$haloalkylsulfonyl, $C_1$–$C_6$alkoxy-$C_1$–$C_6$alkylthio, $C_1$–$C_6$alkoxy-$C_1$–$C_6$alkylsulfinyl, $C_1$–$C_6$alkoxy-$C_1$–$C_6$alkylsulfonyl, $C_2$–$C_{12}$alkenylthio, $C_2$–$C_{12}$alkenylsulfinyl, $C_2$–$C_{12}$alkenyisulfonyl, $C_2$–$C_{12}$alkynylthio, $C_2$–$C_{12}$alkynylsulfinyl, $C_2$–$C_{12}$alkynylsulfonyl, $C_2$–$C_{12}$haloalkenylthio, $C_2$–$C_{12}$haloalkenylsulfinyl, $C_2$–$C_{12}$haloalkenylsulfonyl, $C_1$–$C_4$alkoxycarbonyl-$C_1$–$C_4$alkylthio, $C_1$–$C_4$alkoxycarbonyl-$C_1$–$C_4$alkylsulfinyl, $C_1$–$C_4$alkoxycarbonyl-$C_1$–$C_4$alkylsuflonyl, $(C_1$–$C_4$alkoxy$)_2$P(O)O, $C_1$–$C_4$alkyl-$(C_1$–$C_4$alkoxy)P(O)O, H$(C_1$–$C_4$alkoxy)P(O)O, $R_{44}R_{45}N$, $R_{75}R_{76}NNH$—, $R_{46}R_{47}NC(O)O$—, $R_{77}R_{78}NC(O)NH$—, $C_1$–$C_4$alkyl-S(O)$_2$NR$_{48}$, $C_1$–$C_4$haloalkyl-S(O)$_2$NR$_{49}$, $C_1$–$C_4$alkyl-S(O)$_2$O, $C_1$–$C_4$haloalkyl-S(O)$_2$O, $C_1$–$C_{18}$alkylcarbonyloxy, where the alkyl group may be substituted by halogen, $C_1$–$C_6$alkoxy, $C_1$–$C_6$alkylthio or cyano, $C_2$–$C_{18}$alkenylcarbonyloxy, $C_2$–$C_{18}$alkynylcarbonyloxy, $C_3$–$C_6$cycloalkylcarbonyloxy, $C_1$–$C_{12}$alkoxycarbonyloxy, $C_1$–$C_{12}$alkylthiocarbonyloxy, $C_1$–$C_{12}$alkylthiocarbamoyl, $C_1$–$C_6$alkyl-NH(CS)N$(C_1$–$C_6$alkyl)—NH—, di-$C_1$–$C_6$alkyl-N(CS)N$(C_1$–$C_6$alkyl)—NH—, benzyloxy, benzylthio, benzylsulfinyl, benzylsulfonyl, phenoxy, phenylthio, phenylsulfinyl, phenyisulfonyl, phenylsulfonyloxy or benzoyloxy, where the phenyl groups for their part may each be substituted by $C_1$–$C_4$alkyl, $C_1$–$C_4$haloalkyl, $C_1$–$C_4$alkoxy, $C_1$–$C_4$haloalkoxy, $C_1$–$C_4$alkylcarbonyl, $C_1$–$C_4$alkoxycarbonyl, $C_1$–$C_4$alkylamino, di-$C_1$–$C_4$alkylamino, $C_1$–$C_4$alkylthio, $C_1$–$C_4$alkylsulfinyl, $C_1$–$C_4$alkylsulfonyl, $C_1$–$C_4$alkyl-S(O)$_2$O, $C_1$–$C_4$haloalkylthio, $C_1$–$C_4$haloalkyisulfinyl, $C_1$–$C_4$haloalkylsulfonyl, $C_1$–$C_4$haloalkyl-S(O)$_2$O, $C_1$–$C_4$alkyl-S(O)$_2$NH, $C_1$–$C_4$alkyl-S(O)$_2$N$(C_1$–$C_4$alkyl), halogen, nitro or cyano, or a group Ar$_6$-thio, Ar$_7$-sulfinyl, Ar$_8$-sulfonyl, —OCO—Ar$_9$ or NH—Ar$_{10}$ in which Ar$_6$, Ar$_7$, Ar$_8$, Ar$_9$ and Ar$_{10}$ independently of one another are a five- to ten-membered monocyclic or fused bicyclic ring system which may be aromatic or partially saturated and may contain 1 to 4 heteroatoms selected from the group consisting of nitrogen, oxygen and sulfur, and in which each ring system may not contain more than 2 oxygen atoms and not more than two sulfur atoms, and in which the ring system for its part may be mono-, di- or trisubstituted by $C_1$–$C_6$alkyl, $C_1$–$C_6$haloalkyl, $C_3$–$C_6$alkenyl, $C_3$–$C_6$haloalkenyl, $C_3$–$C_6$alkynyl, $C_3$–$C_6$haloalkynyl, $C_1$–$C_6$alkoxy, $C_1$–$C_6$haloalkoxy, $C_3$–$C_6$alkenyloxy, $C_3$–$C_6$alkynyloxy, mercapto, $C_1$–$C_6$alkylthio, $C_1$–$C_6$haloalkylthio, $C_3$–$C_6$alkenylthio, $C_3$–$C_6$haloalkenylthio, $C_3$–$C_6$alkynylthio, $C_2$–$C_5$alkoxyalkylthio, $C_3$–$C_5$acetylalkylthio, $C_3$–$C_6$alkoxycarbonylalkylthio, $C_2$–$C_4$cyanoalkylthio, $C_1$–$C_6$alkylsulfinyl, $C_1$–$C_6$haloalkylsulfinyl, $C_1$–$C_6$alkylsulfonyl, $C_1$–$C_6$haloalkylsulfonyl, aminosulfonyl, $C_1$–$C_2$alkylaminosulfonyl, $C_2$–$C_4$dialkylaminosulfonyl, $C_1$–$C_3$alkylene-$R_{50}$, NR$_{51}$R$_{52}$, halogen, cyano, nitro, phenyl and benzylthio, where phenyl and benzylthio for their part may be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or nitro, and where substituents on the nitrogen in the heterocyclic ring are different from halogen;

$R_{50}$ is $C_1$–$C_3$alkoxy, $C_2$–$C_4$alkoxycarbonyl, $C_1$–$C_3$alkylthio, $C_1$–$C_3$alkylsulfinyl, $C_1$–$C_3$alkylsulfonyl or phenyl, where phenyl for its part may be substituted by $C_1$–$C_3$alkyl, $C_1$–$C_3$haloalkyl, $C_1$–$C_3$alkoxy, $C_1$–$C_3$haloalkoxy, halogen, cyano or nitro;

$R_{51}$ is hydrogen or $C_1$–$C_6$alkyl;

$R_{52}$ is $C_1$–$C_6$alkyl or $C_1$–$C_6$alkoxy;

$R_{46}$, $R_{44}$, $R_{48}$, $R_{49}$, $R_{75}$ and $R_{77}$ independently of one another are hydrogen or $C_1$–$C_4$alkyl;

$R_{47}$, $R_{45}$, $R_{76}$ and $R_{78}$ independently of one another are hydrogen, $C_1$–$C_{12}$alkyl, hydroxyl, $C_1$–$C_{12}$alkoxy, $C_3$–$C_6$alkenyloxy or $C_3$–$C_6$alkynyloxy; or $R_{44}$ and $R_{45}$ together or $R_{46}$ and $R_{47}$ together or $R_{75}$ and $R_{76}$ together or $R_{77}$ and $R_{78}$ together are pyrrolidino, piperidino, morpholino, thiomorpholino, which may be mono- or polysubstituted by methyl groups; or are the group Q$_3$

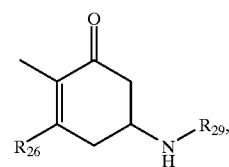

(Q$_3$)

in which
$R_{26}$ is hydroxyl, $O^-M^+$, halogen, cyano, SCN, OCN, $C_1$–$C_{12}$ alkoxy, $C_1$–$C_4$alkoxycarbonyl-$C_1$–$C_4$alkoxy, $C_1$–$C_{12}$alkylthio, $C_1$–$C_{12}$alkylsulfinyl, $C_1$–$C_{12}$alkylsulfonyl, $C_1$–$C_{12}$haloalkylthio, $C_1$–$C_{12}$haloalkylsulfinyl, $C_1$–$C_{12}$haloalkylsulfonyl, $C_1$–$C_6$alkoxy-$C_1$–$C_6$alkylthio, $C_1$–$C_6$alkoxy-$C_1$–$C_6$alkylsulfinyl, $C_1$–$C_6$alkoxy-$C_1$–$C_6$alkylsulfonyl, $C_2$–$C_{12}$alkenylthio, $C_2$–$C_{12}$alkenylsulfinyl, $C_2$–$C_{12}$alkenylsulfonyl, $C_2$–$C_{12}$alkynylthio, $C_2$–$C_{12}$alkynylsulfinyl, $C_2$–$C_{12}$alkynylsulfonyl, $C_2$–$C_{12}$haloalkenylthio, $C_2$–$C_{12}$haloalkenylsulfinyl, $C_2$–$C_{12}$haloalkenylsulfonyl, $C_1$–$C_4$alkoxycarbonyl-$C_1$–$C_4$alkylthio, $C_1$–$C_4$alkoxycarbonyl-$C_1$–$C_4$alkylsulfinyl, $C_1$–$C_4$alkoxycarbonyl-$C_1$–$C_4$alkylsulfonyl, $(C_1$–$C_4$alkoxy$)_2$P(O)O, $C_1$–$C_4$alkyl-$(C_1$–$C_4$alkoxy)P(O)O, H$(C_1$–$C_4$alkoxy)P(O)O, $R_{53}R_{54}N$, $R_{79}R_{80}NNH-$, $R_{55}R_{56}NC(O)O-$, $R_{81}R_{82}NC(O)NH-$, $C_1-C_4alkyl-S(O)_2NR_{57}$, $C_1-C_4haloalkyl-S(O)_2NR_{58}$, $C_1-C_4alkyl-S(O)_2O$, $C_1-C_4haloalkyl-S(O)_2O$, $C_1-C_{18}alkylcarbonyloxy$, where the alkyl group may be substituted by halogen, $C_1-C_6alkoxy$, $C_1-C_6alkylthio$ or cyano, $C_2C_{18}alkenylcarbonyloxy$, $C_2-C_{18}alkynylcarbonyloxy$, $C_3-C_6cycloalkylcarbonyloxy$, $C_1-C_{12}alkoxycarbonyloxy$, $C_1-C_{12}alkylthiocarbonyloxy$, $C_1-C_{12}alkylthiocarbamoyl$, $C_1-C_6alkyl-NH(CS)N(C_1-C_6alkyl)-NH-$, $di-C_1-C_6alkyl-N(CS)N(C_1-C_6alkyl)-NH-$, benzyloxy, benzylthio, benzylsulfinyl, benzylsulfonyl, phenoxy, phenylthio, phenylsulfinyl, phenylsulfonyl, phenylsulfonyloxy or benzoyloxy, where the phenyl groups for their part may each be substituted by $C_1-C_4alkyl$, $C_1-C_4haloalkyl$, $C_1-C_4alkoxy$, $C_1-C_4haloalkoxy$, $C_1-C_4alkylcarbonyl$, $C_1-C_4alkoxycarbonyl$, $C_1-C_4alkylamino$, $di-C_1-C_4alkylamino$, $C_1-C_4alkylthio$, $C_1-C_4alkylsulfinyl$, $C_1-C_4alkylsulfonyl$, $C_1-C_4alkyl-S(O)_2O$, $C_1-C_4haloalkylthio$, $C_1-C_4haloalkylsulfinyl$, $C_1-C_4haloalkylsulfonyl$, $C_1-C_4haloalkyl-S(O)_2O$, $C_1-C_4alkyl-S(O)_2NH$, $C_1-C_4alkyl-S(O)_2N(C_1-C_4alkyl)$, halogen, nitro or cyano, or a group $Ar_{11}$-thio, $Ar_{12}$-sulfinyl, $Ar_{13}$-sulfonyl, $-OCO-Ar_{14}$ or $NH-Ar_{15}$ in which $Ar_{11}$, $Ar_{12}$, $Ar_{13}$, $Ar_{14}$ and $Ar_{15}$ independently of one another are a five- to ten-membered monocyclic or fused bicyclic ring system which may be aromatic or partially saturated and may contain 1 to 4 heteroatoms selected from the group consisting of nitrogen, oxygen and sulfur, and in which each ring system may not contain more than 2 oxygen atoms and not more than two sulfur atoms, and in which the ring system for its part may be mono-, di- or trisubstituted by $C_1-C_6alkyl$, $C_1-C_6haloalkyl$, $C_3-C_6alkenyl$, $C_3-C_6haloalkenyl$, $C_3-C_6alkynyl$, $C_3-C_6haloalkynyl$, $C_1-C_6alkoxy$, $C_1-C_6haloalkoxy$, $C_3-C_6alkenyloxy$, $C_3-C_6alkynyloxy$, mercapto, $C_1-C_6alkylthio$, $C_1-C_6haloalkylthio$, $C_3-C_6alkenylthio$, $C_3-C_6haloalkenylthio$, $C_3-C_6alkynylthio$, $C_2-C_5alkoxyalkylthio$, $C_3-C_5acetylalkylthio$, $C_3-C_6alkoxycarbonylalkylthio$, $C_2-C_4cyanoalkylthio$, $C_1-C_6alkylsulfinyl$, $C_1-C_6haloalkylsulfinyl$, $C_1-C_6alkylsulfonyl$, $C_1-C_6haloalkylsulfonyl$, aminosulfonyl, $C_1-C_2alkylaminosulfonyl$, $C_2-C_4dialkylaminosulfonyl$, $C_1-C_3alkylene-R_{59}$, $NR_{60}R_{61}$, halogen, cyano, nitro, phenyl and benzylthio, where phenyl and benzylthio for their part may be substituted on the phenyl ring by $C_1-C_3alkyl$, $C_1-C_3haloalkyl$, $C_1-C_3alkoxy$, $C_1-C_3haloalkoxy$, halogen, cyano or nitro, and where substituents on the nitrogen in the heterocyclic ring are different from halogen;

$R_{59}$ is $C_1-C_3alkoxy$, $C_2-C_4alkoxycarbonyl$, $C_1-C_3alkylthio$, $C_1-C_3alkylsulfinyl$, $C_1-C_3alkylsulfonyl$ or phenyl, where phenyl for its part may be substituted by $C_1-C_3alkyl$, $C_1-C_3haloalkyl$, $C_1-C_3alkoxy$, $C_1-C_3haloalkoxy$, halogen, cyano or nitro;

$R_{60}$ is hydrogen or $C_1-C_6alkyl$;

$R_{61}$ is $C_1-C_6alkyl$ or $C_1-C_6alkoxy$;

$R_{55}$, $R_{53}$, $R_{57}$, $R_{58}$, $R_{79}$ and $R_{81}$ independently of one another are hydrogen or $C_1-C_4alkyl$;

$R_{56}$, $R_{54}$, $R_{80}$ and $R_{82}$ independently of one another are hydrogen, $C_1-C_{12}alkyl$, hydroxyl, $C_1-C_{12}alkoxy$, $C_3-C_6alkenyloxy$ or $C_3-C_6alkynyloxy$; or $R_{53}$ and $R_{54}$ together or $R_{55}$ and $R_{56}$ together or $R_{79}$ and $R_{80}$ together or $R_{81}$ and $R_{82}$ together are pyrrolidino, piperidino, morpholino, thiomorpholino, which may be mono- or polysubstituted by methyl groups;

$R_{29}$ is hydrogen, $C_1-C_6alkyl$, $C_1-C_4alkylcarbonyl$, $C_1-C_4alkoxycarbonyl$, $(C_1-C_4alkyl)NHCO$, phenylaminocarbonyl, benzylaminocarbonyl or $(C_1-C_4alkyl)_2NCO$, where the phenyl and benzyl groups for their part may each be substituted by $C_1-C_4alkyl$, $C_1-C_4haloalkyl$, $C_1-C_4alkoxy$, $C_1-C_4haloalkoxy$, $C_1-C_4alkylcarbonyl$, $C_1-C_4alkoxycarbonyl$, $C_1-C_4alkylamino$, $di-C_1-C_4alkylamino$, $C_1-C_4alkylthio$, $C_1-C_4alkylsulfinyl$, $C_1-C_4alkylsulfonyl$, $C_1-C_4alkyl-S(O)_2O$, $C_1-C_4haloalkylthio$, $C_1-C_4haloalkylsulfinyl$, $C_1-C_4haloalkylsulfonyl$, $C_1-C_4haloalkyl-S(O)_2O$, $C_1-C_4alkyl-S(O)_2NH$, $C_1-C_4alkyl-S(O)_2N(C_1-C_4alkyl)$, halogen, nitro or cyano;

or is the group $Q_4$

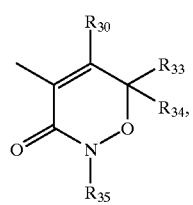

(Q4)

in which $R_{30}$ is hydroxyl, $O^-M^+$, halogen, cyano, SCN, OCN, $C_1-C_{12}alkoxy$, $C_1-C_4alkoxycarbonyl-C_1-C_4alkoxy$, $C_1-C_{12}alkylthio$, $C_1-C_{12}alkylsulfinyl$, $C_1-C_{12}alkylsulfonyl$, $C_1-C_{12}haloalkylthio$, $C_1-C_{12}haloalkylsulfinyl$, $C_1-C_{12}haloalkylsulfonyl$, $C_1-C_6alkoxy-C_1-C_6alkylthio$, $C_1-C_6alkoxy-C_1-C_6alkylsulfinyl$, $C_1-C_6alkoxy-C_1-C_6alkylsulfonyl$, $C_2-C_{12}alkenylthio$, $C_2-C_{12}alkenylsulfinyl$, $C_2-C_{12}alkenylsulfonyl$, $C_2-C_{12}alkynylthio$, $C_2-C_{12}alkynylsulfinyl$, $C_2-C_{12}alkynylsulfonyl$, $C_2-C_{12}haloalkenylthio$, $C_2-C_{12}haloalkenylsulfinyl$, $C_2-C_{12}haloalkenylsulfonyl$, $C_1-C_4alkoxycarbonyl-C_1-C_4alkylthio$, $C_1-C_4alkoxycarbonyl-C_1-C_4alkylsulfinyl$, $C_1-C_4alkoxycarbonyl-C_1-C_4alkylsulfonyl$, $(C_1-C_4alkoxy)_2P(O)O$, $C_1-C_4alkyl-(C_1-C_4alkoxy)P(O)O$, $H(C_1-C_4alkoxy)P(O)O$, $R_{62}R_{63}N$, $R_{83}R_{84}NNH-$, $R_{64}R_{65}NC(O)O-$, $R_{85}R_{86}NC(O)NH-$, $C_1-C_4alkyl-S(O)_2NR_{66}$, $C_1-C_4haloalkyl-S(O)_2NR_{67}$, $C_1-C_4alkyl-S(O)_2O$, $C_1-C_4haloalkyl-S(O)_2O$, $C_1-C_{18}alkylcarbonyloxy$, where the alkyl group may be substituted by halogen, $C_1-C_6alkoxy$, $C_1-C_6alkylthio$ or cyano, $C_2-C_{18}alkenylcarbonyloxy$, $C_2-C_{18}alkynylcarbonyloxy$, $C_3-C_6cycloalkylcarbonyloxy$, $C_1-C_{12}alkoxycarbonyloxy$, $C_1-C_{12}alkylthiocarbonyloxy$, $C_1-C_{12}alkylthiocarbamoyl$, $C_1-C_6alkyl-NH(CS)N(C_1-C_6alkyl)NH-$, $di-C_1-C_6alkyl-N(CS)N(C_1-C_6alkyl)-NH-$, benzyloxy, benzylthio, benzylsulfinyl, benzylsulfonyl, phenoxy, phenylthio, phenylsulfinyl, phenylsulfonyl, phenylsulfonyloxy or benzoyloxy, where the phenyl groups for their part may each be substituted by $C_1-C_4alkyl$, $C_1-C_4haloalkyl$, $C_1-C_4alkoxy$, $C_1-C_4haloalkoxy$, $C_1-C_4alkylcarbonyl$, $C_1$–$C_4$alkoxycarbonyl, $C_1$–$C_4$alkylamino, di-$C_1$–$C_4$alkylamino, $C_1$–$C_4$alkylthio, $C_1$–$C_4$alkylsulfinyl, $C_1$–$C_4$alkylsulfonyl, $C_1$–$C_4$alkyl-S(O)$_2$O, $C_1$–$C_4$haloalkylthio, C i-$C_4$haloalkylsulfinyl, $C_1$–$C_4$haloalkylsulfonyl, $C_1$–$C_4$haloalkyl-S(O)$_2$O, $C_1$–$C_4$alkyl-S(O)$_2$NH, $C_1$–$C_4$alkyl-S(O)$_2$N($C_1$–$C_4$alkyl), halogen, nitro or cyano, or a group Ar$_{16}$-thio, Ar$_{17}$-sulfinyl, Ar$_{18}$-sulfonyl, —OCO—Ar$_{19}$ or NH—Ar$_{20}$ in which Ar$_{16}$, Ar$_{17}$, Ar$_{18}$, Ar$_{19}$ and Ar$_{20}$ independently of one another are a five- to ten-membered monocyclic or fused bicyclic ring system which may be aromatic or partially saturated and may contain 1 to 4 heteroatoms selected from the group consisting of nitrogen, oxygen and sulfur, and in which each ring system may not contain more than 2 oxygen atoms and not more than two sulfur atoms, and in which the ring system for its part may be mono-, di- or trisubstituted by $C_1$–$C_6$alkyl, $C_1$–$C_6$haloalkyl, $C_3$–$C_6$alkenyl, $C_3$–$C_6$haloalkenyl, $C_3$–$C_6$alkynyl, $C_3$–$C_6$haloalkynyl, $C_1$–$C_6$alkoxy, $C_1$–$C_6$haloalkoxy, $C_3$–$C_6$alkenyloxy, $C_3$–$C_6$alkynyloxy, mercapto, $C_1$–$C_6$alkylthio, $C_1$–$C_6$haloalkylthio, $C_3$–$C_6$alkenylthio, $C_3$–$C_6$haloalkenylthio, $C_3$–$C_6$alkynylthio, $C_2$–$C_5$alkoxyalkylthio, $C_3$–$C_5$acetyoalkylthio, $C_3$–$C_6$alkoxycarbonylalkylthio, $C_2$–$C_4$cyanoalkylthio, $C_1$–$C_6$alkylsulfinyl, $C_1$–$C_6$haloalkylsulfinyl, $C_1$–$C_6$alkylsulfonyl, $C_1$–$C_6$haloalkylsulfonyl, aminosulfonyl, $C_1$–$C_2$alkylaminosulfonyl, $C_2$–$C_4$dialkylaminosulfonyl, $C_1$–$C_3$alkylene-R$_{68}$, NR$_{69}$R$_{70}$, halogen, cyano, nitro, phenyl and benzylthio, where phenyl and benzylthio for their part may be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or nitro, and where substituents on the nitrogen in the heterocyclic ring are different from halogen;

R$_{68}$ is $C_1$–$C_3$alkoxy, $C_2$–$C_4$alkoxycarbonyl, $C_1$–$C_3$alkylthio, $C_1$–$C_3$alkylsulfinyl, $C_1$–$C_3$alkylsulfonyl or phenyl, where phenyl for its part may be substituted by $C_1$–$C_3$alkyl, $C_1$–$C_3$haloalkyl, $C_1$–$C_3$alkoxy, $C_1$–$C_3$haloalkoxy, halogen, cyano or nitro;

R$_{70}$ is hydrogen or $C_1$–$C_6$alkyl;

R$_{61}$ is $C_1$–$C_6$alkyl or $C_1$–$C_6$alkoxy;

R$_{64}$, R$_{62}$, R$_{66}$, R$_{67}$, R$_{83}$ and R$_{85}$ independently of one another are hydrogen or $C_1$–$C_4$alkyl;

R$_{65}$, R$_{63}$, R$_{84}$ and R$_{86}$ independently of one another are hydrogen, $C_1$–$C_{12}$alkyl, hydroxyl, $C_1$–$C_{12}$alkoxy, $C_3$–$C_6$alkenyloxy or $C_3$–$C_6$alkynyloxy; or R$_{62}$ and R$_{63}$ together or R$_{64}$ and R$_{65}$ together or R$_{83}$ and R$_{84}$ together or R$_{85}$ and R$_{86}$ together are pyrrolidino, piperidino, morpholino, thiomorpholino, which may be mono- or polysubstituted by methyl groups;

R$_{33}$ and R$_{34}$ independently of one another are hydrogen, $C_1$–$C_4$alkyl, $C_2$–$C_6$alkenyl, $C_2$–$C_6$alkynyl, $C_1$–$C_4$alkoxycarbonyl, $C_1$–$C_6$alkylthio, $C_1$–$C_6$alkylsulfinyl, $C_1$–$C_6$alkylsulfonyl, $C_1$–$C_4$alkyl-NHS(O)$_2$, $C_1$–$C_4$haloalkyl, —NH—$C_1$–$C_4$alkyl, —N($C_1$–$C_4$alkyl)$_2$, $C_1$–$C_6$alkoxy or phenyl, which for its part may be substituted by $C_1$–$C_4$alkyl, $C_1$–$C_4$haloalkyl, $C_1$–$C_4$alkoxy, $C_1$–$C_4$haloalkoxy, $C_1$–$C_4$alkylcarbonyl, $C_1$–$C_4$alkoxycarbonyl, amino, $C_1$–$C_4$alkylamino, di-$C_1$–$C_4$alkylamino, $C_1$–$C_6$alkylthio, $C_1$–$C_6$alkylsulfinyl, $C_1$–$C_6$alkylsulfonyl, $C_1$–$C_6$alkyl-S(O)$_2$O, $C_1$–$C_4$haloalkylthio, $C_1$–$C_4$haloalkylsulfinyl, $C_1$–$C_4$haloalkylsulfonyl, $C_1$–$C_4$haloalkyl-S(O)$_2$O, $C_1$–$C_4$alkyl-S(O)$_2$NH, $C_1$–$C_4$alkyl-S(O)$_2$N($C_1$–$C_4$alkyl), halogen, nitro, COOH or cyano; or R$_{33}$ and R$_{34}$ together form a $C_2$–$C_6$alkylene bridge; and R$_{35}$ is hydrogen, $C_1$–$C_6$alkyl, $C_3$–$C_6$alkenyl, $C_3$–$C_6$alkynyl or benzyl, which for its part may be substituted by halogen, methyl or methoxy, or is $C_1$–$C_4$alkoxycarbonyl or phenyl, which for its part may be substituted by $C_1$–$C_4$alkyl, $C_1$–$C_4$haloalkyl, $C_1$–$C_4$alkoxy, $C_1$–$C_4$haloalkoxy, $C_1$–$C_4$alkylcarbonyl, $C_1$–$C_4$alkoxycarbonyl, amino, $C_1$–$C_4$alkylamino, di-$C_1$–$C_4$alkylamino, $C_1$–$C_4$alkylthio, $C_1$–$C_4$alkylsulfinyl, $C_1$–$C_4$alkylsulfonyl, $C_1$–$C_4$alkyl-S(O)$_2$O, $C_1$–$C_4$haloalkylthio, $C_1$–$C_4$haloalkylsulfinyl, $C_1$–$C_4$haloalkylsulfonyl, $C_1$–$C_4$haloalkyl-S(O)$_2$O, $C_1$–$C_4$alkyl-S(O)$_2$NH, $C_1$–$C_4$alkyl-S(O)$_2$N($C_1$–$C_4$alkyl), halogen, nitro, COOH or cyano;

or is the group Q$_5$

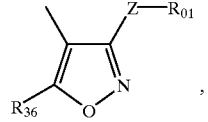

(Q$_5$)

in which

Z is S, SO or SO$_2$;

R$_{01}$ is hydrogen, $C_1$–$C_8$alkyl, $C_1$–$C_8$alkyl substituted by halogen, $C_1$–$C_4$alkoxy, $C_1$–$C_4$alkylthio, $C_1$–$C_4$alkylsulfonyl, $C_1$–$C_4$alkylsulfinyl, —CO$_2$R$_{02}$, —COR$_{03}$, —COSR$_{04}$, —NR$_{05}$R$_{06}$, CONR$_{036}$R$_{037}$ or phenyl, which for its part may be substituted by $C_1$–$C_4$alkyl, $C_1$–$C_6$haloalkyl, $C_1$–$C_4$alkoxy, $C_1$–$C_4$haloalkoxy, $C_2$–$C_6$alkenyl, $C_3$–$C_6$alkynyl, $C_3$–$C_6$alkenyloxy, $C_3$–$C_6$alkynyloxy, halogen, nitro, cyano, —COOH, COOC$_1$–$C_4$alkyl, COOphenyl, $C_1$–$C_4$alkoxy, phenoxy, ($C_1$–$C_4$alkoxy)-$C_1$–$C_4$alkyl, ($C_1$–$C_4$alkylthio)-$C_1$–$C_4$alkyl, ($C_1$–$C_4$alkylsulfinyl)-$C_1$–$C_4$alkyl, ($C_1$–$C_4$alkylsulfonyl)-$C_1$–$C_4$alkyl, NHS)$_2$—$C_1$–$C_4$alkyl, NHSO$_2$-phenyl, N($C_1$–$C_6$alkyl)S)$_2$—$C_1$–$C_4$alkyl, N($C_1$–$C_6$alkyl)SO$_2$-phenyl, N($C_2$–$C_6$alkenyl)S)$_2$—$C_1$–$C_4$alkyl, N($C_2$–$C_6$alkenyl)SO$_2$-phenyl, N($C_3$–$C_6$alkynyl)SO$_2$—$C_1$–$C_4$alkyl, N($C_3$–$C_6$alkynyl)SO$_2$-phenyt, N($C_3$–$C_7$cycloalkyl)SO$_2$—$C_1$–$C_4$alkyl, N($C_3$–$C_7$cycloalkyl)SO$_2$-phenyl, N(phenyl)SO$_2$—$C_1$–$C_4$alkyl, N(phenyl)SO$_2$-phenyl, OSO$_2$—$C_1$–$C_4$alkyl, CONR$_{25}$R$_{26}$, OSO$_2$—$C_1$–$C_4$haloalkyl, OSO$_2$-phenyl, $C_1$–$C_4$alkylthio, $C_1$–$C_4$haloalkylthio, phenytthio, $C_1$–$C_4$alkylsulfonyl, $C_1$–$C_4$haloalkylsulfonyl, phenylsulfonyl, $C_1$–$C_4$alkylsulfinyl, $C_1$–$C_4$haloalkylsulfinyl, phenylsulfinyl, $C_1$–$C_4$alkylene-phenyl or —NR$_{015}$CO$_2$R$_{027}$;

or R$_{01}$ is $C_2$–$C_8$alkenyl or $C_2$–$C_8$alkenyl substituted by halogen, $C_1$–$C_4$alkoxy, $C_1$–$C_4$alkylthio, $C_1$–$C_4$alkylsulfonyl, $C_1$–$C_4$alkylsulfinyl, —CONR$_{032}$R$_{033}$, cyano, nitro, —CHO, —CO$_2$R$_{038}$, —COR$_{039}$, —COS—$C_1$–$C_4$alkyl, —NR$_{034}$R$_{035}$ or phenyl which for its part may be substituted by $C_1$–$C_4$alkyl, $C_1$–$C_6$haloalkyl, $C_1$–$C_4$alkoxy, $C_1$–$C_4$haloalkoxy, $C_2$–$C_6$alkenyl, $C_3$–$C_6$alkynyl, $C_3$–$C_6$alkenyloxy, $C_3$–$C_6$alkynyloxy, halogen, nitro, cyano, —COOH, COOC$_1$–$C_4$alkyl, COOphenyl, $C_1$–$C_4$alkoxy, phenoxy, ($C_1$–$C_4$alkoxy)-$C_1$–$C_4$alkyl, ($C_1$–$C_4$alkylthio)-$C_1$–$C_4$alkyl, ($C_1$–$C_4$alkylsulfinyl)-$C_1$–$C_4$alkyl, ($C_1$–$C_4$alkylsulfonyl)-$C_1$–$C_4$alkyl, NHSO)$_2$—$C_1$–$C_4$alkyl, NHSO$_2$-phenyl, N($C_1$–$C_6$alkyl)SO$_2$—$C_1$–$C_4$alkyl, N($C_1$–$C_6$alkyl)SO$_2$-phenyl, N($C_2$–$C_6$alkenyl)SO$_2$—$C_1$–$C_4$alkyl, N($C_2$–$C_6$alkenyl)SO$_2$-phenyl, N($C_3$–$C_6$alkynyl)SO$_2$—$C_1$–$C_4$alkyl, N($C_3$–$C_6$alkynyl)SO$_2$-phenyl, N($C_3$–$C_7$cycloalkyl)SO$_2$—$C_1$–$C_4$alkyl, alkyl, N($C_3$–$C_7$cycloalkyl)SO$_2$-phenyl, N(phenyl)SO$_2$—$C_1$–$C_4$alkyl, N(phenyl)SO$_2$-phenyl, OSO$_2$—$C_1$–$C_4$alkyl, CONR$_{040}$R$_{041}$, OSO$_2$—$C_1$–$C_4$haloalkyl, OSO$_2$-phenyl, $C_1$–$C_4$alkylthio, $C_1$–$C_4$haloalkylthio, phenylthio, $C_1$–$C_4$alkylsulfonyl, $C_1$–$C_4$haloalkylsulfonyl, phenylsulfonyl, $C_1$–$C_4$alkylsulfinyl, $C_1$–$C_4$haloalkylsulfinyl, phenylsulfinyl, $C_1$–$C_4$alkylene-phenyl or —NR$_{043}$CO$_2$R$_{042}$;

or R$_{01}$ is $C_3$–$C_6$alkynyl or $C_3$–$C_6$alkynyl substituted by halogen, $C_1$–$C_4$haloalkyl, cyano, —CO$_2$R$_{044}$ or phenyl, which for its part may be substituted by $C_1$–$C_4$alkyl, $C_1$–$C_6$haloalkyl, $C_1$–$C_4$alkoxy, $C_1$–$C_4$haloalkoxy, $C_2$–$C_6$alkenyl, $C_3$–$C_6$alkynyl, $C_3$–$C_6$alkenyloxy, $C_3$–$C_6$alkynyloxy, halogen, nitro, cyano, —COOH, COOC$_1$–$C_4$alkyl, COOphenyl, $C_1$–$C_4$alkoxy, phenoxy, ($C_1$–$C_4$alkoxy)-$C_1$–$C_4$alkyl, ($C_1$–$C_4$alkylthio)-$C_1$–$C_4$alkyl, ($C_1$–$C_4$alkylsulfinyl)-$C_1$–$C_4$alkyl, ($C_1$–$C_4$alkylsulfonyl)-$C_1$–$C_4$alkyl, NHSO$_2$—$C_1$–$C_4$alkyl, NHSO$_2$-phenyl, N($C_1$–$C_6$alkyl)SO$_2$—$C_1$–$C_4$alkyl, N($C_1$–$C_6$alkyl)SO$_2$-phenyl, N($C_2$–$C_6$alkenyl)SO$_2$—$C_1$–$C_4$alkyl, N($C_2$–$C_6$alkenyl)SO$_2$-phenyl, N($C_3$–$C_6$alkynyl)SO$_2$—$C_1$–$C_4$alkyl, N($C_3$–$C_6$alkynyl)SO$_2$-phenyl, N($C_3$–$C_7$cycloalkyl)SO$_2$—$C_1$–$C_4$alkyl, N($C_3$–$C_7$cycloalkyl)SO$_2$-phenyl, N(phenyl)SO$_2$—$C_1$–$C_4$alkyl, N(phenyl)SO$_2$-phenyt, OSO$_2$—$C_1$–$C_4$alkyl, CONR$_{028}$R$_{029}$, OSO$_2$—$C_1$–$C_4$haloalkyl, OSO$_2$-phenyl, $C_1$–$C_4$alkylthio, $C_1$–$C_4$haloalkylthio, phenylthio, $C_1$–$C_4$alkylsulfonyl, $C_1$–$C_4$haloalkylsu ifonyl, phenylsulfonyl, $C_1$–$C_4$alkylsulfinyl, $C_1$–$C_4$haloalkylsulfinyl, phenylsulfinyl, $C_1$–$C_4$alkylene-phenyl or —NR$_{031}$CO$_2$R$_{030}$;

or R$_{01}$ is $C_3$–$C_7$cycloalkyl, $C_3$–$C_7$cycloalkyl substituted by $C_1$–$C_4$alkyl, $C_1$–$C_4$alkoxy, $C_1$–$C_4$alkylthio, $C_1$–$C_4$alkylsulfinyl, $C_1$–$C_4$alkylsulfonyl or phenyl, which for its part may be substituted by halogen, nitro, cyano, $C_1$–$C_4$alkoxy, $C_1$–$C_4$haloalkoxy, $C_1$–$C_4$alkylthio, $C_1$–$C_4$haloalkylthio, $C_1$–$C_4$alkyl and $C_1$–$C_4$haloalkyl; or R$_{01}$ is $C_1$–$C_4$alkylene-$C_3$–$C_7$cycloalkyl, phenyl, or phenyl which is substituted by $C_1$–$C_4$alkyl, $C_1$–$C_6$haloalkyl, $C_1$–$C_4$alkoxy, $C_1$–$C_4$haloalkoxy, $C_2$–$C_6$alkenyl, $C_3$–$C_6$alkynyl, $C_3$–$C_6$alkenyloxy, $C_3$–$C_6$alkynyloxy, halogen, nitro, cyano, —COOH, COOC$_1$–$C_4$alkyl, COOphenyl, $C_1$–$C_4$alkoxy, phenoxy, ($C_1$–$C_4$alkoxy)-$C_1$–$C_4$alkyl, ($C_1$–$C_4$alkylthio)-$C_1$–$C_4$alkyl, ($C_1$–$C_4$alkylsulfinyl)-$C_1$–$C_4$alkyl, ($C_1$–$C_4$alkylsulfonyl)-$C_1$–$C_4$alkyl, NHSO$_2$—$C_1$–$C_4$alkyl, NHSO$_2$-phenyl, N($C_1$–$C_6$alkyl)SO$_2$—$C_1$–$C_4$alkyl, N($C_1$–$C_6$alkyl)SO$_2$-phenyl, N($C_2$–$C_6$alkenyl)SO$_2$—$C_1$–$C_4$alkyl, N($C_2$–$C_6$alkenyl)SO$_2$-phenyl, N($C_3$–$C_6$alkynyl)SO$_2$—$C_1$–$C_4$alkyl, N($C_3$–$C_6$alkynyl)SO$_2$-phenyl, N($C_3$–$C_7$cycloalkyl)SO$_2$—$C_1$–$C_4$alkyl, N($C_3$–$C_7$cycloalkyl)SO$_2$-phenyl, N(phenyl)SO$_2$—$C_1$–$C_4$alkyl, N(phenyl)SO$_2$-phenyl, OSO$_2$—$C_1$–$C_4$alkyl, CONR$_{045}$R$_{046}$, OSO$_2$—$C_1$–$C_4$haloalkyl, OSO$_2$-phenyl, $C_1$–$C_4$alkylthio, $C_1$–$C_4$haloalkylthio, phenylthio, $C_1$–$C_4$alkylsulfonyl, $C_1$–$C_4$haloalkylsulfonyl, phenylsutfonyl, $C_1$–$C_4$alkylsulfinyl, $C_1$–$C_4$haloalkylsulfinyl, phenylsulfinyl, or —NR$_{048}$CO$_2$R$_{047}$; or R$_{01}$ is $C_1$–$C_4$alkylene-phenyl, COR$_{07}$ or 4-6-membered heterocyclyl;

R$_{02}$, R$_{038}$, R$_{044}$ and R$_{066}$ independently of one another are hydrogen, $C_1$–$C_4$alkyl, phenyl, or phenyl which is substituted by $C_1$–$C_4$alkyl, $C_1$–$C_6$haloalkyl, $C_1$–$C_4$alkoxy, $C_1$–$C_4$haloalkoxy, $C_2$–$C_6$alkenyl, $C_3$–$C_6$alkynyl, $C_3$–$C_6$alkenyloxy, $C_3$–$C_6$alkynyloxy, halogen, nitro, cyano, —COOH, COOC$_1$–$C_4$alkyl, COOphenyl, $C_1$–$C_4$alkoxy, phenoxy, ($C_1$–$C_4$alkoxy)-$C_1$–$C_4$alkyl, ($C_1$–$C_4$alkylthio)-$C_1$–$C_4$alkyl, ($C_1$–$C_4$alkylsulfinyl)-$C_1$–$C_4$alkyl, ($C_1$–$C_4$alkylsulfonyl)-$C_1$–$C_4$alkyl, NHSO$_2$—$C_1$–$C_4$alkyl, NHSO$_2$-phenyl, N($C_1$–$C_6$alkyl)SO$_2$—$C_1$–$C_4$alkyl, N($C_1$–$C_6$alkyl)SO$_2$-phenyl, N($C_2$–$C_6$alkenyl)SO$_2$—$C_1$–$C_4$alkyl, N($C_2$–$C_6$alkenyl)SO$_2$-phenyl, N($C_3$–$C_6$alkynyl)SO$_2$—$C_1$–$C_4$alkyl, N($C_3$–$C_6$alkynyl)SO$_2$-phenyl, N($C_3$–$C_7$cycloalkyl)SO$_2$—$C_1$–$C_4$alkyl, N($C_3$-C cycloalkyl)SO$_2$-phenyl, N(phenyl)SO$_2$—$C_1$–$C_4$alkyl, N(phenyl)SO$_2$-phenyl, OSO$_2$—$C_1$–$C_4$alkyl, CONR$_{049}$R$_{050}$, OSO$_2$—$C_1$–$C_4$haloalkyl, OSO$_2$-phenyl, $C_1$–$C_4$alkylthio, $C_1$–$C_4$haloalkylthio, phenylthio, $C_1$–$C_4$alkylsuffonyl, $C_1$–$C_4$haloalkylsulfonyl, phenylsulfonyl, $C_1$–$C_4$alkylsulfinyl, $C_1$–$C_4$haioalkylsulfinyl, phenylsultinyl, $C_1$–$C_4$alkylene phenyl or —NR$_{052}$CO$_2$R$_{053}$;

R$_{03}$, R$_{039}$ and R$_{067}$ independently of one another are $C_1$–$C_4$alkyl, phenyl or phenyl which is substituted by $C_1$–$C_4$alkyl, $C_1$–$C_6$haloalkyl, $C_1$–$C_4$alkoxy, $C_1$–$C_4$haloalkoxy, $C_2$–$C_6$alkenyl, $C_3$–$C_6$alkynyl, $C_3$–$C_6$alkenyloxy, $C_3$–$C_6$alkynyloxy, halogen, nitro, cyano, —COOH, COOC$_1$–$C_4$alkyl, COOphenyl, $C_1$–$C_4$alkoxy, phenoxy, ($C_1$–$C_4$alkoxy)-$C_1$–$C_4$alkyl, ($C_1$–$C_4$alkylthio)-$C_1$–$C_4$alkyl, ($C_1$–$C_4$alkylsulfinyl)-$C_1$–$C_4$alkyl, ($C_1$–$C_4$alkylsulfonyl)-$C_1$–$C_4$alkyl, NHSO$_2$—$C_1$–$C_4$alkyl, NHSO$_2$-phenyl, N($C_1$–$C_6$alkyl)SO$_2$—$C_1$–$C_4$alkyl, N($C_1$–$C_6$alkyl)SO$_2$-phenyl, N($C_2$–$C_6$alkenyl)SO$_2$—$C_1$–$C_4$alkyl, N($C_2$–$C_6$alkenyl)SO$_2$-phenyl, N($C_3$–$C_6$alkynyl)SO$_2$—$C_1$–$C_4$alkyl, N($C_3$–$C_6$alkynyl)SO$_2$-phenyl, N($C_3$–$C_7$ cycloalkyl)SO$_2$—$C_1$–$C_4$alkyl, N($C_3$–$C_7$cycloalkyl)SO$_2$-phenyl, N(phenyl)SO$_2$—$C_1$–$C_4$alkyl, N(phenyl)SO$_2$-phenyl, OSO$_2$—$C_1$–$C_4$alkyl, CONRO$_{070}$R$_{054}$, OSO$_2$—$C_1$–$C_4$haloalkyl, OSO$_2$-phenyl, $C_1$–$C_4$alkylthio, $C_1$–$C_4$haloalkylthio, phenylthio, $C_1$–$C_4$alkylsulfonyl, $C_1$–$C_4$haloalkylsulfonyl, phenylsulfonyl, $C_1$–$C_4$alkylsulfinyl, $C_1$–$C_4$haloalkylsulfinyl, phenylsulfinyl, $C_1$–$C_4$alkylene-phenyl or —NR$_{056}$CO$_2$R$_{055}$;

R$_{04}$ is $C_1$–$C_4$alkyl;

R$_{05}$ is hydrogen, $C_1$–$C_4$alkyl, $C_2$–$C_6$alkenyl, $C_3$–$C_6$alkynyl, $C_3$–$C_7$cycloalkyl, phenyl or phenyl which is substituted by $C_1$–$C_4$alkyl, $C_1$–$C_6$haloalkyl, $C_1$–$C_4$alkoxy, $C_1$–$C_4$haloalkoxy, $C_2$–$C_6$alkenyl, $C_3$–$C_6$alkynyl, $C_3$–$C_6$alkenyloxy, $C_3$–$C_6$alkynyloxy, halogen, nitro, cyano, —COOH, COOC$_1$–$C_4$alkyl, COOphenyl, $C_1$–$C_4$alkoxy, phenoxy, ($C_1$–$C_4$alkoxy)-$C_1$–$C_4$alkyl, ($C_1$–$C_4$alkylthio)-$C_1$–$C_4$alkyl, ($C_1$–$C_4$alkylsulfinyl)-$C_1$–$C_4$alkyl, ($C_1$–$C_4$alkylsulfonyl)-$C_1$–$C_4$alkyl, NHSO$_2$—$C_1$–$C_4$alkyl, NHSO$_2$-phenyl, N($C_1$–$C_6$alkyl)SO$_2$—$C_1$–$C_4$alkyl, N($C_1$–$C_6$alkyl)SO$_2$-phenyl, N($C_2$–$C_6$alkenyl)SO$_2$—$C_1$–$C_4$alkyl, N($C_2$–$C_6$alkenyl)

$SO_2$-phenyl, $N(C_3-C_6alkynyl)SO_2H$, $N(C_3-C_6alkynyl)SO_2-C_1-C_4alkyl$, $N(C_3-C_6alkynyl)SO_2$-phenyl, $N(C_3-C_7cycloalkyl)SO_2H$, $N(C_3-C_7cycloalkyl)SO_2-C_1-C_4alkyl$, $N(C_3-C_7cycloalkyl)SO_2$-phenyl, $N(phenyl)SO_2-C_1-C_4alkyl$, $N(phenyl)SO_2$-phenyl, $OSO_2-C_1-C_4alkyl$, $CONR_{057}R_{058}$, $OSO_2-C_1-C_4haloalkyl$, $OSO_2$-phenyl, $C_1-C_4alkylthio$, $C_1-C_4haloalkylthio$, phenylthio, $C_1-C_4alkylsulfonyl$, $C_1-C_4haloalkylsulfonyl$, phenylsulfonyl, $C_1-C_4alkylsulfinyl$, $C_1-C_4haloalkylsulfinyl$, phenylsulfinyl, $C_1-C_4alkylenephenyl$ or $-NR_{060}CO_2R_{059}$;

$R_{06}$ is hydrogen, $C_1-C_4alkyl$, $C_2-C_6alkenyl$, $C_3-C_6alkynyl$, $C_3-C_7cycloalkyl$, phenyl or phenyl which is substituted by $C_1-C_4alkyl$, $C_1-C_6haloalkyl$, $C_1-C_4alkoxy$, $C_1-C_4haloalkoxy$, $C_2-C_6alkenyl$, $C_3-C_6alkynyl$, $C_3-C_6alkenyloxy$, $C_3-C_6alkynyloxy$, halogen, nitro, cyano, $-COOH$, $COOC_1-C_4alkyl$, COOphenyl, $C_1-C_4alkoxy$, phenoxy, $(C_1-C_4alkoxy)-C_1-C_4alkyl$, $(C_1-C_4alkylthio)-C_1-C_4alkyl$, $(C_1-C_4alkylsulfinyl)-C_1-C_4alkyl$, $(C_1-C_4alkylsulfonyl)-C_1-C_4alkyl$, $NHSO_2-C_1-C_4alkyl$, $NHSO_2$-phenyl, $N(C_1-C_6alkyl)SO_2-C_1-C_4alkyl$, $N(C_1-C_6alkyl)SO_2$-phenyl, $N(C_2-C_6alkenyl)SO_2-C_1-C_4alkyl$, $N(C_2-C_6alkenyl)SO_2$-phenyl, $N(C_3-C_6alkynyl)SO_2-C_1-C_4alkyl$, $N(C_3-C_6alkynyl)SO_2$-phenyl, $N(C_3-C_7cycloalkyl)SO_2-C_1-C_4alkyl$, $N(C_3-C_7cycloalkyl)SO_2$-phenyl, $N(phenyl)SO_2-C_1-C_4alkyl$, $N(phenyl)SO_2$-phenyl, $OSO_2-C_1-C_4alkyl$, $CONR_{061}R_{062}$, $OSO_2-C_1-C_4haloalkyl$, $OSO_2$-phenyl, $C_1-C_4alkylthio$, $C_1-C_4haloalkylthio$, phenylthio, $C_1-C_4alkylsulfonyl$, $C_1-C_4haloalkylsulfonyl$, phenylsulfonyl, $C_1-C_4alkylsulfinyl$, $C_1-C_4haloalkylsulfinyl$, phenylsulfinyl, $C_1-C_4alkylene$-phenyl or $-NR_{064}CO_2R_{063}$;

$R_{07}$ is phenyl, substituted phenyl, $C_1-C_4alkyl$, $C_1-C_4alkoxy$ or $-NR_{08}R_{09}$;

$R_{08}$ and $R_{09}$ independently of one another are $C_1-C_4alkyl$, phenyl or phenyl which is substituted by halogen, nitro, cyano, $C_1-C_4alkyl$, $C_1-C_4alkoxy$, $C_1-C_4thioalkyl$, $-CO_2R_{066}$, $-COR_{067}$, $C_1-C_4alkylsulfonyl$, $C_1-C_4alkylsulfinyl$, $C_1-C_4haloalkyl$; or $R_{08}$ and $R_{09}$ together form a 5-6-membered ring which may be interrupted by oxygen, $NR_{065}$ or S, $R_{015}$, $R_{031}$, $R_{043}$, $R_{048}$, $R_{052}$, $R_{056}$, $R_{060}$ and $R_{064}$ independently of one another are hydrogen, $C_1-C_4alkyl$, $C_2-C_6alkenyl$, $C_3C_6alkynyl$ or $C_3-C_7cycloalkyl$;

$R_{025}$, $R_{026}$, $R_{027}$, $R_{028}$, $R_{029}$, $R_{030}$, $R_{032}$, $R_{033}$, $R_{034}$, $R_{035}$, $R_{036}$, $R_{037}$, $R_{040}$, $R_{041}$, $R_{042}$, $R_{045}$, $R_{046}$, $R_{047}$, $R_{049}$, $R_{050}$, $R_{053}$, $R_{054}$, $R_{055}$, $R_{057}$, $R_{058}$, $R_{059}$, $R_{061}$, $R_{062}$, $R_{063}$, $R_{065}$ and $R_{070}$ independently of one another are hydrogen, $C_1-C_4alkyl$, $C_2-C_6alkenyl$, $C_3-C_6alkynyl$, $C_3-C_7cycloalkyl$, phenyl, or phenyl which is substituted by halogen, nitro, cyano, $C_1-C_4alkoxy$, $C_1-C_4haloalkoxy$, $C_1-C_4$ alkylthio, $C_1-C_4haloalkylthio$, $C_1-C_4alkyl$ or $C_1-C_4haloalkyl$; and $R_{36}$ is $C_1-C_4alkyl$, $C_1-C_4haloalkyl$, $C_3-C_6alkenyl$, $C_3-C_6haloalkenyl$, $C_3-C_6alkynyl$, $C_3-C_6haloalkynyl$, $C_3-C_6cycloalkyl$ or $C_3-C_6cycloalkyl$ which is substituted by halogen, $C_1-C_4alkyl$, $C_1-C_4haloalkyl$, $C_3-C_6alkenyl$, $C_3-C_6haloalkenyl$, $C_3-C_6alkynyl$, $C_3-C_6haloalkynyl$, $C_1-C_4alkoxycarbonyl$, $C_1-C_4alkylthio$, $C_1-C_4alkylsulfinyl$, $C_1-C_4alkylsulfonyl$, $C_1-C_4haloalkylthio$, $C_1-C_4haloalkylsulfinyl$, $C_1-C_4haloalkylsulfonyl$, $C_1-C_4alkylcarbonyl$, $di-C_1-C_4alkylamino$, $C_1-C_4alkoxy$, $C_1-C_4haloalkoxy$, $C_1-C_4alkyl-S(O)_2O$, $C_1-C_4haloalkyl-S(O)_2O$ or phenyl which for its part may be substituted by halogen, $C_1-C_4alkyl$, $C_1-C_4haloalkyl$, $C_3-C_6alkenyl$, $C_3-C_6alkynyl$, cyano, nitro or COOH; and agronomically acceptable salts $M^+$ and all stereoisomers and tautomers of the compounds of the formula I.

The compounds of the formula I can be present in different isomeric forms which can be isolated in pure form. The invention therefore also embraces all stereoisomeric forms of the compound of the formula I. Examples of these isomeric forms are the formulae Ix, Ixx, Ixxx and Ixxxx below, in which Q is the group $Q_2$.

Ix
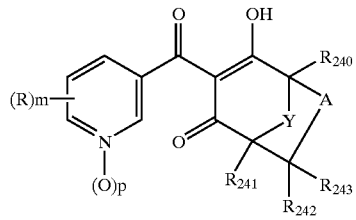

Ixx
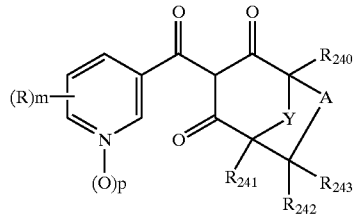

Ixxx
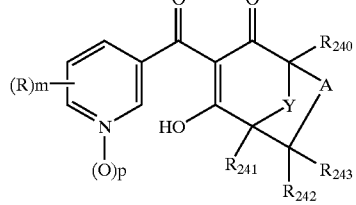

Ixxxx
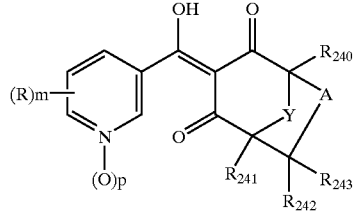

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, heptyl and octyl and their branched isomers. Alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 8 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Suitable haloalkenyl groups are alkenyl groups which are mono- or polysubstituted by halogen, halogen being fluorine, chlorine, bromine and iodine and in particular fluorine and chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl. Among the $C_3$–$C_{20}$alkenyl groups which are mono-, di- or trisubbtuted by halogen, preference is given to those having a chain length of from 3 to 5 carbon atoms.

Suitable haloalkynyl groups are, for example, aikynyl groups which are mono- or polysubstituted by halogen, halogen being bromine, iodine and in particular fluorine and chlorine, for example 3-fluoropropynyl, 3-chloropropynyl, 3-bromopropynyl, 3,3,3-trifluoropropynyl and 4,4,4-trifluorobut-2-yn-1-yl. Among the alkynyl groups which are mono- or polysubstituted by halogen, preference is given to those having a chain length of from 3 to 5 carbon atoms.

Alkoxy groups preferably have a chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals; preferably methoxy and ethoxy. Alkylcarbonyl is preferably acetyl or propionyl. Alkoxycarbonyl is, for example, methoxycarbonyl, ethoxycarbonyl, propoxycarbonyl, isopropoxycarbonyt, n-butoxycarbonyl, isobutoxycarbonyl, sec-butoxycarbonyl or tert-butoxycarbonyl; preferably methoxycarbonyl or ethoxycarbonyl. Haloalkoxy groups preferably have a chain length of from 1 to 8 carbon atoms. Haloalkoxy is, for example, fluoromethoxy, difluoromethoxy, trifluoromethoxy, 2,2,2-trifluoroethoxy, 1,1,2,2-tetrafluoroethoxy, 24luoroethoxy, 2-chloroethoxy, 2,2-difluoroethoxy and 2,2,2-trichloroethoxy; preferably difluoromethoxy, 2-chloroethoxy and trifluoromethoxy. Alkylthio groups preferably have a chain length of from 1 to 8 carbon atoms. Alkylthio is, for example, methylthio, ethylthio, propylthio, isopropylthio, n-butylthio, isobutylthio, sec-butylthio or tert-butylthio, preferably methylthio and ethylthio. Alkylsuffinyl is, for example, methylsulfinyl, ethylsulfinyl, propyisulfinyl, isopropylsulfinyl, n-butylsulfinyl, isobutylsulfiny l, sec-butylsulfinyl, tert-butylsulfinyl; preferably methylsulfinyl and ethylsulfinyl. Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl; preferably methylsulfonyl or ethylsulfonyl. Alkoxyalkoxy groups preferably have a chain length of from 1 to 8 carbon atoms. Examples of alkoxyalkoxy groups are: methoxymethoxy, methoxyethoxy, methoxypropoxy, ethoxymethoxy, ethoxyethoxy, propoxymethoxy or butoxybutoxy. Alkylamino is, for example, methylamino, ethylamino, n-propylamino, isopropylamino or the isomeric butylamines. Dialkylamino is, for example, dimethylamino, methylethylamino, diethylamino, n-propylmethylamino, dibutylamino and diisopropylamino. Preference is given to alkylamino groups having a chain length of from 1 to 4 carbon atoms. Alkoxyalkyl groups have a chain length of preferably from 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl. Alkylthioalkyl groups preferably have from 1 to 8 carbon atoms. Alkylthioalkyl is, for example, methylthiomethyl, methylthioethyl, ethylthiomethyl, ethylthioethyl, n-propylthiomethyl, n-propylthioethyl, isopropylthiomethyl, iso-propylthioethyl, butylthiomethyl, butylthioethyl or butylthiobutyl. The cycloalkyl groups preferably have from 3 to 8 ring carbon atoms, for example cyclopropyl, cyclobutyl, cyclopentyl, cyclohexyl, cycloheptyl and cyclooctyl. Phenyl, also as part of a substituent as phenoxy, benzyl, benzyloxy, benzoyl, phenylthio, phenylalkyl, phenoxyalkyl, may be substituted. In this case, the substituents can be in ortho, meta and/or para position. The preferred substituent positions are the ortho and para positions to the ring attachment point. Heterocyclyl is to be understood as meaning ring systems which, in addition to carbon atoms, contain at least one heteroatom, such as nitrogen, oxygen and/or sulfur. They can be saturated or unsaturated. In the context of the present invention, heterocyclyl ring systems may also be substituted. Suitable substituents are, for example, $C_1$–$C_4$alkyl, $C_1$–$C_4$haloalkyl, $C_1$–$C_4$alkoxy, cyano, nitro, $C_1$–$C_4$alkylsulfonyl, $C_1$–$C_4$alkylsulfinyl, $C_1$–$C_4$alkylthio or $C_3$–$C_6$cycloalkyl.

Heterocyclyl may be, for example, furyl, thiophenyl, pyrrolidyl, piperidinyl, morpholinyl, pyridyl, imidazolyl, tetrahydrofuryl, tetrahydropyranyl, dihydrofuryl, dihydropyranyl, isoxazolyl, oxazolyl, isothiazolyl, 1,2,3-thiadiazolyl, 1,2,4-thiadiazolyl, thiazolyl, pyrazolyl, 1,2,4-triazolyl, 1,2,3-triazolyl, tetrazolyl, pyrimidyl, pyrazinyl, sym. or unsym. triazinyl, piperazinyl, oxazolinyl (for example:

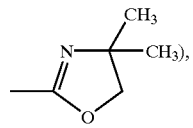

oxazolidinyl, imidazolinyl, imidazolidinyl, dioxanyl, oxetanyl, in particular 2-oxetanyl, or phthalimidyl.

The invention also embraces the salts $M^+$ which can be formed by the compounds of the formula 1, in particular the compounds of the formula I in which $R_{20}$, $R_{23}$, $R_{26}$ and $R_{30}$ are hydroxyl, preferably with amines, alkali metal and alkaline earth metal bases or quaternary ammonium bases. Among the alkali metal and alkaline earth metal bases, the hydroxides of lithium, sodium, potassium, magnesium or calcium, in particular those of sodium or potassium, may be especially emphasized as salt formers. Examples of amines suitable for ammonium salt formation are both ammonia and primary, secondary and tertiary $C_1$–$C_{18}$alkylamines, $C_1$–$C_4$hydroxyalkylamines and $C_2$–$C_4$alkoxyalkylamines, for example methylamine, ethylamine, n-propylamine, isopropylamine, the four isomeric butylamines, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, al iylamine, n-butenyl-2-amine, n-pentenyl-2-amine, 2,3dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amiines, for example pyridine, quinoline, isoquinoline, morpholine, piperidine, pyrrolidine, indoline, quinuclidine and azepine: primary arylamines, for example anilines, methoxyanilines, ethoxyanilines, o,m,p-toluidines, phenylenediamines, naphthylamines and o,m,p-chloroanilines; but in particular triethylamine, isopropylamine and diisopropylamine. Quaternary ammonium bases which are suitable for salt formation are, for example, $[N(R_{a01} R_{b01} R_{c01} R_{d01})]^+ OH^-$, where $R_{a01}, R_{b01}, R_{c01}$ and $R_{d01}$ independently of one anotheer are $C_1$–$C_4$alkyl. Further suitable tetraalkylammonium bases with other anions can be obtained, for example, by anion exchange reactions.

Preferred compounds of the formula I correspond to the formula Ib

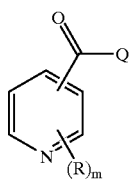

(Ib)

in which
each R independently is $C_1$–$C_6$alkyl, $C_1$–$C_6$alkoxy, $C_1$–$C_6$haloalkoxy, $C_1$–$C_6$alkylthio, $C_1$–$C_6$-alkylsulfinyl, $C_1$–$C_6$alkylsulfonyl, $C_1$–$C_6$haloalkyl, $C_1$–$C_6$haloalkylthio, $C_1$–$C_6$haloalkylsu ffinyl, $C_1$–$C_6$haloalkylsulfonyl, $C_1$–$C_6$alkoxycarbonyl, $C_1$–$C_6$alkylcarbonyl, $C_1$–$C_6$alkylamino, di-$C_1$–$C_6$-alkylamino, $C_1$–$C_6$alkylaminosu ffonyl, di-$C_1$–$C_6$alkylaminosulfonyl, —N($R_1$)—S—$R_2$, —N($R_3$)—SO—$R_4$, —N($R_5$)—$SO_2$—$R_6$, nitro, cyano, halogen, hydroxyl, amino, or a five- to ten-membered monocyclic or fused bicyclic ring system which may be aromatic or partially saturated and may contain 1 to 4 heteroatoms selected from the group consisting of nitrogen, oxygen and sulfur, where the ring system is either attached directly to the pyridine ring or attached via a $C_1$–$C_4$alkylene group to the pyridine ring, and each ring system may not contain more than 2 oxygen atoms and not more than two sulfur atoms, and the ring system for its part may be mono-, di- or trisubstituted by $C_1$–$C_6$alkyl, $C_1$–$C_6$haloalkyl, $C_3$–$C_6$alkenyl, $C_3$–$C_6$haloalkenyl, $C_3$–$C_6$alkynyl, $C_3$–$C_6$haloalkynyl, $C_1$–$C_6$alkoxy, $C_1$–$C_6$haloalkoxy, $C_3$–$C_6$alkenyloxy, $C_3$–$C_6$alkynyloxy, mercapto, $C_1$–$C_6$alkylthio, $C_1$–$C_6$haloalkylthio, $C_3$–$C_6$alkenylthio, $C_3$–$C_6$haloalkenylthio, $C_3$–$C_6$alkynylthio, $C_2$–$C_5$alkoxyalkylthio, $C_3$–$C_6$acetylalkylthio, $C_3$–$C_6$alkoxycarbonylalkylthio, $C_2$–$C_4$-cyanoalkylthio, $C_1$–$C_6$alkylsulfinyl, $C_1$–$C_6$haloalkylsulfinyl, $C_1$–$C_6$alkylsulfonyl, $C_1$–$C_6$-haloalkylsulfonyl, aminosulfonyl, $C_1$–$C_2$alkylaminosulfonyl, $C_2$–$C_4$dialkylaminosulfonyl, $C_1$–$C_3$-alkylene-$R_7$, $NR_8R_9$, halogen, cyano, nitro, phenyl and benzylthio where phenyl and benzylthio for their part may be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or nitro, and where substituents on the nitrogen in the heterocyclic ring are different from halogen;

Q is the group $Q_1$ in which
$R_{20}$ is hydroxyl, $C_1$–$C_4$alkoxy, $C_1$–$C_4$alkylcarbonyloxy, $C_1$–$C_4$alkoxycarbonyloxy, $R_{21}R_{22}N$—C(O)O, phenylthio, $C_1$–$C_4$alky lthio, $C_1$–$C_4$alkyl-S(O)$_2$O, ($C_1$–$C_4$alkoxy)$_2$P(O)O, $C_1$–$C_4$alkyl($C_1$–$C_4$alkoxy)P(O)O, H($C_1$–$C_4$alkoxy)P(O)O or benzoyloxy; and $R_{21}$ and $R_{22}$ independently of one another are hydrogen or $C_1$–$C_4$alkyl; or the group $Q_{2a}$

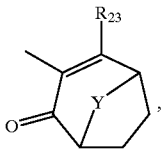

($Q_{2a}$)

in which $R_{23}$ is hydroxyl, $C_1$–$C_4$alkoxy, $C_1$–$C_4$alkylcarbonyloxy, $C_1$–$C_4$alkoxycarbonyloxy, $R_{24}R_{25}N$—C(O)O, phenylthio, $C_1$–$C_4$alkylthio, $C_1$–$C_4$alkyl-S(O)$_2$O, ($C_1$–$C_4$alkoxy)$_2$P(O)O, $C_1$–$C_4$-alkyl($C_1$–$C_4$alkoxy)P(O)O, H($C_1$–$C_4$alkoxy)P(O)O or benzoyloxy; and $R_{24}$ and $R_{25}$ independently of one another are hydrogen or $C_1$–$C_4$alkyl; and Y is oxygen, sulfur, a chemical bond or a $C_1$–$C_4$alkylene bridge;

or the group $Q_3$

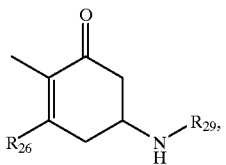

($Q_3$)

in which $R_{26}$ is hydroxyl, $C_1$–$C_4$alkoxy, $C_1$–$C_4$alkylcarbonyloxy, $C_1$–$C_4$alkoxycarbonyloxy, $R_{27}R_{28}N$-C(O)O, phenylthio, $C_1$–$C_4$alkylthio, $C_1$–$C_4$alkyl-S(O)$_2$O, ($C_1$–$C_4$alkoxy)$_2$P(O)O, $C_1$–$C_4$-alkyl($C_1$–$C_4$alkoxy)P(O)O, H($C_1$–$C_4$alkoxy)P(O)O or benzoyloxy; and $R_{27}$ and $R_{28}$ independently of one another are hydrogen or $C_1$–$C_4$alkyl and $R_{29}$ is hydrogen, $C_1$–$C_6$alkyl, $C_1$–$C_4$alkylcarbonyl, $C_1$–$C_4$alkoxycarbonyl, ($C_1$–$C_4$alkyl)NHCO or ($C_1$–$C_4$alkyl)$_2$NCO; or the group $Q_4$

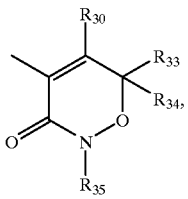

($Q_4$)

in which $R_{30}$ is hydroxyl, $C_1$–$C_4$alkoxy, $C_1$–$C_4$alkylcarbonyloxy, $C_1$–$C_4$alkoxycarbonyloxy, $R_{31}R_{32}N$—C(O)O, phenylthio, $C_1$–$C_4$alkylthio, $C_1$–$C_4$alkyl-S(O)$_2$O, ($C_1$–$C_4$alkoxy)$_2$P(O)O, $C_1$–$C_4$-alkyl ($C_1$–$C_4$alkoxy)P(O)O, H($C_1$–$C_4$alkoxy)P(O)O or benzoyloxy; and $R_{31}$ and $R_{32}$ independently of one another are hydrogen or $C_1$–$C_4$alkyl;

$R_{33}$ and $R_{34}$ independently of one another are hydrogen, $C_1$–$C_4$alkyl, $C_2$–$C_6$alkenyl, C2–$C_6$alkynyl, $C_1$–$C_4$-alkoxycarbonyl, $C_1$–$C_6$alkylthio, $C_1$–$C_6$alkylsulfinyl, $C_1$–$C_6$alkylsulfonyl, $C_1$–$C_4$alkyl-NHS(O)$_2$, $C_1$–$C_4$haloalkyl, —NH—$C_1$–$C_4$alkyl, —N($C_1$–$C_4$alkyl)$_2$, $C_1$–$C_6$alkoxy, or phenyl which for its part may be substituted by $C_1$–$C_4$alkyl, $C_1$–$C_4$haloalkyl, $C_1$–$C_4$alkoxy, $C_1$–$C_4$haloalkoxy, $C_1$–$C_4$alkylcarbonyl, $C_1$–$C_4$alkoxycarbonyl, amino, $C_1$–$C_4$alkylamino, di-$C_1$–$C_4$alkylamino, $C_1$–$C_6$alkylthio, $C_1$–$C_6$-alkylsulfinyl, $C_1$–$C_6$alkylsulfonyl, $C_1$–$C_4$alkyl-S(O)$_2$O, $C_1$–$C_4$haloalkylthio, $C_1$–$C_4$haloalkylsulfinyl, $C_1$–$C_4$haloalkylsulfonyl, $C_1$–$C_4$haloalkyl-S(O)$_2$O, $C_1$–$C_4$alkyl-S(O)$_2$NH, $C_1$–$C_4$alkyl-S(O)$_2$N($C_1$–$C_4$-alkyl), halogen, nitro, COOH or cyano; or $R_{33}$ and $R_{34}$ together form a $C_2$–$C_6$alkylene bridge; and $R_{35}$ is hydrogen, $C_1$–$C_4$alkyl, $C_1$–$C_4$alkoxycarbonyl or phenyl which for its part may be substituted by $C_1$–$C_4$alkyl, $C_1$–$C_4$haloalkyl, $C_1$–$C_4$alkoxy, $C_1$–$C_4$haloalkoxy, $C_1$–$C_4$alkylcarbonyl, $C_1$–$C_4$alkoxycarbonyl, amino, $C_1$–$C_4$alkylamino, di-$C_1$–$C_4$alkylamino, $C_1$–$C_4$alkylthio, $C_1$–$C_4$-alkylsulfinyl, $C_1$–$C_4$alkylsulfonyl, $C_1$–$C_4$alkyl-S(O)$_2$O, $C_0$–$C_4$haloalkylthio, $C_1$–$C_4$haloalkylsulfinyl, $C_1$–$C_4$haloalkylsulfonyl, $C_1$–$C_4$haloalkyl-S(O)$_2$O, $C_1$–$C_4$alkyl-S(O)$_2$NH, $C_1$–$C_4$alkyl-S(O)$_2$N($C_1$–$C_4$-alkyl), halogen, nitro, COOH or cyano; or the group $Q_5$, and also agronomically acceptable salts of these compounds, the other substituents being defined as under formula I in claim 1. Among the compounds of the formula Ib, preference is furthermore given to those in which the group —C(O)—Q is located in the 3 position on the pyridine ring, or in which Q is $Q_2$, $R_{23}$ being, in particular, hydroxyl, Y being a methylene bridge and m being the number 2. Preference is further given to compounds of the formula Ib in which R is $C_1$–$C_6$alkyl or $C_1$–$C_6$haloalkyl.

Preferred compounds of the formula I are characterized in that the group —C(O)Q is in the ortho position to a group R. Preference is furthermore given to compounds of the formula I in which a group R is $C_1$–$C_6$haloalkyl and in the ortho position to the pyridyl nitrogen. Of particular interest are furthermore compounds of the formula I in which the group —C(O)Q is in the 3 position to the pyridyl nitrogen. In the formula 1, p is preferably the number 0. Also to be emphasized are compounds of the formula I in which m is 2 and R is $C_1$–$C_3$alkyl, $C_1$–$C_3$-haloalkyl, $C_1$–$C_2$alkoxymethyl, $C_1$–$C_2$alkythiomethyl, hydroxymethyl, $C_1$–$C_6$alky lcarbonyloxymethyl, benzoyloxymethyl, $C_1$–$C_4$alkoxycarbonyloxymethyl, chlorine, cyano, $C_1$–$C_3$alkoxy, $C_1$–$C_3$haloalkoxy, allyloxy, propargyloxy, $C_1$–$C_3$alkylthio, $C_1$–$C_3$alkylsulfinyl, $C_1$–$C_3$alkylsulfonyl, $C_1$–$C_3$alkylsulfonyloxy, $C_1$–$C_2$alkylsulfinylmethyl or $C_1$–$C_2$alkylsulfonylmethyl. A further group of preferred compounds of the formula I is formed by those compounds in which at least one group R is trifluoromethyl, difluorochloromethyl, pentafluoroethyl or heptafluoro-n-propyl.

Particularly noteworthy compounds of the formula I are those in which Q is a group $Q_1$ and $R_{16}$, $R_{18}$ and $R_{19}$ are $C_1$–$C_3$alkyl and $R_{17}$ is hydrogen, or Q is a group $Q_2$ and Y is —CH$_2$—, —CH$_2$CH$_2$— or oxygen, A is —CH$_2$— and $R_{240}$, $R_{241}$, $R_{242}$ and $R_{243}$ are Mch hydrogen, or Q is a group $Q_3$ and $R_{29}$ is $C_1$–$C_4$alkylcarbonyl, $C_1$–$C_4$alkoxycarbonyl or $C_1$–$C_4$alkylaminocarbonyl or di($C_1$–$C_2$-alkyl) aminocarbonyl, or Q is a group $Q_4$ in which $R_{33}$, $R_{34}$ and $R_{35}$ are $C_1$–$C_3$alkyl. In these noteworthy compounds of the formula I, $R_{20}$, $R_{23}$, $R_{26}$ and $R_{30}$ independently of one another are halogen, thiocyanato, $C_1$–$C_{12}$alkoxy, $C_1$–$C_4$alkoxycarbonyl-$C_1$–$C_2$alkoxy, $C_1$–$C_{12}$-alkylthio, alkylthio, $C_1$–$C_{12}$alkylsulfinyl, $C_1$–$C_{12}$alkylsulfonyl, $C_1$–$C_{12}$haloalkylthio, $C_1$–$C_{12}$haloalkylsulfinyl, $C_1$–$C_{12}$haloalkylsulfonyl, $C_1$–$C_{12}$alkenylthio, $C_2$–$C_{12}$alkenylsulfinyl, $C_2$–$C_{12}$alkenylsulfonyl, $C_2$–$C_{12}$-haloalkenylthio, $C_2$–$C_{12}$haloalkenylsulfinyl, $C_2$–$C_{12}$haloalkenylsulfonyl, $C_2$–$C_{12}$alkynylthio, $C_2$–$C_{12}$alkynylsulfinyl, $C_2$–$C_{12}$alkynylsulfonyl, $C_1$–$C_4$alkoxycarbonyl-$C_1$–$C_2$-alkylthio, $C_1$–$C_4$-alkoxycarbonyl-$C_1$–$C_2$alkylsulfinyl, $C_1$–$C_4$alkoxycarbonyl-$C_1$–$C_2$alkylsulfonyl, $C_1$–$C_4$alkyl-S(O)$_2$NH, $C_1$–$C_4$haloalkyl-S(O)$_2$NH, $C_1$–$C_4$alkyl-S(O)$_2$O, $C_1$–$C_{18}$alkylcarbonyloxy, $C_2$–$C_{18}$-alkenylcarbonyloxy, $C_3$–$C_6$cycloalkylcarbonyloxy, $C_1$–$C_{12}$alkoxycarbonyloxy, $C_1$–$C_{12}$-alkylthiocarbonyloxy, $C_1$–$C_{12}$alkylthiocarbamoyl, $C_1$–$C_6$alkyl-NH(CS)N($C_1$–$C_6$alkyl)—NH—, di-$C_1$–$C_6$alkyl-N(CS)N($C_1$–$C_6$alkyl)—NH—, benzyloxy, benzylthio, benzylsulfinyl, benzylsulfonyl, phenoxy, phenylthio, phenylsulfinyl, phenylsulfonyl, phenylsulfonyloxy or benzoyloxy, where the phenyl groups for their part may in each case be substituted by $C_1$–$C_4$alkyl, $C_1$–$C_4$-haloalkyl, $C_1$–$C_4$alkoxy, $C_1$–$C_4$haloalkoxy, $C_1$–$C_4$alkylcarbonyl, $C_1$–$C_4$alkoxycarbonyl, $C_1$–$C_4$-alkylamino, di-$C_1$–$C_4$alkylamino, $C_1$–$C_4$alkylthio, $C_1$–$C_4$alkylsulfinyl, $C_1$–$C_4$alkylsuonyl, $C_1$–$C_4$-alkyl-S(O)$_2$O, $C_1$–$C_4$haloalkylthio, $C_1$–$C_4$haloalkylsulfinyl, $C_1$–$C_4$haloalky lsulfonyl, $C_1$–$C_4$-haloalkyl-S(O)$_2$O, $C_1$–$C_4$alkyl-S(O)$_2$NH, $C_1$–$C_4$alkyl-S(O)$_2$N($C_1$–$C_4$alkyl), halogen, nitro or cyano, or $R_{20}$, $R_{23}$, $R_{26}$ and $R_{30}$ independently of one another are thienylcarbonyloxy or furylcarbonyloxy which for their part may be substituted by methyl or halogen, or are pyridylcarbonyloxy which for its part may be substituted as stated in claim 1, or $R_{20}$ is $R_{37}R_{37}$N, $R_{71}R_{72}$NNH—, $R_{21}R_{22}$NC(O)O— or $R_{73}R_{74}$NC(O)NH—; or $R_{23}$ is $R_{44}R_{45}$N, $R_{75}R_{76}$NNH—, $R_{46}R_{47}$NC(O)O— or $R_{77}R_{78}$NC(O)NH—; or $R_{26}$ is $R_{53}R_{54}$N, $R_{79}R_{80}$NNH—, $R_{55}R_{56}$NC(O)O— or $R_{81}R_{82}$NC(O)NH—; or $R_{30}$ is $R_{62}R_{63}$N, $R_{83}R_{84}$NNH—, $R_{64}R_{65}$NC(O)O— or $R_{85}R_{86}$NC(O)NH—. Very particularly preferably, $R_{20}$, $R_{23}$, $R_{26}$ or $R_{30}$ are hydroxyl or O$^-$M$^+$.

A further preferred group is formed by those compounds of the formula I in which Q is a group $Q_5$, $R_{36}$ is $C_1$–$C_4$alkyl, $C_1$–$C_4$haloalkyl or cyclopropyl and $R_{01}$ is $C_1$–$C_6$alkyl, $C_1$–$C_4$-alkoxycarbonylmethyl, $C_3$–$C_8$alkenyl, is benzyl or phenyl substituted by methyl, halogen, trifluoromethyl, methoxy, and at least one group R is trifluoromethyl, difluorochloromethyl, pentafluoroethyl or heptafluoro-n-propyl located in the ortho position to the pyridyl nitrogen.

The process according to the invention for preparing compounds of the formula I (I)

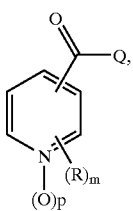

in which R and m are as defined under formula 1; p is 0 and Q is the group (Q₁)

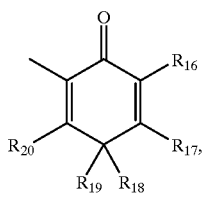

(Q₂)

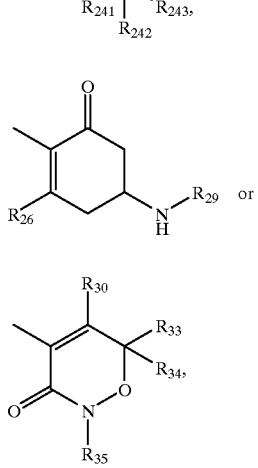

(Q₃)

(Q₄)

is carried out analogously to known processes (for example those described in WO 97/46530 and EP-A-0 353 187) and comprises a) reacting a compound of the formula II (II)

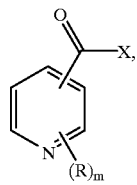

in which R and m are as defined under formula I and X is a leaving group, for example halogen, in an inert organic solvent in the presence of a base with compounds of the formula III, IV, V or VI (III)

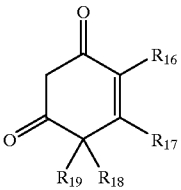

(IV)

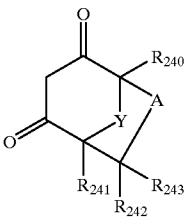

(V)

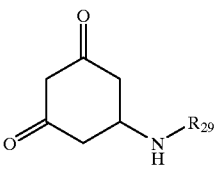

(VI)

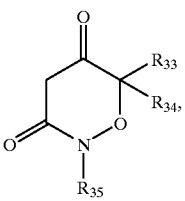

in which $R_{16}$, $R_{17}$, $R_{18}$, $R_{19}$, $R_{29}$, $R_{33}$, $R_{34}$, $R_{35}$, $R_{240}$, $R_{243}$, $R_{242}$, $R_{241}$, A and Y are as defined under formula I to give the compounds of the formula VII, VIII, IX or X (VII)

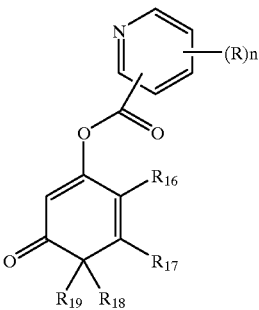

-continued (VIII)
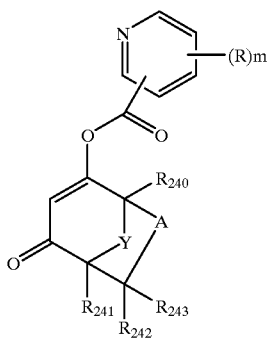

(IX)
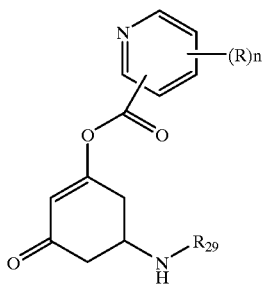

(X)
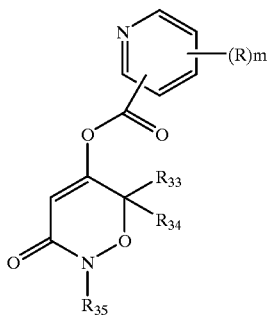

and then isomerizing these compounds, for example in the presence of a base and a catalytic amount of dimethylaminopyridine (DMAP) or a source of cyanide; or b) reacting a compound of the formula XI (XI)
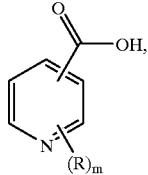

in which R and m are as defined under formula I with compounds of the formula III, IV, V or VI (III)
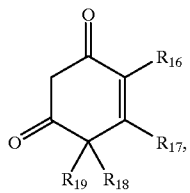

(IV)
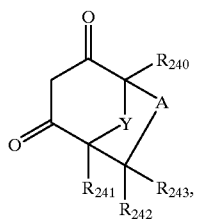

(V)
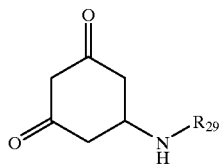

(VI)
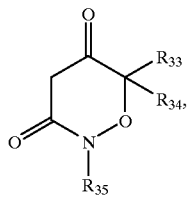

in which $R_{16}$, $R_{17}$, $R_{18}$, $R_{19}$, $R_{29}$, $R_{33}$, $R_{34}$, $R_{35}$, $R_{240}$, $R_{243}$, $R_{242}$, $R_{241}$, A and Y are as defined under formula I in an inert organic solvent in the presence of a base and a coupling agent to give a compound of the formula VII, VIII, IX or X (VII)
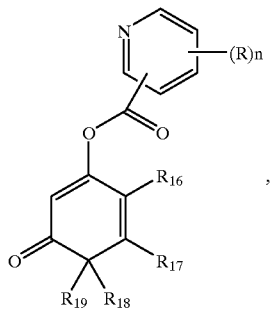

-continued

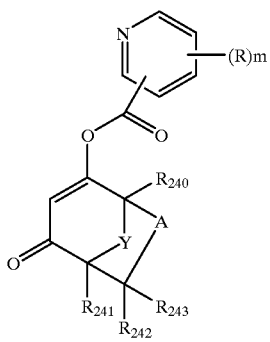
(VIII)

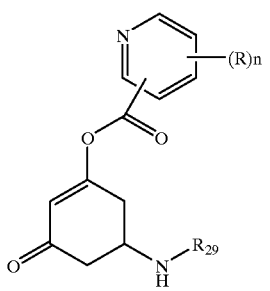
(IX)

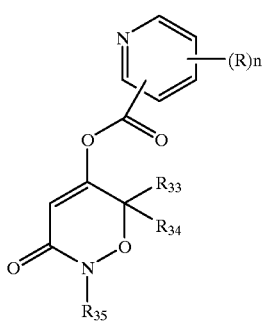
(X)

and then isomerizing these compounds, for example as described under route a).

Compounds of the formula I in which $R_{20}$, $R_{23}$, $R_{26}$ and $R_{30}$ are different from hydroxyl or halogen can be prepared by converesion methods which are generally known from the literature, for example acyclations or carbamoylations with appropriate acyl chlorides, from compounds in which $R_{20}$, $R_{23}$, $R_{26}$ or $R_{30}$ is hydroxyl in the presence of a suitable base, or they can be prepared by nucleophilic substitution reactions on chlorides of the formula I in which $R_{20}$, $R_{23}$, $R_{26}$ or $R_{30}$ is halogen, which are likewise obtainable by known processes by reaction with a chlorinating agent, such as phosgene, thionyl chloride or oxalyl chloride. Here, for example, suitably substituted amines, or hydroxylamines directly, or alkylsulfonamides, mercaptans, thiophenols, phenols, $Ar_1$—$NH_2$ or $Ar_1$—SH, are employed in the presence of a base, for example 5-ethyl-2-methylpyridine, diisopropylethylamine, triethylamine, sodium bicarbonate, sodium acetate or potassium carbonate.

Compounds of the formula I in which $R_{20}$, $R_{23}$, $R_{26}$ or $R_{30}$ comprise thio groups can be oxidized analogously to known standard processes, for example using peracids, for example meta-chloroperbenzoic acid (m-CPBA) or peracetic acid, to give the corresponding sulfones and sulfoxides of the formula I. Here, the degree of oxidation at the sulfur atom (SO— or $SO_2$—) can be controlled by the amount of oxidizing agent.

The process according to the invention for preparing compounds of the formula I in which R and m are as defined under formula I and Q is a group

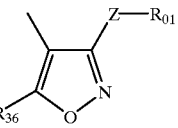
($Q_5$)

in which Z is sulfur, q is 0 and $R_{36}$ and $R_{01}$ are as defined under formula I is carried out analogously to known processes (for example those described in WO 97/43270) and comprises converting a compound of the formula XII

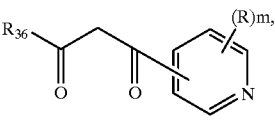
(XII)

in which $R_{36}$, R and m are as defined under formula I in the presence of a base, carbon disulfide and an alkylating agent of the formula XIII $R_{01}$—$X_1$ (XIII), in which $R_{01}$ is as defined under formula I and $X_1$ is a leaving group, for example halogen or sulfonate, into the compound of the formula XIV

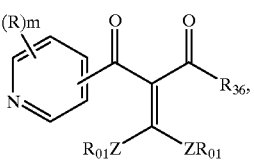
(XIV)

in which Z is sulfur and R, $R_{01}$, $R_{36}$ and m are as defined above and then cyclizing this compound using hydroxylamine hydrochloride, in the presence or absence of a solvent, in the presence of a base to give the compounds of the formulae

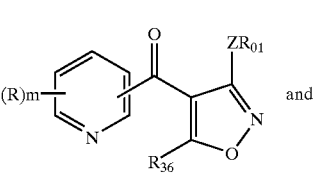
(Ie)

and

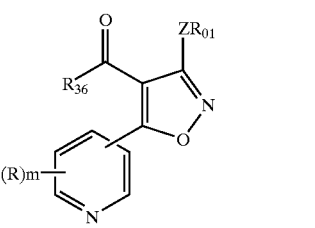
(If)

in which Z is sulfur and R, $R_{36}$, $R_{01}$ and m are as defined above, and then oxidizing these compounds with an oxidizing agent, for example meta-chloroperbenzoic acid (m-CPBA). The isomers of the formulae Ie and If can be separated using column chromatography and a suitable mobile phase and then purified.

The preparation of the compounds of the formula I in which p is 0 is illustrated in more detail in the reaction schemes 1 and 2 below.

Reaction scheme 1

Route a):

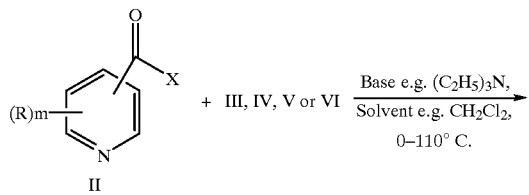

Route b):

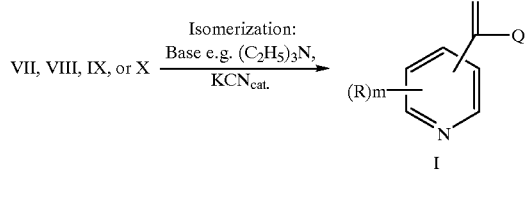

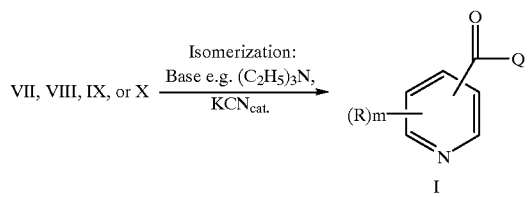

According to this reaction scheme, the compounds of the formula I with the group $Q_1$ in which $R_{20}$ is hydroxyl, the compounds of the formula I with the group $Q_2$ in which $R_{23}$ is hydroxyl, the compounds of the formula I with the group $Q_3$ in which $R_{26}$ is hydroxyl and the compounds of the formula I with the group $Q_4$ in which $R_{30}$ is hydroxyl can preferably be prepared.

Reaction scheme 2

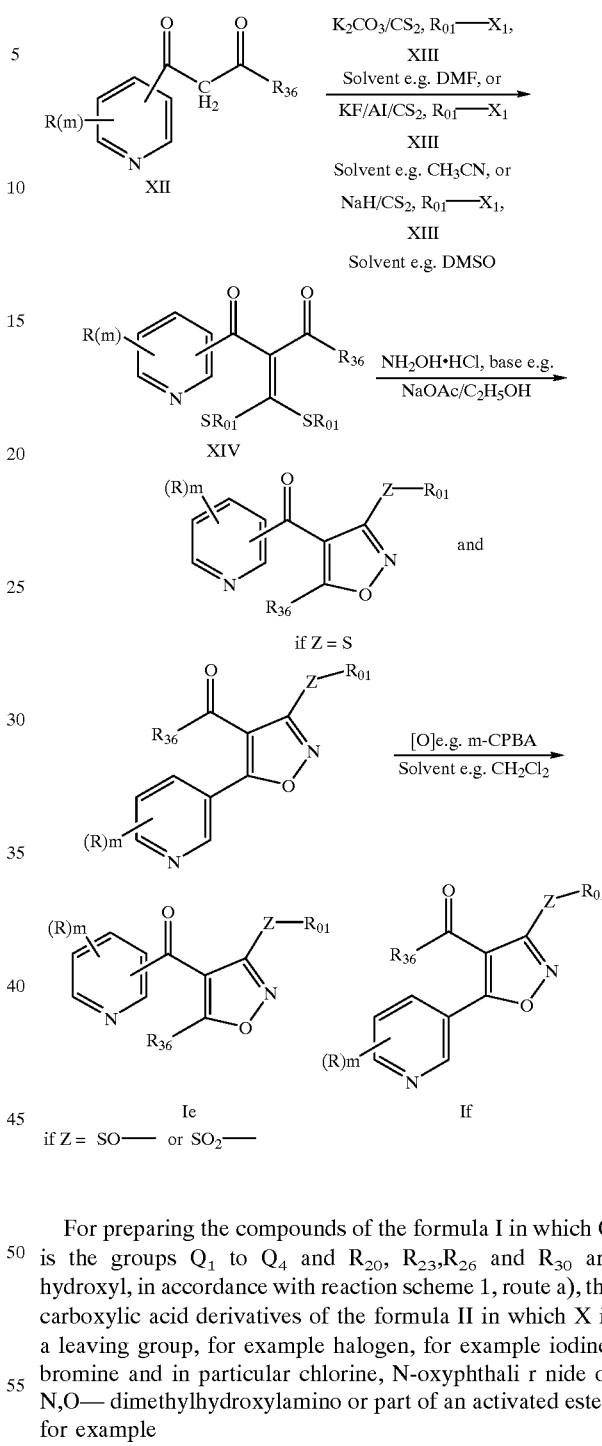

For preparing the compounds of the formula I in which Q is the groups $Q_1$ to $Q_4$ and $R_{20}$, $R_{23}$, $R_{26}$ and $R_{30}$ are hydroxyl, in accordance with reaction scheme 1, route a), the carboxylic acid derivatives of the formula II in which X is a leaving group, for example halogen, for example iodine, bromine and in particular chlorine, N-oxyphthali r nide or N,O— dimethylhydroxylamino or part of an activated ester, for example

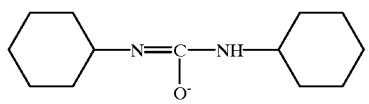

(formed from dicyclohexylcarbodiimide (DCC) and the corresponding carboxylic acid) or

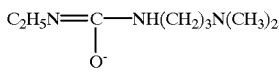

(formed from N-ethyl-N'-(3-dimethyiaminopropyl) carbodiimide (EDC) and the corresponding carboxylic acid) are employed. These compounds are reacted in an inert organic solvent, for example a halogenated hydrocarbon, for example dichloromethane, a nitrile, for example acetonitrile, or an aromatic hydrocarbon, for example toluene, and in the presence of a base, for example an alkylamine, for example triethylamine, an aromatic amine, for example pyridine or 4-dimethyiaminopyridine (DMAP), with the dione derivatives of the formula III, IV, V or VI to give the isomeric enol ethers of the formulae VII, VIII, IX and X. This esterification is carried out at temperatures of from 0° C. to 110° C.

The isomerization of the ester derivatives of the formulae VII, VIII, IX and X to the dione derivatives of the formula I (in which $R_{20}$, $R_{23}$, $R_{26}$ and $R_{30}$ are hydroxyl) can be carried out, for example, analogously to EP 369 803 in the presence of a base, for example an alkylamine, for example triethylamine, a carbonate, for example potassium carbonate, and a catalytic amount of DMAP or a cyanide source, for example acetone cyanohydrin or potassium cyanide.

According to reaction scheme 1, route b), the desired diones of the formula I (in which $R_{20}$, $R_{23}$, $R_{26}$ and $R_{30}$ are hydroxyl) can be obtained, for example, in analogy to Chem. Lett. 1975, 1045 by esterifying the carboxylic acids of the formula Xl with the dione derivatives of the formula III, IV, V or VI in an inert solvent, for example a halogenated hydrocarbon, for example dichloromethane, a nitrile, for example acetonitrile, or an aromatic hydrocarbon, for example toluene, in the presence of a base, for example an alkylamine, for example triethylamine, and a coupling agent, for example 2-chloro-1-methylpyridinium iodide. Depending on the solvent used, this esterification is carried out at temperatures of from 0° C. to 110° C., affording initially, as described under route a), the isomeric ester of the formula I which can be isomerized as described under route a), for example in the presence of a base and a catalytic amount of DMAP, or a cyanide source, to give the desired dione derivative of the formula I ($R_{20}$, $R_{23}$, $R_{26}$ and $R_{30}$ are hydroxyl).

The preparation of the compounds of the formula I in which Q is the group $Q_5$ can be carried out in accordance with reaction scheme 2 by reacting the β-diketone derivative of the formula XII, for example in analogy to Synthesis 1991, 301; ibid. 1988, 793; or Tetrahedron 32, 3055 (1976) with carbon disulfide in the presence of a base, for example a carbonate, for example potassium carbonate, a metal hydride, for example sodium hydride, or potassium fluoride on aluminium, and an alkylating agent of the formula XIII in which $X_1$ is a leaving group, for example halogen, for example iodine, bromine and in particular chlorine,

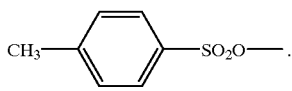

This reaction is preferably carried out in the presence of a solvent, for example an amide, for example N,N-dimethylformamide (DMF), a sulfoxide, for example dimethylsulfoxide (DMSO), or a nitrle, for example acetonitrile. The ketene thioacetal of the formula XIV which is formed is cyclized with the aid of hydroxylamine hydrochloride in the presence of a base, for example sodium acetate, in a solvent, for example an alcohol, for example ethanol, or an ether, for example tetrahydrofuran, to give the compound of the formula le in which Z is sulfur. This cyclization reaction is carried out at temperatures of from 0° C. to 100° C. If appropriate, compounds of the formulae le and If (Z is sulfur) can be oxidized analogously to known standard processes, for example with peracids, for example meta-chloroperbenzoic acid (m-CPBA) or peracetic acid, to give the corresponding sulfones and sulfoxides of the formulae Ie and If (Z=SO— or $SO_2$—). Here, the degree of oxidation at the sulfur atom (Z=SO— or $SO_2$__) can be controlled by the amount of oxidizing agent.

Oxidations to the compounds of the formulae le and If (Z is SO— or $SO_2$__) are carried out as described, for example, in H.O. House, "Modern Synthetic Reactions" W. A. Benjamin, Inc., Menlo Park, Calif., 1972, pages 334–335 and 353–354.

The activated carboxylic acid derivatives of the formula II in reaction scheme 1 (route a) in which X is a leaving group, for example halogen, for example bromine, iodine or in particular chlorine, can be prepared by known standard processes, as described, for example, in C. Ferri "Reaktionen der organischen Synthese" [Reactions of Organic Synthesis], Georg Thieme Verlag, Stuttgart, 1978, page 461 ff. This is shown in reaction scheme 3 below.

Reaction scheme 3

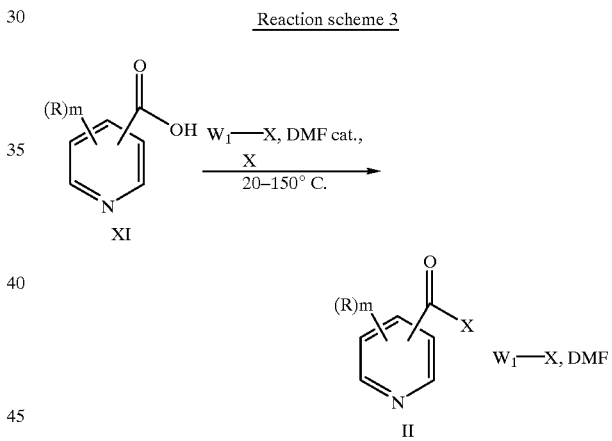

According to reaction scheme 3, the compounds of the formula II (X=leaving group) or II (X=halogen) are prepared, for example, by employing a halogenating agent, for example a thionyl halide, for example thionyl chloride or thionyl bromide; a phosphorus halide or phosphorus oxyhalide, for example phosphorus pentachloride or phosphorus oxychloride or phosphorus pentabromide or phosphoryl bromide; or an oxalyl halide, for example oxalyl chloride, or by employing a reagent for the formation of activated esters, for example N,N'-dicyclohexylcarbodiimide (DCC) or N-ethyl-N'-(3-dimethylaminopropyli)carbodiimide (EDC) of the formula X. For the compound of the formula X used as halogenating agents, X is a leaving group, for example halogen, for example fluorine, bromine or iodine and in particular chlorine, and $W_1$ is, for example, $PCl_2$, SOCl, SOBr or ClCOCO. The reaction is carried out in the presence or absence of an inert organic solvent, for example in aliphatic, halogenated aliphatic, aromatic or halogenated aromatic hydrocarbons, for example n-hexane, benzene, toluene, xylenes, dichloromethane, 1,2-dichloroethane or chlorobenzene, at reaction temperatures in the range of from −20° C. to the reflux temperature of the reaction mixture, preferably at 40–150° C., and in the presence of a catalytic amount of N,N-dimethylformamide. Such reactions are generally known and described in the literature in various variations with respect to the leaving group X.

The compounds of the formulae III, IV, V and VI are known and can be prepared analogously to the methods described, for example, in WO 92/07837, DE-A-3818958, EP-A-0 338 992 and DE-A-3902818.

The compounds of the formula XII in reaction scheme 2 can be obtained by standard processes, for example from the corresponding compounds of the formula II

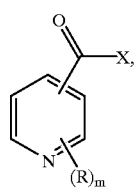

(II)

in which R and m are as defined above and X is a leaving group, for example halogen, for example via Claisen condensation, or from the compounds of the formula II by reaction with a ketocarboxylic acid salt of the formula XV

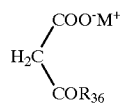

(XV)

in which $R_{36}$ is as defined under formula I and $M^+$ is an alkali metal ion (cf., for example, WO 96/26192).

The compounds of the formulae II and XI are known and can be prepared analogously to the methods described, for example, in WO 97146530, EP-A-0 353 187, Heterocycles, 48, 779 (1998), Heterocycles, 46, 129 (1997), or Tetrahedron Letters, 1749 (1998).

For preparing all other compounds of the formula I functionalized according to the definition of $(R)_m$, there is a large number of known standard processes available, for example alkylation, halogenation, acylation, amidation, oximation, oxidation and reduction, and the choice of the suitable preparation processes depends on the properties (reactivities) of the substituents in the intermediates in question.

All further compounds originating from the scope of the formula I can be prepared in a simple manner, taking into account the chemical properties of the pyridyl or Q moiety.

The end products of the formula I can be isolated in a customary manner by concentration or evaporation of the solvent and be purified by recrystallization or trituration of the solid residue in solvents in which they are only sparingly soluble, such as ethers, aromatic hydrocarbons or chlorinated hydrocarbons, by distillation or by means of column chromatography and a suitable mobile phase.

Furthermore, it is known to the person skilled in the art in which order certain reactions have to be carried out advantageously to avoid possible side reactions. Unless a targeted synthesis is carried out for isolating pure isomers, the product may be obtained as a mixture of two or more isomers. The isomers can be separated by methods known per se.

Compounds of the formula I in which p is 1, i.e. the corresponding N-oxides of the formula I, can be prepared by reacting a compound of the formula I in which p is 0 with a suitable oxidizing agent, for example with the $H_2O_2$ urea adduct, in the presence of an acid anhydride, for example trifluoroacetic anhydride. This reaction sequence is demonstrated using the example of group $Q_2$ below:

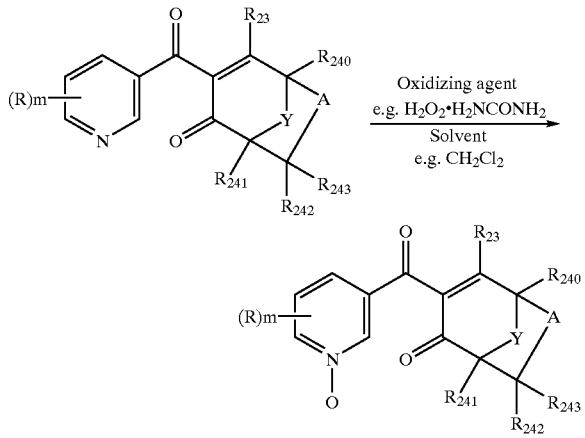

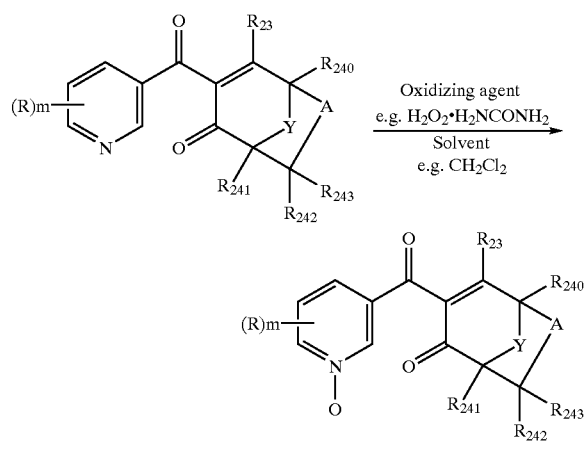

Compounds of the formula I in which R in the ortho position to the pyridine nitrogen is 1-chloro-$C_1$–$C_2$alkyl, 1-hydroxy-$C_1$–$C_2$alkyl, 1-($C_1$–$C_6$alkylcarbonyloxy)-$C_1$–$C_2$alkyl, 1-benzoyloxy-$C_1$–$C_2$alkyl, 1-($C_1$–$C_4$alkoxycarbonyloxy)-$C_1$–$C_2$alkyl, 1-($C_1$–$C_4$alkylthio)-$C_1$–$C_2$alkyl, 1-($C_1$–$C_4$-alkylsulfinyl)-$C_1$–$C_2$alkyl, 1-($C_7$–$C_4$alkylsulfonyl)-$C_1$–$C_2$alkyl, 1-thiocyanato-$C_1$–$C_2$alkyl, 1-cyano-$C_1$–$C_2$alkyl, can also be prepared, for example, by heating an N-oxide of the formula I under known reaction conditions, for example in the presence of tosyl chloride (see, for example, Parham, W. E.; Sloan, K. B.; Reddy, K. R.; Olson, P. E.; *J Org Chem* 1973, 38, 927) or in the presence of an acid anhydride (see, for example, Konno, K.; Hashimoto, K.; Shirahama, H.; Matsumoto, T.; *Heterocycles* 1986, 24, 2169), followed, if appropriate, by subsequent conversion.

The compounds of the formula XXIIa are synthesized analogously to known processes, for example those mentioned in Heterocycles, 46, 129 (1997) or Helvetica Chimica Acta 71, 596 (1988), and comprises either a) acylating a compound of the formula XVI

(XVI)

in which $R_{301}$ is hydrogen or $C_1$–$C_6$alkyl;

$R_{401}$ is hydrogen, $C_1$–$C_6$alkyl $C_2$–$C_6$alkenyl, $C_3$–$C_6$cycloalkyl, $C_1$–$C_6$alkoxy, $C_1$–$C_6$alkylthio, $C_1$–$C_6$alkylsulfinyl, $C_1$–$C_6$haloalkyl, 1-($C_1$–$C_6$alkylcarbonyloxy)-$C_1$–$C_6$alkyl, 1-($C_1$–$C_6$alkylthio)-$C_1$–$C_6$-alkyl, 1-($C_1$–$C_6$alkylsulfinyl)-$C_1$–$C_6$alkyl, 1-($C_1$–$C_6$alkylsulfonyl)-$C_1$–$C_6$alkyl, 1-thiocyanato-$C_1$–$C_6$-alkyl, 1-cyano-$C_1$–$C_6$alkyl, phenyl, where the phenyl groups may be mono- or polysubstituted by halogen, methyl, ethyl, trifluoromethyl, methoxy or nitro, or is a five- to ten-membered monocyclic or fused bicyclic ring system which may be aromatic or partially saturated and may contain 1 to 4 heteroatoms selected from the group consisting of nitrogen, oxygen and sulfur, where the ring system is either attached directly or via a $C_1$–$C_4$alkylene group to the double bond, and each ring system may not contain more than 2 oxygen atoms and not more than two sulfur atoms and the ring system for its part may be mono-, di- or trisubstituted by $C_1$–$C_6$alkyl, $C_1$–$C_6$haloalkyl, $C_3$–$C_6$alkenyl, $C_3$–$C_6$haloalkenyl, $C_3$–$C_6$alkynyl, $C_3$–$C_6$haloalkynyl, $C_1$–$C_6$alkoxy, $C_1$–$C_6$haloalkoxy, $C_3$–$C_6$alkenyloxy, $C_3$–$C_6$alkynyloxy, mercapto, $C_1$–$C_6$alkylthio, $C_1$–$C_6$haloalkylthio, $C_3$–$C_6$alkenylthio, $C_3$–$C_6$haloalkenylthio, $C_3$–$C_6$alkynylthio, $C_2$–$C_5$alkoxyalkylthio, $C_3$–$C_5$acetylalkylthio, $C_3$–$C_6$alkoxycarbonylalkylthio, $C_2$–$C_4$cyanoalkylthio, $C_1$–$C_6$alkylsulfinyl, $C_1$–$C_6$haloalkylsulfinyl, $C_1$–$C_6$alkylsulfonyl, $C_1$–$C_6$haloalkylsulfonyl, aminosulfonyl, $C_1$–$C_2$alkylaminosulfonyl, $C_2$–$C_4$dialkylaminosulfonyl, $C_1$–$C_3$alkylene-$R_{87}$, $NR_{88}R_{89}$, halogen, cyano, nitro, phenyl and benzylthio, where phenyl and benzylthio for their part may be substituted on the phenyl ring by $C_1$–$C_3$alkyl, $C_1$–$C_3$haloalkyl, $C_1$–$C_3$alkoxy, $C_1$–$C_3$-haloalkoxy, halogen, cyano or nitro and where substituents on nitrogen in the heterocyclic ring are different from halogen;

$R_{87}$ is $C_1$–$C_3$alkoxy, $C_2$–$C_4$alkoxycarbonyl, $C_1$–$C_3$alkylthio, $C_1$–$C_3$alkylsulfinyl, $C_1$–$C_3$alkylsulfonyl or phenyl, where phenyl for its part may be substituted by $C_1$–$C_3$alkyl, $C_1$–$C_3$haloalkyl, $C_1$–$C_3$-alkoxy, $C_1$–$C_3$haloalkoxy, halogen, cyano or nitro;

$R_{88}$ is hydrogen or $C_1$–$C_6$alkyl and $R_{89}$ is $C_1$–$C_6$alkyl or $C_1$–$C_6$alkoxy;

with a compound of the formula XVII

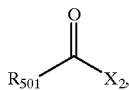

(XVII)

in which $R_{501}$ is $C_1$–$C_6$haloalkyl and $X_2$ is $O(CO)R_{501}$ or halogen to give the compound of the formula XVIII

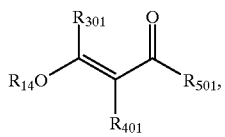

(XVIII)

in which $R_{301}$, $R_{401}$, $R_{501}$, and $R_{14}$ are as defined above, in the presence of a base, for example an aromatic amine, for example pyridine, and subsequently replacing the alkoxy group by the amino group using ammonia in an organic solvent, for example a halogenated hydrocarbon, for example dichloromethane, or a nitrile, for example acetonitrile. The resulting compound of the formula XIX

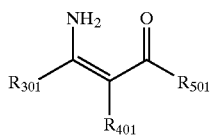

(XIX)

is subsequently condensed with a compound of the formula XX

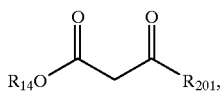

(XX)

in which $R_{201}$ is $C_1$–$C_6$alkyl, $C_2$–$C_6$alkenyl, $C_2$–$C_6$haloalkenyl, $C_2$–$C_6$alkynyl, $C_2$–$C_6$-haloalkynyl, $C_3$–$C_6$cycloalkyl, $C_1$–$C_6$haloalkyl, 1-($C_1$–$C_6$alkylcarbonyloxy)-$C_1$–$C_6$alkyl, 1-($C_1$–$C_6$alkylthio)-$C_1$–$C_6$alkyl, 1-($C_1$–$C_6$alkylsulfinyl)-$C_1$–$C_6$alkyl, 1-($C_1$–$C_6$alkylsulfonyl)$C_1$–$C_6$alkyl, 1-thiocyanato-$C_1$–$C_6$alkyl, 1-cyano-$C_1$–$C_6$alkyl, $C_1$–$C_6$alkoxy-$C_1$–$C_6$alkyl, $C_1$–$C_6$alkoxycarbonyl-$C_1$–$C_6$alkoxy, $C_1$–$C_6$alkylthio-$C_1$–$C_6$alkoxy, phenyl, benzyl, phenoxy, phenylthio, phenylsulfinyl, phenylsulfonyl, benzyithio, benzylsulfinyl or benzylsulfonyl, where the phenyl groups may be mono- or polysubstituted at least by halogen, methyl, ethyl, trifluoromethyl, methoxy or nitro, or is a five- to ten-membered monocyclic or fused bicyclic ring system which may be aromatic or partially saturated and may contain 1 to 4 heteroatoms selected from the group consisting of nitrogen, oxygen and sulfur, where the ring system is attached either directly or via a $C_1$–$C_4$-alkylene group and each ring system may not contain more than 2 oxygen atoms and not more than two sulfur atoms, and the ring system for its part may be mono-, di- or trisubstituted by $C_1$–$C_6$alkyl, $C_1$–$C_6$haloalkyl, $C_3$–$C_6$alkenyl, $C_3$–$C_6$haloalkenyl, $C_3$–$C_6$alkynyl, $C_3$–$C_6$haloalkynyl, $C_1$–$C_6$a lkoxy, $C_1$–$C_6$haloalkoxy, $C_3$–$C_6$alkenyloxy, $C_3$–$C_6$alkynyloxy, mercapto, $C_1$–$C_6$alkylthio, $C_1$–$C_6$haloalkylthio, $C_3$–$C_6$alkenylthio, $C_3$–$C_6$haloalkenylthio, $C_3$–$C_6$alkynylthio, $C_2$–$C_5$alkoxyalkylthio, $C_3$–$C_5$acetylalkylthio, $C_3$–$C_6$alkoxycarbonylalkylthio, $C_2$–$C_4$cyanoalkylthio, $C_1$–$C_6$alkylsulfinyl, $C_1$–$C_6$haloalky lsulfinyl, $C_1$–$C_6$alkylsulfonyl, $C_1$–$C_6$haloalkylsulfonyl, aminosulfonyl, $C_1$–$C_2$alkylaminosulfonyl, $C_2$–$C_4$dialkylaminosulfonyl, $C_1$–$C_3$-$R_{90}$, $NR_{91}R_{92}$, halogen, cyano, nitro, phenyl and benzylthio, where phenyl and benzylthio for their part may be substituted on the phenyl ring by $C_1$–$C_3$alkyl, $C_1$–$C_3$haloalkyl, $C_1$–$C_3$alkoxy, $C_1$–$C_3$-haloalkoxy, halogen, cyano or nitro, and where substituents on nitrogen in the heterocyclic ring are different from halogen;

$R_{90}$ is $C_1$–$C_3$alkoxy, $C_2$–$C_4$alkoxycarbonyl, $C_1$–$C_3$alkylthio, $C_1$–$C_3$alkylsuffinyl, $C_1$–$C_3$alkylsulfonyl or phenyl, where phenyl for its part may be substituted by $C_1$–$C_3$-alkyl, $C_1$–$C_3$haloalkyl, $C_1$–$C_3$-alkoxy, $C_1$–$C_3$haloalkoxy, halogen, cyano or nitro;

$R_{91}$ is hydrogen or $C_1$–$C_6$alkyl and $R_{92}$ is $C_1$–$C_6$alkyl or $C_1$–$C_6$alkoxy and $R_{14}$ is as defined above, and the resulting compound of the formula XXIa

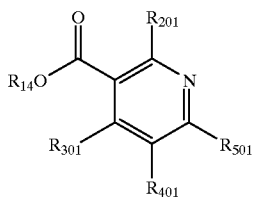
(XXIa)

is subsequently hydrolysed to give the compound of the formula XXIIa

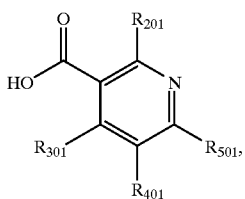
(XXIIa)

in which $R_{201}$, $R_{301}$, $R_{401}$, and $R_{501}$ are as defined above, or b) condensing a compound of the formula XXIII

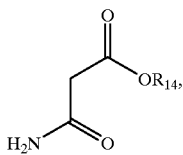
(XXIII)

in which $R_{14}$ is as defined above with a compound of the formula XXIV

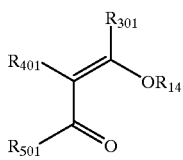
(XXIV)

and chlorinating the resulting compound of the formula XXV

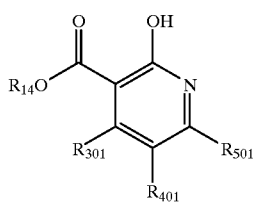
(XXV)

in which $R_{301}$, $R_{401}$ and $R_{501}$ are as defined above and $R_{14}$ is $C_1$–$C_4$alkyl to give compounds of the formula XXVI

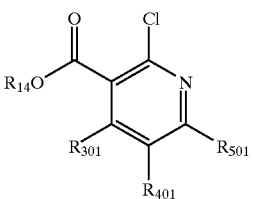
(XXVI)

in which $R_{301}$, $R_{401}$, $R_{501}$ and $R_{14}$ are as defined above (using, for example, $POCl_3$), and subsequently reacting this compound with a nucleophile of the formula XXVII

Z—$R_{150}$ (XXVII)

In which Z is SH, OH or amino and $R_{150}$ is $C_1$–$C_6$alkyl, $C_3$–$C_6$alkeny4 $C_3$–$C_6$halogenalkenyl, $C_3C_6$alkynyl, $C_3$–$C_6$haloalkynyl, $C_1$–$C_6$alkylsulfonyl, $C_1$–$C_6$haloalkyl, phenyl, benzyl, where the phenyl and benzyl groups for their part may be substituted by $C_1$–$C_3$alkyl, $C_1$–$C_3$haloalkyl, $C_1$–$C_3$alkoxy, $C_1$–$C_3$haloalkoxy, halogen, cyano or nitro, is $C_1$–$C_1$alkoxy-$C_1$–$C_4$alkyl or $C_1$–$C_4$-alkylthio-$C_1$–$C_4$alkyl, $C_1$–$C_4$alkylsulfinyl-$C_1$–$C_4$alkyl, $C_1$–$C_4$alkylsulfonyl-$C_1$–$C_4$alkyl, or a five- to ten-membered monocyclic or fused bicyclic ring system which may be aromatic or partially saturated and may contain 1 to 4 heteroatoms selected from the group consisting of nitrogen, oxygen and sulfur, and each ring system may not contain more than 2 oxygen atoms and not more than two sulfur atoms, and the ring system for its part may be mono-, di- or trisubstituted by $C_1$–$C_6$alkyl, $C_1$–$C_6$haloalkyl, $C_3$–$C_6$alkenyl, $C_3$–$C_6$haloalkenyl, $C_3$–$C_6$-alkynyl, $C_3$–$C_6$haloalkynyl, $C_1$–$C_6$alkoxy, $C_1$–$C_6$haloalkoxy, $C_3$–$C_6$alkenyloxy, $C_3$–$C_6$alkynyloxy, mercapto, $C_1$–$C_6$alkylthio, $C_1$–$C_6$haloalkylthio, $C_3$–$C_6$alkenylthio, $C_3$–$C_6$haloalkenylthio, $C_3$–$C_6$-alkynylthio, $C_2$–$C_5$alkoxyalkylthio, $C_3$–$C_5$acetylalkylthio, $C_3$–$C_6$alkoxycarbonylalkylthio, $C_2$–$C_4$-cyanoalkylthio, $C_1$–$C_6$alkylsulfinyl, $C_1$–$C_6$haloalkylsulfinyl, $C_1$–$C_6$alkylsulfonyl, $C_1$–$C_6$-haloalkylsulfonyl, aminosulfonyl, $C_1$–$C_2$alkylaminosulfonyl, $C_2$–$C_4$dialkylaminosulfonyl, $C_1$–$C_3$-alkylene-$R_{93}$, $NR_{94}R_{95}$, halogen, cyano, nitro, phenyl and benzylthio, where phenyl and benzylthio for their part may be substituted on the phenyl ring by $C_1$–$C_3$alkyl, $C_1$–$C_3$-haloalkyl, $C_1$–$C_3$alkoxy, $C_1$–$C_3$haloalkoxy, halogen, cyano or nitro, and where substituents on nitrogen in the heterocyclic ring are different from halogen;

$R_{93}$ is $C_1$–$C_3$alkoxy, $C_2$–$C_4$alkoxycarbonyl, $C_1$–$C_3$alkylthio, $C_1$–$C_3$alkylsulfinyl, $C_1$–$C_3$alkylsulfonyl or phenyl, where phenyl for its part may be substituted by $C_1$–$C_3$alkyl, $C_1$–$C_3$haloalkyl, $C_1$–$C_3$alkoxy, $C_1$–$C_3$haloalkoxy, halogen, cyano or nitro;

$R_{94}$ is hydrogen or $C_1$–$C_6$alkyl and $R_{95}$ is $C_1$–$C_6$alkyl or $C_1$–$C_6$alkoxy;

in the presence of a base to give compounds of the formula XXIb

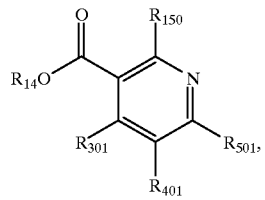

(XXIb)

in which $R_{14}$, $R_{150}$, $R_{301}$, $R_{401}$, and $R_{501}$ are as defined above, and subsequently hydrolysing the resulting compound to give the compound of the formula XXIIb

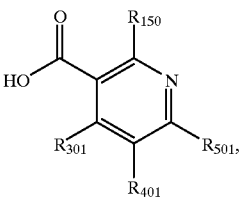

(XXIb)

in which $R_{150}$, $R_{301}$, $R_{401}$ and $R_{501}$ are as defined.

Compounds of the formula XXIb in which $R_{150}$ is fluorine are prepared by reacting a compound of the formula XXVI in the presence of a polar aprotic solvent, for example acetonitrile, dimethylformamide or sulfolane, with potassium fluoride in the presence or absence of a catalytic amount of 18-crown-6. Compounds of the formula XXIc in which $R_{150}$ is hydrogen are preparerd by reducing the chlorine group in the formula XXVI, for example using hydrogen in the presence of a suitable metal catalyst or using ammonium formate in a suitable solvent. The preparation of the compounds of the formula XXIIa, or XXIIb and XXIIc is illustrated in more detail in the reaction schemes 4 and 5 below.

Reaction scheme 4

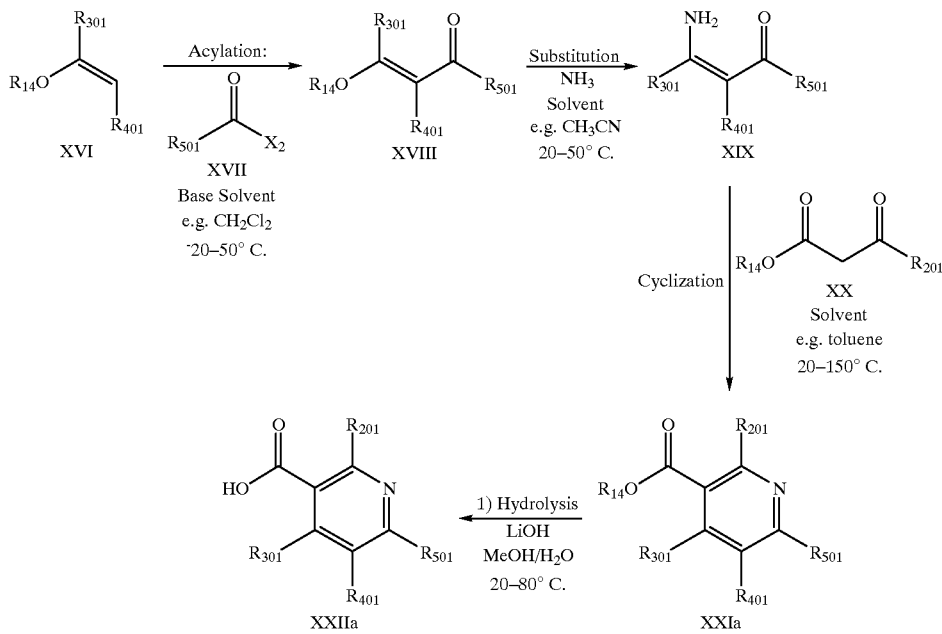

Reaction scheme 5

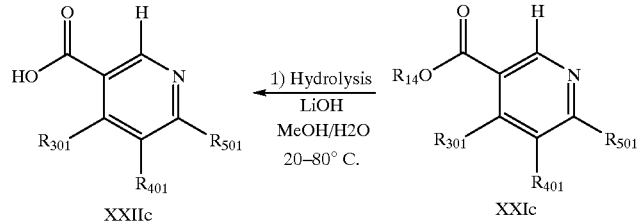

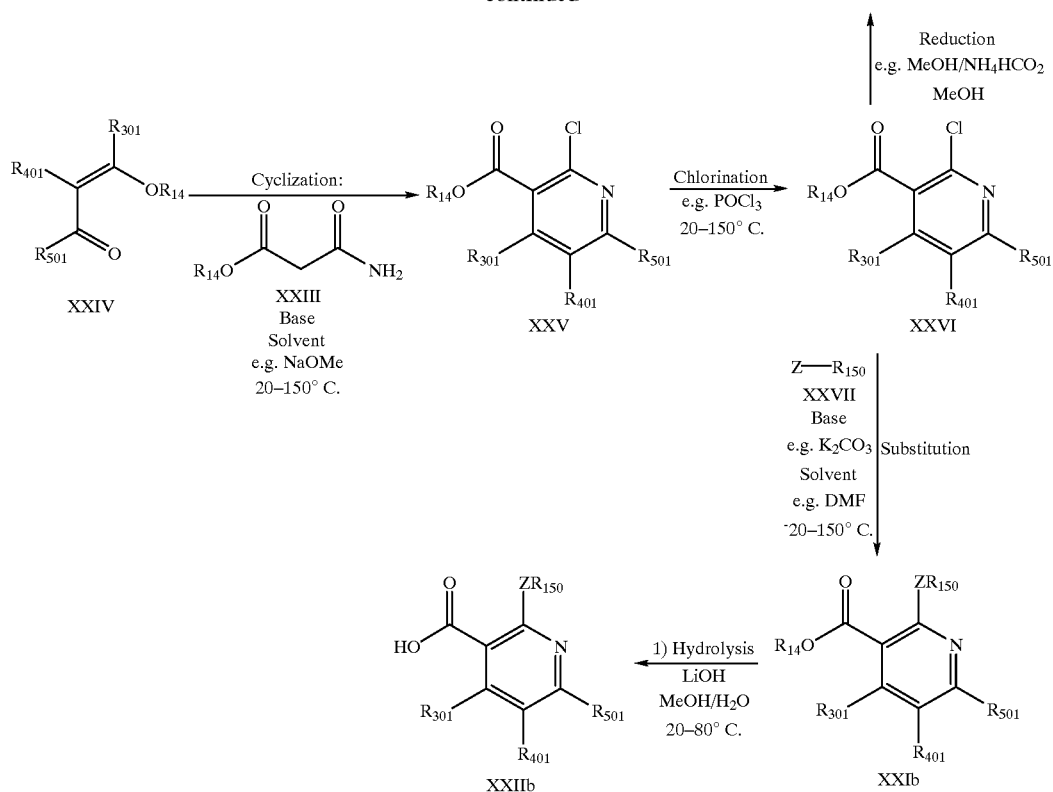

For preparing all other compounds of the formula I which are functionalized according to the definition of $R_{201}$ ($R_{150}$) to $R_{501}$, a large number of known standard processes is suitable, for example alkylation, halogenation, acylation, amidation, oximation, oxidation and reduction, the choice of the suitable preparation processes depending on the properties (reactivities) of the substituents in the intermediates in question.

The novel compounds of the formula IIb in which $R_f$ is trifluoromethyl, difluorochloromethyl, pentafluoroethyl, heptafluoro-n-propyl or trichloromethyl, $R_{X1}$ is $C_1$–$C_6$alkyl and Q and R are as defined under formula I can be prepared by generally known processes via 3-alkoxycarbonyl-4-perhaloalkylpyridine N-oxides of the formula XXVIII according to reaction scheme 5 by preparing, using suitable chlorination conditions and separation processes, the 6-chloro-4-haloalkyl-3-nicotinic esters of the formula XXX and then converting these compounds with a nucleophile of the formula XXXI $$Z_{o1}\text{—}R_{151tm} \quad (XXXI)$$

in which $Z_{o7}$ is SH, hydroxyl, halogen or amino and $R_{151}$ is hydrogen, $C_1$–$C_6$alkyl, $C_3$–$C_6$-alkenyl, $C_3$–$C_6$haloalkenyl, $C_3$–$C_6$alkynyl, halogen, $C_3$–$C_6$haloalkynyl, $C_1$–$C_6$alkylsulfonyl, $C_1$–$C_6$-haloalkyl, phenyl, benzyl, where the phenyl and benzyl groups for their part may be substituted by $C_1$–$C_3$alkyl, $C_1$–$C_3$haloalkyl, $C_1$–$C_3$alkoxy, $C_1$–$C_3$haloalkoxy, halogen, cyano or nitro, is $C_1$–$C_4$alkoxy-$C_1$–$C_4$alkyl or $C_1$–$C_4$alkylthio-$C_1$–$C_4$alkyl, $C_1$–$C_4$alkylsulfinyl-$C_1$–$C_4$alkyl, $C_1$–$C_4$alkylsulfonyl-$C_1$–$C_4$alkyl, or a five- to ten-membered monocyclic or fused bicyclic ring system which may be aromatic or partially saturated and may contain 1 to 4 heteroatoms selected from the group consisting of nitrogen, oxygen and sulfur, and each ring system may not contain more than 2 oxygen atoms and not more than two sulfur atoms, and the ring system for its part may be mono-, di- or trisubstituted by $C_1$–$C_6$alkyl, $C_1$–$C_6$haloalkyl, $C_3$–$C_6$alkenyl, $C_3$–$C_6$haloalkenyl, $C_3$–$C_6$alkynyl, $C_3$–$C_6$-haloalkynyl, $C_1$–$C_6$alkoxy, $C_1$–$C_6$haloalkoxy, $C_3$–$C_6$alkenyloxy, $C_3$–$C_6$alkynyloxy, mercapto, $C_1$–$C_6$alkylthio, $C_1$–$C_6$haloalkylthio, $C_3$–$C_6$alkenylthio, $C_3$–$C_6$haloalkenylthio, $C_3$–$C_6$alkynylthio, $C_2$–$C_5$alkoxyalkylthio, $C_3$–$C_5$acetylalkylthio, $C_3$–$C_6$alkoxycarbonylalkylthio, $C_2$–$C_4$cyanoalkylthio, $C_1$–$C_6$-alkylsulfinyl, $C_1$–$C_6$haloalkylsulfinyl, $C_1$–$C_6$alkylsulfonyl, $C_1$–$C_6$haloalkylsulfonyl, aminosulfonyl, $C_1$–$C_2$alkylaminosulfonyl, $C_2$–$C_4$dialkylaminosulfonyl, $C_1$–$C_3$alkylene-$R_{96}$, $NR_{97}R_{98}$, halogen, cyano, nitro, phenyl or benzylthio, where phenyl and benzylthio for their part may be substituted on the phenyl ring by $C_1$–$C_3$alkyl, $C_1$–$C_3$haloalkyl, $C_1$–$C_3$alkoxy, $C_1$–$C_3$-haloalkoxy, halogen, cyano or nitro, $R_{96}$ is $C_1$–$C_3$alkoxy, $C_2$–$C_4$alkoxycarbonyl, $C_1$–$C_3$alkylthio, $C_1$–$C_3$alkylsulfinyl, $C_1$–$C_3$alkylsulfonyl or phenyl, where phenyl for its part may be substituted by $C_1$–$C_3$alkyl, $C_1$–$C_3$haloalkyl, $C_1$–$C_3$-alkoxy, $C_1$–$C_3$haloalkoxy, halogen, cyano or nitro;

$R_{97}$ is hydrogen or $C_1$–$C_6$alkyl and $R_{98}$ is $C_1$–$C_6$alkyl or $C_1$–$C_6$alkoxy;

and where substituents on nitrogen in the heterocyclic ring are different from halogen, using reaction processses which are generally known to the person skilled in the art, into the 6-substituted 4-perhaloalkylnicotinic acids of the formula XXXII and their subsequent products of the formulae IIb and Ib as described in reaction scheme 1. This is shown in reaction scheme 6 below.

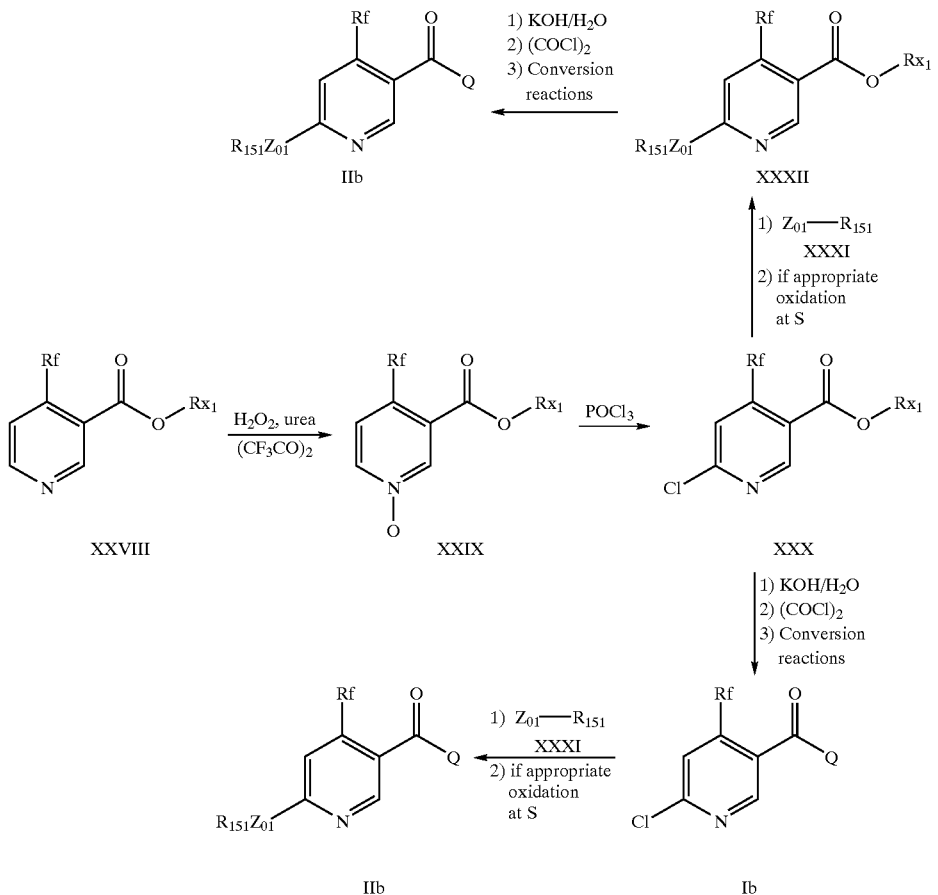

According to this reaction scheme, it is preferably possible to prepare the compounds of the formula I with the group $Q_1$ in which $R_{20}$ is hydroxyl, the compounds of the formula I with the group 02 in which $R_{23}$ is hydroxyl, the compounds of the formula I with the group $Q_3$ in which $R_{26}$ is hydroxyl and the compounds of the formula I with the group $Q_4$ in which $R_{30}$ is hydroxyl.

6-substituted 2-haloalkylnicotinic acid compounds of the formula Ic can be prepared, for example, from the corresponding 2-haloalkyl-3-alkoxycarbonyl-2-pyridines XXXIII in which $R_f$ is trifluoromethyl, difluorochloromethyl, pentafluoroethyl, heptafluoro-n-propyl or trichloromethyl and $R_{1x}$ is $C_1$–$C_6$alkyl and R is as defined under formula I, by hydrolysis into the corresponding carboxylic acids and their subsequent activation, for example by conversion into an acylhalide (IIc). (Reaction scheme 7).

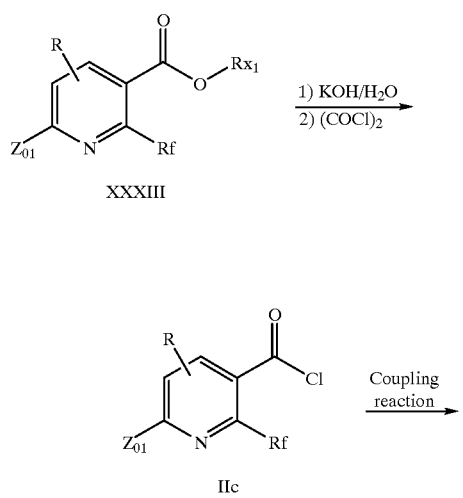

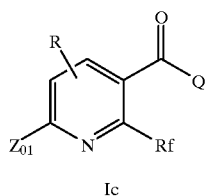

Their precursors of the formulae XXXIIIa, XXXIIIb, XXXIIIc, XXXIIId, XXXIIIe, XXXIIIf, XXXIIIg and XXXIIIh are likewise accessible by conversion processes known to the person skilled in the art (reaction shceme 7). 2-Trifluoromethyl-3-ethoxycarbonyl-2-pyridone (formula XXXIIIa in which R is hydrogen, $R_{1X}$ is ethyl and Rf is trifluoromethyl) in particular is known form Org. Process Research & Developmnet, 1, 370 (1997).

for example using an alkali metal iodide in an inert solvent into the corresponding iodides, or using gaseous hydrobromic acid in lower carboxylic acids, for example conc. acetic acid, into the corresponding bromo derivatives (for example according to U.S. Pat. No. 3,974,166) or using alkali metal fluoride in a dipolar solvent, such as sulfolane, into the corresponding fluoro derivatives.

The compound of the formula XXXIIIe can be prepared by reacting a halo derivative of the formula XXXIIId obtained as described above with an alcohol of the formula $R_{151}$—OH in the presence of a base, such as sodium hydride, or an alkali metal oxide or carbonate, or directly with an alkali metal alkoxide, in an inert solvent such as dimethylformamide or in an excess of the alcohol of the formula $R_{151}$—OH which corresponds to the group to be introduced, at temperatures between –5 and 160° C., or by reacting, to prepare a corresponding 6-thioether of the formula XXXIIIc, analogously to what was described above, either the halide of the formula XXXIIId with a thiol of the

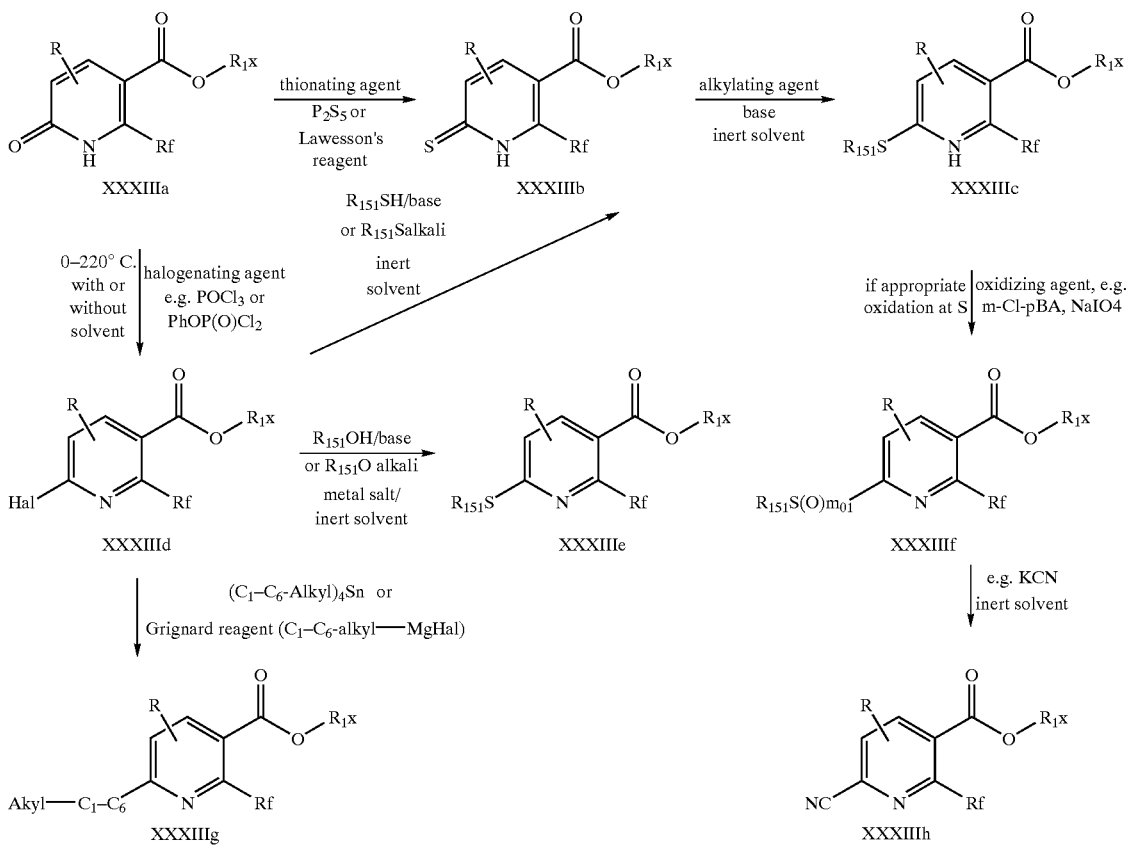

Intermediates of the formulae XXXIIIa to XXXIIIh can be obtained by reacting, for example for preparing a 6-halo derivative of the formula XXXIIId, a pyridone of the formula XXXIIIa (preparation according to Org. Process Research & Development, 1, 370 (1997) or scheme 8) with a halogenating agent, for example phosphorus oxychloride, phosphorus oxybromide or phenyl dichlorophosphate, in the presence or absence of added base, such as a dialkylaniline, in the presence or absence of solvent, if desired in a pressure vessel, at temperatures between 0 and 220° C. (preferably 60-200° C.). It is known to the person skilled in the art how to convert chloro derivatives by nucleophilic substitution, formula $R_{151}$—SH in the presence of a base such as sodium hydride or with an alkali metal salt of a thiol in an inert solvent at –10-150° C., or by preparing, starting from a pyridone XXXIIIa and using a thionating agent, for example Lawesson's reagent, in an inert solvent, such as toluene or acetonitrile, a pyrithione of the formula XXXIIIb and alkylating this with an alkylating agent $R_{151}$-X, where X is a leaving group, such as halide (Cl, Br, I) or $ROSO_3$— or $RSO_2$—, at 20-120° C. in an inert solvent, such as tetrahydrofuran, to give the thioether of the formula XXXIIIc, or, to prepare the corresponding sulfinyl or sulfonyl derivative of the formula XXXIIIf, reacting with an oxidizing agent, such as m-chloroperbenzoic acid or sodium periodate, or sodium perborate, under temperature control known to the person skilled in the art, depending on the degree of oxidation (for example −30° C.-+50° C. for $m_{o1}=1$ or −20° C.-+100° C. for $m_{o1}=2$) in an inert solvent, such as dichloromethane, to give XXXIIIf, or, to prepare 6-alkyl derivatives XXXIIIg according to the invention, reacting a sulfone of the formula XXXIIIf ($m_{o1}=2$) or a halo derivative of the formula XXXIIId in the presence or absence of a Pd(O) catalyst such as Pd(PPh$_3$)$_2$Cl$_2$ with a tetra-$C_1$–$C_6$alkyltin or with a Grignard reagent $C_1$–$C_6$alkyl-MgHal at temperatures between −10° and 180° C., for example analogously to Synlett 1998 (1185), or as described in Organocopper Reagents, R. J. K. Taylor, Oxford University Press 1994, or in Transition Metals in Organic Synthesis, S. Gibson, Oxford Univ. Press,1997, or in Org. React. 50, 1 (Stille reaction), or, to prepare 6-cyano derivatives of the formula XXXIIIh, reacting a halide of the formula XXXIIId or a sulfone of the formula XXXIIIf ($m_{o1}=2$) with an alkali metal or tetraalkylammonium cyanide or copper cyanide in an inert solvent, such as dichloromethane, tetrahydrofuran or dimethylformamide, at temperatures between 0° C. and 220° C.

Some of the compounds of the formula XXXIIIe are also obtainable from the pyridone of the formula XXXIIIa by reacting them analogously to Org. React. 42, 2 with an alcohol $R_{151}$OH in the presence of an azodicarboxylic ester (for example diethyl ester) and triphenylphosphine in an inert solvent, such as tetrahydrofuran or dioxane. (Scheme 9)

Reaction scheme 9

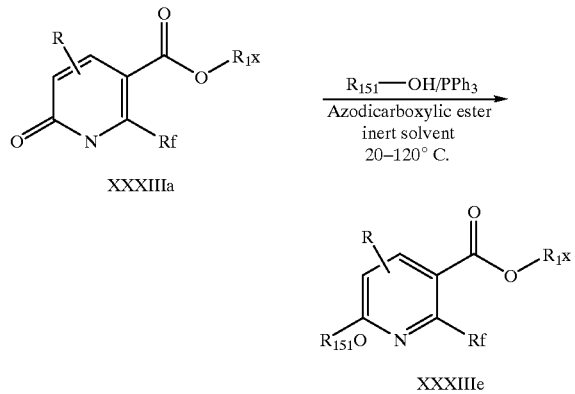

The intermediates of the formula XXXIIIa required in reaction scheme 8 as starting materials are obtainable according to Scheme 10 route A or route B (Org. Process Research & Development, 1, 370 (1997)) or route C.

Reaction scheme 10

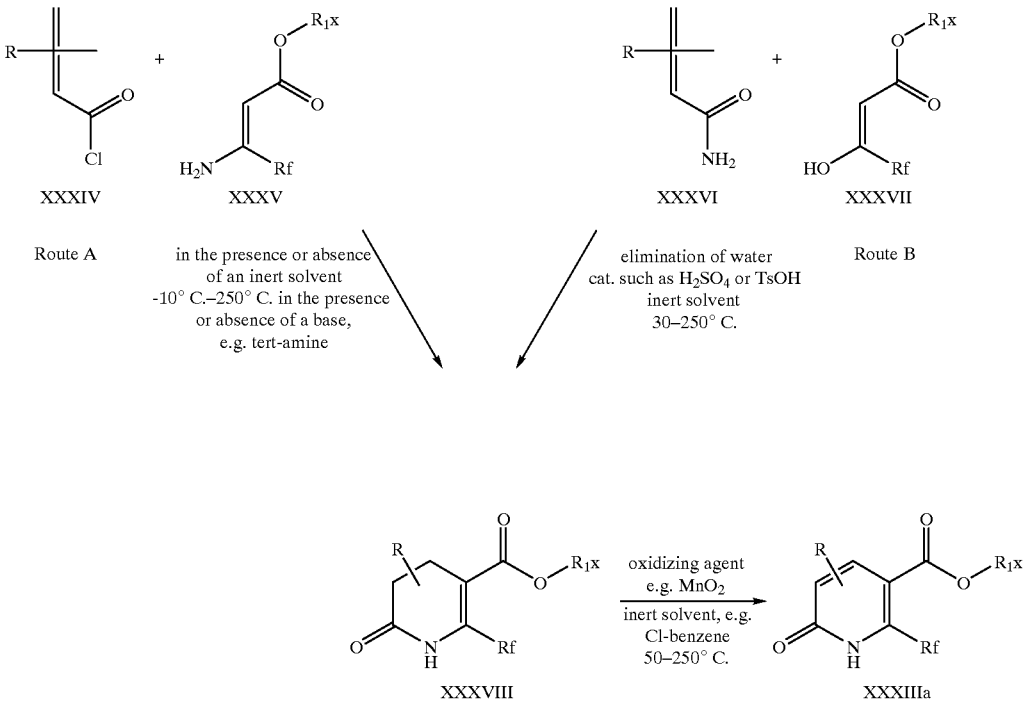

Route C

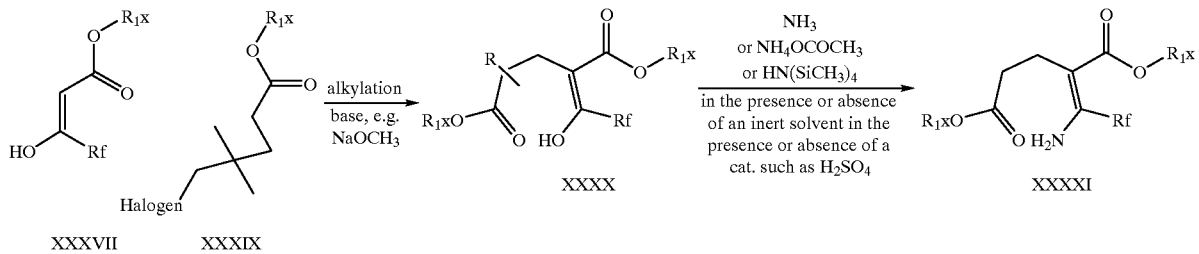

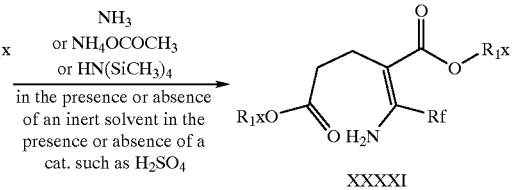

Intermediates of the formula XXXIIIa are obtainable by route A by reacting, to prepare the 3,4-dihydro-5-alkoxycarbonyl-6-haloalkylpyridin-2-ones of the formula XXXVIII, an enamine of the formula XXXV in the presence or, preferably, in the absence of a solvent either in an excess of enamine or in the presence of a base, such as a tert-amine, with an acryloyl chloride of the formula XXXIV at temperatures between −10° and +200° C., or by reacting a keto ester of the formula XXXVII with an acrylamide of the formula XXXVI in the presence of a catalyst such as p-toluenesulfonic acid (=HOTs) in an inert solvent, such as toluene, at temperatures between 30 and 200° C., with removal of the water of reaction formed (for example azeotropic distillation), or by reacting a keto ester of the formula XXXVII in the presence of a base, such as an alkali metal alkoxide or magnesium alkoxide, with a 4-haloketo ester of the formula XXXIX in an inert solvent, such as ethanol, at 0-180° C. to give the intermediate of the formula XXXX, converting this with ammonia or an ammonium salt, such as ammonium acetate, or with a bis-silylamine such as hexamethyldisilazane, in the presence or absence of an acidic catalyst, such as sulfuric acid or p-toluenesulfonic acid or an organic carboxylic acid (for example conc. acetic acid), in an inert solvent and at temperatures between 0° and 180° C. into the corresponding enamine of the formula XXXXI, subsequently cyclizing in the presence of a catalyst, such as p-toluenesulfonic acid or sulfuric acid, if desired with continuous removal of the water of reaction formed in an inert solvent, such as toluene, to give the dihydropyridone of the formula XXXVIII, and finally treating with an oxidizing agent, such as manganese dioxide, in an inert solvent, such as chlorobenzene, at temperatures between 50 and 250° C., to prepare the pyridones XXXIIIa.

The intermediates of the formula IIa

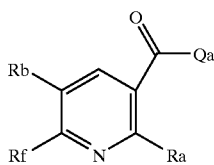
(IIa)

in which $Q_a$ is hydroxyl, halogen, cyano, or a group —$CH_2$(CO)$R_{36}$ or

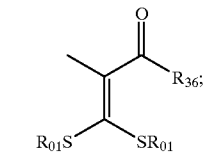

$R_b$ is hydrogen, $C_1$–$C_4$alkyl or halogen;
$R_1$ is trifluoromethyl, difluorochloromethyl, pentafluoroethyl, heptafluoro-n-propyl or trichloromethyl;
$R_a$ is $C_1$–$C_3$alkyl, $C_1$–$C_3$haloalkyl, $C_3$–$C_4$cycloalkyl, $C_1$–$C_2$alkoxy-$C_1$–$C_4$alkyl, $C_1$–$C_2$-alkylthiomethyl, hydroxyl, halogen, cyano, $C_1$–$C_3$alkoxy, $C_1$–$C_3$haloalkoxy, allyloxy, propargyioxy, $C_1$–$C_3$alkylthio, $C_1$–$C_3$alkylsulfinyl, $C_1$–$C_3$alkylsulfonyl or $C_1$–$C_3$alkylsulfonyloxy, and $R_{01}$ and $R_{36}$ are as defined under group $O_5$ of the formula 1, except for the compounds 2,6-bistrifluoromethyinicotinic acid, 2,6-bistrifluoromethyl-5-methoxynicotinic acid and 2-hydroxy-6-trifluoromethyinicotinic acid, are novel and therefore likewise form part of the subject matter of the present invention.

Compounds of the formula IIb

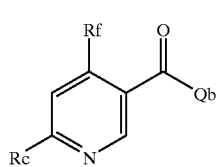
(IIb)

in which $Q_b$ is hydroxyl, halogen, cyano or a group —$CH_2$(CO)$R_{99}$ or

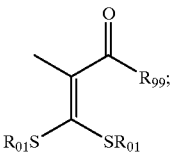

$R_{99}$ is $C_1$–$C_4$alkyl, $C_1$–$C_4$haloalkyl, $C_3$–$C_4$cycloalkyl or $C_1$–$C_4$alkoxy;

$R_f$ is trifluoromethyl, difluorochloromethyl, pentafluoroethyl or heptafluoro-n-propyl; and $R_c$ is $C_1$–$C_3$alkyl, $C_1$–$C_3$haloalkyl, $C_1$–$C_2$alkoxymethyl, $C_1$–$C_1$alkylthiomethyl, hydroxyl, halogen, cyano, $C_1$–$C_3$alkoxy, $C_1$–$C_3$haloalkoxy, allyloxy, propargyloxy, $C_1$–$C_3$alkylthio, $C_1$–$C_3$-alkylsulfinyl, $C_1$–$C_3$alkylsulfonyl or $C_1$–$C_3$alkylsulfonyloxy and $R_{01}$ is as defined under formula I are novel and therefore likewise form part of the subject matter of the present invention.

Preferred compounds of the formula IIa correspond to the formula Ia

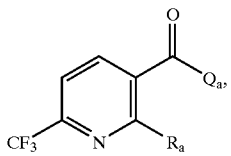

(Ia)

in which $Q_a$ is hydroxyl, halogen, cyano or a group —$CH_2(CO)R_{36}$ or

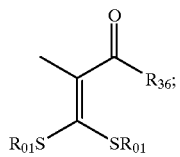

$R_{01}$ and $R_{36}$ are as defined in claim 1 and $R_a$ is $C_1$–$C_3$alkyl.

The compounds of the formula I or compositions comprising them can be used according to the invention in all the application methods customary in agriculture, for example pre-emergence application, postemergence application and seed dressing, and various methods and techniques, for example controlled release of active compounds. To this end, the active compound is absorbed in solution onto mineral granule carriers or polymerized granules (urea/formaldehyde) and dried. If appropriate, a coating which allows the active compound to be released in metered form over a certain period of time can additionally be applied (coated granules).

The compounds of the formula I can be employed as herbicides in unchanged form, i.e. as they are obtained in the synthesis, but they are preferably processed in a customary manner with the auxiliaries conventionally used in the art of formulation, for example to give emulsifiable concentrates, directly sprayable or dilutable solutions, dilute emulsions, wettable powders, soluble powders, dusts, granules or microcapsules. Such formulations are described, for example, in WO 97/34485 on pages 9 to 13. The methods of application, such as spraying, atomizing, dusting, wetting, scattering or watering, in the same way as the nature of the compositions, are chosen according to the aims striven for and the given circumstances.

The formulations, i.e. the compositions, formulations or preparations comprising the active compound of the formula I or at least one active compound of the formula I and as a rule one or more solid or liquid formulation auxiliaries, are prepared in a known manner, for example by intimate mixing and/or grinding of the active compounds with the formulation auxiliaries, for example solvents or solid carriers. Surface-active compounds (surfactants) can furthermore additionally be used during the preparation of the formulations. Examples of solvents and solid carriers are given, for example, in WO 97/34485 on page 6. Depending on the nature of the active compound of the formula I to be formulated, suitable surface-active compounds are nonionic, cationic and/or anionic surfactants and surfactant mixtures having good emulsifying, dispersing and wetting properties.

Examples of suitable anionic, nonionic and cationic surfactants are listed, for example, in WO 97/34485 on pages 7 and 8.

The surfactants conventionally used in the art of formulation and which are suitable to prepare the herbicidal compositions according to the invention are described, inter alia, in "Mc Cutcheon's Detergents and Emulsifiers Annual", MC Publishing Corp., Ridgewood N.J., 1981, Stache, H., "Tensid-Taschenbuch" [Surfactant handbook], Carl Hanser Verag, Munich/Vienna, 1981 and M. and J. Ash, "Encyclopedia of Surfactants", Vol I-III, Chemical Publishing Co., New York, 1980-81.

The herbicidal formulations as a rule comprise 0.1 to 99% by weight, in particular 0.1 to 95% by weight, of herbicide, 1 to 99.9% by weight, in particular 5 to 99.8% by weight, of a solid or liquid formulation auxiliary and 0 to 25% by weight, in particular 0.1 to 25% by weight, of a surfactant. While concentrated compositions are rather preferred as commercial goods, the end user as a rule uses dilute compositions. The compositions can also comprise further additives, such as stabilizers, for example epoxidized or non-epoxidized vegetable oils (epoxidized coconut oil, rapeseed oil or soya oil), defoamers, for example silicone oil, preservatives, viscosity regulators, binders, tackifiers and fertilizers or other active compounds.

The active compounds of the formula I are as a rule applied to the plants or their habitat, at application rates of 0.001 to 4 kg/ha, in particular 0.005 to 2 kg tha. The dosage required for the desired effect can be determined by tests. It depends on the nature of the effect, the development stage of the crop plant and the weed and on the application (location, time, process) and can, as a function of these parameters, vary within wide ranges.

The compounds of the formula I have herbicidal and growth-inhibiting properties, owing to which they can be used in crops of useful plants, in particular in cereals, cotton, soya, sugar beet, sugar cane, plantings, rapeseed, maize and rice, and for the non-selective control of weeds. Crops include those which have been rendered tolerant towards herbicides or herbicide classes by conventional breeding methods or genetical engineering methods. The weeds to be controlled can be both monocotyledonous and dicotyledonous weeds, for example Stellaria, Nasturtium, Agrostis, Digitaria, Avena, Setaria,Sinapis, Lolium, Solanum, Echinochloa, Scirpus, Monochoria, Sagittaria, Bromus, Alopecurus, *Sorghum halepense,* Rottboellia, Cyperus, Abutilon, Sida, Xanthium, Amaranthus, Chenopodium, Ipomoea, Chrysanthemum, Galium, Viola and Veronica.

The examples below illustrate the invention in more detail, without limiting it.

PREPARATION EXAMPLES

Example H1

PreParation of 2-difluoromethoxy-6-trifluoromethylnicotinic acid

At 70° C., 25 g (0.106 mol ) of (3-(ethoxycarbonyl)-6-trifluoromethyl)pyrid-2-one (Helv. Chim. Acta (1988), 71(3), 596 601) in a mixture of 50 ml of dimethylformamide and 20 ml of water are treated, in the presence of 16 g (0.116 mol) of finely powdered potassium carbonate and with efficient stirring, with a continuous stream of gaseous Freon-22. After 6 hours, a further 16 g of potassium carbonate and 20 ml of dimethyl sulfoxide are added, and the mixture is stirred with continuous introduction of Freon-22 gas at a temperature of 100° C for another 4 hours. The mixture is then treated with water and ice and extracted with diethyl ether. The aqueous phase is adjusted to pH 2 using conc. HCl and extracted with ethyl acetate. Diethyl ether is added to the extract, and some (3-(carboxy)-6-trifluoromethyl)pyrid-2-one crystals which have precipitated out are removed by filtration. The filtrate is filtered through a silica gel column (mobile phase ethyl acetate/hexane 1:1) giving, as a crystalline product, pure 2-difluoromethoxy-6-trifluoromethylnicotinic acid: $^1$H NMR (CDCl$_3$, ppm): 8.60, d, J=9 Hz, 1H; 7.62, d, J=9 Hz, 1H; 7.62, t, J=67 Hz, 1H.

Example H2

Preparation of 4-methyl-6-trifluoromethylnicotinic Acid

In the presence of 5.8 ml of phenyl dichlorophosphate, 7.5 g (0.03 mol) of ((3-ethoxycarbonyl)-4-methyl-6-trifluoromethyl)pyrid-2-one (Helv. Chim. Acta (1988), 71 (3), 596-601) are heated in a pressure vessel at a temperature of 170° C. for 3 hours. The cold reaction solution is filtered directly through a short silica gel column (mobile phase: ethyl acetate/hexane 1:9), giving, as an oily product, ethyl 2-chloro-4-methyl-6-trifluoromethylpyridin-3-ylcarboxylate:

$^1$H NMR (CDCl$_3$, ppm): 7.49, s, 1H; 4.48, q, 2H; 2.43, s, 3H, 1.43, t, 3H.

3.0 g (16.8 mmol) of the above product and, in 2 portions, a total of 5 g of ammonium formate are added to a suspension of 0.55 g of 10% Pd/C in 20 ml of methanol, and the mixture is stirred at room temperature for 24 hours. The reaction mixture is then filtered through Celite and, after addition of sodium chloride solution, extracted with ethyl acetate. Chromatographic purification (mobile phase 1:9) gives the 4-methyl-6-trifluoromethylpyridin-3-yl ethyl ester as an oil: $^1$H NMR (CDCl$_3$, ppm): 9.11, s, 1H; 7.56, s, 1H, 4.44, q, 2H; 2.72, s, 3H, 1.42, t, 3H. This is hydrolysed at 40° C. in the presence of aqueous potassium hydroxide solution in dioxane. Extraction with ethyl acetate gives, after acidification to pH 2.7, 4-methyl-6-trifluoromethyinicotinic acid as a crystalline product: $^1$H NMR (CDCl$_3$, ppm): 7.49, s, 1H; 4.48, q, 2H; 2.43, s, 3H, 1.43, t, 3H; 9.32, s, 1 H, 7.62, s, 1 H, 2.79, s, 3H.

Example H3

Preparation of 6-chloro-4-trifluoromethylnicotinic Acid 9.6 g (0.047 mol) of methyl 4-trifluoromethylpyridin-3-ylcarboxylate, dissolved in 50 ml of dichloromethane, are treated with 30% hydrogen peroxide/urea adduct and 17 ml of trifluoroacetic anhydride. The reaction solution is stirred at temperature of 20° C. for 20 hours and then washed once each with dilute sodium hydroxide solution and half-saturated sodium chloride solution. The product obtained is 3-methoxycarbonyl4-trifluoromethyl-3-pyridine N-oxide; $^1$H NMR (CDCl$_3$, ppm): 8.55, s, 1H; 8.31, d, 1H; 7.6, d, 1H; 3.98, s, 3H. 4.85 g (0.022 mol) of the above product are then added to a mixture of 5 ml of phosphorus oxychloride and 4.3 ml of ethyidiisopropylamine in 15 ml of 1,2dichloroethane, and the mixture is heated to a temperature of 60° C. After about 2 hours, another 2 ml of phosphorus oxychloride and 2.8 ml of ethyidiisopropylamine are added, and the mixture is stirred at this temperature for 20 hours. The reaction mixture is subsequently added to icewater, adjusted to pH 3 using 30% NaOH and then extracted with dich ioromethane. Filtration through a little silica gel gives an approximately 5:1 product mixture of the two 6-chloro- and 2-chloro-4-trifluoromethylpyridin-3-yl methyl esters, which can be separated by HPLC into the pure components. Thus, pure methyl 6-chloro-4-trifluoromethylpyridin-3-ylcarboxylate is obtained as the main product; $^1$H NMR (CDCl$_3$, ppm): 8.91, s, 1H; 7.68, s, 1H; 3.98, s, 3H, and pure methyl 2-chloro-4-trifluoromethylpyridin-3-ylcarboxylate is obtained as the byproduct; $^1$H NMR (CDCl$_3$, ppm): 8.64, d, 1H; 7.52, d, 1H; 4.01, s, 3H. In the presence of 0.073 g of potassium hydroxide, 0.22 g of pure methyl 6-chloro-4-trifluoromethylpyridin-3-ylcarboxylate are hydrolysed at room temperature in a 1:1 mixture of 6 ml of dioxane/water. Recrystallization gives the pure 6-chloro-4-trifluoromethyinicotinic acid: m.p. 115-117° C.; $^1$H NMR (CDCl$_3$, ppm): 9.12, s, 1H; 7.24, s, 1H.

Example H4

Preparation of 6-methylthio-4-trifluoromethyinicotinic Acid

In boiling acetone, 0.70 g (2.9 mol) of methyl 6-chloro-4-trifluoromethylpyridin-3-ylcarboxylate is treated in the presence of a catalytic amount of 18-crown-6 with methanethiolate (0.33 g) until no further conversion can be detected by gas chromatographic analysis. The mixture is then filtered through silica gel and evaporated. This gives 0.73 g of methyl 6-methylthio-4-trifluoromethylpyridin-3-yicarboxylate; $^1$H NMR (CDCl$_3$, ppm): 8.98, s, 1H; 7.48, S, 1H; 3.94, s, 3H; 2.64, s, 3H. Hydrolysis under the conditions mentioned above gives 6-methylthio-4-trifluoromethylnicotinic acid: $^1$H NMR (CDCl$_3$, ppm): 9.02, s, 1H; 7.46, s, 1H; 2.64, s, 3H.

Example H5

6-Hydroxy-2-trifluoromethylpyridin-3-yl ethyl ester

Under an atmosphere of nitrogen and with stirring, 33.4 g of 3,4-dihydro-5-ethoxycarbonyl-6-trifluoromethylpyridin-2-one (Org. Res.& Devel. 1,370 (1997)) and 34 g of manganese dioxide in 250 ml of 1,2-dichlorobenzene are heated under reflux for 24 hours. In intervals of about 20 hours, manganese dioxide (total amount of MnO$_2$ used: 213 g) is added six more times over a period of 3 days, and the mixture is in each case heated further under ref lux. The mixture is then cooled, diluted with ethyl acetate, and filtered through silica gel, the filtercake is washed with ethyl ester and the filtrate is concentrated. The solid residue (26.7 g, i.e. 80%), which may still contain about 6% of starting material, is directly reacted further. For complete purification, it is possible to purify, for example, over silica gel (hexane/ethyl acetate 7:3) ($^1$H NMR, CDCl$_3$, ppm): 8.02 (d, 1H); 6.85 (d, 1H); 4.86 (q, 2H); 1.37 (t, 1H).

Example H6

Preparation of ethyl 6-chloro-2-trifluoromethyl pvridin-3-ylcarboxylate

In a bomb tube, 23.5 g of ethyl 6-hydroxy-2trifluoromethylpyridin-3-ylcarboxylate and 23.5 ml of phenyl dichlorophosphate are heated at 170° C. for 3 hours, and the mixture is, after cooling, added to ice-water, stirred for a few minutes and subsequently taken up in ethyl acetate and made slightly alkaline using sodium bicarbonate and then washed neutral with water. The extracts are admixed with a little hexane and filtered through silica gel. The filtrate is evaporated, leaving 21.6 g (85%) of the title compound in the form of a dark oil with $n_D^{30}$, 1.4679. $^1$H NMR (CDCl$_3$, ppm): 8.09 (d,1H); 7.60 (d,1 H); 4.43 (q, 2H); 1.43 (t,3H).

Example H7

Preparation of 6-chloro-2-trifluoromethylpyridin-3-ylcarboxylic acid 2.5 g of the ethyl 6-chloro-2-trifluoromethylpyridin-3-ylcarboxylate obtained above are dissolved in the smallest possible amount of tetrahydrofuran, treated with approximately 20 g of ice and 11 ml of 1N lithium hydroxide and stirred at room temperature until hydrolysed completely. The mixture is then washed with a little ether and the aqueous phase is acidified using 4N hydrochloric acid and extracted with ethyl acetate. The extracts are washed with sodium chloride solution, dried and evaporated. This gives 1.8 g of the title compound of m.p. 154-156° C. The other free carboxylic acids are likewise obtained from their esters in this manner.

Example H8

Preparation of ethyl 6-methylthio-2-trifluoromethylpyridin-3-ylcarboxylate

Under an atmosphere of nitrogen and with stirring, a solution of 1.7 g of 6-chloro-2-trifluoromethylpyridin-3-yl ethyl ester in 60 ml of dimethylformamide is treated a little at a time with 0.52 g of sodium methanethiolate and stirred at room temperature until the reaction has gone to completion. The reaction mixture is then poured into ice-water, made neutral by addition of a little dilute hydrochloric acid and extracted with ethyl acetate. The extracts are diluted with a little hexane, washed with water, dried over sodium sulfate, filtered and, after filtration through a little silica gel, evaporated. This gives 1.4 g (79%) of the title compound in the form of an oil with $n_D^{25}$ 1.5100, $^1$H NMR (CDCl$_3$, ppm): 7.90 (d, 1H); 7.40 (d, 1H); 1.40 (q, 2H); 2.60 (s, 3H); 1.49 (t, 3H).

Example H9

Preparation of ethyl 6-ethylthio-2-trifluoromethylpyridin-3-ylcarboxylate

In an apparatus previously flushed with nitrogen, a solution of 1.8 ml of ethanethiol in 40 ml of dimethylformamide, which had been cooled to 0° C., is treated a little at a time with 0.96 g of sodium hydride oil dispersion (60%), and the mixture is stirred at room temperature. After evolution of hydrogen has ceased, the mixture is cooled to −20° C., and a solution of 5.07 g of 6-chloro-2-trifluoromethylpyridin-3-yl ethyl ester in 10 ml of dimethylformamide is added dropwise at this temperature, and the mixture is stirred slowly until room temperature has been reached. After the reaction has ended (approximately 3 hours), the reaction mixture is added to ice-water and extracted with ethyl acetate. The extracts are washed with water, dried, filtered, evaporated and dried under high vacuum. This gives 5.0 g (89%) of the title compound as a brownish oil. $^1$H NMR (CDCl$_3$, ppm): 7.90 (d, 1H); 7.35 (d, 1H); 4.40 (q, 2H); 3.25 (q, 2H); 1.38 (2t, 6H).

Example H10

Preparation of ethyl 6-ethylsulfinyl-2-trifluoromethylpyridin-3-ylcarboxylate

Under an atmosphere of nitrogen and with stirring and cooling, a solution of 2.5 g of m-chloroperbenzoic acid in 40 ml of methylene chloride is added dropwise at a temperature of −20° C. to a solution of 2.8 g of ethyl 6-ethylthio-2-trifluoromethylpyridin-3-ylcarboxylate, which had been charged initially, and the mixture is stirred at a temperature of +5° C. for 20 hours. The mixture is then evaporated gently and purified over silica gel (hexane:ethyl acetate 7:3). This gives 2.48 g (84%) of 6-ethylsulfinyl-2-trifluoromethylpyridin-3-yl-ethyl ester. $^1$H NMR (CDCl$_3$, ppm): 8.38 (d, 1H); 8.30 (d, 1H); 4.45 (q, 2H); 3.26-3.00 (m, 2H); 1.43 (t, 3H); 1.26 (t, 3H).

Ethyl 6-methylsulfinyl-2-trifluoromethylpyridin-3-ylcarboxylate is obtained in an analogous manner.

Example H11

Preparation of ethyl 6-methylsulfonyl-2-trifluoromethylpyridin-3-ylcarboxylate

Under an atmosphere of nitrogen and with stirring and cooling, 21 g of m-chloroperbenzoic acid are introduced a little at a time over a period of 30 minutes at a temperature of −20° C. into a solution of 3.6 g of 6-methylthio-2-trifluoromethylpyridin-3-yl ethyl ester, which had been charged initially, and the reaction mixture is stirred at room temperature for 5 hours. The mixture is then evaporated and filtered through silica gel (ethyl acetate/methanol/triethylamine 85:10:5). This gives 3.95 g (97%) of ethyl 6-methylsulfonyl-2-trifluoromethylpyridin-3-ylcarboxylate as a brownish solid with m.p. 70-72° C. $^1$H NMR (CDCl$_3$, ppm): 8.40 (1H,d); 8.33 (1H,d); 4.47 (2H,q); 1.43 (3H,t).

Example H12

Preparation of ethyl 6-cyano-2-trifluoromethylpyridin-3-ylcarboxylate

Under an atmosphere of nitrogen and with stirring, a solution of 0.596 g of ethyl 6-methylsulfonyl-2-trifluoromethylpyridin-3-ylcarboxylate in 5 ml of dimethylformamide is treated with 160 mg of solid potassium cyanide and a spatula tipful of 18-crown-6, and the mixture is heated at 80° C. for 3 hours. The mixture is cooled overnight, and the next day another 30 mg of potassium cyanide are added and the mixture is heated further until the starting material has disappeared (approximately 2 hours). The mixture is then cooled, added to ice-water and extracted with ethyl acetate. The extracts are washed with water, dried, evaporated and freed from traces of dimethylformamide under high vacuum at approximately 40° C. This gives 480 mg (yield virtually quantitative) of ethyl 6-cyano-2-trifluoromethylpyridin-3-ylcarboxylate in the form of an oil which slowly solidifies. $^1$H NMR (CDCl$_3$, ppm): 8.29 (1H, d); 7.97 (1H,d); 4.48 (2H, d); 1.43 (3H,t).

Example H13

Preparation of ethyl 6-methyl-2-trifluoromethylpyridin-3-ylcarboxylate

Under an atmosphere of nitrogen and with stirring, a solution of 3.6 g of 6-chloro-2-trifluoromethylpyridin-3-yl ethyl ester in 20 ml of dimethylacetamide is treated with 4.5 ml of tetramethyltin and 200 mg of dichloro (bistriphenylphosphine)palladium, and the mixture is heated to a temperature of 80-90° C. for 24 hours. Then another 1.5 ml of tetramethyltin and 30 mg of dichloro (bistriphenylphosphine)palladium are added and the mixture is heated for another 6 hours. The reaction mixture is then freed from excess tetramethyltin using reduced pressure (destruction by passing through ethanolic sodium hydroxide solution), cooled and added to ice-water. The mixture is extracted with diethyl ether and the extract is washed with water, dried over sodium sulfate, filtered through a little silica gel, evaporated and dried under reduced pressure. This gives the title compound (2.4 g, 73%), which still contains traces of dimethylacetamide, in the form of a dark oil. $^1$H NMR (CDCl$_3$, ppm): 8.00 (1H,d); 7.42 (1H,d); 4.42 (2H, d); 2.68 (3H, s); 1.41 (3H,t). Hydrolysis analogously to the description already mentioned above affords 6-methyl-2-trifluoromethylpyridin-3-ylcarboxylic acid (brown resin) which is directly converted further into the carbonyl chloride.

Example H14

Preparation of 6-methyl-2-trifluoromethyl pvridin-3-ylcarbonyl chloride

A solution of 0.45 g of 6-methyl-2-trifluoromethylpyridin-3-ylcarboxyi ic acid in 20 ml of dichloromethane is charged initially, 3 drops of dimethylformamid c are added and the mixture is subsequently treated with 1.6 ml of oxalyl chloride. After the intensive evolution of gas has ceased, the mixture is kept at a bath temperature of 40° C. for another 1.5 hours and then evaporated. The crude product (0.56 g) that remains as residue can be directly reacted further. $^1$H NMR (CDCl$_3$, ppm): 8.20 (1H,d); 7.51 (1H,d); 2.65 (3H, s).

Example H15

Preparation of 4-oxobicyclo[3.2.1]oct-2-en-2-yl 6-methyl-2- trifluoromethylnicotinate Under an atmosphere of nitrogen and with stirring and cooling, a solution of 0.56 g of 6-methyl-2-trifluoromethylpyridin-3-ylcarbonyl chloride in 10 ml of methylene chloride is added dropwise at 0° C. to a solution of 0.4 g of bicyclo[3.2.1]octane-2,4-dione and 0.72 g of triethylamine in 10 ml of methylene chloride, and the mixture is stirred for 5 hours until room temperature has been reached. The mixture is then diluted with methylene chloride, washed with cold 1N hydrochloric acid, dried and evaporated to give the desired enol ester (0.8 g) as a brown resin which is directly reacted further. $^1$H NMR (CDCl$_3$, ppm): 8.17 (1H,d); 7.51 (1H, d); 5.96 (1H, s); 3.04 (2H, m); 2.75 (3H, s);2.32-1.30 (m).

Example H16

Preparation of 4-hydroxy-3-(6-methyl-2-trifluoromethylpyridin-3-carbonyl)-bicyclo[3.2.1]oct-3-en-2-one Under an atmosphere of nitrogen and with stirring, 0.8 g of the above enol ester is dissolved in 30 ml of acetonitrile at 25° C., and the mixture is treated with 0.5 ml of triethylamine and 0.4 ml of acetone cyanohydrin and stirred at room temperature for 20 hours. The mixture is then diluted with solvent and washed with dilute hydrochloric acid, dried and evaporated, and the residue is purified through a little silica gel (ethyl acetate/methanol/triethylamine 85:10:5).

This gives 371 mg (46%) of the title compound (triethylamine salt) in the form of a yellowish resin. $^1$H NMR (CDCl$_3$, ppm): 7.45 (1H, d); 7.25 (1H, d); 3.80-3.43 (4H, m); 3.18 (6H, m); 2.80 (2H, s(br)); 2.62 (3H, s); 220-1.54 (m).

Example H17

Preparation of ethyl 6-methoxy-2-trifluoromethylpyridin-3-ylcarboxylate

A suspension of 5.65 g of ethyl 6-hydroxy-2-trifluoromethylpyridin-3-ylcarboxylate, 6.0 g of potassium carbonate and 2.7 ml of methyl iodide is, together with a spatula tipful of 18-crown-6, heated to a temperature of 60-70° C. until the reaction has gone to completion. The mixture is then filtered, the filtration residue is washed with acetonitrile and the filtrate is concentrated under reduced pressure. The residue is cooled, admixed with ice-water, neutralized with dilute sulfuric acid and extracted with ethyl acetate. The extracts are washed with water, dried, diluted with a little hexane and filtered through a little silica gel.

The resulting residue is the title compound (3.7 g, 65%) in the form of slightly orange crystals of m.p. 150-152° C. $^1$H NMR (CDCl$_3$, ppm): 8.00 (1H, d); 6.83 (1H, d); 4.38 (2H, q); 4.01 (3H, s);1.39 (3H, t).

Example H18

Preparation of 4-hydroxy-3(2-methyl-6-trifluoromethylpyridin-3-carbonyl)-bicyclo[3.2.1] oct-3-en-2-one 6.68 g (0.0305 mol) of methyl 2-methyl-6-trifluoromethyinicotinate (prepared as described in Heterocycles, 46, 129 (1997)) are dissolved in 250 ml of methanovwater (3:1 mixture), and 1.92 g (0.046 mol) of lithium hydroxide hydrate are added a little at a time at 22° C. After 4 hours at 22° C, the reaction mixture is poured into ethyl acetate and 2N hydrochloric acid, the organic phase is washed three times with water, dried with sodium sulfate and evaporated and the residue is triturated with a little hexane. Filtration gives 5.69 g (90% of theory) of the expected 2-methyl-6-trifluoromethyinicotinic acid of m.p. 147-149° C. The 2-methyl6trifluoromethyinicotinic acid obtained (2.0 g, 0.0098 mol) is dissolved in 20 ml of oxalyl chloride. Three drops of dimethylformamide are added, and the mixture is heated under reflux for 1 hour. The mixture is then concentrated using a rotary evaporator, and the residue (2-methyl-6-trifluoromethyinicotinoyl chloride) is taken up in 30 ml of methylene chloride. At 0° C., 2.7 ml (0.0196 mol) of triethylamine and 0.12 g (0.00098 mol) of dimethylaminopyridine are added. 1.49 g (0.0108 mol) of bicyclo [3.2.1]octane-2,4-dione, dissolved in 20 ml of methylene chloride, are then added dropwise. After 3 hours at 22° C., the reaction mixture is extracted with 2 N hydrochloric acid. The methylene chloride phase is separated off, washed with water and subsequently extracted with 10% aqueous sodium bicarbonate solution, dried over sodium sulfate and evaporated. This gives 3.18 g (100% of theory) of 4-oxobicyclo [3.2.1]oct-2-en-2-yl 2-methyl-6-trifluoromethyinicotinate as an oil, which can be processed further without purification.

3.02 g (0.0093 mol) of 4-oxobicyclo [3.2.1]oct-2en-2-yl 2-methyl-6-trifluoromethyinicotinate and 1.9 ml (0.0136 mo l) of triethylamine are dissolved in 45 ml of acetonitrile. At 22° C., 0.01 ml of acetone cyanohydrin are added. After 18 hours at 22° C., the reaction mixture is poured into dilute hydrochloric acid and extracted with ethyl acetate. The ethyl acetate phase is washed with water and then with brine, dried over sodium sulfate and evaporated, and the residue is dissolved in a little warm acetone. The product crystallizes on standing. Filtration gives 0.99 g (33% of theory) of the expected 4-hydroxy-3-(2-methyl-6-trifluoromethylpyridine-3-carbonyl)bicyclo[3.2.1]oct-3-en-2-one as white crystals (m.p. 75-77° C.).

Example H19

Preparation of 3-(2-methyl-6-trifluoromethylpyridine-3-carbonyl)-4-oxo-bicyclo [3.2.1]oct-2-en-2-yl benzoate At 0° C., a solution of 0.562 g (0.0004 mol) of benzoyl chloride in 1 ml of tetrahydrofuran is added to a solution of 1.14 g (0.0035 mol) of 4-hydroxy-3-(2-methyl-6-trifluoromethylpyridine-3-carbonyl)bicyclo[3.2.1]oct-3-en-2-one and 0.517 g (0.004 mol) of ethyidiisopropylamine in 15 ml of tetrahydrofuran. The reaction mixture is stirred at 25° C. for 2 hours, evaporated and purified over silica gel (hexane/ethyl acetate 1:1). This gives 0.9 g (60%) of the title compound in the form of a yellowish resin. $^1$H NMR (CDCl$_3$, ppm): 7.91-7.87, m, 3H; 7.64, t, J=7.5 Hz, 1 H; 7.5 0-7.40, m, 3H; 3.24, br t, J=4 Hz, 1 H; 3.14, br t, J=4 Hz, 1H; 2.70, s, 3H; 2.47, d, J=13.5 Hz, 1H; 2.40, 2.15, m, 3H; 1.95-1.8, m, 2H.

Example H20

Preparation of 4-hydroxy-3-(2-methyl-1-oxy-6-trifluoromethylpyridine-3-carbonyl)bicyclo[3.2.1] oct-3-en-2-one 16.25 g (0.05 mol) of 4-hydroxy-3-(2-methyl-6-trifluoromethylpyridine-3-carbonyl)-bicyclo[3.2.1]oct-3-en-2-one and 9.4 g (0.1 mol) of urea/hydrogen peroxide complex are dissolved in 150 ml of methylene chloride, and 20.5 ml (0.15 mol) of trifluoroacetic anhydride are added dropwise at 25° C. After 14 hours at 25° C., the reaction mixture is added to ethyl acetate and water, and the organic phase is washed twice with water, dried with sodium sulfate and evaporated. The residue is chromatographed over silica gel (mobile phase: ethyl acetatelmethanol 9/1). This gives 6.8 g (40%) of the desired product as white crystals (m.p. 109-110° C.).

Example H21

Preparation of 4-chloro-3-(2-methyl-6-trifluoromethylpyridine-3-carbonyl)-bicyclo[3.2.1] oct-3-en-2-one 20.15 g (0.062 mo 1) of 4-hydroxy-3-(2-methyl-6-trifluoromethyipyridine-3carbonyl)-bicyclo[3.2.1]oct-3-en-2-one are suspended in 50 ml of oxalyl chloride, and 0.1 ml of dimethylformamide are added dropwise. After the intensive evolution of gas has ceased, the mixture is kept at a bath temperature of 45° C. for another 1.5 hours and then evaporated, and the residue is suspended in a little ethyl acetate and admixed with stirring at 0° C. with hexane. Filtration gives 19.19 g (90% of theory) of 4-chloro-3-(2-methyl-6-trifluoromethyl-pyridine-3-carbonyl)bicyclo [3.2.1]oct-3-en-2-one of m.p. 137-138° C.

Example H22

Preparation of 4-amino-3-(2-methyl-6-trifluoronmethvlpvridine-3-carbonyl)-bicyclo[3.2.1] oct-3-en-2one 1.0 g (0.0029 mol) of 4-chloro-3-(2-methyl-6-trifluoromethylpyridine-3-carbonyl)-bicyclo[3.2.1]oct-3-en-2-one are dissolved in 10 ml of tetrahydrofuran and, at 25° C., treated with 2.0 ml of aqueous ammonia (30%). After 0.5 hours at 25° C., the reaction mixture is added to ethyl acetate and water, the organic phase is washed twice with water, dried with sodium sulfate and evaporated and the residue is triturated with a little ethyl acetate. Filtration gives 0.81 g (86% of theory) of 4-amino-3-(2-methyl-6-trifluoromethylpyridine-3-carbonyl)bicyclo[3.2.1]oct-3en-2-one in the form of white crystals (m.p. 262-263° C). $^1$H NMR (CDCl$_3$, ppm): 10.62 br s 1H; 8.223 br s 1H; 7.41, d, J=8.1 Hz, 1H; 7.35, d, J=8.1 Hz, 1H; 3.03, br t, J=4.8 Hz, 1H; 2.70, br t, J=4.8 Hz, 1H; 2.41, s, 3H; 1.97-2.14, m, 3H; 1.77-1.812, m, 1H; 1.47-1.70, m, 2H.

Example H23

Preparation of 4-(4-chlorophenylsulfanyl)-3-(2-methyl-6-trifluoromethyl-pyridine-3-carbonyl) bicyclo[3.2.1]oct-3-en-2-one 2.0 g (0.0058 mol) of 4-chloro-3-(2-methyl-6-trifluoromethylpyridine-3-carbonyl)-bicyclo[3.2.1]oct-3-en-2-one, 0.07 g of dimethylaminopyridine (0.00058 mol) and 1.61 ml of triethylamine are dissolved in 15 ml of methylene chloride. At 25° C., 0.092 g (0.0064 mol) of 4-chlorothiophenol are added. After 2 hours at 22° C., the reaction mixture is evaporated and purified over silica gel (hexane/ethyl acetate 2:1). Recrystallization (hexane/acetic acid at −25° C.) gives pure 4-(4-chlorophenylsulfanyl)-3-(2-methyl-6-trifluoromethylpyridine-3-carbonyl)bicyclo [3.2.1]oct-3-en-2-one: m.p. 130-131 ° C.

Example H24

Preparation of 4-(4-chlorobenzenesulfonyl)-3-(2-methyl-6-trifluoromethyl-pyridine-3-carbonyl) bicyclo[3.2.1]oct-3-en-2-one 0.6 g (0.00133 mol) of the 4-(4-chlorophenylsul tanyl)-3-(2-methyl-6trifluoromethylpyridine-3-carbonyl)bicyclo [3.2.1]oct-3-en-2-one obtained above is dissolved in methylene chloride, and 0.9 ml of peracetic acid (39% in acetic acid, 0.0053 mol) are added dropwise at 25° C. After 5 hours at 25° C., the reaction mixture is added to ethyl acetate and water, the organic phase is washed with water, dried with sodium sulfate and evaporated and the residue is triturated with a little hexane. Filtration gives 0.56 g (84% of theory) of 4-(4-chlorobenzenesulfonyl)-3-(2-methyl-6-trifluoromethylpyridine-3-carbonyl)bicyclo[3.2.1]oct-3-en-2-one in the form of white crystals (m.p.166-167° C.).

Example H25

Preparation of (5-cyclopropyl-3-methylsulfanylisoxazol-4-yl)-(2-methyl-6-trifluoromethylpyridin-3-yl)methanone and cyclopropyl-[3-methylsulfanyl-5-(2-methyl-6-trifluoromethylpyridin-3-yl)isoxazol4-yl)methanone 14.8 g (0.080 mol) of tert-butyl 3-cyclopropyl-3-oxopropionic acid ester are dissolved in 25 ml of MeOH, and 1.93 g (0 .080 mol) of magnesium are added. With ice-bath cooling, 7 ml of carbon tetrachloride are added dropwise, and the reaction mixture is stirred at a temperature of 22° C. for one hour. After evaporation, the residue is suspended in 100 ml of acetonitrile, and 16.31 g (0.073 mol) of 2-methyl-6-trifluoromethyinicotinoyl chloride (prepared as described in Example H18), dissolved in 50 ml of acetonitrile, are added dropwise at a temperature of 22° C. After 6 hours, the reaction mixture is taken up in ethyl acetate and washed with saturated sodium bicarbonate solution. The ethyl acetate phase is separated off, washed with water, dried over sodium sulfate and evaporated. The residue is dissolved in 160 ml of methylene chloride, and 10 ml of trifluoroacetic acid are added dropwise at a temperature of 22° C. After 18 hours, the reaction mixture is poured into water and extracted with methylene chloride. The methylene chloride phase is washed with water and then with saturated aqueous sodium chloride solution, dried over sodium sulfate and evaporated. This gives 17.3 g (88% of theory) of 1-cyclopropyl-3-(2-methyl-6-trifluoromethylpyridin-3-yl) propane-1,3-dione as an oil, which is processed further without purification. The 1-cyclopropyl-3-(2-methyl-6-trifluoromethylpyridin-3-yl)propane-1,3-dione obtained above (15.0 g, 0.055 mol) is dissolved in 150 ml of dimethylformamide, and 50 g of potassium fluoride on an aluminium oxide support (alumina) (0.0055 movg, 0.276 mol) are added a little at a time at a temperature of 0° C. After 5 minutes, 6.7 g (0.088 mol) of carbon disulfide are added dropwise. After 2 hours, 23.6 g (0.166 mol) of methyl iodide are added dropwise, and the reaction mixture is warmed to a temperature of 22° C. After a further 2 hours, the alumina is filtered off, the filtrate is added to water and the mixture is extracted with ethyl acetate. The ethyl acetate phase is washed with water and then with saturated aqueous sodium chloride solution, dried over sodium sulfate and evaporated. The residue is chromatographed over silica gel (mobile phase: ethyl acetate/hexane 15/1). This gives 12.0 g (60% of theory) of 2-(bismethylsulfanylmethylene)-1-cyclopropyl-3-(2-methyl-6-trifluoromethylpyridin-3-yl)-propane-1,3-dione as a solid. 12.0 g (0.033 mol) of the product obtained above are, together with 5.4 g (0.066 mol) of anhydrous sodium acetate, suspended in 120 ml of ethanol. 4.6 g (0.066 mol) of hydroxylamine hydrochloride are added, and the reaction mixture is kept at a temperature of 22° C. for 5 hours. Another 2.7 g of anhydrous sodium acetate and 2.3 g of hydroxylamine hydrochloride are then added. After 18 hours, the reaction mixture is diluted with water and extracted with ethyl acetate. The ethyl acetate phase is washed with water and then with saturated aqueous sodium chloride solution, dried over sodium sulfate and evaporated. Trituration with a little ethyl acetate gives 9.0 g (79.5%) of the desired product as a 2:1 isomer mixture in the form of white crystals (m.p. 103-104° C.).

Main isomer: $^1$H NMR (CDCl$_3$, ppm) ((5-cyclopropyl-3-methylsulfanylisoxazol-4-yl)-(2-methyl-6-trifluoromethylpyridin-3-yl)methanone) 7.98, d, J=7.8 Hz, 1H; 7.61, d, J=7.8 Hz, 1H; 2.67, s, 3H; 2.50, s, 3H; 2.02-1.93, m, 1 H; 1.34-1.28, m, 2H; 1.18-1.09, m, 2H.

$^1$H NMR (CDCl$_3$, ppm) (cyclopropyl-13-methylsulfanyl-5-(2-methyl6-trifluoromethylpyridin-3-yl)isoxazol-4-yl] methane): 7.95, d, J=7.8 Hz, 1H; 7.69, d, J=7.8 Hz, 1H; 2.67, s, 3H; 2.66, s, 3H; 1.74-1.64, m, 1H; 1.28-1.18, m, 2H; 0.89 4.80, m, 2H.

Example H26

Preparation of (5-cyclopropyl-3-methylsulfinylisoxazol-4-yl)-(2-methyl-6-trifluoromethylpyridin-3-yl)methanone and cylopropyl-[3-methanesulfinyl-5-(2-methyl-6-trifluoromethylpyridin-3-yl)isoxazol-4-yl]methanone 1.50 g (0.0043 mol) of the isomer mixture obtained above are dissolved in 30 ml of acetonelwater (2:1 mixture), and 1.02 g (0.0048 mol) of sodium metaperiodate are added a little at a time at 22° C. After 5 hours, the reaction mixture is evaporated using a rotary evaporator. The residue is taken up in water and ethyl acetate. The ethyl acetate phase is dried over sodium sulfate and evaporated. The residue is chromatographed over silica gel (mobile phase: ethyl acetate/hexane 3/1). This gives initially 0.8 g (51% of theory) of (5-cyclopropyl-3-methylsulfinylisoxazol-4-yl)-(2-methyl-6-trifluoromethylpyridin-3-yl)methanone as white crystals (m.p. 96-97° C.). $^1$H NMR (CDCl$_3$, ppm): 7.86, d, J=7.8 Hz, 1H; 7.59, d, J=7.8 Hz, 1H; 3.078, s, 3H; 2.66, s, 3H; 1.54-1A49, m, IH; 1.32-1.25, m, 2H; 1.13-1.072, m, 2H.

The second product that eiutes consists of 0.34 g (22% of theory) of cyclopropyl-[3-methanesulfinyl-5-(2-methyl-6-trifluoromethylpyridin-3yl)isoxazol4-yl]methanone as white crystals (m.p. 112-113° C.). $^1$H NMR (CDCl$_3$, ppm): 7.97, d, J=7.8 Hz, 1H; 7.67, d, J=7.8 Hz, 1H; 3.128, s, 3H; 2.62, s, 3H; 1.69-1.64, m, 1H; 1.26-1.18, m, 2H; 0.90-0.85, m, 2H.

Example H27

Preparation of (5-cyclopropyl-3-methanesulfonylisoxazol-4-yl)-(2-isopropyl-6-trifluoromethylpyridin-3-yl)methanone 0.15 g (0.0045 mol) of (5-cyclopropyl-3-methylsulfanylisoxazol-4-yl)-(2-isopropyl-6-trifluoromethylpyridin-3-yl)methanone is dissolved in methylene chloride, and 0.28 ml of peracetic acid (39% in acetic acid, 0.0016 mol) are added dropwise at a temperature of 5° C. After 15 hours at 25° C., the reaction mixture is added to ethyl acetate and water, and the organic phase is washed with water, dried with sodium sulfate and evaporated. The residue is chromatographed over silica gel (mobile phase: ethyl acetate/hexane 5/1). This gives 0.121 g (74% of theory) of the expected product as white crystals (m.p.105-106° C.).

In an analogous manner, and according to the methods shown in the general reaction schemes 1-10 and in the references mentioned therein, it is also possible to prepare the compounds listed in the tables below. In these tables, CCH is the ethynyl group, Ph is the phenyl group and Me is the methyl group.

TABLE 1

| Comp. No. | R₁ | R₂ | R₃ | R₄ | R₅ | p |
|---|---|---|---|---|---|---|
| 1.001 | H | $CF_3$ | H | H | OH | 0 |
| 1.002 | F | $CF_3$ | H | H | OH | 0 |
| 1.003 | Cl | $CF_3$ | H | H | OH | 0 |
| 1.004 | Br | $CF_3$ | H | H | OH | 0 |
| 1.005 | $CHF_2$ | $CF_3$ | H | H | OH | 0 |
| 1.006 | $CCl_3$ | $CF_3$ | H | H | OH | 0 |
| 1.007 | $CClF_2$ | $CF_3$ | H | H | OH | 0 |
| 1.008 | $CF_3$ | $CF_3$ | H | H | OH | 0 |
| 1.009 | $CH_3$ | $CF_3$ | H | H | OH | 0 |
| 1.01 | $CH_2CH_3$ | $CF_3$ | H | H | OH | 0 |
| 1.011 | $CH(CH_3)_2$ | $CF_3$ | H | H | OH | 0 |
| 1.012 | $(CH_2)_2CH_3$ | $CF_3$ | H | H | OH | 0 |
| 1.013 | $C(CH_3)_3$ | $CF_3$ | H | H | OH | 0 |
| 1.014 | Ph | $CF_3$ | H | H | OH | 0 |
| 1.015 | $CH_2F$ | $CF_3$ | H | H | OH | 0 |
| 1.016 | $CH_2Cl$ | $CF_3$ | H | H | OH | 0 |
| 1.017 | $CH_2Br$ | $CF_3$ | H | H | OH | 0 |
| 1.018 | $CH_2OH$ | $CF_3$ | H | H | OH | 0 |
| 1.019 | $CH_2OCOCH_3$ | $CF_3$ | H | H | OH | 0 |
| 1.02 | $CH_2OCOPh$ | $CF_3$ | H | H | OH | 0 |
| 1.021 | $CH_2OCH_3$ | $CF_3$ | H | H | OH | 0 |
| 1.022 | $CH_2OCH_2CH_3$ | $CF_3$ | H | H | OH | 0 |
| 1.023 | $CH_2CH_2OCH_3$ | $CF_3$ | H | H | OH | 0 |
| 1.024 | $CH_2SMe$ | $CF_3$ | H | H | OH | 0 |
| 1.025 | $CH_2SOMe$ | $CF_3$ | H | H | OH | 0 |
| 1.026 | $CH_2SO_2Me$ | $CF_3$ | H | H | OH | 0 |
| 1.027 | $CH_2SO_2Ph$ | $CF_3$ | H | H | OH | 0 |
| 1.028 | $SCH_2Ph$ | $CF_3$ | H | H | OH | 0 |
| 1.029 | $SOCH_2Ph$ | $CF_3$ | H | H | OH | 0 |
| 1.03 | $SO_2CH_2Ph$ | $CF_3$ | H | H | OH | 0 |
| 1.031 | $SCH_3$ | $CF_3$ | H | H | OH | 0 |
| 1.032 | $SOCH_3$ | $CF_3$ | H | H | OH | 0 |
| 1.033 | $SO_2CH_3$ | $CF_3$ | H | H | OH | 0 |
| 1.034 | SPh | $CF_3$ | H | H | OH | 0 |
| 1.035 | SOPh | $CF_3$ | H | H | OH | 0 |
| 1.036 | $SO_2Ph$ | $CF_3$ | H | H | OH | 0 |
| 1.037 | $N(CH_3)_2$ | $CF_3$ | H | H | OH | 0 |
| 1.038 | $CH=CH_2$ | $CF_3$ | H | H | OH | 0 |
| 1.039 | $CH_2CH=CH_2$ | $CF_3$ | H | H | OH | 0 |
| 1.04 | $SO_2N(CH_3)_2$ | $CF_3$ | H | H | OH | 0 |
| 1.041 | ethynyl | $CF_3$ | H | H | OH | 0 |
| 1.042 | cyclopropyl | $CF_3$ | H | H | OH | 0 |
| 1.043 | $OCH_3$ | $CF_3$ | H | H | OH | 0 |
| 1.044 | OPh | $CF_3$ | H | H | OH | 0 |
| 1.045 | $OCHF_2$ | $CF_3$ | H | H | OH | 0 |
| 1.046 | $CO_2Me$ | $CF_3$ | H | H | OH | 0 |
| 1.047 | 2-furyl | $CF_3$ | H | H | OH | 0 |
| 1.048 | $OCH_2$ethynyl | $CF_3$ | H | H | OH | 0 |
| 1.049 | 2-pyridyl | $CF_3$ | H | H | OH | 0 |
| 1.05 | 3-pyridyl | $CF_3$ | H | H | OH | 0 |
| 1.051 | 4-pyridyl | $CF_3$ | H | H | OH | 0 |
| 1.052 | H | $CF_3$ | H | H | OH | 1 |
| 1.053 | F | $CF_3$ | H | H | OH | 1 |
| 1.054 | Cl | $CF_3$ | H | H | OH | 1 |
| 1.055 | Br | $CF_3$ | H | H | OH | 1 |
| 1.056 | $CHF_2$ | $CF_3$ | H | H | OH | 1 |
| 1.057 | $CCl_3$ | $CF_3$ | H | H | OH | 1 |
| 1.058 | $CClF_2$ | $CF_3$ | H | H | OH | 1 |
| 1.059 | $CF_3$ | $CF_3$ | H | H | OH | 1 |
| 1.06 | $CH_3$ | $CF_3$ | H | H | OH | 1 |
| 1.061 | $CH_2CH_3$ | $CF_3$ | H | H | OH | 1 |
| 1.062 | $CH(CH_3)_2$ | $CF_3$ | H | H | OH | 1 |
| 1.063 | $(CH_2)_2CH_3$ | $CF_3$ | H | H | OH | 1 |
| 1.064 | $C(CH_3)_3$ | $CF_3$ | H | H | OH | 1 |
| 1.065 | Ph | $CF_3$ | H | H | OH | 1 |

TABLE 1-continued

| Comp. No. | $R_1$ | $R_2$ | $R_3$ | $R_4$ | $R_5$ | p |
|---|---|---|---|---|---|---|
| 1.066 | $CH_2F$ | $CF_3$ | H | H | OH | 1 |
| 1.067 | $CH_2Cl$ | $CF_3$ | H | H | OH | 1 |
| 1.068 | $CH_2Br$ | $CF_3$ | H | H | OH | 1 |
| 1.069 | $CH_2OH$ | $CF_3$ | H | H | OH | 1 |
| 1.07 | $CH_2OCOCH_3$ | $CF_3$ | H | H | OH | 1 |
| 1.071 | $CH_2OCOPh$ | $CF_3$ | H | H | OH | 1 |
| 1.072 | $CH_2OCH_3$ | $CF_3$ | H | H | OH | 1 |
| 1.073 | $CH_2OCH_2CH_3$ | $CF_3$ | H | H | OH | 1 |
| 1.074 | $CH_2CH_2OCH_3$ | $CF_3$ | H | H | OH | 1 |
| 1.075 | $CH_2SMe$ | $CF_3$ | H | H | OH | 1 |
| 1.076 | $CH_2SOMe$ | $CF_3$ | H | H | OH | 1 |
| 1.077 | $CH_2SO_2Me$ | $CF_3$ | H | H | OH | 1 |
| 1.078 | $CH_2SO_2Ph$ | $CF_3$ | H | H | OH | 1 |
| 1.079 | $SCH_2Ph$ | $CF_3$ | H | H | OH | 1 |
| 1.08 | $SOCH_2Ph$ | $CF_3$ | H | H | OH | 1 |
| 1.081 | $SO_2CH_2Ph$ | $CF_3$ | H | H | OH | 1 |
| 1.082 | $SCH_3$ | $CF_3$ | H | H | OH | 1 |
| 1.083 | $SOCH_3$ | $CF_3$ | H | H | OH | 1 |
| 1.084 | $SO_2CH_3$ | $CF_3$ | H | H | OH | 1 |
| 1.085 | SPh | $CF_3$ | H | H | OH | 1 |
| 1.086 | SOPh | $CF_3$ | H | H | OH | 1 |
| 1.087 | $SO_2Ph$ | $CF_3$ | H | H | OH | 1 |
| 1.088 | $N(CH_3)_2$ | $CF_3$ | H | H | OH | 1 |
| 1.089 | $CH=CH_2$ | $CF_3$ | H | H | OH | 1 |
| 1.09 | $CH_2CH=CH_2$ | $CF_3$ | H | H | OH | 1 |
| 1.091 | $SO_2N(CH_3)_2$ | $CF_3$ | H | H | OH | 1 |
| 1.092 | ethynyl | $CF_3$ | H | H | OH | 1 |
| 1.093 | cyclopropyl | $CF_3$ | H | H | OH | 1 |
| 1.094 | $OCH_3$ | $CF_3$ | H | H | OH | 1 |
| 1.095 | OPh | $CF_3$ | H | H | OH | 1 |
| 1.096 | $OCHF_2$ | $CF_3$ | H | H | OH | 1 |
| 1.097 | $CO_2Me$ | $CF_3$ | H | H | OH | 1 |
| 1.098 | 2-furyl | $CF_3$ | H | H | OH | 1 |
| 1.099 | $OCH_2CCH$ | $CF_3$ | H | H | OH | 1 |
| 1.1 | 2-pyridyl | $CF_3$ | H | H | OH | 1 |
| 1.101 | 3-pyridyl | $CF_3$ | H | H | OH | 1 |
| 1.102 | 4-pyridyl | $CF_3$ | H | H | OH | 1 |
| 1.103 | H | $CF_2CF_3$ | H | H | OH | 0 |
| 1.104 | Cl | $CF_2CF_3$ | H | H | OH | 0 |
| 1.105 | $CHF_2$ | $CF_2CF_3$ | H | H | OH | 0 |
| 1.106 | $CCl_3$ | $CF_2CF_3$ | H | H | OH | 0 |
| 1.107 | $CClF_2$ | $CF_2CF_3$ | H | H | OH | 0 |
| 1.108 | $CF_3$ | $CF_2CF_3$ | H | H | OH | 0 |
| 1.109 | $CH_3$ | $CF_2CF_3$ | H | H | OH | 0 |
| 1.11 | $CH_2CH_3$ | $CF_2CF_3$ | H | H | OH | 0 |
| 1.111 | $CH(CH_3)_2$ | $CF_2CF_3$ | H | H | OH | 0 |
| 1.112 | $(CH_2)_2CH_3$ | $CF_2CF_3$ | H | H | OH | 0 |
| 1.113 | $C(CH_3)_3$ | $CF_2CF_3$ | H | H | OH | 0 |
| 1.114 | $CH_2F$ | $CF_2CF_3$ | H | H | OH | 0 |
| 1.115 | $CH_2Cl$ | $CF_2CF_3$ | H | H | OH | 0 |
| 1.116 | $CH_2OH$ | $CF_2CF_3$ | H | H | OH | 0 |
| 1.117 | $CH_2OCOCH_3$ | $CF_2CF_3$ | H | H | OH | 0 |
| 1.118 | $CH_2OCOPh$ | $CF_2CF_3$ | H | H | OH | 0 |
| 1.119 | $CH_2OCH_3$ | $CF_2CF_3$ | H | H | OH | 0 |
| 1.12 | $CH_2OCH_2CH_3$ | $CF_2CF_3$ | H | H | OH | 0 |
| 1.121 | $CH_2SMe$ | $CF_2CF_3$ | H | H | OH | 0 |
| 1.122 | $CH_2SOMe$ | $CF_2CF_3$ | H | H | OH | 0 |
| 1.123 | $CH_2SO_2Me$ | $CF_2CF_3$ | H | H | OH | 0 |
| 1.124 | $CH_2SO_2Ph$ | $CF_2CF_3$ | H | H | OH | 0 |
| 1.125 | $N(CH_3)_2$ | $CF_2CF_3$ | H | H | OH | 0 |
| 1.126 | $CH=CH_2$ | $CF_2CF_3$ | H | H | OH | 0 |
| 1.127 | $CH_2CH=CH_2$ | $CF_2CF_3$ | H | H | OH | 0 |
| 1.128 | $SO_2N(CH_3)_2$ | $CF_2CF_3$ | H | H | OH | 0 |
| 1.129 | CCH | $CF_2CF_3$ | H | H | OH | 0 |
| 1.13 | cyclopropyl | $CF_2CF_3$ | H | H | OH | 0 |

TABLE 1-continued

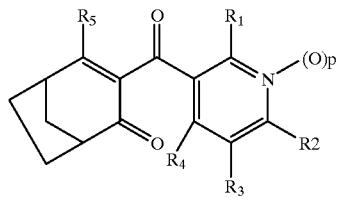

| Comp. No. | $R_1$ | $R_2$ | $R_3$ | $R_4$ | $R_5$ | p |
|---|---|---|---|---|---|---|
| 1.131 | OPh | $CF_2CF_3$ | H | H | OH | 0 |
| 1.132 | $OCH_3$ | $CF_2CF_3$ | H | H | OH | 0 |
| 1.133 | $CO_2Me$ | $CF_2CF_3$ | H | H | OH | 0 |
| 1.134 | $OCH_2CCH$ | $CF_2CF_3$ | H | H | OH | 0 |
| 1.135 | 2-pyridyl | $CF_2CF_3$ | H | H | OH | 0 |
| 1.136 | 3-pyridyl | $CF_2CF_3$ | H | H | OH | 0 |
| 1.137 | 4-pyridyl | $CF_2CF_3$ | H | H | OH | 0 |
| 1.138 | H | $CF_2CF_3$ | H | H | OH | 1 |
| 1.139 | Cl | $CF_2CF_3$ | H | H | OH | 1 |
| 1.14 | $CHF_2$ | $CF_2CF_3$ | H | H | OH | 1 |
| 1.141 | $CCl_3$ | $CF_2CF_3$ | H | H | OH | 1 |
| 1.142 | $CClF_2$ | $CF_2CF_3$ | H | H | OH | 1 |
| 1.143 | $CF_3$ | $CF_2CF_3$ | H | H | OH | 1 |
| 1.144 | $CH_3$ | $CF_2CF_3$ | H | H | OH | 1 |
| 1.145 | $CH_2CH_3$ | $CF_2CF_3$ | H | H | OH | 1 |
| 1.146 | $CH(CH_3)_2$ | $CF_2CF_3$ | H | H | OH | 1 |
| 1.147 | $(CH_2)_2CH_3$ | $CF_2CF_3$ | H | H | OH | 1 |
| 1.148 | $C(CH_3)_3$ | $CF_2CF_3$ | H | H | OH | 1 |
| 1.149 | $CH_2F$ | $CF_2CF_3$ | H | H | OH | 1 |
| 1.15 | $CH_2Cl$ | $CF_2CF_3$ | H | H | OH | 1 |
| 1.151 | $CH_2OH$ | $CF_2CF_3$ | H | H | OH | 1 |
| 1.152 | $CH_2OCOCH_3$ | $CF_2CF_3$ | H | H | OH | 1 |
| 1.153 | $CH_2OCOPh$ | $CF_2CF_3$ | H | H | OH | 1 |
| 1.154 | $CH_2OCH_3$ | $CF_2CF_3$ | H | H | OH | 1 |
| 1.155 | $CH_2OCH_2CH_3$ | $CF_2CF_3$ | H | H | OH | 1 |
| 1.156 | $CH_2SMe$ | $CF_2CF_3$ | H | H | OH | 1 |
| 1.157 | $CH_2SOMe$ | $CF_2CF_3$ | H | H | OH | 1 |
| 1.158 | $CH_2SO_2Me$ | $CF_2CF_3$ | H | H | OH | 1 |
| 1.159 | $CH_2SO_2Ph$ | $CF_2CF_3$ | H | H | OH | 1 |
| 1.16 | $N(CH_3)_2$ | $CF_2CF_3$ | H | H | OH | 1 |
| 1.161 | $CH=CH_2$ | $CF_2CF_3$ | H | H | OH | 1 |
| 1.162 | $CH_2CH=CH_2$ | $CF_2CF_3$ | H | H | OH | 1 |
| 1.163 | $SO_2N(CH_3)_2$ | $CF_2CF_3$ | H | H | OH | 1 |
| 1.164 | CCH | $CF_2CF_3$ | H | H | OH | 1 |
| 1.165 | cyclopropyl | $CF_2CF_3$ | H | H | OH | 1 |
| 1.166 | OPh | $CF_2CF_3$ | H | H | OH | 1 |
| 1.167 | $OCH_3$ | $CF_2CF_3$ | H | H | OH | 1 |
| 1.168 | $CO_2Me$ | $CF_2CF_3$ | H | H | OH | 1 |
| 1.169 | $OCH_2CCH$ | $CF_2CF_3$ | H | H | OH | 1 |
| 1.17 | 2-pyridyl | $CF_2CF_3$ | H | H | OH | 1 |
| 1.171 | 3-pyridyl | $CF_2CF_3$ | H | H | OH | 1 |
| 1.172 | 4-pyridyl | $CF_2CF_3$ | H | H | OH | 1 |
| 1.173 | H | $CF_2CF_2CF_3$ | H | H | OH | 0 |
| 1.174 | $CHF_2$ | $CF_2CF_2CF_3$ | H | H | OH | 0 |
| 1.175 | $CF_3$ | $CF_2CF_2CF_3$ | H | H | OH | 0 |
| 1.176 | $CH_3$ | $CF_2CF_2CF_3$ | H | H | OH | 0 |
| 1.177 | $CH_2CH_3$ | $CF_2CF_2CF_3$ | H | H | OH | 0 |
| 1.178 | $(CH_2)_2CH_3$ | $CF_2CF_2CF_3$ | H | H | OH | 0 |
| 1.179 | $CH_2Cl$ | $CF_2CF_2CF_3$ | H | H | OH | 0 |
| 1.18 | $CH_2OCH_3$ | $CF_2CF_2CF_3$ | H | H | OH | 0 |
| 1.181 | H | $CF_2CF_2CF_3$ | H | H | OH | 1 |
| 1.182 | $CHF_2$ | $CF_2CF_2CF_3$ | H | H | OH | 1 |
| 1.183 | $CF_3$ | $CF_2CF_2CF_3$ | H | H | OH | 1 |
| 1.184 | $CH_3$ | $CF_2CF_2CF_3$ | H | H | OH | 1 |
| 1.185 | $CH_2CH_3$ | $CF_2CF_2CF_3$ | H | H | OH | 1 |
| 1.186 | $(CH_2)_2CH_3$ | $CF_2CF_2CF_3$ | H | H | OH | 0 |
| 1.187 | $CH_2Cl$ | $CF_2CF_2CF_3$ | H | H | OH | 1 |
| 1.188 | $CH_2OCH_3$ | $CF_2CF_2CF_3$ | H | H | OH | 1 |
| 1.189 | H | $CF_2Cl$ | H | H | OH | 0 |
| 1.19 | Cl | $CF_2Cl$ | H | H | OH | 0 |
| 1.191 | $CHF_2$ | $CF_2Cl$ | H | H | OH | 0 |
| 1.192 | $CCl_3$ | $CF_2Cl$ | H | H | OH | 0 |
| 1.193 | $CClF_2$ | $CF_2Cl$ | H | H | OH | 0 |
| 1.194 | $CF_3$ | $CF_2Cl$ | H | H | OH | 0 |
| 1.195 | $CH_3$ | $CF_2Cl$ | H | H | OH | 0 |

TABLE 1-continued

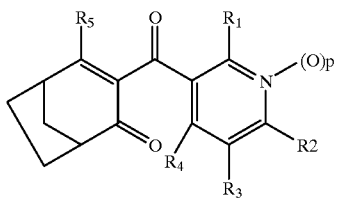

| Comp. No. | R₁ | R₂ | R₃ | R₄ | R₅ | p |
|---|---|---|---|---|---|---|
| 1.196 | CH₂CH₃ | CF₂Cl | H | H | OH | 0 |
| 1.197 | CH(CH₃)₂ | CF₂Cl | H | H | OH | 0 |
| 1.198 | (CH₂)₂CH₃ | CF₂Cl | H | H | OH | 0 |
| 1.199 | C(CH₃)₃ | CF₂Cl | H | H | OH | 0 |
| 1.2 | CH₂F | CF₂Cl | H | H | OH | 0 |
| 1.201 | CH₂Cl | CF₂Cl | H | H | OH | 0 |
| 1.202 | CH₂OH | CF₂Cl | H | H | OH | 0 |
| 1.203 | CH₂OCOCH₃ | CF₂Cl | H | H | OH | 0 |
| 1.204 | CH₂OCOPh | CF₂Cl | H | H | OH | 0 |
| 1.205 | CH₂OCH₃ | CF₂Cl | H | H | OH | 0 |
| 1.206 | CH₂OCH₂CH₃ | CF₂Cl | H | H | OH | 0 |
| 1.207 | CH₂SMe | CF₂Cl | H | H | OH | 0 |
| 1.208 | CH₂SOMe | CF₂Cl | H | H | OH | 0 |
| 1.209 | CH₂SO₂Me | CF₂Cl | H | H | OH | 0 |
| 1.21 | CH₂SO₂Ph | CF₂C | H | H | OH | 0 |
| 1.211 | N(CH₃)₂ | CF₂Cl | H | H | OH | 0 |
| 1.212 | CH=CH₂ | CF₂Cl | H | H | OH | 0 |
| 1.213 | CH₂CH=CH₂ | CF₂Cl | H | H | OH | 0 |
| 1.214 | SO₂N(CH₃)₂ | CF₂Cl | H | H | OH | 0 |
| 1.215 | CCH | CF₂Cl | H | H | OH | 0 |
| 1.216 | cyclopropyl | CF₂Cl | H | H | OH | 0 |
| 1.217 | OPh | CF₂Cl | H | H | OH | 0 |
| 1.218 | OCH₃ | CF₂Cl | H | H | OH | 0 |
| 1.219 | CO₂Me | CF₂Cl | H | H | OH | 0 |
| 1.22 | OCH₂CCH | CF₂Cl | H | H | OH | 0 |
| 1.221 | 2-pyridyl | CF₂Cl | H | H | OH | 0 |
| 1.222 | 3-pyridyl | CF₂Cl | H | H | OH | 0 |
| 1.223 | 4-pyridyl | CF₂Cl | H | H | OH | 0 |
| 1.224 | H | CF₂Cl | H | H | OH | 1 |
| 1.225 | Cl | CF₂Cl | H | H | OH | 1 |
| 1.226 | CHF₂ | CF₂Cl | H | H | OH | 1 |
| 1.227 | CCl₃ | CF₂Cl | H | H | OH | 1 |
| 1.228 | CClF₂ | CF₂Cl | H | H | OH | 1 |
| 1.229 | CF₃ | CF₂Cl | H | H | OH | 1 |
| 1.23 | CH₃ | CF₂Cl | H | H | OH | 1 |
| 1.231 | CH₂CH₃ | CF₂Cl | H | H | OH | 1 |
| 1.232 | CH(CH₃)₂ | CF₂Cl | H | H | OH | 1 |
| 1.233 | (CH₂)₂CH₃ | CF₂Cl | H | H | OH | 1 |
| 1.234 | C(CH₃)₃ | CF₂Cl | H | H | OH | 1 |
| 1.235 | CH₂F | CF₂Cl | H | H | OH | 1 |
| 1.236 | CH₂Cl | CF₂Cl | H | H | OH | 1 |
| 1.237 | CH₂OH | CF₂Cl | H | H | OH | 1 |
| 1.238 | CH₂OCOCH₃ | CF₂Cl | H | H | OH | 1 |
| 1.239 | CH₂OCOPh | CF₂Cl | H | H | OH | 1 |
| 1.24 | CH₂OCH₃ | CF₂Cl | H | H | OH | 1 |
| 1.241 | CH₂OCH₂CH₃ | CF₂Cl | H | H | OH | 1 |
| 1.242 | CH₂SMe | CF₂Cl | H | H | OH | 1 |
| 1.243 | CH₂SOMe | CF₂Cl | H | H | OH | 1 |
| 1.244 | CH₂SO₂Me | CF₂Cl | H | H | OH | 1 |
| 1.245 | CH₂SO₂Ph | CF₂Cl | H | H | OH | 1 |
| 1.246 | N(CH₃)₂ | CF₂Cl | H | H | OH | 1 |
| 1.247 | CH=CH₂ | CF₂Cl | H | H | OH | 1 |
| 1.248 | CH₂CH=CH₂ | CF₂Cl | H | H | OH | 1 |
| 1.249 | SO₂N(CH₃)₂ | CF₂Cl | H | H | OH | 1 |
| 1.25 | CCH | CF₂Cl | H | H | OH | 1 |
| 1.251 | cyclopropyl | CF₂Cl | H | H | OH | 1 |
| 1.252 | OPh | CF₂Cl | H | H | OH | 1 |
| 1.253 | OCH₃ | CF₂Cl | H | H | OH | 1 |
| 1.254 | CO₂Me | CF₂Cl | H | H | OH | 1 |
| 1.255 | OCH₂CCH | CF₂Cl | H | H | OH | 1 |
| 1.256 | H | CCl₃ | H | H | OH | 0 |
| 1.257 | Cl | CCl₃ | H | H | OH | 0 |
| 1.258 | CH₃ | CCl₃ | H | H | OH | 0 |
| 1.259 | CH₂CH₃ | CCl₃ | H | H | OH | 0 |
| 1.26 | CH(CH₃)₂ | CCl₃ | H | H | OH | 0 |

TABLE 1-continued

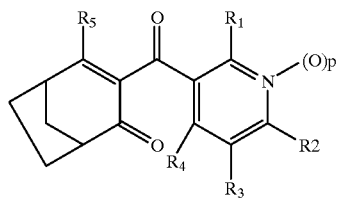

| Comp. No. | $R_1$ | $R_2$ | $R_3$ | $R_4$ | $R_5$ | p |
|---|---|---|---|---|---|---|
| 1.261 | (CH$_2$)$_2$CH$_3$ | CCl$_3$ | H | H | OH | 0 |
| 1.262 | CH$_2$F | CCl$_3$ | H | H | OH | 0 |
| 1.263 | CH$_2$Cl | CCl$_3$ | H | H | OH | 0 |
| 1.264 | CH$_2$OH | CCl$_3$ | H | H | OH | 0 |
| 1.265 | CH$_2$OCOCH$_3$ | CCl$_3$ | H | H | OH | 0 |
| 1.266 | CH$_2$OCOPh | CCl$_3$ | H | H | OH | 0 |
| 1.267 | CH$_2$OCH$_3$ | CCl$_3$ | H | H | OH | 0 |
| 1.268 | CH$_2$OCH$_2$CH$_3$ | CCl$_3$ | H | H | OH | 0 |
| 1.269 | CH$_2$SMe | CCl$_3$ | H | H | OH | 0 |
| 1.27 | CH$_2$SOMe | CCl$_3$ | H | H | OH | 0 |
| 1.271 | CH$_2$SO$_2$Me | CCl$_3$ | H | H | OH | 0 |
| 1.272 | CH$_2$SO$_2$Ph | CCl$_3$ | H | H | OH | 0 |
| 1.273 | cyclopropyl | CCl$_3$ | H | H | OH | 0 |
| 1.274 | OPh | CCl$_3$ | H | H | OH | 0 |
| 1.275 | OCH$_3$ | CCl$_3$ | H | H | OH | 0 |
| 1.276 | CO$_2$Me | CCl$_3$ | H | H | OH | 0 |
| 1.277 | OCH$_2$OCH | CCl$_3$ | H | H | OH | 0 |
| 1.278 | H | CCl$_3$ | H | H | OH | 1 |
| 1.279 | Cl | CCl$_3$ | H | H | OH | 1 |
| 1.28 | CH$_3$ | CCl$_3$ | H | H | OH | 1 |
| 1.281 | CH$_2$CH$_3$ | CCl$_3$ | H | H | OH | 1 |
| 1.282 | CH(CH$_3$)$_2$ | CCl$_3$ | H | H | OH | 1 |
| 1.283 | (CH$_2$)$_2$CH$_3$ | CCl$_3$ | H | H | OH | 1 |
| 1.284 | CH$_2$F | CCl$_3$ | H | H | OH | 1 |
| 1.285 | CH$_2$Cl | CCl$_3$ | H | H | OH | 1 |
| 1.286 | CH$_2$OH | CCl$_3$ | H | H | OH | 1 |
| 1.287 | CH$_2$OCOCH$_3$ | CCl$_3$ | H | H | OH | 1 |
| 1.288 | CH$_2$OCOPh | CCl$_3$ | H | H | OH | 1 |
| 1.289 | CH$_2$OCH$_3$ | CCl$_3$ | H | H | OH | 1 |
| 1.29 | CH$_2$OCH$_2$CH$_3$ | CCl$_3$ | H | H | OH | 1 |
| 1.291 | CH$_2$SMe | CCl$_3$ | H | H | OH | 1 |
| 1.292 | CH$_2$SOMe | CCl$_3$ | H | H | OH | 1 |
| 1.293 | CH$_2$SO$_2$Me | CCl$_3$ | H | H | OH | 1 |
| 1.294 | CH$_2$SO$_2$Ph | CCl$_3$ | H | H | OH | 1 |
| 1.295 | cyclopropyl | CCl$_3$ | H | H | OH | 1 |
| 1.296 | OPh | CCl$_3$ | H | H | OH | 1 |
| 1.297 | OCH$_3$ | CCl$_3$ | H | H | OH | 1 |
| 1.298 | CO$_2$Me | CCl$_3$ | H | H | OH | 1 |
| 1.299 | OCH$_2$CCH | CCl$_3$ | H | H | OH | 1 |
| 1.3 | CF$_3$ | CHF$_2$ | H | H | OH | 0 |
| 1.301 | CH$_3$ | CHF$_2$ | H | H | OH | 0 |
| 1.302 | CH$_2$OCH$_3$ | CHF$_2$ | H | H | OH | 0 |
| 1.303 | CH$_2$Cl | CHF$_2$ | H | H | OH | 0 |
| 1.304 | CH$_2$F | CHF$_2$ | H | H | OH | 0 |
| 1.305 | CF$_3$ | CHF$_2$ | H | H | OH | 1 |
| 1.306 | CH$_3$ | CHF$_2$ | H | H | OH | 1 |
| 1.307 | CH$_2$OCH$_3$ | CHF$_2$ | H | H | OH | 1 |
| 1.308 | CH$_2$Cl | CHF$_2$ | H | H | OH | 1 |
| 1.309 | CH$_2$F | CHF$_2$ | H | H | OH | 1 |
| 1.31 | CH$_3$ | CF$_3$ | H | CH$_3$ | OH | 0 |
| 1.311 | CH$_3$ | CF$_3$ | H | CH$_3$ | OH | 1 |
| 1.312 | Cl | CF$_3$ | H | CH$_3$ | OH | 0 |
| 1.313 | CH$_3$ | CF$_3$ | CH$_3$ | H | OH | 0 |
| 1.314 | CH$_3$ | CF$_3$ | Ph | H | OH | 0 |
| 1.315 | CH$_3$ | CF$_3$ | Cl | H | OH | 0 |
| 1.316 | CH$_3$ | CF$_3$ | CO$_2$CH$_2$CH$_3$ | H | OH | 0 |
| 1.317 | CH$_3$ | CF$_3$ | CO$_2$CH$_2$Ph | H | OH | 0 |
| 1.318 | CH$_3$ | CF$_3$ | CH$_3$ | H | OH | 1 |
| 1.319 | CH$_3$ | CF$_3$ | Ph | H | OH | 1 |
| 1.32 | CH$_3$ | CF$_3$ | Cl | H | OH | 1 |
| 1.321 | CH$_3$ | CF$_3$ | CO$_2$CH$_2$CH$_3$ | H | OH | 1 |
| 1.322 | CH$_3$ | CF$_3$ | CO$_2$CH$_2$Ph | H | OH | 1 |
| 1.323 | OCH$_3$ | CF$_3$ | CH$_3$ | H | OH | 0 |
| 1.324 | CH$_2$OCH$_3$ | CF$_3$ | CH$_3$ | H | OH | 0 |
| 1.325 | CH$_2$OCH$_3$ | CF$_3$ | Ph | H | OH | 0 |

TABLE 1-continued

| Comp. No. | R₁ | R₂ | R₃ | R₄ | R₅ | p |
|---|---|---|---|---|---|---|
| 1.326 | CH₂OCH₃ | CF₃ | Cl | H | OH | 0 |
| 1.327 | CH₂OCH₃ | CF₃ | CO₂CH₂CH₃ | H | OH | 0 |
| 1.328 | CH₂OCH₃ | CF₃ | CO₂CH₂Ph | H | OH | 0 |
| 1.329 | CH₂OCH₃ | CF₃ | CH₃ | H | OH | 1 |
| 1.33 | CH₂OCH₃ | CF₃ | Ph | H | OH | 1 |
| 1.331 | CH₂OCH₃ | CF₃ | Cl | H | OH | 1 |
| 1.332 | CH₂OCH₃ | CF₃ | CO₂CH₂CH₃ | H | OH | 1 |
| 1.333 | CH₂OCH₃ | CF₃ | CO₂CH₂Ph | H | OH | 1 |
| 1.334 | COOCH₃ | H | H | H | OH | 0 |
| 1.335 | CF₃ | SCH₃ | H | H | OH | 0 |
| 1.336 | CH₃ | SCH₃ | H | H | OH | 0 |
| 1.337 | CF₃ | SOCH₃ | H | H | OH | 0 |
| 1.338 | CH₃ | SOCH₃ | H | H | OH | 0 |
| 1.339 | CF₃ | SO₂CH₃ | H | H | OH | 0 |
| 1.34 | CH₃ | SO₂CH₃ | H | H | OH | 0 |
| 1.341 | CF₃ | SCH₂CH₃ | H | H | OH | 0 |
| 1.342 | CH₃ | SCH₂CH₃ | H | H | OH | 0 |
| 1.343 | CF₃ | SOCH₂CH₃ | H | H | OH | 0 |
| 1.344 | CH₃ | SOCH₂CH₃ | H | H | OH | 0 |
| 1.345 | CF₃ | SO₂CH₂CH₃ | H | H | OH | 0 |
| 1.346 | CH₃ | SO₂CH₂CH₃ | H | H | OH | 0 |
| 1.347 | CF₃ | OCH₃ | H | H | OH | 0 |
| 1.348 | CH₃ | OCH₃ | H | H | OH | 0 |
| 1.349 | CF₃ | OCH₂CF₃ | H | H | OH | 0 |
| 1.35 | CH₃ | OCH₂CF₃ | H | H | OH | 0 |
| 1.351 | CF₃ | OCH₂CCH | H | H | OH | 0 |
| 1.352 | CH₃ | OCH₂CCH | H | H | OH | 0 |
| 1.353 | CF₃ | CN | H | H | OH | 0 |
| 1.354 | CH₃ | CN | H | H | OH | 0 |
| 1.355 | CF₃ | Cl | H | H | OH | 0 |
| 1.356 | CF₃ | Cl | H | H | O-NEt₃+ | 0 |
| 1.357 | CH₃ | Cl | H | H | OH | 0 |
| 1.358 | H | Cl | H | H | OH | 0 |
| 1.359 | CF₃ | OCH₃ | H | H | OH | 0 |
| 1.36 | CH₃ | OCH₃ | H | H | OH | 0 |
| 1.361 | CF₃ | CH₃ | H | H | OH | 0 |
| 1.362 | H | CF₃ | H | CH₃ | OH | 0 |
| 1.363 | H | CF₃ | H | CF₃ | OH | 0 |
| 1.364 | H | CF₃ | H | CH₂CH₃ | OH | 0 |
| 1.365 | H | CF₃ | H | CF₃ | OH | 0 |
| 1.366 | H | CF₃ | H | SCH₃ | OH | 0 |
| 1.367 | H | CF₃ | H | SOCH₃ | OH | 0 |
| 1.368 | H | CF₃ | H | SO₂CH₃ | OH | 0 |
| 1.369 | H | CF₃ | H | Cl | OH | 0 |
| 1.37 | H | CF₃ | H | OCH₃ | OH | 0 |
| 1.371 | H | CH₃ | H | CF₃ | OH | 0 |
| 1.372 | H | Cl | H | CF₃ | OH | 0 |
| 1.373 | H | OCH₃ | H | CF₃ | OH | 0 |
| 1.374 | H | SCH₃ | H | CF₃ | OH | 0 |
| 1.375 | H | SOCH₃ | H | CF₃ | OH | 0 |
| 1.376 | CH₃ | CF₃ | H | H | O-K+ | 0 |
| 1.377 | CH₃ | CF₃ | H | H | S(CH₂)₇CH₃ | 0 |
| 1.378 | CH₃ | CF₃ | H | H | S(CH₂)₇CH₃ | 0 |
| 1.379 | CH₃ | CF₃ | H | H | SO(CH₂)₇CH₃ | 0 |
| 1.38 | CH₃ | CF₃ | H | H | SO₂(CH₂)₇CH₃ | 0 |
| 1.381 | CH₃ | CF₃ | H | H | SPh | 0 |
| 1.382 | CH₃ | CF₃ | H | H | SOPh | 0 |
| 1.383 | CH₃ | CF₃ | H | H | SO₂Ph | 0 |
| 1.384 | CH₃ | CF₃ | H | H | NOCH₃ | 0 |
| 1.385 | CH₃ | CF₃ | H | H | NOCH₂Ph | 0 |
| 1.386 | CH₃ | CF₃ | H | H | NOCH₂CH=CH₂ | 0 |
| 1.387 | CH₃ | CF₃ | H | H | NOC(CH₃)₃ | 0 |
| 1.388 | CH₃ | CF₃ | H | H | NOCH₂CH₃ | 0 |
| 1.389 | CH₃ | CF₃ | H | H | NCH₂CH₂SH | 0 |
| 1.39 | CH₃ | CF₃ | H | H | NN(CH₃)₂ | 0 |

TABLE 1-continued

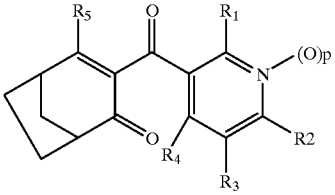

| Comp. No. | R₁ | R₂ | R₃ | R₄ | R₅ | p |
|---|---|---|---|---|---|---|
| 1.391 | CH₃ | CF₃ | H | H | NN(CH₃)C(S)NH₂ | 0 |
| 1.392 | CH₃ | CF₃ | H | H | N-morpholino | 0 |
| 1.393 | CH₃ | CF₃ | H | H | NHCOCH₃ | 0 |
| 1.394 | CH₃ | CF₃ | H | H | NHCO(CH₂)₇CH₃ | 0 |
| 1.395 | CH₃ | CF₃ | H | H | NHCOPh | 0 |
| 1.396 | CH₃ | CF₃ | H | H | NHSO₂CH₃ | 0 |
| 1.397 | CH₃ | CF₃ | H | H | NH(CO)S(CH₂)₇CH₃ | 0 |
| 1.398 | CH₃ | CF₃ | H | H | Cl | 0 |
| 1.399 | CH₃ | CF₃ | H | H | NH₂ | 0 |
| 1.4 | CH₃ | CF₃ | H | H | OCOC(CH₃)₃ | 0 |
| 1.401 | CH₃ | CF₃ | H | H | OCOCH₃ | 0 |
| 1.402 | CH₃ | CF₃ | H | H | OCOPh | 0 |
| 1.403 | CH₃ | CF₃ | H | H | OCO-cyclopropyl | 0 |
| 1.404 | CH₃ | CF₃ | H | H | OCOCH₂CH₃ | 0 |
| 1.405 | CH₃ | CF₃ | H | H | OCOCH=CH₂ | 0 |
| 1.406 | CH₃ | CF₃ | H | H | OCOCH=CHCH₃ | 0 |
| 1.407 | CH₃ | CF₃ | H | H | O(CO)SCH₃ | 0 |
| 1.408 | CH₃ | CF₃ | H | H | O(CO)S(CH₂)₇CH₃ | 0 |
| 1.409 | CH₃ | CF₃ | H | H | O(CO)OCH₂CH₃ | 0 |
| 1.41 | CH₃ | CF₃ | H | H | O(CO)N(CH₂CH₃)₂ | 0 |
| 1.411 | CH₃ | (CF₂)₃CF₃ | H | H | OH | 0 |
| 1.412 | CH₃ | CF₃ | H | H | S-(4-Cl-phenyl) | 0 |
| 1.413 | CH₃ | CF₃ | H | H | SO-(4-Cl-phenyl) | 0 |
| 1.414 | CH₃ | CF₃ | H | H | SO₂-(4-Cl-phenyl) | 0 |
| 1.415 | CH₃ | CF₃ | H | H | S-(4-CF₃-phenyl) | 0 |
| 1.416 | CH₃ | CF₃ | H | H | SO-(4-CF₃-phenyl) | 0 |
| 1.417 | CH₃ | CF₃ | H | H | SO₂-(4-CF₃-phenyl) | 0 |
| 1.418 | CH₃ | CF₃ | H | H | S-(4-NO₂-phenyl) | 0 |
| 1.419 | CH₃ | CF₃ | H | H | SO-(4-NO₂-phenyl) | 0 |
| 1.42 | CH₃ | CF₃ | H | H | SO₂-(4-NO₂-phenyl) | 0 |
| 1.421 | CH₃ | CF₃ | H | H | 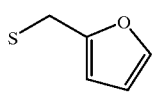 | 0 |
| 1.422 | CH₃ | CF₃ | H | H | 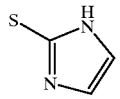 | 0 |
| 1.423 | CH₃ | CF₃ | H | H | 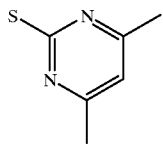 | 0 |
| 1.424 | CH₃ | CF₃ | H | H | 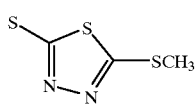 | 0 |
| 1.425 | CF₂H | SCH₃ | H | H | OH | 0 |
| 1.426 | CF₂Cl | SCH₃ | H | H | OH | 0 |
| 1.427 | CF₂H | SOCH₃ | H | H | OH | 0 |
| 1.428 | CF₂Cl | SOCH₃ | H | H | OH | 0 |
| 1.429 | CF₂H | SO₂CH₃ | H | H | OH | 0 |
| 1.43 | CF₂Cl | SO₂CH₃ | H | H | OH | 0 |
| 1.431 | CF₂H | SCH₂CH₃ | H | H | OH | 0 |
| 1.432 | CF₂Cl | SCH₂CH₃ | H | H | OH | 0 |
| 1.433 | CF₂H | SOCH₂CH₃ | H | H | OH | 0 |

TABLE 1-continued

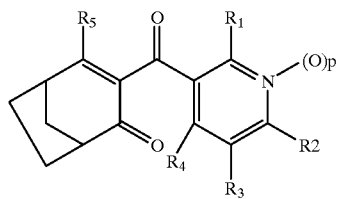

| Comp. No. | R₁ | R₂ | R₃ | R₄ | R₅ | p |
|---|---|---|---|---|---|---|
| 1.434 | CF₂Cl | SOCH₂CH₃ | H | H | OH | 0 |
| 1.435 | CF₂H | SO₂CH₂CH₃ | H | H | OH | 0 |
| 1.436 | CF₂Cl | SO₂CH₂CH₃ | H | H | OH | 0 |
| 1.437 | CF₂H | OCH₃ | H | H | OH | 0 |
| 1.438 | CF₂Cl | OCH₃ | H | H | OH | 0 |
| 1.439 | CF₂H | OCH₂CF₃ | H | H | OH | 0 |
| 1.44 | CF₂Cl | OCH₂CF₃ | H | H | OH | 0 |
| 1.441 | CF₂H | OCH₂CCH | H | H | OH | 0 |
| 1.442 | CF₂Cl | OCH₂CCH | H | H | OH | 0 |
| 1.443 | CF₂H | CN | H | H | OH | 0 |
| 1.444 | CF₂Cl | CN | H | H | OH | 0 |
| 1.445 | CF₂H | Cl | H | H | OH | 0 |
| 1.446 | CF₂Cl | Cl | H | H | OH | 0 |
| 1.447 | CF₂H | OCH₃ | H | H | OH | 0 |
| 1.448 | CF₂Cl | OCH₃ | H | H | OH | 0 |
| 1.449 | CF₃ | CH₂OCH₃ | H | H | OH | 0 |
| 1.45 | CF₃ | CH₂OCH₃ | H | H | OH | 1 |
| 1.451 | CF₂Cl | CH₂OCH₃ | H | H | OH | 0 |
| 1.452 | CF₂Cl | CH₂OCH₃ | H | H | OH | 1 |
| 1.453 | CF₂H | CH₂OCH₃ | H | H | OH | 0 |
| 1.454 | CF₂H | CH₂OCH₃ | H | H | OH | 1 |
| 1.455 | CN | CF₃ | H | H | OH | 0 |

TABLE 2

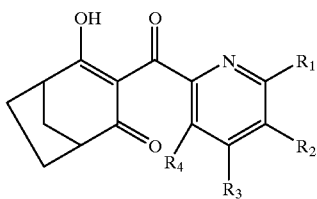

| Comp. No. | R₁ | R₂ | R₃ | R₄ |
|---|---|---|---|---|
| 2.001 | H | CF₃ | H | H |
| 2.002 | F | CF₃ | H | H |
| 2.003 | Cl | CF₃ | H | H |
| 2.004 | Br | CF₃ | H | H |
| 2.005 | CHF₂ | CF₃ | H | H |
| 2.006 | CCl₃ | CF₃ | H | H |
| 2.007 | CClF₂ | CF₃ | H | H |
| 2.008 | CF₃ | CF₃ | H | H |
| 2.009 | CH₃ | CF₃ | H | H |
| 2.01 | CH₂CH₃ | CF₃ | H | H |
| 2.011 | CH(CH₃)₂ | CF₃ | H | H |
| 2.012 | (CH₂)₂CH₃ | CF₃ | H | H |
| 2.013 | Ph | CF₃ | H | H |
| 2.014 | CH₂F | CF₃ | H | H |
| 2.015 | CH₂Cl | CF₃ | H | H |
| 2.016 | CH₂Br | CF₃ | H | H |
| 2.017 | CH₂OH | CF₃ | H | H |
| 2.018 | CH₂OCOCH₃ | CF₃ | H | H |
| 2.019 | CH₂OCOPh | CF₃ | H | H |
| 2.02 | CH₂OCH₃ | CF₃ | H | H |
| 2.021 | CH₂OCH₂CH₃ | CF₃ | H | H |
| 2.022 | CH₂CH₂OCH₃ | CF₃ | H | H |
| 2.023 | CH₂SMe | CF₃ | H | H |

TABLE 2-continued

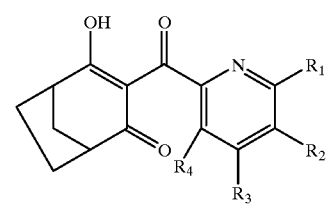

| Comp. No. | R₁ | R₂ | R₃ | R₄ |
|---|---|---|---|---|
| 2.024 | CH₂SOMe | CF₃ | H | H |
| 2.025 | CH₂SO₂Me | CF₃ | H | H |
| 2.026 | CH₂SO₂Ph | CF₃ | H | H |
| 2.027 | SCH₂ph | CF₃ | H | H |
| 2.028 | SOCH₂Ph | CF₃ | H | H |
| 2.029 | SO₂CH₂Ph | CF₃ | H | H |
| 2.03 | SCH₃ | CF₃ | H | H |
| 2.031 | SOCH₃ | CF₃ | H | H |
| 2.032 | SO₂CH₃ | CF₃ | H | H |
| 2.033 | N(CH₃)₂ | CF₃ | H | H |
| 2.034 | CH=CH₂ | CF₃ | H | H |
| 2.035 | CH₂CH=CH₂ | CF₃ | H | H |
| 2.036 | SO₂N(CH₃)₂ | CF₃ | H | H |

TABLE 2-continued

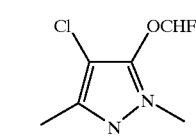

| Comp. No. | R₁ | R₂ | R₃ | R₄ |
|---|---|---|---|---|
| 2.037 | CCH | CF₃ | H | H |
| 2.038 | OCH₃ | CF₃ | H | H |
| 2.039 | OPh | CF₃ | H | H |
| 2.04 | OCHF₂ | CF₃ | H | H |
| 2.041 | CO₂Me | CF₃ | H | H |
| 2.042 | OCH₂CCH | CF₃ | H | H |
| 2.043 | OCH₂CF₃ | CF₃ | H | H |
| 2.044 | H | CF₃ | H | Cl |
| 2.045 | (Cl, OCHF₂-pyrazole) | F | H | Cl |
| 2.046 | CN | CF₃ | H | H |
| 2.047 | H | CHF₂ | H | H |
| 2.048 | CH₃ | CHF₂ | H | H |
| 2.049 | CH₂CH₃ | CHF₂ | H | H |
| 2.05 | CH₂OCH₃ | CHF₂ | H | H |
| 2.051 | H | CF₂Cl | H | H |
| 2.052 | CH₃ | CF₂Cl | H | H |
| 2.053 | CH₂CH₃ | CF₂Cl | H | H |
| 2.054 | CH₂OCH₃ | CF₂Cl | H | H |

TABLE 3

| Comp. No. | R₁ | R₂ | R₃ | R₄ |
|---|---|---|---|---|
| 3.001 | H | CF₃ | H | H |
| 3.002 | F | CF₃ | H | H |
| 3.003 | Cl | CF₃ | H | H |
| 3.004 | Br | CF₃ | H | H |
| 3.005 | CHF₂ | CF₃ | H | H |
| 3.006 | CCl₃ | CF₃ | H | H |
| 3.007 | CClF₂ | CF₃ | H | H |
| 3.008 | CF₃ | CF₃ | H | H |
| 3.009 | CH₃ | CF₃ | H | H |
| 3.01 | CH₂CH₃ | CF₃ | H | H |
| 3.011 | CH(CH₃)₂ | CF₃ | H | H |
| 3.012 | (CH₂)₂CH₃ | CF₃ | H | H |
| 3.013 | Ph | CF₃ | H | H |
| 3.014 | CH₂F | CF₃ | H | H |
| 3.015 | CH₂Cl | CF₃ | H | H |
| 3.016 | CH₂Br | CF₃ | H | H |
| 3.017 | CH₂OH | CF₃ | H | H |

TABLE 3-continued

| Comp. No. | R₁ | R₂ | R₃ | R₄ |
|---|---|---|---|---|
| 3.018 | CH₂OCOCH₃ | CF₃ | H | H |
| 3.019 | CH₂OCOPh | CF₃ | H | H |
| 3.02 | CH₂OCH₃ | CF₃ | H | H |
| 3.021 | CH₂OCH₂CH₃ | CF₃ | H | H |
| 3.022 | CH₂CH₂OCH₃ | CF₃ | H | H |
| 3.023 | CH₂SMe | CF₃ | H | H |
| 3.024 | CH₂SOMe | CF₃ | H | H |
| 3.025 | CH₂SO₂Me | CF₃ | H | H |
| 3.026 | CH₂SO₂Ph | CF₃ | H | H |
| 3.027 | SCH₂Ph | CF₃ | H | H |
| 3.028 | SOCH₂Ph | CF₃ | H | H |
| 3.029 | SO₂CH₂Ph | CF₃ | H | H |
| 3.03 | SCH₃ | CF₃ | H | H |
| 3.031 | SOCH₃ | CF₃ | H | H |
| 3.032 | SO₂CH₃ | CF₃ | H | H |
| 3.033 | N(CH₃)₂ | CF₃ | H | H |
| 3.034 | CH=CH₂ | CF₃ | H | H |
| 3.035 | CH₂CH=CH₂ | CF₃ | H | H |
| 3.036 | SO₂N(CH₃)₂ | CF₃ | H | H |
| 3.037 | CCH | CF₃ | H | H |
| 3.038 | OCH₃ | CF₃ | H | H |
| 3.039 | OPh | CF₃ | K | H |
| 3.04 | OCHF₂ | CF₃ | H | H |
| 3.041 | CO₂Me | CF₃ | H | H |
| 3.042 | OCH₂CCH | CF₃ | H | H |
| 3.043 | OCH₂CF₃ | CF₃ | H | H |
| 3.044 | H | CF₃ | H | H |
| 3.045 | CN | CF₃ | H | H |
| 3.046 | H | CHF₂ | H | H |
| 3.047 | CH₃ | CHF₂ | H | H |
| 3.048 | CH₂CH₃ | CHF₂ | H | H |
| 3.049 | CH₂OCH₃ | CHF₂ | H | H |
| 3.05 | H | CF₂Cl | H | H |
| 3.051 | CH₃ | CF₂Cl | H | H |
| 3.052 | CH₂CH₃ | CF₂Cl | H | H |
| 3.053 | CH₂OCH₃ | CF₂Cl | H | H |
| 3.054 | Cl | CH₃ | H | H |
| 3.055 | CN | SCH₃ | H | H |
| 3.056 | CN | SO₂CH₃ | H | H |

TABLE 4

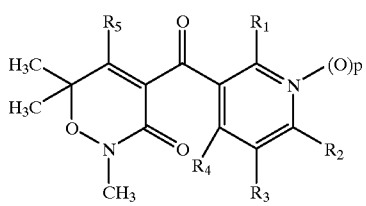

| Comp. No. | R₁ | R₂ | R₃ | R₄ | R₅ | P |
|---|---|---|---|---|---|---|
| 4.001 | H | CF₃ | H | H | OH | 0 |
| 4.002 | F | CF₃ | H | H | OH | 0 |
| 4.003 | Cl | CF₃ | H | H | OH | 0 |
| 4.004 | Br | CF₃ | H | H | OH | 0 |
| 4.005 | CHF₂ | CF₃ | H | H | OH | 0 |
| 4.006 | CCl₃ | CF₃ | H | H | OH | 0 |
| 4.007 | CClF₂ | CF₃ | H | H | OH | 0 |
| 4.008 | CF₃ | CF₃ | H | H | OH | 0 |
| 4.009 | CH₃ | CF₃ | H | H | OH | 0 |
| 4.01 | CH₂CH₃ | CF₃ | H | H | OH | 0 |
| 4.011 | CH(CH₃)₂ | CF₃ | H | H | OH | 0 |
| 4.012 | (CH₂)₂CH₃ | CF₃ | H | H | OH | 0 |
| 4.013 | C(CH₃)₃ | CF₃ | H | H | OH | 0 |
| 4.014 | Ph | CF₃ | H | H | OH | 0 |
| 4.015 | CH₂F | CF₃ | H | H | OH | 0 |
| 4.016 | CH₂Cl | CF₃ | H | H | OH | 0 |
| 4.017 | CH₂Br | CF₃ | H | H | OH | 0 |
| 4.018 | CH₂OH | CF₃ | H | H | OH | 0 |
| 4.019 | CH₂OCOCH₃ | CF₃ | H | H | OH | 0 |
| 4.02 | CH₂OCOPh | CF₃ | H | H | OH | 0 |
| 4.021 | CH₂OCH₃ | CF₃ | H | H | OH | 0 |
| 4.022 | CH₂OCH₂CH₃ | CF₃ | H | H | OH | 0 |
| 4.023 | CH₂CH₂OCH₃ | CF₃ | H | H | OH | 0 |
| 4.024 | CH₂SMe | CF₃ | H | H | OH | 0 |
| 4.025 | CH₂SOMe | CF₃ | H | H | OH | 0 |
| 4.026 | CH₂SO₂Me | CF₃ | H | H | OH | 0 |
| 4.027 | CH₂SO₂Ph | CF₃ | H | H | OH | 0 |
| 4.028 | N(CH₃)₂ | CF₃ | H | H | OH | 0 |
| 4.029 | CH=CH₂ | CF₃ | H | H | OH | 0 |
| 4.03 | CH₂CH=CH₂ | CF₃ | H | H | OH | 0 |
| 4.031 | SO₂N(CH₃)₂ | CF₃ | H | H | OH | 0 |
| 4.032 | CCH | CF₃ | H | H | OH | 0 |
| 4.033 | cyclopropyl | CF₃ | H | H | OH | 0 |
| 4.034 | OCH₃ | CF₃ | H | H | OH | 0 |
| 4.035 | OPh | CF₃ | H | H | OH | 0 |
| 4.036 | OCHF₂ | CF₃ | H | H | OH | 0 |
| 4.037 | CO₂Me | CF₃ | H | H | OH | 0 |
| 4.038 | OCH₂CCH | CF₃ | H | H | OH | 0 |
| 4.039 | H | CF₃ | H | H | OH | 1 |
| 4.04 | F | CF₃ | H | H | OH | 1 |
| 4.041 | Cl | CF₃ | H | H | OH | 1 |
| 4.042 | Br | CF₃ | H | H | OH | 1 |
| 4.043 | CHF₂ | CF₃ | H | H | OH | 1 |
| 4.044 | Cl₃ | CF₃ | H | H | OH | 1 |
| 4.045 | CClF₂ | CF₃ | H | H | OH | 1 |
| 4.046 | CF₃ | CF₃ | H | H | OH | 1 |
| 4.047 | CH₃ | CF₃ | H | H | OH | 1 |
| 4.048 | CH₂CH₃ | CF₃ | H | H | OH | 1 |
| 4.049 | CH(CH₃)₂ | CF₃ | H | H | OH | 1 |
| 4.05 | (CH₂)₂CH₃ | CF₃ | H | H | OH | 1 |
| 4.051 | C(CH₃)₃ | CF₃ | H | H | OH | 1 |
| 4.052 | Ph | CF₃ | H | H | OH | 1 |
| 4.053 | CH₂F | CF₃ | H | H | OH | 1 |
| 4.054 | CH₂Cl | CF₃ | H | H | OH | 1 |
| 4.055 | CH₂Br | CF₃ | H | H | OH | 1 |
| 4.056 | CH₂OH | CF₃ | H | H | OH | 1 |
| 4.057 | CH₂OCOCH₃ | CF₃ | H | H | OH | 1 |
| 4.058 | CH₂OCOPh | CF₃ | H | H | OH | 1 |
| 4.059 | CH₂OCH₃ | CF₃ | H | H | OH | 1 |
| 4.06 | CH₂OCH₂CH₃ | CF₃ | H | H | OH | 1 |
| 4.061 | CH₂CH₂OCH₃ | CF₃ | H | H | OH | 1 |
| 4.062 | CH₂SMe | CF₃ | H | H | OH | 1 |
| 4.063 | CH₂SOMe | CF₃ | H | H | OH | 1 |
| 4.064 | CH₂SO₂Me | CF₃ | H | H | OH | 1 |
| 4.065 | CH₂SO₂Ph | CF₃ | H | H | OH | 1 |

TABLE 4-continued

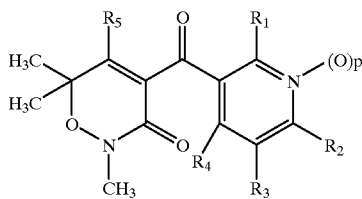

| Comp. No. | R₁ | R₂ | R₃ | R₄ | R₅ | P |
|---|---|---|---|---|---|---|
| 4.066 | N(CH₃)₂ | CF₃ | H | H | OH | 1 |
| 4.067 | CH=CH₂ | CF₃ | H | H | OH | 1 |
| 4.068 | CH₂CH=CH₂ | CF₃ | H | H | OH | 1 |
| 4.069 | SO₂N(CH₃)₂ | CF₃ | H | H | OH | 1 |
| 4.07 | CCH | CF₃ | H | H | OH | 1 |
| 4.071 | cyclopropyl | CF₃ | H | H | OH | 1 |
| 4.072 | OCH₃ | CF₃ | H | H | OH | 1 |
| 4.073 | OPh | CF₃ | H | H | OH | 1 |
| 4.074 | OCHF₂ | CF₃ | H | H | OH | 1 |
| 4.075 | CO₂Me | CF₃ | H | H | OH | 1 |
| 4.076 | 2-furyl | CF₃ | H | H | OH | 1 |
| 4.077 | OCH₂CCH | CF₃ | H | H | OH | 1 |
| 4.078 | H | CF₂CF₃ | H | H | OH | 0 |
| 4.079 | Cl | CF₂CF₃ | H | H | OH | 0 |
| 4.08 | CHF₂ | CF₂CF₃ | H | H | OH | 0 |
| 4.081 | CCl₃ | CF₂CF₃ | H | H | OH | 0 |
| 4.082 | CClF₂ | CF₂CF₃ | H | H | OH | 0 |
| 4.083 | CF₃ | CF₂CF₃ | H | H | OH | 0 |
| 4.084 | CH₃ | CF₂CF₃ | H | H | OH | 0 |
| 4.085 | CH₂CH₃ | CF₂CF₃ | H | H | OH | 0 |
| 4.086 | CH(CH₃)₂ | CF₂CF₃ | H | H | OH | 0 |
| 4.087 | (CH₂)₂CH₃ | CF₂CF₃ | H | H | OH | 0 |
| 4.088 | C(CH₃)₃ | CF₂CF₃ | H | H | OH | 0 |
| 4.089 | CH₂F | CF₂CF₃ | H | H | OH | 0 |
| 4.09 | CH₂Cl | CF₂CF₃ | H | H | OH | 0 |
| 4.091 | CH₂OH | CF₂CF₃ | H | H | OH | 0 |
| 4.092 | CH₂OCOCH₃ | CF₂CF₃ | H | H | OH | 0 |
| 4.093 | CH₂OCOPh | CF₂CF₃ | H | H | OH | 0 |
| 4.094 | CH₂OCH₃ | CF₂CF₃ | H | H | OH | 0 |
| 4.095 | CH₂OCH₂CH₃ | CF₂CF₃ | H | H | OH | 0 |
| 4.096 | CH₂SMe | CF₂CF₃ | H | H | OH | 0 |
| 4.097 | CH₂SOMe | CF₂CF₃ | H | H | OH | 0 |
| 4.098 | CH₂SO₂Me | CF₂CF₃ | H | H | OH | 0 |
| 4.099 | CH₂SO₂Ph | CF₂CF₃ | H | H | OH | 0 |
| 4.1 | N(CH₃)₂ | CF₂CF₃ | H | H | OH | 0 |
| 4.101 | CH=CH₂ | CF₂CF₃ | H | H | OH | 0 |
| 4.102 | CH₂CH=CH₂ | CF₂CF₃ | H | H | OH | 0 |
| 4.103 | SO₂N(CH₃)₂ | CF₂CF₃ | H | H | OH | 0 |
| 4.104 | CCH | CF₂CF₃ | H | H | OH | 0 |
| 4.105 | cyclopropyl | CF₂CF₃ | H | H | OH | 0 |
| 4.106 | OPh | CF₂CF₃ | H | H | OH | 0 |
| 4.107 | OCH₃ | CF₂CF₃ | H | H | OH | 0 |
| 4.108 | CO₂Me | CF₂CF₃ | H | H | OH | 0 |
| 4.109 | OCH₂CCH | CF₂CF₃ | H | H | OH | 0 |
| 4.11 | H | CF₂CF₂CF₃ | H | H | OH | 0 |
| 4.111 | CHF₂ | CF₂CF₂CF₃ | H | H | OH | 0 |
| 4.112 | CF₃ | CF₂CF₂CF₃ | H | H | OH | 0 |
| 4.113 | CH₃ | CF₂CF₂CF₃ | H | H | OH | 0 |
| 4.114 | CH₂CH₃ | CF₂CF₂CF₃ | H | H | OH | 0 |
| 4.115 | (CH₂)₂CH₃ | CF₂CF₂CF₃ | H | H | OH | 0 |
| 4.116 | CH₂Cl | CF₂CF₂CF₃ | H | H | OH | 0 |
| 4.117 | CH₂OCH₃ | CF₂CF₂CF₃ | H | H | OH | 0 |
| 4.118 | H | CF₂Cl | H | H | OH | 0 |
| 4.119 | Cl | CF₂Cl | H | H | OH | 0 |
| 4.12 | CHF₂ | CF₂Cl | H | H | OH | 0 |
| 4.121 | CCl₃ | CF₂Cl | H | H | OH | 0 |
| 4.122 | CClF₂ | CF₂Cl | H | H | OH | 0 |
| 4.123 | CF₃ | CF₂Cl | H | H | OH | 0 |
| 4.124 | CH₃ | CF₂Cl | H | H | OH | 0 |
| 4.125 | CH₂CH₃ | CF₂Cl | H | H | OH | 0 |
| 4.126 | CH(CH₃)₂ | CF₂Cl | H | H | OH | 0 |
| 4.127 | (CH₂)₂CH₃ | CF₂Cl | H | H | OH | 0 |
| 4.128 | C(CH₃)₃ | CF₂Cl | H | H | OH | 0 |
| 4.129 | CH₂F | CF₂Cl | H | H | OH | 0 |
| 4.13 | CH₂Cl | CF₂Cl | H | H | OH | 0 |

TABLE 4-continued

| Comp. No. | R₁ | R₂ | R₃ | R₄ | R₅ | P |
|---|---|---|---|---|---|---|
| 4.131 | CH$_2$OH | CF$_2$Cl | H | H | OH | 0 |
| 4.132 | CH$_2$OCOCH$_3$ | CF$_2$Cl | H | H | OH | 0 |
| 4.133 | CH$_2$OCOPh | CF$_2$Cl | H | H | OH | 0 |
| 4.134 | CH$_2$OCH$_3$ | CF$_2$Cl | H | H | OH | 0 |
| 4.135 | CH$_2$OCH$_2$CH$_3$ | CF$_2$Cl | H | H | OH | 0 |
| 4.136 | CH$_2$SMe | CF$_2$Cl | H | H | OH | 0 |
| 4.137 | CH$_2$SOMe | CF$_2$Cl | H | H | OH | 0 |
| 4.138 | CH$_2$SO$_2$Me | CF$_2$Cl | H | H | OH | 0 |
| 4.139 | CH$_2$SO$_2$Ph | CF$_2$Cl | H | H | OH | 0 |
| 4.14 | N(CH$_3$)$_2$ | CF$_2$Cl | H | H | OH | 0 |
| 4.141 | CH=CH$_2$ | CF$_2$Cl | H | H | OH | 0 |
| 4.142 | CH$_2$CH=CH$_2$ | CF$_2$Cl | H | H | OH | 0 |
| 4.143 | SO$_2$N(CH$_3$)$_2$ | CF$_2$Cl | H | H | OH | 0 |
| 4.144 | CCH | CF$_2$Cl | H | H | OH | 0 |
| 4.145 | cyclopropyl | CF$_2$Cl | H | H | OH | 0 |
| 4.146 | OPh | CF$_2$Cl | H | H | OH | 0 |
| 4.147 | OCH$_3$ | CF$_2$Cl | H | H | OH | 0 |
| 4.148 | CO$_2$Me | CF$_2$Cl | H | H | OH | 0 |
| 4.149 | OCH$_2$CCH | CF$_2$Cl | H | H | OH | 0 |
| 4.15 | CH$_3$ | CF$_2$Cl | H | H | OH | 1 |
| 4.151 | CH$_2$OCH$_3$ | CF$_2$Cl | H | H | OH | 1 |
| 4.152 | H | CCl$_3$ | H | H | OH | 0 |
| 4.153 | Cl | CCl$_3$ | H | H | OH | 0 |
| 4.154 | CH$_3$ | CCl$_3$ | H | H | OH | 0 |
| 4.155 | CH$_2$CH$_3$ | CCl$_3$ | H | H | OH | 0 |
| 4.156 | CH(CH$_3$)$_2$ | CCl$_3$ | H | H | OH | 0 |
| 4.157 | (CH$_2$)$_2$CH$_3$ | CCl$_3$ | H | H | OH | 0 |
| 4.158 | CH$_2$F | CCl$_3$ | H | H | OH | 0 |
| 4.159 | CH$_2$Cl | CCl$_3$ | H | H | OH | 0 |
| 4.16 | CH$_2$OH | CCl$_3$ | H | H | OH | 0 |
| 4.161 | CH$_2$OCOCH$_3$ | CCl$_3$ | H | H | OH | 0 |
| 4.162 | CH$_2$OCOPh | CCl$_3$ | H | H | OH | 0 |
| 4.163 | CH$_2$OCH$_3$ | CCl$_3$ | H | H | OH | 0 |
| 4.164 | CH$_2$OCH$_2$CH$_3$ | CCl$_3$ | H | H | OH | 0 |
| 4.165 | CH$_2$SMe | CCl$_3$ | H | H | OH | 0 |
| 4.166 | CH$_2$SOMe | CCl$_3$ | H | H | OH | 0 |
| 4.167 | CH$_2$SO$_2$Me | CCl$_3$ | H | H | OH | 0 |
| 4.168 | CH$_2$SO$_2$Ph | CCl$_3$ | H | H | OH | 0 |
| 4.169 | cyclopropyl | CCl$_3$ | H | H | OH | 0 |
| 4.17 | OPh | CCl$_3$ | H | H | OH | 0 |
| 4.171 | OCH$_3$ | CCl$_3$ | H | H | OH | 0 |
| 4.172 | CO$_2$Me | CCl$_3$ | H | H | OH | 0 |
| 4.173 | OCH$_2$CCH | CCl$_3$ | H | H | OH | 0 |
| 4.174 | CF$_3$ | CHF$_2$ | H | H | OH | 0 |
| 4.175 | CH$_3$ | CHF$_2$ | H | H | OH | 0 |
| 4.176 | CH$_2$OCH$_3$ | CHF$_2$ | H | H | OH | 0 |
| 4.177 | CH$_2$Cl | CHF$_2$ | H | H | OH | 0 |
| 4.178 | CH$_2$F | CHF$_2$ | H | H | OH | 0 |
| 4.179 | CF$_3$ | CHF$_2$ | H | H | OH | 1 |
| 4.18 | CH$_3$ | CHF$_2$ | H | H | OH | 1 |
| 4.181 | CH$_2$OCH$_3$ | CHF$_2$ | H | H | OH | 1 |
| 4.182 | CH$_2$Cl | CHF$_2$ | H | H | OH | 1 |
| 4.183 | CH$_2$F | CHF$_2$ | H | H | OH | 1 |
| 4.184 | CH$_3$ | CF$_3$ | H | CH$_3$ | OH | 0 |
| 4.185 | CH$_3$ | CF$_3$ | H | CH$_3$ | OH | 1 |
| 4.186 | Cl | CF$_3$ | H | CH$_3$ | OH | 0 |
| 4.187 | CH$_3$ | CF$_3$ | CH$_3$ | H | OH | 0 |
| 4.188 | CH$_3$ | CF$_3$ | Ph | H | OH | 0 |
| 4.189 | CH$_3$ | CF$_3$ | Cl | H | OH | 0 |
| 4.19 | CH$_3$ | CF$_3$ | CO$_2$CH$_2$CH$_3$ | H | OH | 0 |
| 4.191 | CH$_3$ | CF$_3$ | CO$_2$CH$_2$Ph | H | OH | 0 |
| 4.192 | CH$_3$ | CF$_3$ | CH$_3$ | H | OH | 1 |
| 4.193 | CH$_3$ | CF$_3$ | Ph | H | OH | 1 |
| 4.194 | CH$_3$ | CF$_3$ | Cl | H | OH | 1 |
| 4.195 | CH$_3$ | CF$_3$ | CO$_2$CH$_2$CH$_3$ | H | OH | 1 |

TABLE 4-continued

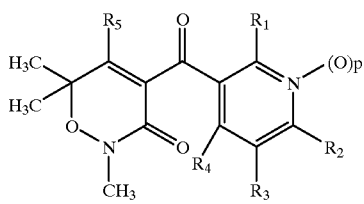

| Comp. No. | R₁ | R₂ | R₃ | R₄ | R₅ | p |
|---|---|---|---|---|---|---|
| 4.196 | CH₃ | CF₃ | OC₂CH₂Ph | H | OH | 1 |
| 4.197 | OCH₃ | CF₃ | CH₃ | H | OH | 0 |
| 4.198 | CH₂OCH₃ | CF₃ | CH₃ | H | OH | 0 |
| 4.199 | CH₂OCH₃ | CF₃ | Ph | H | OH | 0 |
| 4.2 | CH₂OCH₃ | CF₃ | Cl | H | OH | 0 |
| 4.201 | CH₂OCH₃ | CF₃ | CO₂CH₂CH₃ | H | OH | 0 |
| 4.202 | CH₂OCH₃ | CF₃ | CO₂CH₂Ph | H | OH | 0 |
| 4.203 | CH₂OCH₃ | CF₃ | CH₃ | H | OH | 1 |
| 4.204 | CH₂OCH₃ | CF₃ | Ph | H | OH | 1 |
| 4.205 | CH₂OCH₃ | CF₃ | Cl | H | OH | 1 |
| 4.206 | CH₂OCH₃ | CF₃ | CO₂CH₂CH₃ | H | OH | 1 |
| 4.207 | CH₂OCH₃ | CF₃ | CO₂CH₂Ph | H | OH | 1 |
| 4.208 | COOCH₃ | H | H | H | OH | 0 |
| 4.209 | CF₃ | SCH₃ | H | H | OH | 0 |
| 4.21 | CH₃ | SCH₃ | H | H | OH | 0 |
| 4.211 | CF₃ | SOCH₃ | H | H | OH | 0 |
| 4.212 | CH₃ | SOCH₃ | H | H | OH | 0 |
| 4.213 | CF₃ | SO₂CH₃ | H | H | OH | 0 |
| 4.214 | CH₃ | SO₂CH₃ | H | H | OH | 0 |
| 4.215 | CF₃ | SCH₂CH₃ | H | H | OH | 0 |
| 4.216 | CH₃ | SCH₂CH₃ | H | H | OH | 0 |
| 4.217 | CF₃ | SOCH₂CH₃ | H | H | OH | 0 |
| 4.218 | CH₃ | SOCH₂CH₃ | H | H | OH | 0 |
| 4.219 | CF₃ | SO₂CH₂CH₃ | H | H | OH | 0 |
| 4.22 | CH₃ | SO₂CH₂CH₃ | H | H | OH | 0 |
| 4.221 | CF₃ | OCH₃ | H | H | OH | 0 |
| 4.222 | CH₃ | OCH₃ | H | H | OH | 0 |
| 4.223 | CF₃ | OCH₂CF₃ | H | H | OH | 0 |
| 4.224 | CH₃ | OCH₂CF₃ | H | H | OH | 0 |
| 4.225 | CF₃ | OCH₂CCH | H | H | OH | 0 |
| 4.226 | CH₃ | OCH₂CCH | H | H | OH | 0 |
| 4.227 | CF₃ | CN | H | H | OH | 0 |
| 4.228 | CH₃ | CN | H | H | OH | 0 |
| 4.229 | CF₃ | Cl | H | H | OH | 0 |
| 4.23 | CH₃ | Cl | H | H | OH | 0 |
| 4.231 | H | Cl | H | H | OH | 0 |
| 4.232 | CF₃ | OCH₃ | H | H | OH | 0 |
| 4.233 | CH₃ | OCH₃ | H | H | OH | 0 |
| 4.234 | CF₃ | CH₃ | H | H | OH | 0 |
| 4.235 | H | CF₃ | H | CH₃ | OH | 0 |
| 4.236 | H | CF₃ | H | CF₃ | OH | 0 |
| 4.237 | H | CF₃ | H | CH₂CH₃ | OH | 0 |
| 4.238 | H | CF₃ | H | CF₃ | OH | 0 |
| 4.239 | H | CF₃ | H | SCH₃ | OH | 0 |
| 4.24 | H | CF₃ | H | SOCH₃ | OH | 0 |
| 4.241 | H | CF₃ | H | SO₂CH₃ | OH | 0 |
| 4.242 | H | CF₃ | H | Cl | OH | 0 |
| 4.243 | H | CF₃ | H | OCH₃ | OH | 0 |
| 4.244 | H | CH₃ | H | CF₃ | OH | 0 |
| 4.245 | H | Cl | H | CF₃ | OH | 0 |
| 4.246 | H | OCH₃ | H | CF₃ | OH | 0 |
| 4.247 | H | SCH₃ | H | CF₃ | OH | 0 |
| 4.248 | H | SOCH₃ | H | CF₃ | OH | 0 |
| 4.249 | CH₃ | CF₃ | H | H | S(CH₂)₇CH₃ | 0 |
| 4.25 | CH₃ | CF₃ | H | H | S(CH₂)₇CH₃ | 0 |
| 4.251 | CH₃ | CF₃ | H | H | SO(CH₂)₇CH₃ | 0 |
| 4.252 | CH₃ | CF₃ | H | H | SO₂(CH₂)₇CH₃ | 0 |
| 4.253 | CH₃ | CF₃ | H | H | SPh | 0 |
| 4.254 | CH₃ | CF₃ | H | H | SOPh | 0 |
| 4.255 | CH₃ | CF₃ | H | H | SO₂Ph | 0 |
| 4.256 | CH₃ | CF₃ | H | H | NOCH₃ | 0 |
| 4.257 | CH₃ | CF₃ | H | H | NOCH₂Ph | 0 |
| 4.258 | CH₃ | CF₃ | H | H | NOCH₂CH=CH₂ | 0 |
| 4.259 | CH₃ | CF₃ | H | H | NOC(CH₃)₃ | 0 |
| 4.26 | CH₃ | CF₃ | H | H | NOCH₂CH₃ | 0 |

TABLE 4-continued

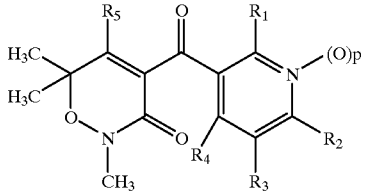

| Comp. No. | R₁ | R₂ | R₃ | R₄ | R₅ | P |
|---|---|---|---|---|---|---|
| 4.261 | CH₃ | CF₃ | H | H | NCH₂CH₂SH | 0 |
| 4.262 | CH₃ | CF₃ | H | H | NN(CH₃)₂ | 0 |
| 4.263 | CH₃ | CF₃ | H | H | NN(CH₃)C(S)NH₂ | 0 |
| 4.264 | CH₃ | CF₃ | H | H | N-morpholino | 0 |
| 4.265 | CH₃ | CF₃ | H | H | NHCOCH₃ | 0 |
| 4.266 | CH₃ | CF₃ | H | H | NHCO(CH₂)₇CH₃ | 0 |
| 4.267 | CH₃ | CF₃ | H | H | NHCOPh | 0 |
| 4.268 | CH₃ | CF₃ | H | H | NHSO₂CH₃ | 0 |
| 4.269 | CH₃ | CF₃ | H | H | NH(CO)S(CH₂)₇CH₃ | 0 |
| 4.27 | CH₃ | CF₃ | H | H | Cl | 0 |
| 4.271 | CH₃ | CF₃ | H | H | NH₂ | 0 |
| 4.272 | CH₃ | CF₃ | H | H | OCOC(CH₃)₃ | 0 |
| 4.273 | CH₃ | CF₃ | H | H | OCOCH₃ | 0 |
| 4.274 | CH₃ | CF₃ | H | H | OCOPh | 0 |
| 4.275 | CH₃ | CF₃ | H | H | OCO-cyclopropyl | 0 |
| 4.276 | CH₃ | CF₃ | H | H | OCOCH₂CH₃ | 0 |
| 4.277 | CH₃ | CF₃ | H | H | OCOCH=CH₂ | 0 |
| 4.278 | CH₃ | CF₃ | H | H | OCOCH=CHCH₃ | 0 |
| 4.279 | CH₃ | CF₃ | H | H | O(CO)SCH₃ | 0 |
| 4.28 | CH₃ | CF₃ | H | H | O(CO)S(CH₂)₇CH₃ | 0 |
| 4.281 | CH₃ | CF₃ | H | H | O(CO)OCH₂CH₃ | 0 |
| 4.282 | CH₃ | CF₃ | H | H | O(CO)N(CH₂CH₃)₂ | 0 |
| 4.283 | CH₃ | (CF₂)₃CF₃ | H | H | OH | 0 |
| 4.284 | CH₃ | CF₃ | H | H | S-(4-Cl-phenyl) | 0 |
| 4.285 | CH₃ | CF₃ | H | H | SO-(4-Cl-phenyl) | 0 |
| 4.286 | CH₃ | CF₃ | H | H | SO₂-(4-Cl-phenyl) | 0 |
| 4.287 | CH₃ | CF₃ | H | H | S-(4-CF₃-phenyl) | 0 |
| 4288 | CH₃ | CF₃ | H | H | SO-(4-CF₃-phenyl) | 0 |
| 4.289 | CH₃ | CF₃ | H | H | SO₂-(4-CF₃-phenyl) | 0 |
| 4.29 | CH₃ | CF₃ | H | H | S-(4-NO₂-phenyl) | 0 |
| 4.291 | CH₃ | CF₃ | H | H | SO-(4-NO₂-phenyl) | 0 |
| 4.292 | CH₃ | CF₃ | H | H | SO₂-(4-NO₂-phenyl) | 0 |
| 4.293 | CH₃ | CF₃ | H | H | 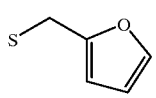 | 0 |
| 4.294 | CH₃ | CF₃ | H | H | 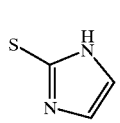 | 0 |
| 4.295 | CH₃ | CF₃ | H | H | 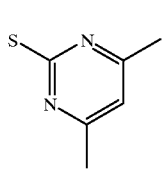 | 0 |
| 4.296 | CH₃ | CF₃ | H | H | 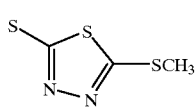 | 0 |
| 4.297 | CF₂H | SCH₃ | H | H | OH | 0 |
| 4.298 | CF₂Cl | SCH₃ | H | H | OH | 0 |
| 4.299 | CF₂H | SOCH₃ | H | H | OH | 0 |
| 4.3 | CF₂Cl | SOCH₃ | H | H | OH | 0 |
| 4.301 | CF₂H | SO₂CH₃ | H | H | OH | 0 |
| 4.302 | CF₂Cl | SO₂CH₃ | H | H | OH | 0 |

TABLE 4-continued

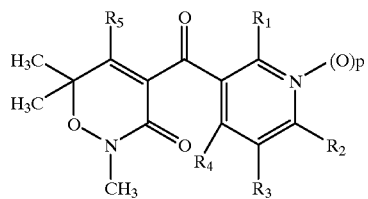

| Comp. No. | $R_1$ | $R_2$ | $R_3$ | $R_4$ | $R_5$ | P |
|---|---|---|---|---|---|---|
| 4.303 | $CF_2H$ | $SCH_2CH_3$ | H | H | OH | 0 |
| 4.304 | $CF_2Cl$ | $SCH_2CH_3$ | H | H | OH | 0 |
| 4.305 | $CF_2H$ | $SOCH_2CH_3$ | H | H | OH | 0 |
| 4.306 | $CF_2Cl$ | $SOCH_2CH_3$ | H | H | OH | 0 |
| 4.307 | $CF_2H$ | $SO_2CH_2CH_3$ | H | H | OH | 0 |
| 4.308 | $CF_2Cl$ | $SO_2CH_2CH_3$ | H | H | OH | 0 |
| 4.309 | $CF_2H$ | $OCH_3$ | H | H | OH | 0 |
| 4.31 | $CF_2Cl$ | $OCH_3$ | H | H | OH | 0 |
| 4.311 | $CF_2H$ | $OCH_2CF_3$ | H | H | OH | 0 |
| 4.312 | $CF_2Cl$ | $OCH_2CF_3$ | H | H | OH | 0 |
| 4.313 | $CF_2H$ | $OCH_2CCH$ | H | H | OH | 0 |
| 4.314 | $CF_2Cl$ | $OCH_2CCH$ | H | H | OH | 0 |
| 4.315 | $CF_2H$ | CN | H | H | OH | 0 |
| 4.316 | $CF_2Cl$ | CN | H | H | OH | 0 |
| 4.317 | $CF_2H$ | Cl | H | H | OH | 0 |
| 4.318 | $CF_2Cl$ | Cl | H | H | OH | 0 |
| 4.319 | $CF_2H$ | $OCH_3$ | H | H | OH | 0 |
| 4.32 | $CF_2Cl$ | $OCH_3$ | H | H | OH | 0 |
| 4.321 | $CF_3$ | $CH_2OCH_3$ | H | H | OH | 0 |
| 4.322 | $CF_3$ | $CH_2OCH_3$ | H | H | OH | 1 |
| 4.323 | $CF_2Cl$ | $CH_2OCH_3$ | H | H | OH | 0 |
| 4.324 | $CF_2Cl$ | $CH_2OCH_3$ | H | H | OH | 1 |
| 4.325 | $CF_2H$ | $CH_2OCH_3$ | H | H | OH | 0 |
| 4.326 | $CF_2H$ | $CH_2OCH_3$ | H | H | OH | 1 |
| 4.327 | CN | $CF_3$ | H | H | OH | 0 |
| 4.328 | $SCH_3$ | H | H | H | OH | 0 |

TABLE 5

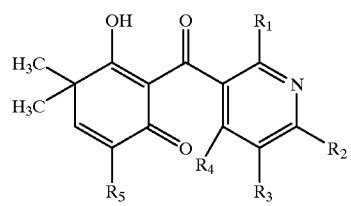

TABLE 5-continued

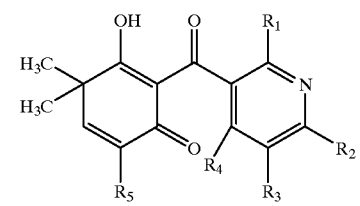

| Comp. No. | $R_1$ | $R_2$ | $R_3$ | $R_4$ | $R_5$ |
|---|---|---|---|---|---|
| 5.001 | H | $CF_3$ | H | H | $CH_3$ |
| 5.002 | F | $CF_3$ | H | H | $CH_3$ |
| 5.003 | Cl | $CF_3$ | H | H | $CH_3$ |
| 5.004 | $CHF_2$ | $CF_3$ | H | H | $CH_3$ |
| 5.005 | $CCl_3$ | $CF_3$ | H | H | $CH_3$ |
| 5.006 | $CClF_2$ | $CF_3$ | H | H | $CH_3$ |
| 5.007 | $CF_3$ | $CF_3$ | H | H | $CH_3$ |
| 5.008 | $CH_3$ | $CF_3$ | H | H | $CH_3$ |
| 5.009 | $CH_2CH_3$ | $CF_3$ | H | H | $CH_3$ |
| 5.01 | $CH(CH_3)2$ | $CF_3$ | H | H | $CH_3$ |
| 5.011 | $(CH_2)_2CH_3$ | $CF_3$ | H | H | $CH_3$ |
| 5.012 | $CH_2F$ | $CF_3$ | H | H | $CH_3$ |
| 5.013 | $CH_2Cl$ | $CF_3$ | H | H | $CH_3$ |
| 5.014 | $CH_2Br$ | $CF_3$ | H | H | $CH_3$ |
| 5.015 | $CH_2OCOCH_3$ | $CF_3$ | H | H | $CH_3$ |
| 5.016 | $CH_2OCH_3$ | $CF_3$ | H | H | $CH_3$ |
| 5.017 | $CH_2CH_2OCH_3$ | $CF_3$ | H | H | $CH_3$ |
| 5.018 | $CH_2SMe$ | $CF_3$ | H | H | $CH_3$ |
| 5.019 | $CH_2SOMe$ | $CF_3$ | H | H | $CH_3$ |
| 5.02 | $CH_2SO_2Me$ | $CF_3$ | H | H | $CH_3$ |
| 5.021 | $N(CH_3)_2$ | $CF_3$ | H | H | $CH_3$ |
| 5.022 | $CH=CH_2$ | $CF_3$ | H | H | $CH_3$ |
| 5.023 | $CH_2CH=CH_2$ | $CF_3$ | H | H | $CH_3$ |
| 5.024 | $SO_2N(CH_3)_2$ | $CF_3$ | H | H | $CH_3$ |
| 5.025 | CCH | $CF_3$ | H | H | $CH_3$ |
| 5.026 | cyclopropyl | $CF_3$ | H | H | $CH_3$ |
| 5.027 | $OCH_3$ | $CF_3$ | H | H | $CH_3$ |
| 5.028 | OPh | $CF_3$ | H | H | $CH_3$ |
| 5.029 | $OCHF_2$ | $CF_3$ | H | H | $CH_3$ |
| 5.03 | $CO_2Me$ | $CF_3$ | H | H | $CH_3$ |
| 5.031 | $OCH_2CCH$ | $CF_3$ | H | H | $CH_3$ |
| 5.032 | $CF_3$ | $SCH_3$ | H | H | $CH_3$ |
| 5.033 | $CH_3$ | $SCH_3$ | H | H | $CH_3$ |
| 5.034 | $CF_3$ | $SOCH_3$ | H | H | $CH_3$ |
| 5.035 | $CH_3$ | $SOCH_3$ | H | H | $CH_3$ |
| 5.036 | $CF_3$ | $SO_2CH_3$ | H | H | $CH_3$ |
| 5.037 | $CH_3$ | $SO_2CH_3$ | H | H | $CH_3$ |
| 5.038 | $CF_3$ | $OCH_3$ | H | H | $CH_3$ |
| 5.039 | $CH_3$ | $OCH_3$ | H | H | $CH_3$ |
| 5.04 | $CF_3$ | $OCH_2CF_3$ | H | H | $CH_3$ |

TABLE 5-continued

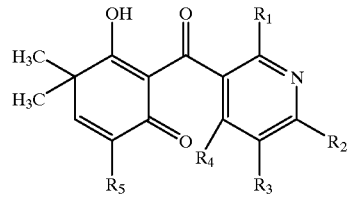

| Comp. No. | R₁ | R₂ | R₃ | R₄ | R₅ |
|---|---|---|---|---|---|
| 5.041 | CH₃ | OCH₂CF₃ | H | H | CH₃ |
| 5.042 | CF₃ | OCH₂CCH | H | H | CH₃ |
| 5.043 | CH₃ | OCH₂CCH | H | H | CH₃ |
| 5.044 | CF₃ | CN | H | H | CH₃ |
| 5.045 | CH₃ | CN | H | H | CH₃ |
| 5.046 | CF₃ | Cl | H | H | CH₃ |
| 5.047 | CH₃ | Cl | H | H | CH₃ |
| 5.048 | H | Cl | H | H | CH₃ |
| 5.049 | CF₃ | OCH₃ | H | H | CH₃ |
| 5.05 | CH₃ | OCH₃ | H | H | CH₃ |
| 5.051 | CF₃ | CH₃ | H | H | CH₃ |
| 5.052 | H | CF₃ | H | CH₃ | CH₃ |
| 5.053 | H | CF₃ | H | CF₃ | CH₃ |
| 5.054 | H | CF₃ | H | CH₂CH₃ | CH₃ |
| 5.055 | H | CF₃ | H | CF₃ | CH₃ |
| 5.056 | H | CF₃ | H | SCH₃ | CH₃ |
| 5.057 | H | CF₃ | H | SOCH₃ | CH₃ |
| 5.058 | H | CF₃ | H | SO₂CH₃ | CH₃ |
| 5.059 | H | CF₃ | H | Cl | CH₃ |
| 5.06 | H | CF₃ | H | OCH₃ | CH₃ |
| 5.061 | H | CH₃ | H | CF₃ | CH₃ |
| 5.062 | H | Cl | H | CF₃ | CH₃ |
| 5.063 | H | OCH₃ | H | CF₃ | CH₃ |
| 5.064 | H | SCH₃ | H | CF₃ | CH₃ |
| 5.065 | H | SOCH₃ | H | CF₃ | CH₃ |
| 5.066 | CF₂Cl | CH₃ | H | H | CH₃ |
| 5.067 | CF₂Cl | CH₂CH₃ | H | H | CH₃ |
| 5.068 | CF₂Cl | SCH₃ | H | H | CH₃ |
| 5.069 | CF₂Cl | SOCH₃ | H | H | CH₃ |
| 5.07 | CF₂Cl | SO₂CH₃ | H | H | CH₃ |
| 5.071 | CF₂Cl | OCH₃ | H | H | CH₃ |
| 5.072 | CF₂Cl | OCH₂CF₃ | H | H | CH₃ |
| 5.073 | CF₂Cl | OCH₂CCH | H | H | CH₃ |
| 5.074 | CF₂Cl | CN | H | H | CH₃ |
| 5.075 | CF₂Cl | Cl | H | H | CH₃ |
| 5.076 | CF₂Cl | OCH₃ | H | H | CH₃ |
| 5.077 | CF₃ | CH₂OCH₃ | H | H | CH₃ |
| 5.078 | CF₂Cl | CH₂OCH₃ | H | H | CH₃ |
| 5.079 | CF₂H | CH₂OCH₃ | H | H | CH₃ |
| 5.08 | CN | CF₃ | H | H | CH₃ |
| 5.081 | CH₃ | CF₃ | H | H | CH₂CH₃ |
| 5.082 | CH₃ | CF₃ | H | H | SCH₃ |
| 5.083 | CH₃ | CF₃ | H | H | SOCH₃ |
| 5.084 | CH₃ | CF₃ | H | H | SO₂CH₃ |
| 5.085 | CH₃ | CF₃ | H | H | H |

TABLE 6

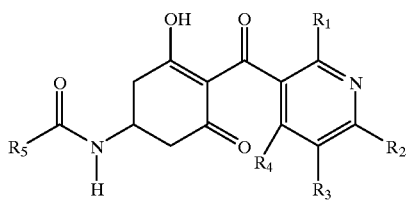

| Comp. No. | R₁ | R₂ | R₃ | R₄ | R₅ |
|---|---|---|---|---|---|
| 6.001 | Cl | CF₃ | H | H | CH₂CH₃ |
| 6.002 | CHF₂ | CF₃ | H | H | CH₂CH₃ |
| 6.003 | CCl₃ | CF₃ | H | H | CH₂CH₃ |

TABLE 6-continued

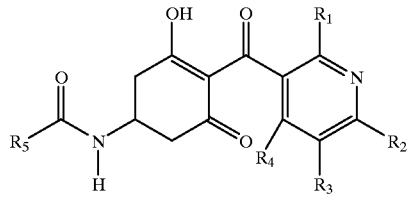

| Comp. No. | R₁ | R₂ | R₃ | R₄ | R₅ |
|---|---|---|---|---|---|
| 6.004 | CClF₂ | CF₃ | H | H | CH₂CH₃ |
| 6.005 | CF₃ | CF₃ | H | H | CH₂CH₃ |
| 6.006 | CH₃ | CF₃ | H | H | CH₂CH₃ |
| 6.007 | CH₂CH₃ | CF₃ | H | H | CH₂CH₃ |
| 6.008 | (CH₂)₂CH₃ | CF₃ | H | H | CH₂CH₃ |
| 6.009 | CH₂F | CF₃ | H | H | CH₂CH₃ |
| 6.01 | CH₂Cl | CF₃ | H | H | CH₂CH₃ |
| 6.011 | CH₂OCH₃ | CF₃ | H | H | CH₂CH₃ |
| 6.012 | CH₂SMe | CF₃ | H | H | CH₂CH₃ |
| 6.013 | CH₂SO₂Me | CF₃ | H | H | CH₂CH₃ |
| 6.014 | CH=CH₂ | CF₃ | H | H | CH₂CH₃ |
| 6.015 | CH₂CH=CH₂ | CF₃ | H | H | CH₂CH₃ |
| 6.016 | CCH | CF₃ | H | H | CH₂CH₃ |
| 6.017 | CF₃ | SCH₃ | H | H | CH₂CH₃ |
| 6.018 | CF₃ | SOCH₃ | H | H | CH₂CH₃ |
| 6.019 | CF₃ | SO₂CH₃ | H | H | CH₂CH₃ |
| 6.02 | CF₃ | OCH₃ | H | H | CH₂CH₃ |
| 6.021 | CF₃ | CN | H | H | CH₂CH₃ |
| 6.022 | CF₃ | Cl | H | H | CH₂CH₃ |
| 6.023 | CF₃ | OCH₃ | H | H | CH₂CH₃ |
| 6.024 | CF₃ | CH₃ | H | H | CH₂CH₃ |
| 6.025 | H | CF₃ | H | CH₃ | CH₂CH₃ |
| 6.026 | H | CF₃ | H | CF₃ | CH₂CH₃ |
| 6.027 | H | CF₃ | H | SCH₃ | CH₂CH₃ |
| 6.028 | H | CF₃ | H | SOCH₃ | CH₂CH₃ |
| 6.029 | H | CF₃ | H | SO₂CH₃ | CH₂CH₃ |
| 6.03 | H | CF₃ | H | Cl | CH₂CH₃ |
| 6.031 | H | CF₃ | H | OCH₃ | CH₂CH₃ |
| 6.032 | H | CH₃ | H | CF₃ | CH₂CH₃ |
| 6.033 | H | Cl | H | CF₃ | CH₂CH₃ |
| 6.034 | H | OCH₃ | H | CF₃ | CH₂CH₃ |
| 6.035 | CN | CF₃ | H | H | CH₂CH₃ |
| 6.036 | Cl | CF₃ | H | H | CH(CH₃)₂ |
| 6.037 | CHF₂ | CF₃ | H | H | CH(CH₃)₂ |
| 6.038 | CCl₃ | CF₃ | H | H | CH(CH₃)₂ |
| 6.039 | CClF₂ | CF₃ | H | H | CH(CH₃)₂ |
| 6.04 | CF₃ | CF₃ | H | H | CH(CH₃)₂ |
| 6.041 | CH₃ | CF₃ | H | H | CH(CH₃)₂ |
| 6.042 | CH₂CH₃ | CF₃ | H | H | CH(CH₃)₂ |
| 6.043 | (CH₂)₂CH₃ | CF₃ | H | H | CH(CH₃)₂ |
| 6.044 | CH₂F | CF₃ | H | H | CH(CH₃)₂ |
| 6.045 | CH₂Cl | CF₃ | H | H | CH(CH₃)₂ |
| 6.046 | CH₂OCH₃ | CF₃ | H | H | CH(CH₃)₂ |
| 6.047 | CH₂SMe | CF₃ | H | H | CH(CH₃)₂ |
| 6.048 | CH₂SO₂Me | CF₃ | H | H | CH(CH₃)₂ |
| 6.049 | CH=CH₂ | CF₃ | H | H | CH(CH₃)₂ |
| 6.05 | CH₂CH=CH₂ | CF₃ | H | H | CH(CH₃)₂ |
| 6.051 | CCH | CF₃ | H | H | CH(CH₃)₂ |
| 6.052 | CF₃ | SCH₃ | H | H | CH(CH₃)₂ |
| 6.053 | CF₃ | SOCH₃ | H | H | CH(CH₃)₂ |
| 6.054 | CF₃ | SO₂CH₃ | H | H | CH(CH₃)₂ |
| 6.055 | CF₃ | OCH₃ | H | H | CH(CH₃)₂ |
| 6.056 | CF₃ | CN | H | H | CH(CH₃)₂ |
| 6.057 | CF₃ | Cl | H | H | CH(CH₃)₂ |
| 6.058 | CF₃ | OCH₃ | H | H | CH(CH₃)₂ |
| 6.059 | CF₃ | CH₃ | H | H | CH(CH₃)₂ |
| 6.06 | H | CF₃ | H | CH₃ | CH(CH₃)₂ |
| 6.061 | H | CF₃ | H | CF₃ | CH(CH₃)₂ |
| 6.062 | H | CF₃ | H | SCH₃ | CH(CH₃)₂ |
| 6.063 | H | CF₃ | H | SOCH₃ | CH(CH₃)₂ |
| 6.064 | H | CF₃ | H | SO₂CH₃ | CH(CH₃)₂ |
| 6.065 | H | CF₃ | H | Cl | CH(CH₃)₂ |
| 6.066 | H | CF₃ | H | OCH₃ | CH(CH₃)₂ |
| 6.067 | H | CH₃ | H | CF₃ | CH(CH₃)₂ |
| 6.068 | H | Cl | H | CF₃ | CH(CH₃)₂ |
| 6.069 | H | OCH₃ | H | CF₃ | CH(CH₃)₂ |

TABLE 6-continued

| Comp. No. | R₁ | R₂ | R₃ | R₄ | R₅ |
|---|---|---|---|---|---|
| 6.07 | CN | CF₃ | H | H | CH(CH₃)₂ |
| 6.071 | Cl | CF₃ | H | H | HNPh |
| 6.072 | CHF₂ | CF₃ | H | H | HNPh |
| 6.073 | CCl₃ | CF₃ | H | H | HNPh |
| 6.074 | CClF₂ | CF₃ | H | H | HNPh |
| 6.075 | CF₃ | CF₃ | H | H | HNPh |
| 6.076 | CH₃ | CF₃ | H | H | HNPh |
| 6.077 | CH₂CH₃ | CF₃ | H | H | HNPh |
| 6.078 | (CH₂)₂CH₃ | CF₃ | H | H | HNPh |
| 6.079 | CH₂F | CF₃ | H | H | HNPh |
| 6.08 | CH₂Cl | CF₃ | H | H | HNPh |
| 6.081 | CH₂OCH₃ | CF₃ | H | H | HNPh |
| 6.082 | CH₂SMe | CF₃ | H | H | HNPh |
| 6.083 | CH₂SO₂Me | CF₃ | H | H | HNPh |
| 6.084 | CH=CH₂ | CF₃ | H | H | HNPh |
| 6.085 | CH₂CH=CH₂ | CF₃ | H | H | HNPh |
| 6.086 | CCH | CF₃ | H | H | HNPh |
| 6.087 | CF₃ | SCH₃ | H | H | HNPh |
| 6.088 | CF₃ | SOCH₃ | H | H | HNPh |
| 6.089 | CF₃ | SO₂CH₃ | H | H | HNPh |
| 6.09 | CF₃ | OCH₃ | H | H | HNPh |
| 6.091 | CF₃ | CN | H | H | HNPh |
| 6.092 | CF₃ | Cl | H | H | HNPh |
| 6.093 | CF₃ | OCH₃ | H | H | HNPh |
| 6.094 | CF₃ | CH₃ | H | H | HNPh |
| 6.095 | H | CF₃ | H | CH₃ | HNPh |
| 6.096 | H | CF₃ | H | CF₃ | HNPh |
| 6.097 | H | CF₃ | H | SCH₃ | HNPh |
| 6.098 | H | CF₃ | H | SOCH₃ | HNPh |
| 6.099 | H | CF₃ | H | SO₂CH₃ | HNPh |
| 6.1 | H | CF₃ | H | Cl | HNPh |
| 6.101 | H | CF₃ | H | OCH₃ | HNPh |
| 6.102 | H | CH₃ | H | CF₃ | HNPh |
| 6.103 | H | Cl | H | CF₃ | HNPh |
| 6.104 | H | OCH₃ | H | CF₃ | HNPh |
| 6.105 | CN | CF₃ | H | H | HNPh |
| 6.106 | Cl | CF₃ | H | H | HNC(CH₃)₃ |
| 6.107 | CHF₂ | CF₃ | H | H | HNC(CH₃)₃ |
| 6.108 | CCl₃ | CF₃ | H | H | HNC(CH₃)₃ |
| 6.109 | CClF₂ | CF₃ | H | H | HNC(CH₃)₃ |
| 6.11 | CF₃ | CF₃ | H | H | HNC(CH₃)₃ |
| 6.111 | CH₃ | CF₃ | H | H | HNC(CH₃)₃ |
| 6.112 | CH₂CH₃ | CF₃ | H | H | HNC(CH₃)₃ |
| 6.113 | (CH₂)₂CH₃ | CF₃ | H | H | HNC(CH₃)₃ |
| 6.114 | CH₂F | CF₃ | H | H | HNC(CH₃)₃ |
| 6.115 | CH₂Cl | CF₃ | H | H | HNC(CH₃)₃ |
| 6.116 | CH₂OCH₃ | CF₃ | H | H | HNC(CH₃)₃ |
| 6.117 | CH₂SMe | CF₃ | H | H | HNC(CH₃)₃ |
| 6.118 | CH₂SO₂Me | CF₃ | H | H | HNC(CH₃)₃ |
| 6.119 | CH=CH₂ | CF₃ | H | H | HNC(CH₃)₃ |
| 6.12 | CH₂CH=CH₂ | CF₃ | H | H | HNC(CH₃)₃ |
| 6.121 | CCH | CF₃ | H | H | HNC(CH₃)₃ |
| 6.122 | CF₃ | SCH₃ | H | H | HNC(CH₃)₃ |
| 6.123 | CF₃ | SOCH₃ | H | H | HNC(CH₃)₃ |
| 6.124 | CF₃ | SO₂CH₃ | H | H | HNC(CH₃)₃ |
| 6.125 | CF₃ | OCH₃ | H | H | HNC(CH₃)₃ |
| 6.126 | CF₃ | CN | H | H | HNC(CH₃)₃ |
| 6.127 | CF₃ | Cl | H | H | HNC(CH₃)₃ |
| 6.128 | CF₃ | OCH₃ | H | H | HNC(CH₃)₃ |
| 6.129 | CF₃ | CH₃ | H | H | HNC(CH₃)₃ |
| 6.13 | H | CF₃ | H | CH₃ | HNC(CH₃)₃ |
| 6.131 | H | CF₃ | H | CF₃ | HNC(CH₃)₃ |
| 6.132 | H | CF₃ | H | SCH₃ | HNC(CH₃)₃ |
| 6.133 | H | CF₃ | H | SOCH₃ | HNC(CH₃)₃ |
| 6.134 | H | CF₃ | H | SO₂CH₃ | HNC(CH₃)₃ |
| 6.135 | H | CF₃ | H | Cl | HNC(CH₃)₃ |
| 6.136 | H | CF₃ | H | OCH₃ | HNC(CH₃)₃ |
| 6.137 | H | CH₃ | H | CF₃ | HNC(CH₃)₃ |
| 6.138 | H | Cl | H | CF₃ | HNC(CH₃)₃ |
| 6.139 | H | OCH₃ | H | CF₃ | HNC(CH₃)₃ |
| 6.14 | CN | CF₃ | H | H | HNC(CH₃)₃ |

TABLE 7

A

B

| Comp. No. | R₁ | R₂ | R₃ | R₄ | p |
|---|---|---|---|---|---|
| 7.001 | H | CF₃ | H | H | 0 |
| 7.002 | F | CF₃ | H | H | 0 |
| 7.003 | Cl | CF₃ | H | H | 0 |
| 7.004 | Br | CF₃ | H | H | 0 |
| 7.005 | CHF₂ | CF₃ | H | H | 0 |
| 7.006 | CCl₃ | CF₃ | H | H | 0 |
| 7.007 | CClF₂ | CF₃ | H | H | 0 |
| 7.008 | CF₃ | CF₃ | H | H | 0 |
| 7.009 | CH₃ | CF₃ | H | H | 0 |
| 7.01 | CH₂CH₃ | CF₃ | H | H | 0 |
| 7.011 | CH(CH₃)₂ | CF₃ | H | H | 0 |
| 7.012 | (CH₂)₂CH₃ | CF₃ | H | H | 0 |
| 7.013 | C(CH₃)₃ | CF₃ | H | H | 0 |
| 7.014 | Ph | CF₃ | H | H | 0 |
| 7.015 | CH₂F | CF₃ | H | H | 0 |
| 7.016 | CH₂Cl | CF₃ | H | H | 0 |
| 7.017 | CH₂Br | CF₃ | H | H | 0 |
| 7.018 | CH₂OH | CF₃ | H | H | 0 |
| 7.019 | CH₂OCOCH₃ | CF₃ | H | H | 0 |
| 7.02 | CH₂OCOPh | CF₃ | H | H | 0 |
| 7.021 | CH₂OCH₃ | CF₃ | H | H | 0 |
| 7.022 | CH₂OCH₂CH₃ | CF₃ | H | H | 0 |
| 7.023 | CH₂CH₂OCH₃ | CF₃ | H | H | 0 |
| 7.024 | CH₂SMe | CF₃ | H | H | 0 |
| 7.025 | CH₂SOMe | CF₃ | H | H | 0 |
| 7.026 | CH₂SO₂Me | CF₃ | H | H | 0 |
| 7.027 | CH₂SO₂Ph | CF₃ | H | H | 0 |

TABLE 7-continued

A:

Structure A: methylsulfonyl(O)p-isoxazole with cyclopropyl at R4 position, connected via carbonyl to pyridine bearing R1, R2, R3, R4 substituents.

B:

Structure B: methylsulfonyl(O)p-isoxazole-4-carbonyl-cyclopropyl, with isoxazole-5-yl linked to pyridine bearing R1, R2, R3, R4.

| Comp. No. | R₁ | R₂ | R₃ | R₄ | p |
|---|---|---|---|---|---|
| 7.028 | SCH₃ | CF₃ | H | H | 0 |
| 7.029 | SOCH₃ | CF₃ | H | H | 0 |
| 7.03 | SO₂CH₃ | CF₃ | H | H | 0 |
| 7.031 | N(CH₃)₂ | CF₃ | H | H | 0 |
| 7.032 | CH=CH₂ | CF₃ | H | H | 0 |
| 7.033 | CH₂CH=CH₂ | CF₃ | H | H | 0 |
| 7.034 | SO₂N(CH₃)₂ | CF₃ | H | H | 0 |
| 7.035 | CCH | CF₃ | H | H | 0 |
| 7.036 | cyclopropyl | CF₃ | H | H | 0 |
| 7.037 | OCH₃ | CF₃ | H | H | 0 |
| 7.038 | OCHF₂ | CF₃ | H | H | 0 |
| 7.039 | OCH₂CCH | CF₃ | H | H | 0 |
| 7.04 | H | CF₂CF₃ | H | H | 0 |
| 7.041 | Cl | CF₂CF₃ | H | H | 0 |
| 7.042 | CHF₂ | CF₂CF₃ | H | H | 0 |
| 7.043 | CCl₃ | CF₂CF₃ | H | H | 0 |
| 7.044 | CClF₂ | CF₂CF₃ | H | H | 0 |
| 7.045 | CF₃ | CF₂CF₃ | H | H | 0 |
| 7.046 | CH₃ | CF₂CF₃ | H | H | 0 |
| 7.047 | CH₂CH₃ | CF₂CF₃ | H | H | 0 |
| 7.048 | CH(CH₃)₂ | CF₂CF₃ | H | H | 0 |
| 7.049 | (CH₂)₂CH₃ | CF₂CF₃ | H | H | 0 |
| 7.05 | C(CH₃)₃ | CF₂CF₃ | H | H | 0 |
| 7.051 | CH₂F | CF₂CF₃ | H | H | 0 |
| 7.052 | CH₂Cl | CF₂CF₃ | H | H | 0 |
| 7.053 | CH₂OH | CF₂CF₃ | H | H | 0 |
| 7.054 | CH₂OCOCH₃ | CF₂CF₃ | H | H | 0 |
| 7.055 | CH₂OCOPh | CF₂CF₃ | H | H | 0 |
| 7.056 | CH₂OCH₃ | CF₂CF₃ | H | H | 0 |
| 7.057 | CH₂OCH₂CH₃ | CF₂CF₃ | H | H | 0 |
| 7.058 | CH₂SMe | CF₂CF₃ | H | H | 0 |
| 7.059 | CH₂SOMe | CF₂CF₃ | H | H | 0 |
| 7.06 | CH₂SO₂Me | CF₂CF₃ | H | H | 0 |
| 7.061 | CH₂SO₂Ph | CF₂CF₃ | H | H | 0 |
| 7.062 | N(CH₃)₂ | CF₂CF₃ | H | H | 0 |
| 7.063 | CH=CH₂ | CF₂CF₃ | H | H | 0 |
| 7.064 | CH₂CH=CH₂ | CF₂CF₃ | H | H | 0 |
| 7.065 | SO₂N(CH₃)₂ | CF₂CF₃ | H | H | 0 |
| 7.066 | CCH | CF₂CF₃ | H | H | 0 |
| 7.067 | cyclopropyl | CF₂CF₃ | H | H | 0 |
| 7.068 | OCH₃ | CF₂CF₃ | H | H | 0 |
| 7.069 | CO₂Me | CF₂CF₃ | H | H | 0 |
| 7.07 | OCH₂CCH | CF₂CF₃ | H | H | 0 |
| 7.071 | H | CF₂Cl | H | H | 0 |
| 7.072 | Cl | CF₂Cl | H | H | 0 |
| 7.073 | CHF₂ | CF₂Cl | H | H | 0 |
| 7.074 | CCl₃ | CF₂Cl | H | H | 0 |
| 7.075 | CClF₂ | CF₂Cl | H | H | 0 |
| 7.076 | CF₃ | CF₂Cl | H | H | 0 |
| 7.077 | CH₃ | CF₂Cl | H | H | 0 |
| 7.078 | CH₂CH₃ | CF₂Cl | H | H | 0 |
| 7.079 | CH(CH₃)₂ | CF₂Cl | H | H | 0 |
| 7.08 | (CH₂)₂CH₃ | CF₂Cl | H | H | 0 |
| 7.081 | C(CH₃)₃ | CF₂Cl | H | H | 0 |
| 7.082 | CH₂F | CF₂Cl | H | H | 0 |
| 7.083 | CH₂Cl | CF₂Cl | H | H | 0 |
| 7.084 | CH₂OH | CF₂Cl | H | H | 0 |
| 7.085 | CH₂OCOCH₃ | CF₂Cl | H | H | 0 |
| 7.086 | CH₂OCOPh | CF₂Cl | H | H | 0 |
| 7.087 | CH₂OCH₃ | CF₂Cl | H | H | 0 |
| 7.088 | CH₂OCH₂CH₃ | CF₂Cl | H | H | 0 |
| 7.089 | CH₂SMe | CF₂Cl | H | H | 0 |
| 7.09 | CH₂SOMe | CF₂Cl | H | H | 0 |
| 7.091 | CH₂SO₂Me | CF₂Cl | H | H | 0 |
| 7.092 | CH₂SO₂Ph | CF₂Cl | H | H | 0 |
| 7.093 | N(CH₃)₂ | CF₂Cl | H | H | 0 |
| 7.094 | CH=CH₂ | CF₂Cl | H | H | 0 |
| 7.095 | CH₂CH=CH₂ | CF₂Cl | H | H | 0 |
| 7.096 | SO₂N(CH₃)₂ | CF₂Cl | H | H | 0 |
| 7.097 | CCH | CF₂Cl | H | H | 0 |
| 7.098 | cyclopropyl | CF₂Cl | H | H | 0 |
| 7.099 | OCH₃ | CF₂Cl | H | H | 0 |
| 7.1 | OCH₂CCH | CF₂Cl | H | H | 0 |
| 7.101 | CF₃ | CHF₂ | H | H | 0 |
| 7.102 | CH₃ | CHF₂ | H | H | 0 |
| 7.103 | CH₂OCH₃ | CHF₂ | H | H | 0 |
| 7.104 | CH₂Cl | CHF₂ | H | H | 0 |
| 7.105 | CH₂F | CHF₂ | H | H | 0 |
| 7.106 | CH₃ | CF₃ | H | CH₃ | 0 |
| 7.107 | Cl | CF₃ | H | CH₃ | 0 |
| 7.108 | CH₃ | CF₃ | CH₃ | H | 0 |
| 7.109 | CH₃ | CF₃ | Cl | H | 0 |
| 7.11 | OCH₃ | CF₃ | CH₃ | H | 0 |
| 7.111 | CH₂OCH₃ | CF₃ | CH₃ | H | 0 |
| 7.112 | CH₂OCH₃ | CF₃ | Cl | H | 0 |
| 7.113 | COOCH₃ | H | H | H | 0 |
| 7.114 | CF₃ | SCH₃ | H | H | 0 |
| 7.115 | CH₃ | SCH₃ | H | H | 0 |
| 7.116 | CF₃ | SOCH₃ | H | H | 0 |
| 7.117 | CH₃ | SOCH₃ | H | H | 0 |
| 7.118 | CF₃ | SO₂CH₃ | H | H | 0 |
| 7.119 | CH₃ | SO₂CH₃ | H | H | 0 |
| 7.12 | CF₃ | OCH₃ | H | H | 0 |
| 7.121 | CH₃ | OCH₃ | H | H | 0 |
| 7.122 | CF₃ | OCH₂CF₃ | H | H | 0 |
| 7.123 | CH₃ | OCH₂CF₃ | H | H | 0 |
| 7.124 | CF₃ | OCH₂CCH | H | H | 0 |
| 7.125 | CH₃ | OCH₂CCH | H | H | 0 |
| 7.126 | CF₃ | CN | H | H | 0 |
| 7.127 | CH₃ | CN | H | H | 0 |

TABLE 7-continued

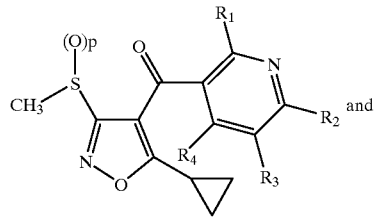

A

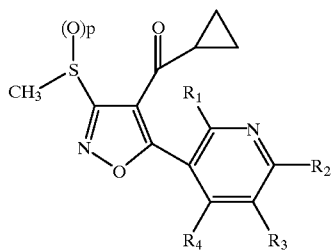

B

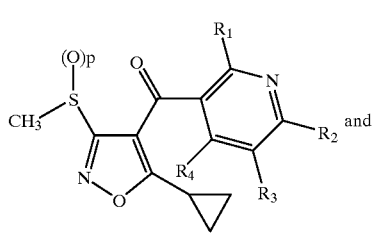

A

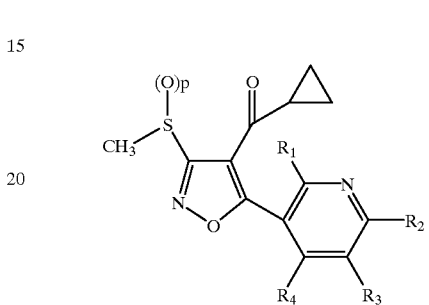

B

| Comp. No. | R₁ | R₂ | R₃ | R₄ | p |
|---|---|---|---|---|---|
| 7.128 | CF₃ | Cl | H | H | 0 |
| 7.129 | CF₃ | Cl | H | H | 0 |
| 7.13 | CH₃ | Cl | H | H | 0 |
| 7.131 | H | Cl | H | H | 0 |
| 7.132 | CF₃ | OCH₃ | H | H | 0 |
| 7.133 | CH₃ | OCH₃ | H | H | 0 |
| 7.134 | CF₃ | CH₃ | H | H | 0 |
| 7.135 | H | CF₃ | H | CH₃ | 0 |
| 7.136 | H | CF₃ | H | CF₃ | 0 |
| 7.137 | H | CF₃ | H | CH₂CH₃ | 0 |
| 7.138 | H | CF₃ | H | CF₃ | 0 |
| 7.139 | H | CF₃ | H | SCH₃ | 0 |
| 7.14 | H | CF₃ | H | SOCH₃ | 0 |
| 7.141 | H | CF₃ | H | SO₂CH₃ | 0 |
| 7.142 | H | CF₃ | H | Cl | 0 |
| 7.143 | H | CF₃ | H | OCH₃ | 0 |
| 7.144 | H | CH₃ | H | CF₃ | 0 |
| 7.145 | H | Cl | H | CF₃ | 0 |
| 7.146 | H | OCH₃ | H | CF₃ | 0 |
| 7.147 | H | SCH₃ | H | CF₃ | 0 |
| 7.148 | H | SOCH₃ | H | CF₃ | 0 |
| 7.149 | CH₃ | (CF₂)₃CF₃ | H | H | 0 |
| 7.15 | CF₂H | SCH₃ | H | H | 0 |
| 7.151 | CF₂Cl | SCH₃ | H | H | 0 |
| 7.152 | CF₂H | SOCH₃ | H | H | 0 |
| 7.153 | CF₂Cl | SOCH₃ | H | H | 0 |
| 7.154 | CF₂H | SO₂CH₃ | H | H | 0 |
| 7.155 | CF₂Cl | SO₂CH₃ | H | H | 0 |
| 7.156 | CF₂H | OCH₃ | H | H | 0 |
| 7.157 | CF₂Cl | OCH₃ | H | H | 0 |
| 7.158 | CF₂H | OCH₂CF₃ | H | H | 0 |
| 7.159 | CF₂Cl | OCH₂CF₃ | H | H | 0 |
| 7.16 | CF₂H | OCH₂CCH | H | H | 0 |
| 7.161 | CF₂Cl | OCH₂CCH | H | H | 0 |
| 7.162 | CF₂H | CN | H | H | 0 |
| 7.163 | CF₂Cl | CN | H | H | 0 |
| 7.164 | CF₂H | Cl | H | H | 0 |
| 7.165 | CF₂Cl | Cl | H | H | 0 |
| 7.166 | CF₂H | OCH₃ | H | H | 0 |
| 7.167 | CF₂Cl | OCH₃ | H | H | 0 |
| 7.168 | CF₃ | CH₂OCH₃ | H | H | 0 |
| 7.169 | CF₂Cl | CH₂OCH₃ | H | H | 0 |
| 7.17 | CF₂H | CH₂OCH₃ | H | H | 0 |
| 7.171 | CN | CF₃ | H | H | 0 |
| 7.172 | H | CF₃ | H | H | 2 |
| 7.173 | F | CF₃ | H | H | 2 |
| 7.174 | Cl | CF₃ | H | H | 2 |
| 7.175 | Br | CF₃ | H | H | 2 |
| 7.176 | CHF₂ | CF₃ | H | H | 2 |
| 7.177 | CCl₃ | CF₃ | H | H | 2 |

| Comp. No. | R₁ | R₂ | R₃ | R₄ | p |
|---|---|---|---|---|---|
| 7.178 | CClF₂ | CF₃ | H | H | 2 |
| 7.179 | CF₃ | CF₃ | H | H | 2 |
| 7.18 | CH₃ | CF₃ | H | H | 2 |
| 7.181 | CH₂CH₃ | CF₃ | H | H | 2 |
| 7.182 | CH(CH₃)₂ | CF₃ | H | H | 2 |
| 7.183 | (CH₂)₂CH₃ | CF₃ | H | H | 2 |
| 7.184 | C(CH₃)₃ | CF₃ | H | H | 2 |
| 7.185 | Ph | CF₃ | H | H | 2 |
| 7.186 | CH₂F | CF₃ | H | H | 2 |
| 7.187 | CH₂Cl | CF₃ | H | H | 2 |
| 7.188 | CH₂Br | CF₃ | H | H | 2 |
| 7.189 | CH₂OH | CF₃ | H | H | 2 |
| 7.19 | CH₂OCOCH₃ | CF₃ | H | H | 2 |
| 7.191 | CH₂OCOPh | CF₃ | H | H | 2 |
| 7.192 | CH₂OCH₃ | CF₃ | H | H | 2 |
| 7.193 | CH₂OCH₂CH₃ | CF₃ | H | H | 2 |
| 7.194 | CH₂CH₂OCH₃ | CF₃ | H | H | 2 |
| 7.195 | CH₂SMe | CF₃ | H | H | 2 |
| 7.196 | CH₂SOMe | CF₃ | H | H | 2 |
| 7.197 | CH₂SO₂Me | CF₃ | H | H | 2 |
| 7.198 | CH₂SO₂Ph | CF₃ | H | H | 2 |
| 7.199 | SCH₃ | CF₃ | H | H | 2 |
| 7.2 | SOCH₃ | CF₃ | H | H | 2 |
| 7.201 | SO₂CH₃ | CF₃ | H | H | 2 |
| 7.202 | N(CH₃)₂ | CF₃ | H | H | 2 |
| 7.203 | CH=CH₂ | CF₃ | H | H | 2 |
| 7.204 | CH₂CH=CH₂ | CF₃ | H | H | 2 |
| 7.205 | SO₂N(CH₃)₂ | CF₃ | H | H | 2 |
| 7.206 | CCH | CF₃ | H | H | 2 |
| 7.207 | cyclopropyl | CF₃ | H | H | 2 |
| 7.208 | OCH₃ | CF₃ | H | H | 2 |
| 7.209 | OCHF₂ | CF₃ | H | H | 2 |
| 7.21 | OCH₂CCH | CF₃ | H | H | 2 |

TABLE 8

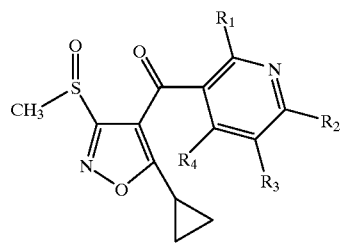

| Comp. No. | R₁ | R₂ | R₃ | R₄ |
|---|---|---|---|---|
| 8.001 | H | $CF_3$ | H | H |
| 8.002 | F | $CF_3$ | H | H |
| 8.003 | Cl | $CF_3$ | H | H |
| 8.004 | Br | $CF_3$ | H | H |
| 8.005 | $CHF_2$ | $CF_3$ | H | H |
| 8.006 | $CCl_3$ | $CF_3$ | H | H |
| 8.007 | $CClF_2$ | $CF_3$ | H | H |
| 8.008 | $CF_3$ | $CF_3$ | H | H |
| 8.009 | $CH_3$ | $CF_3$ | H | H |
| 8.01 | $CH_2CH_3$ | $CF_3$ | H | H |
| 8.011 | $CH(CH_3)_2$ | $CF_3$ | H | H |
| 8.012 | $(CH_2)_2CH_3$ | $CF_3$ | H | H |
| 8.013 | $C(CH_3)_3$ | $CF_3$ | H | H |
| 8.014 | Ph | $CF_3$ | H | H |
| 8.015 | $CH_2F$ | $CF_3$ | H | H |
| 8.016 | $CH_2Cl$ | $CF_3$ | H | H |
| 8.017 | $CH_2Br$ | $CF_3$ | H | H |
| 8.018 | $CH_2OH$ | $CF_3$ | H | H |
| 8.019 | $CH_2OCOCH_3$ | $CF_3$ | H | H |
| 8.02 | $CH_2OCOPh$ | $CF_3$ | H | H |
| 8.021 | $CH_2OCH_3$ | $CF_3$ | H | H |
| 8.022 | $CH_2OCH_2CH_3$ | $CF_3$ | H | H |
| 8.023 | $CH_2CH_2OCH_3$ | $CF_3$ | H | H |
| 8.024 | $CH_2SMe$ | $CF_3$ | H | H |
| 8.025 | $CH_2SOMe$ | $CF_3$ | H | H |
| 8.026 | $CH_2SO_2Me$ | $CF_3$ | H | H |
| 8.027 | $CH_2SO_2Ph$ | $CF_3$ | H | H |
| 8.028 | $SCH_3$ | $CF_3$ | H | H |
| 8.029 | $SOCH_3$ | $CF_3$ | H | H |
| 8.03 | $SO_2CH_3$ | $CF_3$ | H | H |
| 8.031 | $N(CH_3)_2$ | $CF_3$ | H | H |
| 8.032 | $CH=CH_2$ | $CF_3$ | H | H |
| 8.033 | $CH_2CH=CH_2$ | $CF_3$ | H | H |
| 8.034 | $SO_2N(CH_3)_2$ | $CF_3$ | H | H |
| 8.035 | CCH | $CF_3$ | H | H |
| 8.036 | cyclopropyl | $CF_3$ | H | H |
| 8.037 | $OCH_3$ | $CF_3$ | H | H |
| 8.038 | $OCHF_2$ | $CF_3$ | H | H |
| 8.039 | $OCH_2CCH$ | $CF_3$ | H | H |

TABLE 9

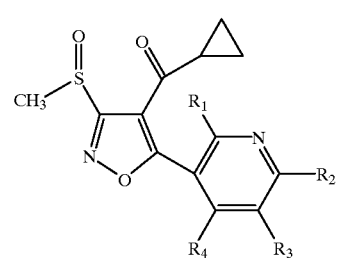

| Comp. No. | R₁ | R₂ | R₃ | R₄ |
|---|---|---|---|---|
| 9.001 | H | $CF_3$ | H | H |
| 9.002 | F | $CF_3$ | H | H |
| 9.003 | Cl | $CF_3$ | H | H |
| 9.004 | Br | $CF_3$ | H | H |

TABLE 9-continued

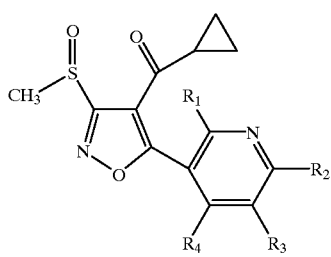

| Comp. No. | R₁ | R₂ | R₃ | R₄ |
|---|---|---|---|---|
| 9.005 | $CHF_2$ | $CF_3$ | H | H |
| 9.006 | $CCl_3$ | $CF_3$ | H | H |
| 9.007 | $CClF_2$ | $CF_3$ | H | H |
| 9.008 | $CF_3$ | $CF_3$ | H | H |
| 9.009 | $CH_3$ | $CF_3$ | H | H |
| 9.01 | $CH_2CH_3$ | $CF_3$ | H | H |
| 9.011 | $CH(CH_3)_2$ | $CF_3$ | H | H |
| 9.012 | $(CH_2)_2CH_3$ | $CF_3$ | H | H |
| 9.013 | $C(CH_3)_3$ | $CF_3$ | H | H |
| 9.014 | Ph | $CF_3$ | H | H |
| 9.015 | $CH_2F$ | $CF_3$ | H | H |
| 9.016 | $CH_2Cl$ | $CF_3$ | H | H |
| 9.017 | $CH_2Br$ | $CF_3$ | H | H |
| 9.018 | $CH_2OH$ | $CF_3$ | H | H |
| 9.019 | $CH_2OCOCH_3$ | $CF_3$ | H | H |
| 9.02 | $CH_2OCOPh$ | $CF_3$ | H | H |
| 9.021 | $CH_2OCH_3$ | $CF_3$ | H | H |
| 9.022 | $CH_2OCH_2CH_3$ | $CF_3$ | H | H |
| 9.023 | $CH_2CH_2OCH_3$ | $CF_3$ | H | H |
| 9.024 | $CH_2SMe$ | $CF_3$ | H | H |
| 9.025 | $CH_2SOMe$ | $CF_3$ | H | H |
| 9.026 | $CH_2SO_2Me$ | $CF_3$ | H | H |
| 9.027 | $CH_2SO_2Ph$ | $CF_3$ | H | H |
| 9.028 | $SCH_3$ | $CF_3$ | H | H |
| 9.029 | $SOCH_3$ | $CF_3$ | H | H |
| 9.03 | $SO_2CH_3$ | $CF_3$ | H | H |
| 9.031 | $N(CH_3)_2$ | $CF_3$ | H | H |
| 9.032 | $CH=CH_2$ | $CF_3$ | H | H |
| 9.033 | $CH_2CH=CH_2$ | $CF_3$ | H | H |
| 9.034 | $SO_2N(CH_3)_2$ | $CF_3$ | H | H |
| 9.035 | CCH | $CF_3$ | H | H |
| 9.036 | cyclopropyl | $CF_3$ | H | H |
| 9.037 | $OCH_3$ | $CF_3$ | H | H |
| 9.038 | $OCHF_2$ | $CF_3$ | H | H |
| 9.039 | $OCH_2CCH$ | $CF_3$ | H | H |

Physical data (melting points in ° C.):

| Comp. No. | |
|---|---|
| 1.001 | resin |
| 1.005 | crystals m.p. 61–62 |
| 1.008 | oil |
| 1.009 | crystals m.p. 75–77 |
| 1.01 | oil |
| 1.011 | crystals m.p. 111–112 |
| 1.012 | crystals m.p. 87–88 |
| 1.013 | crystals m.p. 112–114 |
| 1.014 | oil |
| 1.021 | crystals m.p. 128–129 |
| 1.023 | crystals m.p. 91–92 |
| 1.024 | oil |
| 1.026 | amorphous |
| 1.028 | amorphous |
| 1.03 | resin |
| 1.031 | crystals m.p. 145–146 |
| 1.042 | oil |
| 1.043 | crystals m.p. 107–110 |

-continued

Physical data (melting points in °C.):

| Comp. No. | |
|---|---|
| 1.047 | crystals m.p. 155–156 |
| 1.048 | viscous |
| 1.05 | crystals m.p. 51–53 |
| 1.06 | crystals m.p. >220 |
| 1.109 | oil |
| 1.195 | oil |
| 1.258 | crystals m.p. 119–121 |
| 1.31 | crystals m.p. 92–94 |
| 1.312 | viscous |
| 1.313 | crystals m.p. 137–138 |
| 1.314 | oil |
| 1.316 | resin |
| 1.323 | oil |
| 1.334 | resin |
| 1.335 | crystals m.p. 140–142 |
| 1.339 | crystals m.p. 137–139 |
| 1.341 | resin |
| 1.343 | crystals m.p. 97–99 |
| 1.347 | crystals m.p. 135–137 |
| 1.349 | oil, $n_D$ 1.4965 |
| 1.351 | crystals m.p. 125–127 |
| 1.353 | resin, $n_D$ 1.5289 |
| 1.355 | crystals m.p. 90–92 |
| 1.356 | resin |
| 1.358 | resin |
| 1.361 | oil |
| 1.362 | crystals m.p. 139–142 |
| 1.371 | crystals m.p. 96–97 |
| 1.372 | resin |
| 1.373 | resin |
| 1.374 | crystals m.p. 116–1199 |
| 1.375 | resin |
| 1.376 | crystals m.p. >270 |
| 1.381 | crystals m.p. 117–118 |
| 1.383 | crystals m.p. 172–173 |
| 1.384 | resin |
| 1.385 | resin |
| 1.386 | resin |
| 1.387 | resin |
| 1.388 | crystals m.p. 102–104 |
| 1.389 | crystals m.p. 143–145 |
| 1.39 | crystals m.p. 195–197 |
| 1.391 | solid |
| 1.392 | crystals m.p. 202–206 |
| 1.398 | crystals m.p. 137–138 |
| 1.399 | crystals m.p. 262–263 |
| 1.4 | oil |
| 1.401 | oil |
| 1.402 | oil |
| 1.403 | oil |
| 1.404 | oil |
| 1.405 | viscous |
| 1.406 | oil |
| 1.408 | oil |
| 1.409 | oil |
| 1.41 | oil |
| 1.411 | crystals m.p. 98–100 |
| 1.412 | crystals m.p. 130–131 |
| 1.413 | crystals m.p. 167–170 |
| 1.414 | crystals m.p. 166–167 |
| 1.415 | crystals m.p. 91–93 |
| 1.418 | crystals m.p. 149–150 |
| 1.421 | crystals m.p. 88–89 |
| 1.422 | crystals m.p. 175–177 |
| 1.423 | crystals m.p. 45–47 |
| 1.424 | crystals m.p. 102–104 |
| 2.001 | resin |
| 2.003 | oil |
| 2.03 | crystals m.p. 107–110 |
| 2.038 | crystals m.p. 111–113 |
| 2.043 | resin |
| 2.044 | crystals m.p. 105–106 |
| 2.045 | amorphous |
| 3.001 | crystals m.p. 95–97 |

-continued

Physical data (melting points in °C.):

| Comp. No. | |
|---|---|
| 3.054 | oil |
| 3.055 | crystals m.p. 108–110 |
| 3.056 | resin, $D_D$ 1.5509 |
| 4.009 | crystals m.p. 107–109 |
| 4.01 | oil |
| 4.011 | oil |
| 4.014 | crystals m.p. 148–149 |
| 4.021 | crystals m.p. 44–45 |
| 4.033 | crystals m.p. 46–48 |
| 4.124 | crystals m.p. 46–48 |
| 4.328 | oil |
| 5.008 | resin |
| 5.081 | resin |
| 5.083 | crystals m.p. 161–162 |
| 5.084 | crystals m.p. 215–216 |
| 5.085 | resin |
| 6.006 | crystals m.p. 176–177 |
| 6.041 | crystals m.p. 186–187 |
| 6.076 | crystals m.p. 195–196 |
| 6.111 | crystals m.p. 163–164 |
| 7.009 | ratio A: B = 2:1. H-NMR(CDCl$_3$,ppm) SCH$_3$: A: 2.50; B: 2.66. |
| 7.01 | ratio A: B = 5:1. H-NMR(CDCl$_3$,ppm) SCH$_3$: A: 2.50; B: 2.64. |
| 7.011 | ratio A: B = 9:1. H-NMR(CDCl$_3$,ppm) SCH$_3$: A: 2.46; B: 2.59. |
| 7.021 | ratio A: B = 3:1. H-NMR(CDCl$_3$,ppm) SCH$_3$: A: 2.50; B: 2.62. |
| 7.18 | ratio A: B = 2:. H-NMR(CDCl$_3$,ppm) SO$_2$CH$_3$: A: 3.40; B: 3.58. |
| 7.182 | ratio A: B = 9:1. H-NMR(CDCl$_3$,ppm) SO$_2$CH$_3$: A: 3.32; B: 3.50. |
| 7.192 | ratio A: B = 3:1. H-NMR(CDCl$_3$,ppm) SO$_2$CH$_3$: A: 3.40; B: 3.58. |
| 8.009 | crystals m.p. 96–97 |
| 8.01 | amorphous |
| 8.011 | oil |
| 8.021 | oil |
| 9.009 | crystals m.p. 112–113 |
| 9.01 | amorphous |
| 9.011 | amorphous |
| 9.021 | oil |

Biological Examples

Example B1

Herbical action before emergence of the plants
(pre-emergence action)

Monocotyledonous and dicotyledonous test plants are sown in standard soil in plastic pots. Immediately after sowing, the test substances are sprayed on (500 l of water/ha) as an aqueous suspension (prepared from a 25% wettable powder (Example F3, b) according to WO 97/34485) or emulsion (prepared from a 25% emulsion concentrate (Example F1, c)), corresponding to a dosage of 2 kg of AS/ha. The test plants are then grown under optimum conditions in a greenhouse. After a test period of 3 weeks, the test is evaluated with a nine-level scale of ratings (1=complete damage, 9=no effect). Ratings of 1 to 4 (in particular 1 to 3) mean good to very good herbicidal action.

TABLE B1 pre-emergence action:

| Active compound No. | Test plant | | | | | |
|---|---|---|---|---|---|---|
| | Avena | Cyperus | Setaria | Sinapis | Solanum | Stellaria |
| 1.009 | 2 | 1 | 1 | 2 | 1 | 2 |
| 1.376 | 2 | 1 | 1 | 2 | 1 | 2 |
| 4.009 | 1 | 2 | 1 | 2 | 1 | 3 |
| 7.009 | 4 | 2 | 1 | 3 | 1 | 2 |
| 1.381 | 4 | 1 | 2 | 2 | 1 | 1 |
| 1.011 | 2 | 1 | 1 | 1 | 1 | 1 |
| 5.008 | 2 | 1 | 1 | 2 | 1 | 2 |
| 4.021 | 2 | 1 | 2 | 2 | 1 | 2 |
| 1.010 | 2 | 1 | 1 | 1 | 1 | 2 |
| 1.021 | 4 | 2 | 1 | 1 | 1 | 3 |
| 1.398 | 2 | 1 | 1 | 1 | 1 | 1 |
| 1.195 | 2 | 1 | 1 | 1 | 1 | 2 |
| 4.124 | 2 | 1 | 2 | 2 | 1 | 2 |
| 1.411 | 3 | 2 | 1 | 2 | 1 | 2 |
| 1.042 | 4 | 2 | 2 | 1 | 1 | 4 |
| 1.023 | 2 | 2 | 2 | 1 | 1 | 2 |
| 1.109 | 2 | 2 | 2 | 2 | 1 | 3 |
| 1.313 | 3 | 1 | 2 | 1 | 1 | 2 |
| 1.401 | 2 | 1 | 1 | 2 | 1 | 2 |
| 1.404 | 2 | 1 | 1 | 2 | 1 | 2 |
| 1.400 | 2 | 1 | 1 | 2 | 1 | 2 |
| 1.403 | 2 | 1 | 1 | 1 | 1 | 2 |
| 1.405 | 2 | 1 | 1 | 1 | 1 | 2 |
| 1.406 | 2 | 1 | 1 | 1 | 1 | 2 |
| 1.402 | 2 | 1 | 1 | 2 | 1 | 2 |
| 1.005 | 4 | 1 | 1 | 1 | 1 | 1 |
| 1.043 | 4 | 2 | 1 | 2 | 1 | 2 |
| 1.409 | 1 | 1 | 1 | 1 | 1 | 1 |
| 1.41 | 2 | 1 | 1 | 1 | 1 | 1 |
| 1.06 | 2 | 1 | 1 | 2 | 1 | 1 |
| 7.192 | 4 | 2 | 2 | 3 | 2 | 2 |
| 7.021 | 1 | 1 | 1 | 1 | 1 | 1 |

The same results are obtained when the compounds of the formula I are formulated according to Examples F2 and F4 to F8 according to WO 97/34485.

Example B2

Post-emeroence Herbicidal Action

Monocotyledonous and dicotyledonous test plants are grown in plastic pots with standard soil in a greenhouse and, in the 4- to 6-leaf stage, are sprayed with an aqueous suspension of the test substances of the formula 1, prepared from a 25% wettable powder (Example F3, b) according to WO 97134485) or with an emulsion of the test substances of the formula I, prepared from a 25% emulsion concentrate (Example F1, c) according to WO 97/34485), corresponding to a dosage of 2 kg of AS/ha (500 l of water/ha). The test plants are then grown further under optimum conditions in a greenhouse. After a test period of about 18 days, the test is evaluated with a nine-level scale of rating (1=complete damage, 9=no effect). Ratings of 1 to 4 (in particular 1 to 3) mean good to very good herbicidal action. In this test, the compounds of the formula I show strong herbicidal action.

TABLE B2 post-emergence action:

| Active compound No. | Test plant | | | | |
|---|---|---|---|---|---|
| | Avena | Setaria | Solanum | Sinapis | Stellaria |
| 1.009 | 1 | 1 | 1 | 1 | 2 |
| 1.376 | 1 | 2 | 2 | 1 | 2 |
| 4.009 | 1 | 1 | 1 | 1 | 1 |
| 1.026 | 3 | 1 | 1 | 1 | 2 |
| 7.009 | 3 | 2 | 1 | 1 | 1 |
| 1.381 | 2 | 2 | 2 | 2 | 2 |
| 1.011 | 2 | 2 | 2 | 2 | 2 |
| 5.008 | 2 | 3 | 1 | 1 | 2 |
| 5.085 | 3 | 2 | 2 | 1 | 2 |
| 4.021 | 2 | 2 | 1 | 1 | 2 |
| 1.012 | 3 | 2 | 2 | 1 | 2 |
| 1.010 | 2 | 2 | 2 | 1 | 4 |
| 4.010 | 3 | 3 | 2 | 2 | 2 |
| 1.021 | 2 | 4 | 2 | 1 | 2 |
| 1.398 | 2 | 2 | 2 | 1 | 2 |
| 1.195 | 2 | 2 | 2 | 1 | 2 |
| 4.124 | 2 | 2 | 1 | 1 | 2 |
| 1.411 | 2 | 2 | 2 | 1 | 2 |
| 1.008 | 2 | 2 | 2 | 1 | 2 |
| 6.006 | 2 | 5 | 2 | 2 | 2 |
| 5.081 | 3 | 2 | 1 | 1 | 2 |
| 1.042 | 2 | 2 | 2 | 1 | 2 |
| 1.023 | 2 | 2 | 2 | 1 | 2 |
| 1.109 | 2 | 2 | 2 | 1 | 2 |
| 1.313 | 2 | 2 | 2 | 1 | 2 |
| 1.401 | 2 | 2 | 2 | 2 | 2 |
| 1.404 | 2 | 2 | 1 | 1 | 2 |
| 1.400 | 2 | 2 | 2 | 1 | 2 |
| 1.403 | 2 | 2 | 2 | 1 | 2 |
| 1.403 | 2 | 2 | 2 | 1 | 2 |
| 1.405 | 2 | 2 | 2 | 1 | 2 |
| 1.406 | 2 | 2 | 1 | 1 | 2 |
| 1.402 | 2 | 2 | 2 | 1 | 2 |
| 1.001 | 3 | 2 | 2 | 1 | 2 |
| 1.005 | 2 | 2 | 2 | 1 | 2 |
| 1.362 | 3 | 2 | 2 | 1 | 2 |
| 1.043 | 2 | 2 | 2 | 1 | 2 |
| 1.409 | 2 | 1 | 1 | 1 | 2 |
| 1.410 | 1 | 1 | 1 | 1 | 1 |
| 1.060 | 2 | 1 | 1 | 1 | 2 |
| 7.192 | 2 | 3 | 3 | 2 | 2 |
| 7.021 | 1 | 2 | 1 | 1 | 2 |
| 1.048 | 2 | 1 | 1 | 1 | 2 |

The same results are obtained when the compounds of the formula I are formulated according to Examples F2 and F4 to F8 according to WO 97/34485.

Example B3

Herbicidal action before emergence of the plants (pre-emergence action)

Monocotyledonous and dicotyledonous test plants are sown in pots in standard soil. Immediately after sowing, the test substances are sprayed on (500 l of spray liquorlha) as an aqueous suspension, prepared from a wettable powder WP10 corresponding to the desired dosage (250 g of a.i./ha).

The test plants are then grown under optimum conditions in a greenhouse. After a test period of 3 weeks, the test is evaluated with a nine -evel scale of ratings (1=complete damage, 9=no effect). Ratings of 1 to 4 (in particular 1 to 3) mean good to very good herbicidal action, 7-9 mean good tolerance.

TABLE B3

Pre-emergence action:

| Active compound No. | Abut-ilon | Amar-anthus | Cheno-podium | Kochia | Sida | Stellaria | Dose [g of AS/ha] |
|---|---|---|---|---|---|---|---|
| 1.355 | 1 | 1 | 1 | 1 | 2 | 2 | 250 |
| 1.347 | 2 | 2 | 1 | 1 | 4 | 1 | 250 |
| 1.335 | 1 | 2 | 1 | 5 | 2 | 7 | 250 |
| 1.349 | 1 | 3 | 1 | 4 | 2 | 5 | 250 |
| 1.339 | 2 | 1 | 1 | 7 | 2 | 1 | 250 |
| 1.341 | 3 | 9 | 1 | 9 | 4 | 1 | 250 |
| 1.343 | 1 | 4 | 1 | 9 | 3 | 5 | 250 |

The same results are obtained when the compounds of the formula I are formulated according to Examples F2 and F4 to F8 according to WO 97/34485.

Example B4

Herbicidal action after the emergence of the plants (post-emer gence action)

Monocotyledonous and dicotyledonous test plants are sown in pots in standard soil. In the 2-3- leaf stage of the test plants, the test substances are sprayed on (500 l of spray liquor/ha) as an aqueous suspension, prepared from a wettable powder WP10 according to the desired dosage (250 g of a.i./ha). 0.2% of X77 is added as wetting agent to the spray liquor. The test plants are then grown under optimum conditions in a greenhouse.

After a test period of 3 weeks, the test is evaluated with a nine4evel scale of ratings (1=complete damage, 9=no effect). Ratings of 1 to 4 (in particular 1 to 3) mean good to very good herbicidal action, 7-9 mean good tolerance.

TABLE B4

Post-emergence action:

| Active compound No. | Abut-ilon | Amar-anthus | Cheno-podium | Kochia | Sida | Stellaria | Dose [g of AS/ha] |
|---|---|---|---|---|---|---|---|
| 1.355 | 2 | 2 | 2 | 3 | 2 | 3 | 250 |
| 1.347 | 3 | 2 | 2 | 2 | 3 | 3 | 250 |
| 1.335 | 3 | 2 | 2 | 2 | 2 | 3 | 250 |
| 1.349 | 2 | 2 | 2 | 2 | 2 | 3 | 250 |
| 1.339 | 2 | 2 | 3 | 1 | 4 | 3 | 250 |
| 1.351 | 5 | 2 | 3 | 3 | 3 | 3 | 250 |
| 1.341 | 5 | 2 | 3 | 4 | 5 | 4 | 250 |
| 1.343 | 3 | 2 | 2 | 3 | 9 | 3 | 250 |
| 1.361 | 2 | 2 | 2 | 2 | 2 | 3 | 250 |

The same results are obtained when the compounds of the formula I are formulated according to Examples F2 and F4 to F8 according to WO 97/34485.

What is claimed is:
1. A compound of the formula I

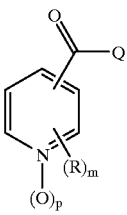

(I)

in which
each R independently is $C_1$–$C_6$alkyl, $C_1$–$C_6$alkenyl, $C_2$–$C_6$haloalkenyl, $C_2$–$C_6$alkynyl, $C_2$–$C_6$ haloalkynyl, $C_3$–$C_6$cycloalkyl, $C_1$–$C_6$alkoxy, $C_1$–$C_6$haloalkoxy, $C_1$–$C_6$alkylthio, $C_1$–$C_6$alkylsulfinyl, $C_1$–$C_6$alkylsulfonyl, $C_1$–$C_6$haloalkyl, $C_1$–$C_6$haloalkylthio, $C_1$–$C_6$haloalkylsulfinyl, $C_1$–$C_6$haloalkylsulfonyl, $C_1$–$C_6$alkoxycarbonyl, $C_1$–$C_6$alkylcarbonyl, $C_1$–$C_6$alkylamino, di-$C_1$–$C_6$ alkylamino, $C_1$–$C_6$alkylaminosulfonyl, di-$C_1$–$C_6$alkylaminosulfonyl, —N($R_1$)—S—$R_2$, —N($R_3$)—SO—$R_4$, —N($R_5$)—$SO_2$—$R_6$, nitro, cyano, halogen, hydroxyl, amino, formyl, hydroxy-$C_1$–$C_6$alkyl, $C_1$–$C_6$ alkoxy-$C_1$–$C_6$alkyl, $C_1$–$C_6$alkoxycarbonyloxy-$C_1$–$C_6$alkyl, $C_1$–$C_6$alkytthio-$C_1$–$C_6$alkyl, $C_1$–$C_6$ alkylsulfinyl-$C_1$–$C_6$alkyl, $C_1$–$C_6$alkylsulfonyl-$C_1$–$C_6$alkyl, thiocyanato-$C_1$–$C_6$alkyl, cyano-$C_1$–$C_6$ alkyl, oxiranyl, $C_3$–$C_6$alkenyloxy, $C_3$–$C_6$alkynyloxy, $C_1$–$C_6$alkoxy-$C_1$–$C_6$alkoxy, cyano-$C_1$–$C_6$ alkenyloxy, $C_1$–$C_6$alkoxycarbonyloxy-$C_1$–$C_6$alkoxy, $C_3$–$C_6$alkynyloxy, cyano-$C_1$–$C_6$lkoxy, $C_1$–$C_6$ alkoxycarbonyl-$C_1$–$C_6$alkoxy, $C_1$–$C_6$alkylthio-$C_1$–$C_6$alkoxy, alkoxycarbonyl-$C_1$–$C_6$alkylthio, alkoxycarbonyl-$C_1$–$C_6$alkylsulfinyl, alkoxycarbonyl-$C_1$–$C_6$alkylsulfonyl, $C_1$–$C_6$alkylsulfonyloxy, $C_1$–$C_6$haloalkylsulfonyloxy, phenyl, benzyl, phenoxy, phenylthio, phenylsulfinyl, phenylsulfonyl, benzylthio, benzylsulfinyl or benzylsulfonyl, where the phenyl groups may be mono- or polysubs ttuted by halogen, methyl, ethyl, trifluoromethyl, methoxy or nitro, or R is a five- to ten-membered monocyclic or fused bicyclic ring system, which may be aromatic or partially saturated and may contain 1 to 4 heteroatoms selected from the group consisting of nitrogen, oxygen and sulfur, where the ring system is either attached directly to the pyridine ring or attached to the pyridine ring via a $C_1$–$C_4$alkylene group, and where each ring system may not contain more than 2 oxygen atoms and not more than two sulfur atoms, and where the ring system for its part may be mono-, di- or trisubstituted by $C_1$–$C_6$alkyl, $C_1$–$C_6$haloalkyl, $C_3$–$C_6$alkenyl, $C_3$–$C_6$haloalkenyl, $C_3$–$C_6$alkynyl, $C_3$–$C_6$haloalkynyl, $C_1$–$C_6$alkoxy, $C_1$–$C_6$ haloalkoxy, $C_3$–$C_6$alkenyloxy, $C_3$–$C_6$alkynyloxy, mercapto, $C_1$–$C_6$alkylthio, $C_1$–$C_6$haloalkylthio, $C_3$–$C_6$alkeny fthio, $C_3$–$C_6$haloalkenylthio, $C_3$–$C_6$alkynylthio, $C_2$–$C_5$alkoxyalkylthio, $C_3$–$C_5$acetylalkylthio, $C_3$–$C_6$alkoxycarbonylalky lthio, $C_2$–$C_4$cyanoalkylthio, $C_1$–$C_6$alkylsulfinyl, $C_1$–$C_6$ haloalkylsulfinyl, $C_1$–$C_6$alkylsulfonyl, $C_1$–$C_6$haloalkylsulfonyl, aminosulfonyl, $C_1$–$C_2$ alkylaminosulfonyl, $C_2$–$C_4$dialkylaminosulfonyl, $C_1$–$C_3$alkylene-$R_7$, $NR_8R_9$, halogen, cyano, nitro, phenyl and benzylthio, where phenyl and benzylthio for their part may be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or nitro, and where substituents on the nitrogen in the heterocyclic ring are different from halogen;

m is 1, 2, 3 or 4;

p is 0 or 1;

$R_1$, $R_3$ and $R_5$ independently of one another are hydrogen or $C_1$–$C_6$alkyl;

$R_2$ is $NR_{10}R_{11}$, $C_1$–$C_6$alkoxy, $C_1$–$C_6$haloalkoxy, $C_1$–$C_6$alkyl, $C_1$–$C_6$haloalkyl, $C_3$–$C_6$alkenyl, $C_3$–C6 haloalkenyl, $C_3$–$C_6$alkynyl, $C_3$–$C_6$haloalkynyl, $C_3$–$C_6$cycloalkyl or phenyl, where phenyl for its part may be substituted by $C_1$–$C_3$alkyl, $C_1$–$C_3$haloalkyl, $C_1$–$C_3$alkoxy, $C_1$–$C_3$haloalkoxy, halogen, cyano or nitro;

$R_4$ is $NR_{12}R_{13}$, $C_1$–$C_6$alkoxy, $C_1$–$C_6$haloalkoxy, $C_1$–$C_6$alkyl, $C_1$–$C_6$haloalkyl, $C_3$–$C_6$alkenyl, $C_3$–$C_6$haloalkenyl, $C_3$–$C_6$alkynyl, $C_3$–$C_6$haloalkynyl, $C_3$–$C_6$cycloalkyl or phenyl, where phenyl for its part may be substituted by $C_1$–$C_3$alkyl, $C_1$–$C_3$haloalkyl, $C_1$–$C_3$alkoxy, $C_1$–$C_3$haloalkoxy, halogen, cyano or nitro;

$R_6$ is $NR_{14}R_{15}$, $C_1$–$C_6$alkoxy, $C_1$–$C_6$haloalkoxy, $C_1$–$C_6$alkyl, $C_1$–$C_6$haloalkyl, $C_3$–$C_6$alkenyl, $C_3$–$C_8$haloalkenyl, $C_3$–$C_6$alkynyl, $C_3$–$C_6$haloalkynyl, $C_3$–$C_6$cycloalkyl or phenyl, where phenyl for its part may be substituted by $C_1$–$C_3$alkyl, $C_1$–$C_3$haloalkyl, $C_1$–$C_3$alkoxy, $C_1$–$C_3$haloalkoxy, halogen, cyano or nitro;

$R_7$ is $C_1$–$C_3$alkoxy, $C_2$–$C_4$alkoxycarbonyl, $C_1$–$C_3$alkylthio, $C_1$–$C_3$alkylsulfinyl, $C_1$–$C_3$alkylsulfonyl or phenyl, where phenyl for its part may be substituted by $C_1$–$C_3$alkyl, $C_1$–$C_3$haloalkyl, $C_1$–$C_3$ alkoxy, $C_1$–$C_3$haloalkoxy, halogen, cyano or nitro;

$R_8$, $R_{10}$, $R_{12}$ and $R_{14}$ independently of one another are hydrogen or $C_1$–$C_6$alkyl;

$R_9$, $R_{11}$, $R_{13}$ and $R_{15}$ independently of one another are $C_1$–$C_6$alkyl or $C_1$–$C_6$alkoxy;

Q is the group $Q_1$

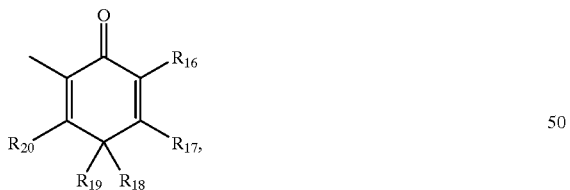

(Q₁)

in which $R_{16}$, $R_{17}$, $R_{18}$ and $R_{19}$ independently of one another are hydrogen, hydroxyl, $C_1$–$C_4$alkyl, $C_2$–$C_6$ alkenyl, $C_2$–$C_6$alkynyl, $C_1$–$C_4$alkoxycarbonyl, $C_1$–$C_6$alkylthio, $C_1$–$C_6$alkylsulfinyl, $C_1$–$C_6$ alkylsulfonyl, $C_1$–$C_4$alkyl-NHS(O)$_2$, $C_1$–$C_4$haloalkyl, —NH—$C_1$–$C_4$alkyl, —N($C_1$–$C_4$alkyl)$_2$, $C_1$–$C_6$ alkoxy, cyano, nitro, halogen or phenyl, which for its part may be substituted by $C_1$–$C_4$alkyl, $C_1$–$C_4$haloalkyl, $C_1$–$C_4$alkoxy, $C_1$–$C_4$haloalkoxy, $C_1$–$C_4$alkylcarbonyl, $C_1$–$C_4$alkoxycarbonyl, amino, $C_1$–$C_4$alkylamino, di-$C_1$–$C_4$alkylamino, $C_1$–$C_6$alkylthio, $C_1$–$C_6$alkylsulfinyl, $C_1$–$C_6$ alkylsulfonyl, $C_1$–$C_4$alkyl-$S(O)_2O$, $C_1$–$C_4$haloalkylthio, $C_1$–$C_4$haloalkylsulfinyl, $C_1$–$C_4$ haloalkylsulfonyl, $C_1$–$C_4$haloalkyl-$S(O)_2O$, $C_1$–$C_4$alkyl-$S(O)_2NH$, $C_1$–$C_4$alkyl-$S(O)_2N(C_1$–$C_4$ alkyl), halogen, nitro, COOH or cyano; or two adjacent substituents from the group consisting of $R_{16}$, $R_{17}$, $R_{18}$ and $R_{19}$ form a $C_2$–$C_6$alkylene bridge;

$R_{20}$ is hydroxyl, $O^-M^+$, halogen, cyano, SCN, OCN, $C_1$–$C_{12}$alkoxy, $C_1$–$C_4$alkoxycarbonyl-$C_1$–$C_4$ alkoxy, $C_1$–$C_{12}$alkylthio, $C_1$–$C_{12}$alkylsulfinyl, $C_1$–$C_{12}$alkylsulfonyl, $C_1$–$C_{12}$haloalkylthio, $C_1$–$C_{12}$haloalkylsulfinyl, $C_1$–$C_{12}$haloalkylsulfonyl, $C_1$–$C_6$alkoxy-$C_1$–$C_6$alkylthio, $C_1$–$C_6$alkoxy-$C_1$–$C_6$alkylsulfinyl, $C_1$–$C_6$alkoxy-$C_1$–$C_6$alkylsulfonyl, $C_2$–$C_{12}$alkenylthio, $C_2$–$C_{12}$alkenylsulfinyl, $C_2$–$C_{12}$alkenylsulfonyl, $C_2$–$C_{12}$alkynylthio, $C_2$–$C_{12}$alkynylsulfinyl, $C_2$–$C_{12}$alkynylsulfonyl, $C_2$–$C_{12}$ haloalkenylthio, $C_2$–$C_{12}$haloalkenylsulfinyl, $C_2$–$C_{12}$haloalkenylsulfonyl, $C_1$–$C_4$alkoxycarbonyl-$C_1$–$C_4$alkylthio, $C_1$–$C_4$alkoxycarbonyl-$C_1$–$C_4$alkylsulfinyl, $C_1$–$C_4$alkoxycarbonyl-$C_1$–$C_4$alkylsulfonyl, ($C_1$–$C_4$alkoxy)$_2$P(O)O, $C_1$–$C_4$alkyl-($C_1$–$C_4$alkoxy)P(O)O, H($C_1$–$C_4$alkoxy)P(O)O, $R_{37}R_{38}N$, $R_{71}R_{72}NNH$—, $R_{21}R_{22}NC(O)O$—, $R_{73}R_{74}NC(O)NH$—, $C_1$–$C_4$alkyl-$S(O)_2NR_{39}$, $C_1$–$C_4$ haloalkyl-$S(O)_2NR_{40}$, $C_1$–$C_4$alkyl-$S(O)_2O$, $C_1$–$C_4$haloalkyl-$S(O)_2O$, $C_1$–$C_{18}$alkylcarbonyloxy, where the alkyl group may be substituted by halogen, $C_1$–$C_6$alkoxy, $C_1$–$C_6$alkylthio or cyano, $C_2$–$C_{18}$alkenylcarbonyloxy, $C_2$–$C_{18}$alkynylcarbonyloxy, $C_3$–$C_6$cycloalkylcarbonyloxy, $C_1$–$C_{12}$alkoxycarbonyloxy, $C_1$–$C_{12}$alkylthiocarbonyloxy, $C_1$–$C_{12}$alkylthiocarbamoyl, $C_1$–$C_6$alkyl-NH(CS)N($C_1$–$C_6$alkyl)—NH—, di-$C_1$–$C_6$alkyl-N(CS)N($C_1$–$C_6$alkyl)—NH—, benzyloxy, benzylthio, benzylsulfinyl, benzylsulfonyl, phenoxy, phenylthio, phenylsulfinyl, phenylsulfonyl, phenylsulfonyloxy or benzoyloxy, where the phenyl groups for their part may each be substituted by $C_1$–$C_4$alkyl, $C_1$–$C_4$haloalkyl, $C_1$–$C_4$alkoxy, $C_1$–$C_4$haloalkoxy, $C_1$–$C_4$alkylcarbonyl, $C_1$–$C_4$alkoxycarbonyl, $C_1$–$C_4$alkylamino, di-$C_1$–$C_4$alkylamino, $C_1$–$C_4$alkylthio, $C_1$–$C_4$alkylsulfinyl, $C_1$–$C_4$alkylsulfonyl, $C_1$–$C_4$alkyl-$S(O)_2O$, $C_1$–$C_4$hatoalkylthio, $C_1$–$C_4$haloalkylsulfinyl, $C_1$–$C_4$ haloalkylsulfonyl, $C_1$–$C_4$haloalkyl-$S(O)_2O$, $C_1$–$C_4$alkyl-$S(O)_2NH$, $C_1$–$C_4$alkyl-$S(O)_2N(C_1$–$C_4$ alkyl), halogen, nitro or cyano, or a group $Ar_1$-thio, $Ar_2$-sulfinyl, $Ar_3$-sulfonyl, —OCO—$Ar_4$ or NH—$Ar_5$ in which $Ar_1$, $Ar_2$, $Ar_3$, $Ar_4$ and $Ar_5$ independently of one another are a five- to ten-membered monocyclic or fused bicyclic ring system which may be aromatic or partially saturated and may contain 1 to 4 heteroatoms selected from the group consisting of nitrogen, oxygen and sulfur, and in which each ring system may not contain more than 2 oxygen atoms and not more than two sulfur atoms, and in which the ring system for its part may be mono-, di- or trisubstituted by $C_1$–$C_6$alkyl, $C_1$–$C_6$haloalkyl, $C_3$–$C_6$alkenyl, $C_3$–$C_6$haloalkenyl, $C_3$–$C_6$alkynyl, $C_3$–$C_6$haloalkynyl, $C_1$–$C_6$alkoxy, $C_1$–$C_6$haloalkoxy, $C_3$–$C_6$alkenyloxy, $C_3$–$C_6$alkynyloxy, mercapto, $C_1$–$C_6$alkylthio, $C_1$–$C_6$haloalkylthio, $C_3$–$C_6$alkenylthio, $C_3$–$C_6$haloalkenylthio, $C_3$–$C_6$alkynyfthio, $C_2$–$C_5$ alkoxyalkylthio, $C_3$–$C_5$acetylalkylthio, $C_3$–$C_6$alkoxycarbonylalkylthio, $C_2$–$C_4$cyanoalkylthio, $C_1$–$C_6$alkylsulfinyl, $C_1$–$C_6$haloalkylsulfinyl, $C_1$–$C_6$alkylsulfonyl, $C_1$–$C_6$haloalkylsulfonyl, aminosulfonyl, $C_1$–$C_2$alkylaminosulfonyl, $C_2$–$C_4$dialkylaminosulfonyl, $C_1$–$C_3$alkylene-$R_{41}$, $NR_{42}R_{43}$, halogen, cyano, nitro, phenyl and benzylthio, where phenyl and benzylthio for their part may be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or nitro, and where substituents on the nitrogen in the heterocyclic ring are different from halogen;

$R_{41}$ is $C_1$–$C_3$alkoxy, $C_2$–$C_4$alkoxycarbonyl, $C_1$–$C_3$alkylthio, $C_1$–$C_3$alkylsulfinyl, $C_1$–$C_3$ alkylsulfonyl or phenyl, where phenyl for its part may be substituted by $C_1$–$C_3$alkyl, $C_1$–$C_3$ haloalkyl, $C_1$–$C_3$alkoxy, $C_1$–$C_3$haloalkoxy, halogen, cyano or nitro;

$R_{42}$ is hydrogen or $C_1$–$C_6$alkyl;

$R_{43}$ is $C_1$–$C_6$alkyl or $C_1$–$C_6$alkoxy;

$R_{21}$, $R_{37}$, $R_{39}$, $R_{40}$, $R_{71}$ and $R_{73}$ independently of one another are hydrogen or $C_1$–$C_4$alkyl;

$R_{22}$, $R_{38}$, $R_{72}$ and $R_{74}$ independently of one another are hydrogen, $C_1$–$C_{12}$alkyl, hydroxyl, $C_1$–$C_{12}$alkoxy, $C_3$–$C_6$alkenyloxy or $C_3$–$C_6$alkynyloxy; or $R_{21}$ and $R_{22}$ together or $R_{37}$ and $R_{38}$ together or $R_{71}$ and $R_{72}$ together or $R_{73}$ and $R_{74}$ together are pyrrolidino, piperidino, morpholino, thiomorpholino, which may be mono- or polysubstituted by methyl groups; or are the group $Q_2$

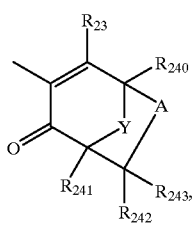

($Q_2$)

in which

Y is a chemical bond, an alkylene group A 1, carbonyl, oxygen, sulfur, sulfinyl, suifonyl, —$NHR_{248}$ or $NH(CO)R_{249}$;

$A_1$ is $C(R_{246}R_{247})m_{01}$;

A is $C(R_{244}R_{245})r$;

r and $m_{01}$ independently of one another are 1 or 2;

$R_{240}$ is hydrogen, methyl or $C_1$–$C_3$alkoxycarbonyl;

$R_{241}$, $R_{242}$, $R_{243}$, $R_{244}$, $R_{245}$, $R_{246}$ and $R_{247}$ independently of one another are hydrogen, halogen or methyl, or $R_{243}$ together with an adjacent group $R_{245}$ or $R_{247}$ is a chemical bond;

$R_{248}$ and $R_{249}$ independently of one another are hydrogen or $C_1$–$C_4$alkyl;

$R_{23}$ is hydroxyl, $O^-M^+$, halogen, cyano, SCN, OCN, $C_1$–$C_{12}$alkoxy, $C_1$–$C_4$alkoxycarbonyl-$C_1$–$C_4$ alkoxy, $C_1$–$C_{12}$alkylthio, $C_1$–$C_{12}$alkylsulfinyl, $C_1$–$C_{12}$alkylsulfonyl, $C_1$–$C_{12}$haloalkylthio, $C_1$–$C_{12}$haloalkylsulfinyl, $C_1$–$C_{12}$haloalkylsulfonyl, $C_1$–$C_6$alkoxy-$C_1$–$C_6$alkylthio, $C_1$–$C_6$alkoxy-$C_1$–$C_6$alkylsulfinyl, $C_1$–$C_6$alkoxy-$C_1$–$C_6$alkylsulfonyl, $C_2$–$C_{12}$alkenylthio, $C_2$–$C_{12}$alkenylsulfinyl, $C_2$–$C_{12}$alkenylsulfonyl, $C_2$–$C_{12}$alkynylthio, $C_2$–$C_{12}$alkynylsulfinyl, $C_2$–$C_{12}$alkynylsulfonyl, $C_2$–$C_{12}$ haloalkenylthio, $C_2$–$C_{12}$haloalkenylsulfinyl, $C_2$–$C_{12}$haloalkenylsulfonyl, $C_1$–$C_4$alkoxycarbonyl-$C_1$–$C_4$alkylthio, $C_1$–$C_4$alkoxycarbonyl-$C_1$–$C_4$alkylsulfinyl, $C_1$–$C_4$alkoxycarbonyl-$C_1$–$C_4$alkylsulfonyl, $(C_1$–$C_4$alkoxy$)_2$P(O)O, $C_1$–$C_4$alky 1-$(C_1$–$C_4$alkoxy)P(O)O, H$(C_1$–$C_4$alkoxy)P(O)O, $R_{44}R_{45}$N, $R_{75}R_{76}$NNH—, $R_{46}R_{47}$NC(O)O—, $R_{77}R_{78}$NC(O)NH—, $C_1$–$C_4$alkyl-S(O)$_2$NR$_{48}$, $C_1$–$C_4$ haloalkyl-S(O)$_2$NR$_{49}$, $C_1$–$C_4$alkyl-S(O)$_2$O, $C_1$–$C_4$haloalkyl-S(O)$_2$O, $C_1$–$C_{18}$alkylcarbonyloxy, where the alkyl group may be substituted by halogen, $C_1$–$C_6$alkoxy, $C_1$–$C_6$alkylthio or cyano, $C_2$–$C_{18}$alkenylcarbonyloxy, $C_2$–$C_{18}$alkynylcarbonyloxy, $C_3$–$C_6$cycloalkylcarbonyioxy, $C_1$–$C_{12}$alkoxycarbonyloxy, $C_1$–$C_{12}$alkylthiocarbonyloxy, $C_1$–$C_{12}$alkylthiocarbamoyl, $C_1$–$C_6$alkyl-NH(CS)N($C_1$–$C_6$alkyl)—NH—, di-$C_1$–$C_6$alkyl-N(CS)N($C_1$–$C_6$alkyl)—NH—, benzyloxy, benzylthio, benzyisulfinyl, benzylsulfonyl, phenoxy, phenylthio, phenylsulfinyl, phenylsulfonyl, phenylsulfonyloxy or benzoyloxy, where the phenyl groups for their part may each be substituted by $C_1$–$C_4$alkyl, $C_1$–$C_4$haloalkyl, $C_1$–$C_4$alkoxy, $C_1$–$C_4$haloalkoxy, $C_1$–$C_4$alkylcarbonyl, $C_1$–$C_4$alkoxycarbonyl, $C_1$–$C_4$alkylamino, di-$C_1$–$C_4$alkylamino, $C_1$–$C_4$alkylthio, $C_1$–$C_4$alkylsulfinyl, $C_1$–$C_4$alkylsulfonyl, $C_1$–$C_4$alkyl-S(O)$_2$O, $C_1$–$C_4$haloalkylthio, $C_1$–$C_4$haloalkylsulfinyl, $C_1$–$C_4$ haloalkylsulfonyl, $C_1$–$C_4$haloalkyl-S(O)$_2$O, $C_1$–$C_4$alkyl-S(O)$_2$NH, $C_1$–$C_4$alkyl-S(O)$_2$N($C_1$–$C_4$ alkyl), halogen, nitro or cyano, or a group $Ar_6$-thio, $Arr$sulfinyl, $Ar_8$-sulfonyl, —OCO—$Ar_9$ or NH—$Ar_{10}$ in which $Ar_6$, $Ar_7$, $Ar_8$, $Ar_9$ and $Ar_{10}$ independently of one another are a five- to ten-membered monocyclic or fused bicyclic ring system which may be aromatic or partially saturated and may contain 1 to 4 heteroatoms selected from the group consisting of nitrogen, oxygen and sulfur, and in which each ring system may not contain more than 2 oxygen atoms and not more than two sulfur atoms, and in which the ring system for its part may be mono-, di- or trisubstituted by $C_1$–$C_6$alkyl, $C_1$–$C_6$haloalkyl, $C_3$–$C_6$alkenyl, $C_3$–$C_6$haloalkenyl, $C_3$–$C_6$alkynyl, $C_3$–$C_6$haloalkynyl, $C_1$–$C_6$alkoxy, $C_1$–$C_6$haloalkoxy, $C_3$–$C_6$alkenyloxy, $C_3$–$C_6$alkyny toxy, mercapto, $C_1$–$C_6$alkylthio, $C_1$–$C_6$haloalkylthio, $C_3$–$C_6$alkenylthio, $C_3$–$C_6$haloalkenylthio, $C_3$–$C_6$alkynylthio, $C_2$–$C_5$ alkoxyalkylthio, $C_3$–$C_5$acetylalkylthio, $C_3$–$C_6$alkoxycarbonylalkylthio, $C_2$–$C_4$cyanoalkylthio, $C_1$–$C_6$alkylsulfinyl, $C_1$–$C_6$haloalkylsulfinyl, $C_1$–$C_6$alkylsulfonyl, $C_1$–$C_6$haloalkylsulfonyl, aminosulfonyl, $C_1$–$C_2$alkylaminosulfonyl, $C_2$–$C_4$dialkylaminosulfonyl, $C_1$–$C_3$alkylene-$R_{50}$, $NR_{51}R_{52}$, halogen, cyano, nitro, phenyl and benzylthio, where phenyl and benzylthio for their part may be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or nitro, and where substituents on the nitrogen in the heterocyclic ring are different from halogen;

$R_{50}$ is $C_1$–$C_3$alkoxy, $C_2$–$C_4$alkoxycarbonyl, $C_1$–$C_3$alkylthio, $C_1$–$C_3$alkylsulfinyl, $C_1$–$C_3$alkylsulfonyl or phenyl, where phenyl for its part may be substituted by $C_1$–$C_3$alkyl, $C_1$–$C_3$haloalkyl, $C_1$–$C_3$ alkoxy, $C_1$–$C_3$haloalkoxy, halogen, cyano or nitro;

$R_{51}$ is hydrogen or $C_1$–$C_6$alkyl;

$R_{52}$ is $C_1$–$C_6$alkyl or $C_1$–$C_6$alkoxy;

$R_{46}$, $R_{44}$, $R_{48}$, $R_{49}$, $R_{75}$ and $R_{77}$ independently of one another are hydrogen or $C_1$–$C_4$alkyl;

$R_{47}$, $R_{45}$, $R_{76}$ and $R_{78}$ independently of one another are hydrogen, $C_1$–$C_{12}$alkyl, hydroxyl, $C_1$–$C_{12}$alkoxy, $C_3$–$C_6$alkenyloxy or $C_3$–$C_6$alkynyloxy; or $R_{44}$ and $R_{45}$ together or $R_{46}$ and $R_{47}$ together or $R_{75}$ and $R_{76}$ together or $R_{77}$ and $R_{78}$ together are pyrro tidino, piperidino, morpholino, thiomorpholino, which may be mono- or polysubstituted by methyl groups; or are the group $Q_3$

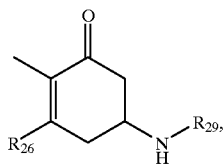

(Q$_3$)

in which $R_2$ is hydroxyl, $O^-M^+$, halogen, cyano, SCN, OCN, $C_1$–$C_{12}$alkyl, $C_1$–$C_4$alkoxycarbonyl-$C_1$–$C_4$ alkoxy, $C_1$–$C_{12}$alkylthio, $C_1$–$C_{12}$alkylsulfinyl, $C_1$–$C_{12}$alkylsulfonyl, $C_1$–$C_{12}$haloalkylthio, $C_1$–$C_{12}$haloalkylsulfinyl, $C_1$–$C_{12}$haloalkylsulfonyl, $C_1$–$C_6$alkoxy-$C_1$–$C_6$alkylthio, $C_1$–$C_6$alkoxy-$C_1$–$C_6$alkylsulfinyl, $C_1$–$C_6$alkoxy-$C_1$–$C_6$alkylsulfonyl, $C_2$–$C_{12}$alkenylthio, $C_2$–$C_{12}$alkenylsulfinyl, $C_2$–$C_{12}$alkenylsulfonyl, $C_2$–$C_{12}$alkynylthio, $C_2$–$C_{12}$alkynylsulfinyl, $C_2$–$C_{12}$alkynylsulfonyl, $C_2$–$C_{12}$ haloalkenylthio, $C_2$–$C_{12}$haloalkenyisulfinyl, $C_1$–$C_{12}$haloalkenylsulfonyl, $C_1$–$C_4$alkoxycarbonyl-$C_1$–$C_4$alkylthio, $C_1$–$C_4$alkoxycarbonyl-$C_1$–$C_4$alkylsulfinyl, $C_1$–$C_4$alkoxycarbonyl-$C_1$–$C_4$alkylsulfonyl, $(C_1$–$C_4$alkoxy$)_2$P(O)O, $C_1$–$C_4$alkyl-$(C_1$–$C_4$alkoxy)P(O)O, H$(C_1$–$C_4$alkoxy)P(O)O, $R_{53}R_{54}$N, $R_{79}R_{80}$NNH—, $R_{55}R_{56}$NC(O)O—, $R_{81}R_{82}$NC(O)NH—, $C_1$–$C_4$alkyl-S(O)$_2$NR$_{57}$, $C_1$–$C_4$ haloalkyl-S(O)$_2$NR$_{58}$, $C_1$–$C_4$alkyl-S(O)$_2$O, $C_1$–$C_4$haloalkyl-S(O)$_2$O, $C_1$–$C_{18}$alkylcarbonyloxy, where the alkyl group may be substituted by halogen, $C_1$–$C_6$alkoxy, $C_1$–$C_6$alkylthio or cyano, $C_2$–$C_{18}$alkenyicarbonyloxy, $C_2$–$C_{18}$alkynylcarbonyloxy, $C_3$–$C_6$cycloalkylcarbonyloxy, $C_1$–$C_{12}$alkoxycarbonyloxy, $C_1$–$C_{12}$alkylthiocarbonyloxy, $C_1$–$C_{12}$alkylthiocarbamoyl, $C_1$–$C_6$alkyl-NH(CS)N$(C_1$–$C_6$alkyl)—NH—, di-$C_1$–$C_6$alkyl-N(CS)N$(C_1$–$C_6$alkyl)—NH—, benzyloxy, benzylthio, benzylsulfinyl, benzylsulfonyl, phenoxy, phenylthio, phenylsulfinyl, phenylsulfonyl, phenylsulfonyloxy or benzoyloxy, where the phenyl groups for their part may each be substituted by $C_1$–$C_4$alkyl, $C_1$–$C_4$haloalkyl, $C_1$–$C_4$alkoxy, $C_1$–$C_4$haloalkoxy, $C_1$–$C_4$alkylcarbonyl, $C_1$–$C_4$alkoxycarbonyl, $C_1$–$C_4$alkylamino, di-$C_1$–$C_4$alkylamino, $C_1$–$C_4$alkylthio, $C_1$–$C_4$alkylsulfinyl, $C_1$–$C_4$alkylsulfonyl, $C_1$–$C_4$alkyl-S(O)$_2$O, $C_1$–$C_4$haloalkylthio, $C_1$–$C_4$haloalkylsulfinyl, $C_1$–$C_4$ haloalkylsulfonyl, $C_1$–$C_4$haloalkyl-S(O)$_2$O, $C_1$–$C_4$alkyl-S(O)$_2$NH, $C_1$–$C_4$alkyl-S(O)$_2$N($C_1$–$C_4$ alkyl), halogen, nitro or cyano, or a group $Ar_{11}$-thio, $Ar_{12}$-sulfinyl, $Ar_{13}$-sulfonyl, —OCO—$Ar_{14}$ or NH—$Ar_{15}$ in which $Ar_{11}$, $Ar_{12}$, $Ar_{13}$, $Ar_{14}$ and $Ar_{15}$ independently of one another are a five- to ten-membered monocyclic or fused bicyclic ring system which may be aromatic or partially saturated and may contain 1 to 4 heteroatoms selected from the group consisting of nitrogen, oxygen and sulfur, and in which each ring system may not contain more than 2 oxygen atoms and not more than two sulfur atoms, and in which the ring system for its part may be mono-, di- or trisubstituted by $C_1$–$C_6$alkyl, $C_1$–$C_6$haloalkyl, $C_3$–$C_6$alkenyl, $C_3$–$C_6$haloalkenyl, $C_3$–$C_6$alkynyl, $C_3$–$C_6$haloalkynyl, $C_1$–$C_6$alkoxy, $C_1$–$C_6$haloalkoxy, $C_3$–$C_6$alkenyloxy, $C_3$–$C_6$alkynyloxy, mercapto, $C_1$–$C_6$alkylthio, $C_1$–$C_6$haloalkylthio, $C_3$–$C_6$alkenylthio, $C_3$–$C_6$haloalkenylthio, $C_3$–$C_6$alkynylthio, $C_2$–$C_5$ alkoxyalkylthio, $C_3$–$C_5$acetylalkylthio, $C_3$–$C_6$alkoxycarbonylalkylthio, $C_2$–$C_4$cyanoalkylthio, $C_1$–$C_6$alkylsulfinyl, $C_1$–$C_6$haloalkylsulfinyl, $C_1$–$C_6$alkylsulfonyl, $C_1$–$C_6$haloalkylsu ffonyl, aminosulfonyl, $C_1$–$C_2$alkylaminosulfonyl, $C_2$–$C_4$dialkylaminosulfonyl, $C_1$–$C_3$alkylene-$R_{59}$, $NR_{60}R_{61}$, halogen, cyano, nitro, phenyl and benzylthio, where phenyl and benzylthio for their part may be substituted on the phenyl ring by $C_1$–$C_3$alkyl, $C_1$–$C_3$haloalkyl, $C_1$–$C_3$alkoxy, $C_1$–$C_3$haloalkoxy, halogen, cyano or nitro, and where substituents on the nitrogen in the heterocyclic ring are different from halogen;

$R_{59}$ is $C_1$–$C_3$alkoxy, $C_2$–$C_4$alkoxycarbonyl, $C_1$–$C_3$alkylthio, $C_1$–$C_3$alkylsulfinyl, $C_1$–$C_3$alkylsulfonyl or phenyl, where phenyl for its part may be substituted by $C_1$–$C_3$alkyl, $C_1$–$C_3$haloalkyl, $C_1$–$C_3$ alkoxy, $C_1$–$C_3$haloalkoxy, halogen, cyano or nitro;

$R_{60}$ is hydrogen or $C_1$–$C_6$alkyl;

$R_{61}$ is $C_1$–$C_6$alkyl or $C_1$–$C_6$alkoxy;

$R_{55}$, $R_{53}$, $R_{57}$, $R_{58}$, $R_{79}$ and $R_{81}$ independently of one another are hydrogen or $C_1$–$C_4$alkyl; $R_{56}$, $R_{54}$, $R_{80}$ and $R_{82}$ independently of one another are hydrogen, $C_1$–$C_{12}$alkyl, hydroxyl, $C_1$–$C_{12}$alkoxy, $C_3$–$C_6$alkenyloxy or $C_3$–$C_6$alkynyloxy; or $R_{53}$ and $R_{54}$ together or $R_{55}$ and $R_{56}$ together or $R_{79}$ and $R_{80}$ together or $R_{81}$ and $R_{82}$ together are pyrrolidino, piperidino, morpholino, thiomorpholino, which may be mono- or polysubstituted by methyl groups; $R_{29}$ is hydrogen, $C_1$–$C_6$alkyl, $C_1$–$C_4$alkylcarbonyl, $C_1$–$C_4$alkoxycarbonyl, $(C_1$–$C_4$alkyl)NHCO, phenylaminocarbonyl, benzylaminocarbonyl or $(C_1$–$C_4$alkyl)$_2$NCO, where the phenyl and benzyl groups for their part may each be substituted by $C_1$–$C_4$alkyl, $C_1$–$C_4$haloalkyl, $C_1$–$C_4$ alkoxy, $C_1$–$C_4$haloalkoxy, $C_1$–$C_4$alkylcarbonyl, $C_1$–$C_4$alkoxycarbonyl, $C_1$–$C_4$alkylamino, di-$C_1$–$C_4$ alkylamino, $C_1$–$C_4$alkylthio, $C_1$–$C_4$alkylsulfinyl, $C_1$–$C_4$alkylsulfonyl, $C_1$–$C_4$alkyl-S(O)$_2$O, $C_1$–$C_4$ haloalkylthio, $C_1$–$C_4$haloalkylsulfinyl, $C_1$–$C_4$haloalkylsulfonyl, $C_1$–$C_4$haloalkyl-S(O)$_2$O, $C_1$–$C_4$ alkyl-S(O)$_2$NH, $C_1$–$C_4$alkyl-S(O)$_2$N$(C_1$–$C_4$alkyl), halogen, nitro or cyano;

or is the group $Q_4$ (Q4)

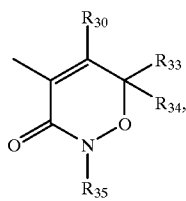

in which

R$_{30}$ is hydroxyl, O$^-$M$^+$, halogen, cyano, SCN, OCN, C$_1$–C$_{12}$alkoxy, C$_1$–C$_4$alkoxycarbonyl-C$_1$–C$_4$ alkoxy, C$_1$–C$_{12}$alkylthio, C$_1$–C$_{12}$alkylsulfinyl, C$_1$–C$_{12}$alkyisulfonyl, C$_1$–C$_{12}$haloalkylthio, C$_1$–C$_{12}$ haloalkylsulfinyl, C$_1$–C$_{12}$haloalkylsulfonyl, C$_1$–C$_6$alkoxy-C$_1$–C$_6$alkylthio, C$_1$–C$_6$alkoxy-C$_1$–C$_6$alkylsu ifinyl, C$_1$–C$_6$alkoxy-C$_1$–C$_6$alkylsulfonyl, C$_2$–C$_{12}$alkenylthio, C$_2$–C$_{12}$alkenylsulfinyl, C$_2$–C$_{12}$ alkenylsulfonyl, C$_2$–C$_{12}$alkynylthio, C$_2$–C$_{12}$alkynylsulfinyl, C$_2$–C$_2$alkynylsulfonyl, C$_2$–C$_{12}$ haloalkenylthio, C$_2$–C$_{12}$haloalkenylsulfinyl, C$_2$–C$_{12}$haloalkenylsulfonyl, C$_1$–C$_4$alkoxycarbonyl-C$_1$–C$_4$alkylthio, C$_1$–C$_4$alkoxycarbonyl-C$_1$–C$_4$alkylsulfinyl, C$_1$–C$_4$alkoxycarbonyl-C$_1$–C$_4$alkylsulfonyl, (C$_1$–C$_4$alkoxy)$_2$P(O)O, C$_1$–C$_4$alkyl-(C$_1$–C$_4$alkoxy)P(O)O, H(C$_1$–C$_4$alkoxy)P(O)O, R$_{62}$R$_{63}$N, R$_{83}$R$_{84}$NNH—, R$_{64}$R$_{65}$NC(O)—, R$_{85}$R$_{86}$NC(O)NH—, C$_1$–C$_4$alkyl-S(O)$_2$NR$_{66}$, C$_1$–C$_4$ haloalkyl-S(O)$_2$NR$_{67}$, C$_1$–C$_4$alkyl-S(O)$_2$O, C$_1$–C$_4$haloalkyl-S(O)$_2$O, C$_1$–C$_{18}$alkylcarbonyloxy, where the alkyl group may be substituted by halogen, C$_1$–C$_6$alkoxy, C$_1$–C$_6$alkylthio or cyano, C$_2$–C$_{18}$alkenylcarbonyloxy, C$_2$–C$_{18}$alkynylcarbonyloxy, C$_3$–C$_6$cycloalkylcarbonyloxy, C$_1$–C$_{12}$alkoxycarbonyloxy, C$_1$–C$_{12}$alkylthiocarbonyloxy, C$_1$–C$_{12}$alkylthiocarbamoyl, C$_1$–C$_6$alkyl-NH(CS)N(C$_1$–C$_6$alkyl)—NH—, di-C$_1$–C$_6$alkyl-N(CS)N(C$_1$–C$_6$alkyl)—NH—, benzyloxy, benzylthio, benzylsulfinyl, benzylsulfonyl, phenoxy, phenylthio, phenylsulfinyl, phenylsulfonyl, phenylsulfonyloxy or benzoyloxy, where the phenyl groups for their part may each be substituted by C$_1$–C$_4$alkyl, C$_1$–C$_4$haloalkyl, C$_1$–C$_4$alkoxy, C$_1$–C$_4$haloalkoxy, C$_1$–C$_4$alkylcarbonyl, C$_1$–C$_4$alkoxycarbonyl, C$_1$–C$_4$alkylamino, di-C$_1$–C$_4$alkylamino, C$_1$–C$_4$alkylthio, C$_1$–C$_4$alkylsulfinyl, C$_1$–C$_4$alkylsulfonyl, C$_1$–C$_4$alkyl-S(O)$_2$O, C$_1$–C$_4$haloalkylthio, C$_1$–C$_4$haloalkylsulfinyl, C$_1$–C$_4$ haloalkylsulfonyl, C$_1$–C$_4$haloalkyl-S(O)$_2$O, C$_1$–C$_4$alkyl-S(O)$_2$NH, C$_1$–C$_4$alkyl-S(O)$_2$N(C$_1$–C$_4$alkyl), halogen, nitro or cyano, or a group Ar$_{16}$-thio, Ar$_{17}$sulfinyl, Ar$_{18}$-sulfonyl, —OCO—Ar$_{19}$ or NH—Ar$_{20}$ in which Ar$_{16}$, Ar$_{17}$, Ar$_{18}$, Ar$_{19}$ and Ar$_{20}$ independently of one another are a five- to ten-membered monocyclic or fused bicyclic ring system which may be aromatic or partially saturated and may contain 1 to 4 heteroatoms selected from the group consisting of nitrogen, oxygen and sulfur, and in which each ring system may not contain more than 2 oxygen atoms and not more than two sulfur atoms, and in which the ring system for its part may be mono-, di- or trisubstituted by C$_1$–C$_6$alkyl, C$_1$–C$_6$haloalkyl, C$_3$–C$_6$alkenyl, C$_3$–C$_6$haloalkenyl, C$_3$–C$_6$alkynyl, C$_3$–C$_6$haloalkynyl, C$_1$–C$_6$alkoxy, C$_1$–C$_6$haloalkoxy, C$_3$–C$_6$alkenyloxy, C$_3$–C$_6$alkynyloxy, mercapto, C$_1$–C$_6$alkylthio, C$_1$–C$_6$haloalkylthio, C$_3$–C$_6$alkenylthio, C$_3$–C$_6$haloalkenylthio, C$_3$–C$_6$alkynylthio, C$_2$–C$_5$ alkoxyalkylthio, C$_3$–C$_5$acetylalkylthio, C$_3$–C$_6$alkoxycarbonylalkylthio, C$_2$–C$_4$cyanoalkylthio, C$_1$–C$_6$alkylsulfinyl, C$_1$–C$_6$haloalkylsulfinyl, C$_1$–C$_6$alkylsulfonyl, C$_1$–C$_6$haioalkyisulfonyl, aminosulfonyl, C$_1$–C$_2$alkylaminosulfonyl, C$_2$–C$_4$dialkylaminosulfonyl, C$_1$–C$_3$alkylene-R$_{68}$, NR$_{69}$R$_{70}$, halogen, cyano, nitro, phenyl and benzylthio, where phenyl and benzylthio for their part may be substituted on the phenyl ring by C$_1$–C$_3$alkyl, C$_1$–C$_3$haloalkyl, C$_1$–C$_3$alkoxy, C$_1$–C$_3$haloalkoxy, halogen, cyano or nitro, and where substituents on the nitrogen in the heterocyclic ring are different from halogen;

R$_{68}$ is C$_1$–C$_3$alkoxy, C$_2$C$_4$alkoxycarbonylt, C$_1$–C$_3$alkylthio, C$_1$–C$_3$alkylsulfinyl, C$_1$–C$_3$alkylsulfonyl or phenyl, where phenyl for its part may be substituted by C$_1$–C$_3$alkyl, C$_1$–C$_3$haloalkyl, C$_1$–C$_3$ alkoxy, C$_1$–C$_3$haloalkoxy, halogen, cyano or nitro;

R$_{70}$ is hydrogen or C$_1$–C$_6$alkyl;

R$_{61}$ is C$_1$–C$_6$alkyl or C$_1$–C$_6$alkoxy;

R$_{64}$, R$_{62}$, R$_{66}$, R$_{67}$, R$_{83}$ and R$_{85}$ independently of one another are hydrogen or C$_1$–C$_4$alkyl;

R$_{65}$, R$_{63}$, R$_{84}$ and R$_{86}$ independently of one another are hydrogen, C$_1$–C$_{12}$alkyl, hydroxyl, C$_1$–C$_{12}$alkoxy, C$_3$–C$_6$alkenyloxy or C$_3$–C$_6$alkynyloxy; or R$_{62}$ and R$_{63}$ together or R$_{64}$ and R$_{65}$ together or R$_{83}$ and R$_{84}$ together or R$_{85}$ and R$_{86}$ together are pyrrolidino, piperidino, morpholino, thiomorpholino, which may be mono- or polysubstituted by methyl groups;

R$_{33}$ and R$_{34}$ independently of one another are hydrogen, C$_1$–C$_4$alkyl, C$_2$–C$_6$alkenyl, C$_2$–C$_6$ alkynyl, C$_1$–C$_4$alkoxycarbonyl, C$_1$–C$_6$alkylthio, C$_1$–C$_6$alkylsulfinyl, C$_1$–C$_6$alkylsulfonyl, C$_1$–C$_4$ alkyl-NHS(O)$_2$, C$_1$–C$_4$haloalkyl, —NH—C$_1$–C$_4$alkyl, —N(C$_1$–C$_4$alkyl)$_2$, C$_1$–C$_6$alkoxy or phenyl, which for its part may be substituted by C$_1$–C$_4$alkyl, C$_1$–C$_4$haloalkyl, C$_1$–C$_4$alkoxy, C$_1$–C$_4$haloalkoxy, C$_1$–C$_4$alkylcarbonyl, C$_1$–C$_4$alkoxycarbonyl, amino, C$_1$–C$_4$alkylamino, di-C$_1$–C$_4$alkylamino, C$_1$–C$_6$alkylthio, C$_1$–C$_6$alkylsulfinyl, C$_1$–C$_6$alkylsulfonyl, C$_1$–C$_4$alkyl-S(O)$_2$O, C$_1$–C$_4$haloalkylthio, C$_1$–C$_4$ haloalkylsulfinyl, C$_1$–C$_4$haloalkylsulfonyl, C$_1$–C$_4$haloalkyl-S(O)$_2$O, C$_1$–C$_4$alkyl-S(O)$_2$NH, C$_1$–C$_4$ alkyl-S(O)$_2$N(C$_1$–C$_4$alkyl), halogen, nitro, COOH or cyano; or R$_{33}$ and R$_{34}$ together form a C$_2$–C$_6$alkylene bridge; and R$_{35}$ is hydrogen, C$_1$–C$_6$alkyl, C$_3$–C$_6$alkenyl, C$_3$–C$_6$alkynyl or benzyl, which for its part may be substituted by halogen, methyl or methoxy, or is C$_1$–C$_4$alkoxycarbonyl or phenyl, which for its part may be substituted by C$_1$–C$_4$alkyl, C$_1$–C$_4$haloalkyl, C$_1$–C$_4$alkoxy, C$_1$–C$_4$haloalkoxy, C$_1$–C$_4$ alkylcarbonyl, C$_1$–C$_4$alkoxycarbonyl, amino, C$_1$–C$_4$alkylamino, di-C$_1$–C$_4$alkylamino, C$_1$–C$_4$ alkylthio, C$_1$–C$_4$alkylsulfinyl, C$_1$–C$_4$alkylsulfonyl, C$_1$–c$_4$alkyl-S(O)$_2$O, C$_1$–C$_4$haloalkylthio, C$_1$–C$_4$ haloalkylsulfinyl, C$_1$–C$_4$haloalkylsulfonyl, C$_1$–C$_4$haloalkyl-S(O)$_2$O, C$_1$–C$_4$alkyl-S(O)$_2$NH, C$_1$–C$_4$ alkyl-S(O)$_2$N(C$_1$–C$_4$alkyl), halogen, nitro, COOH or cyano;

or is the group $Q_5$

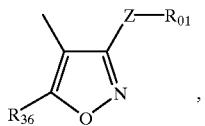

($Q_5$)

in which $Z$ is S, SO or $SO_2$;

$R_{01}$ is hydrogen, $C_1$–$C_8$alkyl, $C_1$–$C_8$alkyl substituted by halogen, $C_1$–$C_4$alkoxy, $C_1$–$C_4$alkylthio, $C_1$–$C_4$alkylsulfonyl, $C_1$–$C_4$alkylsulfinyl, —$CO_2R_{02}$, —$COR_{03}$, —$COSR_{04}$, —$NR_{05}R_{06}$, $CONR_{036}R_{037}$ or phenyl, which for its part may be substituted by $C_1$–$C_4$alkyl, $C_1$–$C_6$haloalkyl, $C_1$–$C_4$alkoxy, $C_1$–$C_4$haloalkoxy, $C_2$–$C_6$alkenyl, $C_3$–$C_6$alkynyl, $C_3$–$C_6$alkenyloxy, $C_3$–$C_6$alkynyloxy, halogen, nitro, cyano, —COOH, $COOC_1$–$C_4$alkyl, COOphenyl, $C_1$–$C_4$alkoxy, phenoxy, ($C_1$–$C_4$alkoxy)-$C_1$–$C_4$ alkyl, ($C_1$–$C_4$alkylthio)-$C_1$–$C_4$alkyl, ($C_1$–$C_4$alkylsulfinyl)-$C_1$–$C_4$alkyl, ($C_1$–$C_4$alkylsulfonyl)-$C_1$–$C_4$ aikyl, $NHSO_2$—$C_1$–$C_4$alkyl, $NHSO_2$-phenyl, $N(C_1$–$C_6$alkyl)$SO_2$—$C_1$–$C_4$alkyl, $N(C_1$–$C_6$alkyl)$SO_2$-phenyl, $N(C_2$–$C_6$alkenyl)$SO_2$—$C_1$–$C_4$alkyl, $N(C_2$–$C_6$alkenyl)$SO_2$-phenyl, $N(C_3$–$C_6$alkynyl)$SO_2$—$C_1$–$C_4$alkyl, $N(C_3$–$C_6$alkynyl)$SO_2$-phenyl, $N(C_3$–$C_7$cycloalkyl)$SO_2$—$C_1$–$C_4$alkyl, $N(C_3$–$C_7$ cycloalkyl)$SO_2$-phenyl, $N(phenyl)SO_2$—$C_1$–$C_4$alkyl, $N(phenyl)SO_2$-phenyl, $OSO_2$—$C_1$–$C_4$alkyl, $CONR_{25}R_{26}$, $OSO_2$—$C_1$–$C_4$haloalkyl, $OSO_2$-phenyl, $C_1$–$C_4$alkylthio, $C_1$–$C_4$haloalkylthio, phenylthio, $C_1$–$C_4$alkylsulfonyl, $C_1$–$C_4$haloalkylsulfonyl, phenylsulfonyl, $C_1$–$C_4$alkylsulfinyl, $C_1$–$C_4$haloalkylsulfinyl, phenylsulfinyl, $C_1$–$C_4$alkylene-phenyl or —$NR_{015}CO_2R_{027}$;

or $R_{01}$ is $C_2$–$C_8$alkenyl or $C_2$–$C_8$alkenyl substituted by halogen, $C_1$–$C_4$alkoxy, $C_1$–$C_4$alkylthio, $C_1$–$C_4$alkylsulfonyl, $C_1$–$C_4$alkylsulfinyl, —$CONR_{032}R_{033}$, cyano, nitro, —CHO, —$CO_2R_{038}$, —$COR_{039}$, —COS—$C_1$–$C_4$alkyl, —$NR_{034}R_{035}$ or phenyl which for its part may be substituted by $C_1$–$C_4$alkyl, $C_1$–$C_6$haloalkyl, $C_1$–$C_4$alkoxy, $C_1$–$C_4$haloalkoxy, $C_2$–$C_6$alkenyl, $C_3$–$C_6$alkynyl, $C_3$–$C_6$alkenyloxy, $C_3$–$C_6$alkynyloxy, halogen, nitro, cyano, —COOH, $COOC_1$–$C_4$alkyl, COOphenyl, $C_1$–$C_4$alkoxy, phenoxy, ($C_1$–$C_4$alkoxy)-$C_1$–$C_4$alkyl, ($C_1$–$C_4$alky fthio)-$C_1$–$C_4$alkyl, ($C_1$–$C_4$alkylsulfinyl)-$C_1$–$C_4$alkyl, ($C_1$–$C_4$alkylsulfonyl)-$C_1$–$C_4$alkyl, $NHSO_2$—$C_1$–$C_4$alkyl, $NHSO_2$-phenyl, $N(C_1$–$C_6$alkyl)$SO_2$—$C_1$–$C_4$ alkyl, $N(C_1$–$C_6$alkyl)$SO_2$-phenyl, $N(C_2$–$C_6$alkenyl)$SO_2$—$C_1$–$C_4$alkyl, $N(C_2$-C ralkenyl)$SO_2$-phenyl, $N(C_3$–$C_6$alkynyl)$SO_2$—$C_1$–$C_4$alkyl, $N(C_3$–$C_6$alkynyl)$SO_2$-phenyl, $N(C_3$–$C_7$cycloalkyl)$SO_2$—$C_1$–$C_4$ alkyl, $N(C_3$–$C_7$cycloalkyl)$SO_2$-phenyl, $N(phenyl)SO_2$—$C_1$–$C_4$alkyl, $N(phenyl)SO_2$-phenyl, $OSO_2$-$C_1$–$C_4$alkyl, $CONR_{040}R_{041}$, $OSO_2$—$C_1$–$C_4$haloalkyl, $OSO_2$-phenyl, $C_1$–$C_4$alkylthio, $C_1$–$C_4$ haioalkylthio, phenylthio, $C_1$–$C_4$alkylsulfonyl, $C_1$–$C_4$haloalkylsulfonyl, phenylsulfonyl, $C_1$–$C_4$alkylsulfinyl, $C_1$–$C_4$haloalkylsulfinyl, phenylsulfinyl, $C_1$–$C_4$alkylene-phenyl or —$NR_{043}CO_2R_{042}$;

or $R_{01}$ is $C_3$–$C_6$alkynyl or $C_3$–$C_6$alkynyl substituted by halogen, $C_1$–$C_4$haloalkyl, cyano, —$CO_2R_{044}$ or phenyl, which for its part may be substituted by $C_1$–$C_4$alkyl, $C_1$–$C_6$haloalkyl, $C_l$–$C_4$ alkoxy, $C_1$–$C_4$haloalkoxy, $C_2$–$C_6$alkenyl, $C_3$–$C_6$alkynyl, $C_3$–$C_6$alkenyloxy, $C_3$–$C_6$alkynyloxy, halogen, nitro, cyano, —COOH, $COOC_1$–$C_4$alkyl, COOphenyl, $C_1$–$C_4$alkoxy, phenoxy, ($C_1$–$C_4$ alkoxy)-$C_1$–$C_4$alkyl, ($C_1$–$C_4$alkylthio)-$C_1$–$C_4$alkyl, ($C_1$–$C_4$alkylsulfinyl)-$C_1$–$C_4$alkyl, ($C_1$–$C_4$ alkylsulfonyl)-$C_1$–$C_4$alkyl, $NHSO_2$—$C_1$–$C_4$alkyl, $NHSO_2$-phenyl, $N(C_1$–$C_6$alkyl)$SO_2$—$C_1$–$C_4$alkyl, $N(C_1$–$C_6$alkyl)$SO_2$-phenyl, $N(C_2$–$C_6$alkenyl)$SO_2$—$C_1$–$C_4$alkyl, $N(C_2$–$C_6$alkenyl)$SO_2$-phenyl, $N(C_3$–$C_6$alkynyl)$SO_2$—$C_1$–$C_4$alkyl, $N(C_3$–$C_7$cycloalkyl)$SO_2$—$C_1$–$C_4$alkyl, $N(C_3$–$C_7$cycloalkyl)$SO_2$-phenyl, $N(phenyl)SO_2$—$C_1$–$C_4$alkyl, $N(phenyl)SO_2$-phenyl, $OS_2O$-$C_1$–$C_4$ alkyl, $CONR_{028}R_{029}$, $OSO_2$—$C_1$–$C_4$haloalkyl, $OSO_2$-phenyl, $C_1$–$C_4$alkylthio, $C_1$–$C_4$haloalkylthio, phenylthio, $C_1$–$C_4$alkylsulfonyl, $C_1$–$C_4$haloalkylsulfonyl, phenylsulfonyl, $C_1$–$C_4$alkylsulfinyl, $C_1$–$C_4$haloalkylsulfinyl, phenylsulfinyl, $C_1$–$C_4$alkylene-phenyl or —$NR_{031}CO_2R_{030}$;

or $R_{01}$ is $C_3$–$C_7$cycloalkyl, $C_3$–$C_7$cycloalkyl substituted by $C_1$–$C_4$alkyl, $C_1$–$C_4$alkoxy, $C_1$–$C_4$ alkylthio, $C_1$–$C_4$alkylsulfinyl, $C_1$–$C_4$alkylsulfonyl or phenyl, which for its part may be substituted by halogen, nitro, cyano, $C_1$–$C_4$alkoxy, $C_1$–$C_4$haloalkoxy, $C_1$–$C_4$alkylthio, $C_1$–$C_4$haloalkylthio, $C_1$–$C_4$alkyl and $C_1$–$C_4$haloalkyl; or $R_{01}$ is $C_1$–$C_4$alkylene-$C_3$–$C_7$cycloalkyl, phenyl, or phenyl which is substituted by $C_1$–$C_4$alkyl, $C_1$–$C_6$haloalkyl, $C_1$–$C_4$alkoxy, $C_1$–$C_4$haloalkoxy, $C_2$–$C_6$alkenyl, $C_3$–$C_6$alkynyl, $C_3$–$C_6$alkenyloxy, $C_3$–$C_6$alkynyloxy, halogen, nitro, cyano, —COOH, $COOC_1$–$C_4$alkyl, COOphenyl, $C_1$–$C_4$alkoxy, phenoxy, ($C_1$–$C_4$alkoxy)-$C_1$–$C_4$alkyl, ($C_1$–$C_4$alkylthio)-$C_1$–$C_4$alkyl, ($C_1$–$C_4$alkylsulfinyl)-$C_1$–$C_4$alkyl, ($C_1$–$C_4$alkylsulfonyl)-$C_1$–$C_4$alkyl, $NHSO_2$—$C_1$–$C_4$alkyl, $NHSO_2$-phenyl, $N(C_1$–$C_6$alkyl)$SO_2$-$C_1$–$C_4$ alkyl, $N(C_1$–$C_6$alkyl)$SO_2$-phenyl, $N(C_2$–$C_6$alkenyl)$SO_2$—$C_1$–$C_4$alkyl, $N(C_2$–$C_6$alkenyl)$SO_2$-phenyl, $N(C_3$–$C_6$alkynyl)$SO_2$—$C_1$–$C_4$alkyl, $N(C_3$–$C_6$alkynyl)$SO_2$-phenyl, $N(C_3$–$C_7$cycloalkyl)$SO_2$—$C_1$–$C_4$ alkyl, $N(C_3$–$C_7$cycloalkyl)$SO_2$-phenyl, $N(phenyl)SO_2$—$C_1$–$C_4$alkyl, $N(phenyl)SO_2$-phenyl, $OSO_2$—$C_1$–$C_4$alkyl, $CONR_{045}R_{046}$, $OSO_2$—$C_1$–$C_4$haloalkyl, $OSO_2$-phenyl, $C_1$–$C_4$alkylthio, $C_1$–$C_4$ haloalkylthio, phenylthio, $C_1$–$C_4$alkylsulfonyl, $C_1$–$C_4$haloalkylsulfonyl, phenylsulfonyl, $C_1$–$C_4$alkylsulfinyl, $C_1$–$C_4$haloalkylsulfinyl, phenylsulfinyl, or —$NR_{048}CO_2R_{047}$; or $R_{01}$ is $C_1$–$C_4$alkylene-phenyl, $COR_{07}$ or 4-6-membered heterocyclyl;

$R_{02}$, $R_{038}$, $R_{044}$ and $R_{066}$ independently of one another are hydrogen, $C_1$–$C_4$alkyl, phenyl, or phenyl which is substituted by $C_1$–$C_4$alkyl, $C_1$–$C_6$haloalkyl, $C_1$–$C_4$alkoxy, $C_1$–$C_4$haloalkoxy, $C_2$–$C_6$alkenyl, $C_3$–$C_6$alkynyl, $C_3$–$C_6$alkenyloxy, $C_3$–$C_6$alkynyloxy, halogen, nitro, cyano, —COOH, $COOC_1$–$C_4$alkyl, Coophenyl, $C_1$–$C_4$alkoxy, phenoxy, ($C_1$–$C_4$alkoxy)-$C_1$–$C_4$alkyl, ($C_1$–$C_4$ alkylthio)-$C_1$–$C_4$alkyl, ($C_1$–$C_4$alkylsulfinyl)-$C_1$–$C_4$alkyl, ($C_1$–$C_4$alkylsulfonyi)-$C_1$–$C_4$alkyl, $NHSO_2$—$C_1$–$C_4$alkyl, $NHSO_2$-phenyl, $N(C_1$–$C_6$alkyl)$SO_2$—$C_1$–$C_4$alkyl, $N(C_1$–$C_6$alkyl)$SO_2$-phenyl, $N(C_2$–$C_6$alkenyl)$SO_2$—$C_1$–$C_4$alkyl, $N(C_2$–$C_6$alkenyl)$SO_2$-phenyl, $N(C_3$–$C_6$alkynyl)$SO_2$—$C_1$–$C_4$alkyl, $N(C_3$–$C_6$alkynyl)$SO_2$-phenyl, $N(C_3$–$C_7$cycloalkyl)$SO_2$—

$C_1$–$C_4$alkyl, $N(C_3$–$C_7$Cyloalkyl)$SO_2$-phenyl, $N$(phenyl)$SO_2$—$C_1$–$C_4$alkyl, $N$(phenyl)$SO_2$-phenyl, $OSO_2$–$C_1$–$C_4$alkyl, $CONR_{049}R_{050}$, $OSO_2$—$C_1$–$C_4$ haloalkyl, $OSO_2$-phenyl, $C_1$–$C_4$alkylthio, $C_1$–$C_4$haloalkylthio, phenylthio, $C_1$–$C_4$alkylsulfonyl, $C_1$–$C_4$haloalkylsulfonyl, phenylsulfonyl, $C_1$–$C_4$alkylsulfinyl, $C_1$–$C_4$haloalkylsulfinyl, phenylsulfinyl, $C_1$–$C_4$alkylene-phenyl or —$NR_{052}CO_2R_{053}$;

$R_{03}$, $R_{039}$ and $R_{067}$ independently of one another are $C_1$–$C_4$alkyl, phenyl or phenyl which is substituted by $C_1$–$C_4$alkyl, $C_1$–$C_6$haloalkyl, $C_1$–$C_4$alkoxy, $C_1$–$C_4$haloalkoxy, $C_2$–$C_6$alkenyl, $C_3$–$C_6$ alkynyl, $C_3$–$C_6$alkenyloxy, $C_3$–$C_6$alkynyloxy, halogen, nitro, cyano, —COOH, $COOC_1$–$C_4$alkyl, COOphenyl, $C_1$–$C_4$alkoxy, phenoxy, ($C_1$–$C_4$alkoxy)-$C_1$–$C_4$alkyl, ($C_1$–$C_4$alkylthio)-$C_1$–$C_4$alkyl, ($C_1$–$C_4$alkylsulfinyl)-$C_1$–$C_4$alkyl, ($C_1$–$C_4$alkylsulfonyl)-$C_1$–$C_4$alkyl, $NHSO_2$—$C_1$–$C_4$alkyl, $NHSO_2$-phenyl, $N(C_1$–$C_6$alkyl)$SO_2$—$C_1$–$C_4$alkyl, $N(C_1$–$C_6$alkyl)$SO_2$-phenyl, $N(C_2$–$C_6$alkenyl)$SO_2$—$C_1$–$C_4$alkyl, $N(C_2$–$C_6$alkenyl)$S)_2$-phenyl, $N(C_3$–$C_6$alkynyl)$SO_2$—$C_1$–$C_4$alkyl, $N(C_3$–$C_6$alkynyl)$SO_2$-phenyl, $N(C_3$–$C_7$ cycloalkyl)$SO_2$—$C_1$–$C_4$alkyl, $N(C_3$-$_7$cycloalkyl)$SO_2$-phenyl, $N$(phenyl)$SO_2$—$C_1$–$C_4$alkyl, $N$(phenyl)$SO_2$-phenyl, $OSO_2$–$C_1$–$C_4$alkyl, $CONR_{070}R_{054}$, $OSO_2$—$C_1$–$C_4$haloalkyl, $OSO_2$-phenyl, $C_1$–$C_4$alkylthio, $C_1$–$C_4$haloalkylthio, phenylthio, $C_1$–$C_4$alkylsulfonyl, $C_1$–$C_4$haloalkylsulfonyl, phenylsulfonyl, $C_1$–$C_4$alkylsulfinyl, $C_1$–$C_4$haloalkylsulfinyl, phenylsulfinyl, $C_1$–$C_4$alkylene-phenyl or —$NR_{056}CO_2R_{055}$;

$R_{04}$ is $C_1$–$C_4$alkyl;

$R_{05}$ is hydrogen, $C_1$–$C_4$alkyl, $C_2$–$C_6$alkenyl, $C_3$–$C_6$alkynyl, $C_3$–$C_7$cycloalkyl, phenyl or phenyl which is substituted by $C_1$–$C_4$alkyl, $C_1$–$C_6$haloalkyl, $C_1$–$C_4$alkoxy, $C_1$–$C_4$haloalkoxy, $C_2$–$C_6$ alkenyl, $C_3$–$C_6$alkynyl, $C_3$–$C_6$alkenyloxy, $C_3$–$C_6$alkynyloxy, halogen, nitro, cyano, —COOH, $COOC_1$–$C_4$alkyl, COOphenyl, $C_1$–$C_4$alkoxy, phenoxy, ($C_1$–$C_4$alkoxy)-$C_1$–$C_4$alkyl, ($C_1$–$C_4$ alkylthio)-$C_1$–$C_4$alkyl, ($C_1$–$C_4$alkylsulfinyl)-$C_1$–$C_4$alkyl, ($C_1$–$C_4$alkylsulfonyl)-$C_1$–$C_4$alkyl, $NHSO_2$—$C_1$–$C_4$alkyl, $NHSO_2$-phenyl, $N(C_1$–$C_6$alkyl)$SO_2$—$C_1$–$C_4$alkyl, $N(C_1$–$C_6$alkyl)$SO_2$-phenyl, $N(C_2$–$C_6$ alkenyl)$SO_2$—$C_1$–$C_4$alkyl, $N(C_2$–$C_6$alkenyl)$SO_2$-phenyl, $N(C_3$–$C_6$alkynyl)$SO_2H$, $N(C_3$–$C_6$ alkynyl)$SO_2$—$C_1$–$C_4$alkyl, $N(C_3$–$C_6$alkynyl)$SO_2$phenyl, $N(C_3$–$C_7$cycloalkyl)$SO_2H$, $N(C_3$–$C_7$ cycloalkyl)$SO_2$—$C_1$–$C_4$alkyl, $N(C_3$–$C_7$cycloalkyl)$SO_2$-phenyl, $N$(phenyl)$SO_2$—$C_1$–$C_4$alkyl, $N$(phenyl)$SO_2$-phenyl, $OSO_2$–$C_1$–$C_4$alkyl, $CONR_{057}R_{058}$, $OSO_2$—$C_1$–$C_4$haloalkyl, $OSO_2$-phenyl, $C_1$–$C_4$alkylthio, $C_1$–$C_4$ha hoalkylthio, phenylthio, $C_1$–$C_4$alkylsulfonyl, $C_1$–$C_4$haloalkylsulfonyl, phenylsulfonyl, $C_1$–$C_4$alkylsulfinyl, $C_1$–$C_4$haloalkylsulfinyl, phenylsulfinyl, $C_1$–$C_4$alkylenephenyl or —$NR_{060}CO_2R_{059}$;

$R_{06}$ is hydrogen, $C_1$–$C_4$alkyl, $C_2$–$C_6$aikenyl, $C_3$–$C_6$alkynyl, $C_3$–$C_7$cycloalkyl, phenyl or phenyl which is substituted by $C_1$–$C_4$alkyl, $C_1$–$C_6$haloalkyl, $C_1$–$C_4$alkoxy, $C_1$–$C_4$haloalkoxy, $C_2$–$C_6$ alkenyl, $C_3$–$C_6$alkynyl, $C_3$–$C_6$alkenyloxy, $C_3$–$C_6$alkyny loxy, halogen, nitro, cyano, —COOH, $COOC_1$–$C_4$alkyl, COOphenyl, $C_1$–$C_4$alkoxy, phenoxy, ($C_1$–$C_4$alkoxy)-$C_1$–$C_4$alkyl, ($C_1$–$C_4$ alkylthio)-$C_1$–$C_4$alkyl, ($C_1$–$C_4$alkylsulfinyl)$C_1$–$C_4$alkyl, ($C_1$–$C_4$alkylsulfonyl)-$C_1$–$C_4$alkyl, $NHSO_2$—$C_1$–$C_4$alkyl, $NHSO_2$-phenyl, $N(C_1$–$C_6$alkyl)$SO_2$—$C_1$–$C_4$alky 1, $N(C_1$–$C_6$alkyl)$SO_2$-phenyl, $N(C_2$–$C_6$ alkenyl)$SO_2$—$C_1$–$C_4$alkyl, $N(C_2$–$C_6$alkenyl)$SO_2$-phenyl, $N(C_3$–$C_6$alkynyl)$SO_2$—$C_1$–$C_4$alkyl, $N(C_3$–$C_6$ alkynyl)$SO_2$-phenyl, $N(C_3$–$C_7$cycloalkyl)$SO_2$—$C_1$–$C_4$alkyl, $N(C_3$–$C_7$cycloalkyl)$SO_2$-phenyl, $N$(phenyl)$SO_2$—$C_1$–$C_4$alkyl, $N$(phenyl)$SO_2$-phenyl, $OS_{02}$–$C_1$–$C_4$alkyl, $CONR_{061}R_{062}$, $OSO_2$—$C_1$–$C_4$ haloalkyl, $OSO_2$-phenyl, $C_1$–$C_4$alkylthio, $C_1$–$C_4$haloalkylthio, phenylthio, $C_1$–$C_4$alkylsulfonyl, $C_1$–$C_4$haloalkylsulfonyl, phenylsulfonyl, $C_1$–$C_4$alkylsulfinyl, $C_1$–$C_4$haloalkylsulfinyl, phenylsulfinyl, $C_1$–$C_4$alkylene-phenyl or —$NR_{064}CO_2R_{063}$;

$R_{07}$ is phenyl, substituted phenyl, $C_1$–$C_4$alkyl, $C_1$–$C_4$alkoxy or —$NR_{08}R_{09}$;

$R_{08}$ and $R_{09}$ independently of one another are $C_1$–$C_4$alkyl, phenyl or phenyl which is substituted by halogen, nitro, cyano, $C_1$–$C_4$alkyl, $C_1$–$C_4$alkoxy, $C_1$–$C_4$thioalkyl, —$CO_2R_{066}$, —$COR_{067}$, $C_1$–$C_4$alkylsulfonyl, $C_1$–$C_4$alkylsulfinyl, $C_1$–$C_4$haloalkyl; or $R_{08}$ and $R_{09}$ together form a 5-6-membered ring which may be interrupted by oxygen, $NR_{065}$ or S, $R_{015}$, $R_{031}$, $R_{043}$, $R_{048}$, $R_{052}$, $R_{056}$, $R_{060}$ and $R_{064}$ independently of one another are hydrogen, $C_1$–$C_4$alkyl, $C_2$–$C_6$alkenyl, $C_3$–$C_6$alkynyl or $C_3$–$C_7$cycloalkyl;

$R_{025}$, $R_{026}$, $R_{027}$, $R_{028}$, $R_{029}$, $R_{030}$, $R_{032}$, $R_{033}$, $R_{034}$, $R_{035}$, $R_{036}$, $R_{037}$, $R_{040}$, $R_{041}$, $R_{042}$, $R_{045}$, $R_{046}$, $R_{047}$, $R_{049}$, $R_{050}$, $R_{053}$, $R_{054}$, $R_{055}$, $R_{057}$, $R_{058}$, $R_{059}$, $R_{061}$, $R_{062}$, $R_{063}$, $R_{065}$ and $R_{070}$ independently of one another are hydrogen, $C_1$–$C_4$alkyl, $C_2$–$C_6$alkenyl, $C_3$–$C_6$alkynyl, $C_3$–$C_7$cycloalkyl, phenyl, or phenyl which is substituted by halogen, nitro, cyano, $C_1$–$C_4$alkoxy, $C_1$–$C_4$haloalkoxy, $C_1$–$C_4$ alkylthio, $C_1$–$C_4$haloalkylthio, $C_1$–$C_4$alkyl or $C_1$–$C_4$haloalkyl; and $R_{36}$ is $C_1$–$C_4$alkyl, $C_1$–$C_4$haloalkyl, $C_3$–$C_6$alkenyl, $C_3C_6$haloalkenyl, $C_3$–$C_6$alkynyl, $C_3$–$C_6$ haloalkynyl, $C_3$–$C_6$cycloalkyl or $C_3$–$C_6$cycloalkyl which is substituted by halogen, $C_1$–$C_4$alkyl, $C_1$–$C_4$haloalkyl, $C_3$–$C_6$alkenyl, $C_3$–$C_6$haloalkenyl, $C_3$–$C_6$alkynyl, $C_3$–$C_6$haloalkynyt, $C_1$–$C_4$ alkoxycarbonyl, $C_1$–$C_4$alkylthio, $C_1$–$C_4$alkylsulfinyl, $C_1$–$C_4$alkylsulfonyl, $C_1$–$C_4$haloalkylthio, $C_1$–$C_4$haloalkylsulfinyl, $C_1$–$C_4$haloalkylsulfonyl, $C_1$–$C_4$alkylcarbonyl, di-$C_1$–$C_4$alkylamino, $C_1$–$C_4$ alkoxy, $C_1$–$C_4$haloalkoxy, $C_1$–$C_4$alkyl-S(O)$_2$O, $C_1$–$C_4$haloalkyl-S(O)$_2$O or phenyl which for its part may be substituted by halogen, $C_1$–$C_4$alkyl, $C_1$–$C_4$haloalkyl, $C_3$–$C_6$alkenyl, $C_3$–$C_6$alkynyl, cyano, nitro or COOH; and agronomically acceptable salts $M^+$ and all stereoisomers and tautomers of the compounds of the formula I.

2. A herbicidal and plant-growth-inhibiting composition, which contains a herbicidally effective amount of a compound of the formula I, according to claim 1, on an inert carrier.

3. A method for controlling undesirable plant growth, wherein a herbicidally effective amount of an active compound of the formula I, according to claim 1, or a composition which contains this active compound is applied to the plants or their habitat.

4. A method for inhibiting plant growth, wherein a herbicidally effective amount of an active compound of the formula I, according to claim 1, or a composition which contains this active compound is applied to the plants or their habitat.

* * * * *